(12) United States Patent
Saribas et al.

(10) Patent No.: US 8,822,191 B2
(45) Date of Patent: Sep. 2, 2014

(54) METHODS OF REFOLDING MAMMALIAN GLYCOSYLTRANSFERASES

(75) Inventors: Sami Saribas, Philadelphia, PA (US); David Hakes, Willow Grove, PA (US); Scott Willett, Doylestown, PA (US); Karl F. Johnson, Hatboro, PA (US); Daniel James Bezila, Quakertown, PA (US); Shawn DeFrees, North Wales, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 149 days.

(21) Appl. No.: 10/587,769

(22) PCT Filed: Feb. 4, 2005

(86) PCT No.: PCT/US2005/003856
§ 371 (c)(1),
(2), (4) Date: Jul. 28, 2006

(87) PCT Pub. No.: WO2005/089102
PCT Pub. Date: Sep. 29, 2005

(65) Prior Publication Data
US 2007/0269879 A1 Nov. 22, 2007

Related U.S. Application Data

(60) Provisional application No. 60/542,210, filed on Feb. 4, 2004, provisional application No. 60/599,406, filed on Aug. 6, 2004, provisional application No. 60/627,406, filed on Nov. 12, 2004.

(51) Int. Cl.
*C12P 21/06* (2006.01)
*C12N 9/10* (2006.01)

(52) U.S. Cl.
CPC .................. *C12N 9/1048* (2013.01)
USPC .......................... 435/193; 435/68.1

(58) Field of Classification Search
USPC ................. 435/68.1, 193
See application file for complete search history.

(56) References Cited

U.S. PATENT DOCUMENTS 5,858,751 A * 1/1999 Paulson et al. ............... 435/193

FOREIGN PATENT DOCUMENTS

WO      WO 99/31224 A      6/1999
WO      WO2004000992       * 11/2004

OTHER PUBLICATIONS

U.S. Appl. No. 60/377,730, filed May 2003, Bayer et al.*
Ramakrishnan et al (J. Biol. Chem. 2001, 276, 37665-37671).*
Anton Middelberg Trend in Biotechnol 2002, 20, pp. 437-443.*
Bach, Horacio et al.; "*Escherichia coli* Maltose-binding Protein as a Molecular Chaperone for Recombinant Intracellular Cytoplasmic Single-chain Antibodies"; 2001, *J. Mol. Bio.*, vol. 312, pp. 79-93.
Bennett, Eric Paul et al.; "cDNA Cloning and Expression of a Novel Human UDP-N-acetyl-α-D-galactosamine"; 1996, *The Journal of Biological Chemistry*, vol. 271, No. 29, pp. 17006-17012.
Bennett, Eric Paul et al.; "Genomic organization and chromosomal localization of three members of the UDP-*N*-Acetylglucosaminyltransferase: polypeptide *N*-Acetylglucosaminyltransferase family"; 1998, *Glycobiology*, vol. 8, No. 6, pp. 547-555.
Boeggeman, Elizabeth E. et al.; "Expression of deletion constructs of bovine β-1,4-galactosyltransferase in *Escherichia coli*: importance of Cys134 for its activity"; 1993, *Protein Engineering*, vol. 6, No. 7, pp. 779-785.
Chen, Wei et al.; "Independent Lec1A CHO Glycosylation Mutants Arise from Point Mutations in *N*-Acetylglucosaminyltransferase I That Reduce Affinity for Both Substrates. Molecular Consequences Based on the Crystal Structure of GlcNAc-TI"; 2001, *Biochemistry*, vol. 40, pp. 8765-8772.
Chen, Wei et al.; "Five Lec1 CHO cell mutants have distinct *Mgat1* gene mutations that encode truncated N-acetylglucosaminyltransferase I"; 2003, *Glycobiology*, vol. 13, No. 1, pp. 43-50.
Clark, Eliana De Bernardez; "Protein refolding for industrial processes"; 2001, *Current Opinion in Biotechnology*, vol. 12, pp. 202-207.
Coffman, Birgit L. et al.; "Analysis of Opioid Binding to UDP-Glucuronosyltransferase 2B7 Fusion Proteins Using Nuclear Magnetic Resonance Spectroscopy"; 2001, *Molecular Pharmacology*, vol. 59, No. 6, pp. 1464-1469.
Colland, Frederic et al.; Functional Proteomics Mapping of a Human Signaling Pathway; 2004, *Genome Research*, vol. 14, pp. 1324-1332.
Collins, Francis S.; "Generation and initial analysis of more that 15,000 full-length human and mouse cDNA sequences"; 2002, *PNAS*, vol. 99, No. 26, pp. 16899-16903.
D'Agostaro, Giacomo et al.; "Cloning of cDNA encoding the membrane-bound form of bovine β1,4-galactosyltransferase"; 1989, *Eur. J. Biochem.*, vol. 183, pp. 211-217.
Lee, Young-Choon et al.; "Molecular Cloning and Functional Expression of Two Members of Mouse NeuAcα2,3Galβ1,3GalNAc GalNAcα2,6-Sialyltransferase Family, ST6GalNAc III and IV"; 1999, *The Journal of Biological Chemistry*, vol. 274, No. 17, pp. 11958-11967.
Fujiyama, Kazuhito et al; "Human N-Acetylglucosaminyltransferase I. Expression in *Escherichia coli* as a Soluble Enzyme, and Application as an Immobilized Enzyme for the Chemoenzymatic Synthesis of N-Linked Oligosaccharides"; 2001, *Journal of Bioscience and Bioengineering*, vol. 92, No. 6, pp. 569-574.
Gillespie, William et al.; "Cloning and Expression of the Galβ1,3GalNAc α2,3-Sialyltransferase"; 1992, *The Journal of Biological Chemistry*, vol. 267, No. 29, pp. 21004-21010.

(Continued)

*Primary Examiner* — Tekchand Saidha
*Assistant Examiner* — Md. Younus Meah
(74) *Attorney, Agent, or Firm* — Leydig, Voit & Mayer, Ltd.

(57) ABSTRACT

The present invention provides methods of refolding mammalian glycosyltransferases that have been produced in bacterial cells, and methods to use such refolded glycosyltransferases, including glycosyltransferase mutants that have enhanced ability to be refolded. The invention also provides methods of refolding more than one glycosyltransferase in a single vessel, methods to use such refolded glycosyltransferases, and reaction mixtures comprising the refolded glycosyltransferases.

16 Claims, 54 Drawing Sheets

(56) References Cited

OTHER PUBLICATIONS

Hellman, Jukka et al.; "In Vitro Refolding of Cyclomaltodextrin Glucanotransferase from Cytoplasmic Inclusion Bodies Formed upon Expression in *Escherichia coli*"; 1995, *Protein Expression and Purification*, vol. 6, pp. 56-62.

Ju, Tongzhong et al.; "Cloning and Expression of Human Core 1 β1,3-Galactosyltransferase"; 2002, *The Journal of Biological Chemistry*, vol. 277, No. 1, pp. 178-186.

Kapust, Rachel B. et al.; "*Escherichia coli* maltose-binding protein is uncommonly effective at promoting the solubility of polypeptides to which it is fused"; 1999, *Protein Science*, vol. 8, pp. 1668-1674.

Koprivova, A. et al.; "N-Glycosylation in the Moss *Physcomitrella patens* is Organized Similarly to that in Higher Plants"; 2003, *Plant Biology*, vol. 5, pp. 582-591.

Kurosawa, Nobuyuki et al.; "Molecular Cloning and Genomic Analysis of Mouse GalNAc α2,6-Sialytransferase (ST6GalNAc I)"; 2000, *J. Biochem.*, vol. 127, pp. 845-854.

Mucha, Jan et al.; "Tissues of the clawed frog *Xenopus laevis* contain two closely related forms of UDP-GlcNAc:α3-D-mannoside β-1,2-N-Acetylglucosaminyltransferase I"; 2001, *Glycobiology*, vol. 11, No. 9, pp. 769-778.

Nishiu, Jun et al.; "Characterization of Rat N-Acetylglucosaminyltransferase I Expressed in *Escherichia coli*"; 1995, *Biosci. Biotech. Biochem.*, vol. 59, No. 9, pp. 1750-1752.

Nozaki, Hirofumi et al.; "Are there two forms of β2-N-Acetylglucosaminyltransferase I in rat testicular and epididymal fluids"; 2003, *Biochimica et Biophysica Acta*, vol. 1649, pp. 140-145.

Opat, Andrew S. et al.: "Genetic defect in N-Acetylglucosaminyltransferase I gene of a ricin-resistant baby hamster kidney mutant"; 1998, *Biochem. J.*, vol. 336, pp. 593-598.

Puthalakath, Hamsa et al.; "Glycosylation Defect in Lec1 Chinese Hamster Ovary Mutant Is Due to a Point Mutation in N-Acetylglucosaminyltransferase I Gene"; 1996, *The Journal of Biological Chemistry*, vol. 271, No. 44, pp. 27818-27822.

Quesneville, Hadi et al.; "Combined Evidence Annotation of Transposable Elements in Genome Sequences"; 2005, *PLoS Computational Biology*, vol. 1, No. 2, pp. 166-175.

Ramakrishnan, Boopathy et al.; "Structure-based Design of β1,4-Galactosyltransferase I (β4Gal-T1) with Equally Efficient N-Acetylglucosaminyltransferase Activity"; 2002, *The Journal of Biological Chemistry*, vol. 277, No. 23, pp. 20833-20839.

Sarkar, M. et al.; "Removal of 106 amino acids from the N-terminus of UDP-GlcNAc: α-3-D-mannoside β-1,2-N-Acetylglucosaminyltransferase I does not inactivate the enzyme"; 1998, *Glycoconjugate Journal*, vol. 15, pp. 193-197.

Sarkar, M. et al.; "Molecular cloning and expression of cDNA encoding the enzyme that controls conversion of high-mannose to hybrid and complex N-glycans: UDP N-Acetylglucosaminyltransferase: α-3-D-mannoside β-1,2 N-Acetylglucosaminyltransferase I"; 1991, *PNAS*, vol. 88, pp. 234-238.

Sasaki, Katsutoshi et al.; "Expression Cloning of a Novel Galβ(1-3/1-4)GlcNAc α2,3-Sialytransferase Using Lectin Resistance Selection"; 1993, *The Journal of Biological Chemistry*, vol. 268, No. 30, pp. 22782-22787.

Tenno, Mari et al.; "Identification of two cysteine residues involved in the binding of UDP-GalNAc to UDP-GalNAc:polypeptide N-Acetylglucosaminyltransferase I (GalNAc-T1)"; 2002, *Eur. J. Biochem.*, vol. 269, pp. 4308-4316.

Unligil, Ulig M. et al.; "X-ray crystal structure of rabbit N-Acetylglucosaminyltransferase I: catalytic mechanism and a new protein superfamily"; 2000, *The EMBO Journal*, vol. 19, No. 20, pp. 5269-5280.

Uehara, Kazuyoshi et al.; "Molecular cloning and characterization of β-1,4 galactosyltransferase expressed in mouse testis"; 1997, *Eur. J. Biochem.*, vol. 244, pp. 706-712.

Yang, Xiaojing et al.; "Soluble human core 2 β6-N-Acetylglucosaminyltransferase C2GnT1 requires its conserved cysteine residues for full activity"; 2003, *Biochimica et Biophysica Acta*, vol. 1648, pp. 62-74.

Wen, Dawn X. et al.; "Primary Structure of Galβ1,3(4)GlcNAc α2,3-Sialytransferase Determined by Mass Spectrometry Sequence Analysis and Molecular Cloning"; 1992, *The Journal of Biological Chemistry*, vol. 267, No. 29, pp. 21011-21019.

White, Thayer et al.: "Purification and cDNA Cloning of a Human UDP-N-acetyl-α-D-galactosamine:polypeptide N-Acetylglucosaminyltransferase"; 1995, *The Journal of Biological Chemistry*, vol. 270, No. 41, pp. 24156-24165.

Wong, Chi-Huey; "Carbohydrate-based Drug Discovery"; 2003, *The Scripps Research Institute*, pp. 129-136.

"FoldIt Screen: User Guide"; 2000, *Hampton Research*, 6 pages.

NCBI accession XM 315359.3, 2 pages.

NCBI accession NM 065318.2, 2 pages.

NCBI accession AJ249878.1, 2 pages.

NCBI accession AJ249883.1, 2 pages.

NCBI accession AJ295993.1, 2 pages.

NCBI accession NM 119986.3, 2 pages.

Boeggeman et al., "Expression of Deletion Constructs of Bovine β-1,4-Galactosyltranseferase in *Escherichia coli*: Importance of Cys134 for its Activity," *Protein Engineering*, 6(7): 779-785 (1993).

Boeggeman et al., "The N-terminal Stem Region of Bovine and Human β1,4-Galactosyltranseferase I Increases the In Vitro Folding Efficiency of their Catalytic Domain from Inclusion Bodies," *Protein Expression and Purification*, 30: 219-229 (2003).

Fujiyama et al., "Human N-Acetylglucosaminyltransferase I. Expression in *Escherichia coli* as a Soluble Enzyme, and Application as an Immobilized Enzyme for the Chemoenzymatic Synthesis of N-Linked Oligosaccharides," *J. Bioscience and Bioengineering*, 92(6): 569-574 (2001).

Higa et al., "Sialylation of Glycoprotein Oligosaccharides with N-Acetyl-,N-Glycolyl-, and N-O-Diacetylneuraminic Acids," *J. Biological Chemistry*, 260(15): 8838-8849 (1985).

Kapust et al., "*Escherichia coli* Maltose-Binding Protein is Uncommonly Effective at Promoting the Solubility of Polypeptides to which it is Fused," *Protein Science*, 8: 1668-1674 (1999).

Paulson et al., "Enzymatic Properties of β-D-Galactoside α2→6 Sialyltransferase from Bovine Colostrum," *J. Biological Chemistry*, 252(7): 2363-2371 (1997).

Shan et al., "Expression, Refolding, and Activation of the Catalytic Domain of Human Blood Coagulation Factor XII," *Protein Expression and Purification*, 27: 143-149 (2003).

Shibatani et al., "Production and Characterization of Active Soluble Human β-1,4-Galactosyltranseferase in *Escherichia coli* as a Useful Catalyst in Synthesis of the Gal β1→4 GlcNAc Linkage," *J. Bioscience and Bioengineering*, 91(1): 85-87 (2001).

Sunitha et al., "Refolding and Purification of *Zymomonas mobilis* Levansucrase Produced as Inclusion Bodies in Fed-Batch Culture of Recombinant *Escherichia coli*," *Protein Expression and Purification*, 18: 388-393 (2000).

Weinstein et al., "Sialylation of Glycoprotein Oligasaccharides N-linked to Asparagine," *J. Biological Chemistry*, 257(22): 13845-13853 (1982).

Williams et al., "Large-Scale Expression of Recombinant Sialyltransferases and Comparison of the Kinetic Properties with Native Enzymes," *Glyconjugate J.*, 12: 755-761 (1995).

Zhang et al., "Characterization of Folded, Intermediate, and Unfolded States of Recombinant Human Interstitial Collagenase," *J. Biol. Chem.*, 271(14): 8015-8021 (1996).

Krzewinski-Recchi, M, et al, Identification and functional expression of a second human β-galactoside α2,6-sialyltransferase ST6Gal II, Eur J. Biochem., 2003, pp. 950-961, vol. 270, No. 5.

Paik, J et al, A putative monofunctional glycosyltransferase is expressed in *Ralstonia eutropha*, J. Bacteriology, Jun. 1997, pp. 4061-4065, vol. 179, No. 12.

Gilbert, M et al, The synthesis of sialylated oligosaccharides using a CMP-Neu5Ac synthetase/sialyltransferase fusion, Nature Biotechnology, Aug. 1998, pp. 769-772, vol. 16, No. 8.

Kroliczewski, J et al, In vitro reconstitution of the spinach chloroplast cytocrhome b6 protein from a fusion protein expressed in *Escherichia coli*, Jul. 2002, pp. 177-184, vol. 1598, No. 1-2.

(56) References Cited

OTHER PUBLICATIONS

Saribas, S et al, In vitro N-glycosylation of glycoproteins using refolded glycosyltransferases, Glycobiology, Nov. 2004, p. 1180, vol. 14, No. 11, Conference Abstracts, Joint Meeting of the society for glycobiology and the Japanese society of carbohydrate research.
Maras, M et al, In vivo synthesis of complex N-glycans by expression of human N-acetylglucosaminyltransferase I in the filamentous fungus *Trichoderma reesei*, FEBS Letters, Jun. 1999, pp. 365-370, vol. 452, No. 3.
Kang, Tie-Jun et al., Heterologous proteins folding in *Escherichia coli*. Institute of Biotechnology, Academy of Military Medical Sciences, 2002, 12, 26(4):304-307 (abstract in English).
Dall'Olio et al., "Sialyltransferases in Cancer," *Glycoconjugate J.*, 18: 841-850 (2001).
Grahn et al., "Cloning and Sequencing of Nineteen Transcript Isoforms of the Human α2,3-Sialyltransferase Gene, ST3Gal III: Its Genomic Organisation and Expression in Human Tissues," *Glycoconjugate J.*, 19: 197-210 (2003).
Harduin-Lepers et al., "The Human Sialyltransferase Family," *Biochimie*, 83: 727-737 (2001).
Jeanneau et al., "Structure-Function Analysis of the Human Sialyltransferase ST3Gal I," *J. Biol. Chem.*, 279(14): 13461-13466 (2004).
Breton et al., "Structural and Functional Features of Glycosyltransferases," *Biochimie*, 83: 713-718 (2001).
Fritz et al., "Dynamic Association Between the Catalytic and Lectin Domains of Human UDP-GalNAc:Polypeptide α-N-Acetylgalactosaminyltransferase-2," *J. Biol. Chem.*, 281(13): 8613-8619 (2006).
Fritz et al., "The Beginning of Mucin Biosynthesis: The Crystal Structure of UDP-GalNAc:Polypeptide α-N-Acetylgalactosaminyltransferase-T1," *Proc. Natl. Acad. Sci, U.S.A.*, 101(43): 15307-15312 (2004).
Mazzoni et al., "A Truncated Form of K1Lsm4p and the Absence of Factors Involved in mRNA Decapping Trigger Apoptosis in Yeast," *Molecular Biology of the Cell*, 14: 721-729 (2003).
Tu et al., "Localization of Golgi-Resident Glycosyltransferases," *Cell. Mol. Life Sci.*, 67: 29-41 (2010).

\* cited by examiner

| # | 1 mM GSH | 0.1 mM GSSG | 0.3 mM LM | mM NaCl | mM KCl | 0.055% PEG 3350 | 550 mM GndHCl | 1.1 mM EDTA | 2.2 mM MgCl₂ | 2.2 mM CaCl₂ | 440 mM Sucrose | 550 mM L-Arg | Activity U/g IB |
|---|---|---|---|---|---|---|---|---|---|---|---|---|---|
| #2 (55 mM MES pH 6.5) | + | + | + | 10.56 | 0.44 | 0 | + | 0 | + | + | 0 | 0 | 0 |
| #3 (55 mM MES pH 6.5) | + | + | 0 | 10.56 | 0.44 | + | + | + | 0 | 0 | + | + | 0 |
| #5 (55 mM MES pH 6.5) | + | + | 0 | 264 | 11 | 0 | 0 | 0 | + | + | + | 0 | 0 |
| #8 (55 mM MES pH 6.5) | + | + | + | 264 | 11 | + | 0 | + | 0 | 0 | 0 | + | 40.00 |
| #10 (55 mM MES pH 8.2) | + | + | + | 10.56 | 0.44 | 0 | 0 | + | 0 | + | + | 0 | 0 |
| #11 (55 mM Tris pH 8.2) | + | + | 0 | 10.56 | 0.44 | + | + | + | + | 0 | 0 | + | 105.26 |
| #13 (55 mM Tris pH 8.2) | + | + | 0 | 264 | 11 | 0 | + | 0 | 0 | + | 0 | 0 | 15.65 |
| #16 (55 mM Tris pH 8.2) | + | + | + | 264 | 11 | + | + | 0 | + | + | + | + | 48.70 |

FIG. 1

GlycoPEGylation (20 K) of EPO

```
              10        20        30        40        50        60
/usr/t  MLKKQSAGLVLWGAILFVAWNALLLLFFWTRPAPGRPPSVSALDGDPASLTREVIRLAQD
        ::::::::::::::::::::::::::::::::.:.: :: .:::  :::::::::::::
P27115  MLKKQSAGLVLWGAILFVAWNALLLLFFWTRPVPSRLPSDNALDDDPASLTREVIRLAQD
              10        20        30        40        50        60

70        80        90       100       110
/usr/t  AEVELERQRGLLQQIGD--ALSSQRGRVPTAAPPAQPRVPVTPAPAVIPILVIACDRSTV
        ::::::::::::::: .   ::  :::  .:::::::::,::::: ::::::::::::::
P27115  AEVELERQRGLLQQIREHHALWSQRWKVPTAAPPAQPHVPVTPPPAVIPILVIACDRSTV
              70        80        90       100       110       120

120       130       140       150       160       170
/usr/t  RRCLDKLLHYRPSAELFPIIVSQDCGHEETAQAIASYGSAVTHIRQPDLSSIAVPPDHRK
        :::::::::::::::::::::::::::::::::.:::::::::::::::.::: :::::
P27115  RRCLDKLLHYRPSAELFPIIVSQDCGHEETAQVIASYGSAVTHIRQPDLSNIAVQPDHRK
             130       140       150       160       170       180

180       190       200       210       220       230
/usr/t  FQGYYKIARHYRWALGQVFRQFRFPAAVVVEDDLEVAPDFFEYFRATYPLLKADPSLWCV
        ::::::::::::::::::.:  .:::::::::::::::::::::::.:::::::::::::
P27115  FQGYYKIARHYRWALGQIFHNFNYPAAVVVEDDLEVAPDFFEYFQATYPLLKADPSLWCV
             190       200       210       220       230       240

240       250       260       270       280       290
/usr/t  SAWNDNGKEQMVDASRPELLYRTDFFPGLGWLLLAELWAELEPKWPKAFWDDWMRRPEQR
        ::::::::::::::.::::::::::::::::::::::::::::::::::::::::::::
P27115  SAWNDNGKEQMVDSSKPELLYRTDFFPGLGWLLLAELWAELEPKWPKAFWDDWMRRPEQR
             250       260       270       280       290       300

300       310       320       330       340       350
/usr/t  QGRACIRPEISRTMTFGRKGVSHGQFFDQHLKFIKLNQQFVHFTQLDLSYLQREAYDRDF
         :::: :::::::::::::::::::::::::::::::::::: ::::::::: ::::::
P27115  KGRACVRPEISRTMTFGRKGVSHGQFFDQHLKFIKLNQQFVPFTQLDLSYLQQEAYDRDF
             310       320       330       340       350       360

360       370       380       390       400       410
/usr/t  LARVYGAPQLQVEKVRTNDRKELGEVRVQYTGRDSFKAFAKALGVMDDLKSGVPRAGYRG
        ::::::::::::::::::::::::::::::::::::::::::::::::::::::::::::
P27115  LARVYGAPQLQVEKVRTNDRKELGEVRVQYTGRDSFKAFAKALGVMDDLKSGVPRAGYRG
             370       380       390       400       410       420

420       430       440
/usr/t  IVTFQFRGRRVHLAPPPTWEGYDPSWN
        :::: ::::::::::::: ::::::::.
P27115  IVTFLFRGRRVHLAPPQTWDGYDPSWT
             430       440
```

FIG. 6

GnT1 Cys121Ser mutant avipilviacdrstvrrsldkillhyrpsaelfpiivsqdcgheetaqaiasygsavthirqpdllssiavppdhrkfqgyykiarhyrwa
lgqvfrqfrfpaavvveddllevapdffeyfratypllkadpslwcvsawndngkeqmvdasrpellyrtdffpglgwlllaelwae
lepkwpkafwddwmrrpeqrqgracirpeisrtmtfgrkgvshgqffdqhlkfiklnqqfvhftqldlsylqreaydrdflarvyg
apqlqvekvrtndrkelgevrvqytgrdsfkafakalgvmddlksgvpragyrgivtfqfpgrrvhlappptwegydpswn*

Gcggtgattccatcctggtcatcgcctgtgaccgcagcactgttcggcctgctctctagacaagctgctgcattatcggccctcggctga
gctcttcccccatcatcgttagccaggacgcgggcaggagagacggccaccaggccatcgcctcctacgcagccagcggtcacgcaca
tccggcagccgacctgagcagcagcattgcgtgccgccgaccacacgcaagttccaggctactacaagatcgcgcgccactaccg
ctgggcgctggggccagttccgcagttcttcggcagtttcgcttccccgcgcgtgttgttggaggatgaccttgaggtggccccgacttctt
cgagtactttcgggccacctatccgctgaaggccgatctgctgaaccaagcctctgcctccctggctggtgtcgtcgcctggcgtctgggct
gatggtggacgcaggcaggcccaagtggccaaaaggcctctgggacgactgatgcgcggccgggagcagcagcggcaggggcctgcatacg
ccctgagatctcaagaacgatgacctttggccgcaagggtgagccacggcagttcttgaccagcaacctcaagtttatcaagctga
accagcagttgtgtgcacttcaccaccagctgagacctgctctcctacctgccagcggagagaggggctgggggagagctgggggggcgcaggga
gctcccccagtcgcaggtgagtgagaaagtgaggagccaatgaccgaaagaccggaaagagagctgggggggtccgagagctgggggtcagtatacggcaggga
cagcttcaaggctttcgccaaggtctgtgggtgtcatgatgacctaagtcggggttccgagagctggctaccggggtattgtcactt
ccagttccccgggccgccgtgtccacctggcgcgcccccaccgactgtggaggctatgatcctagctggaattag

FIG. 7

GnT1 Cys121Asp avipilviacdrstvrrdldkllhyrpsaelfpiivsqdcgheetaqaiasygsavthirqpdlssiavppdhrkfqgyykiarhyrwa
lgqvfrqfrfpaavvveddlevapdffeyfratypllkadpslwcvsawndngkeqmvdasrpellyrtdffpglgwlllaelwae
lepkwpkafwddwmrrpeqrqgracirpeisrtmtfgrkgvshgqffdqhlkfiklnqqfvhftqldlsylqreaydrdflarvyg
apqlqvekvrtndrkelgevrvqytgrdsfkafakalgvmddlksgvpragyrgivtfqfpgrrvhlappptwegydpswn*

Gcggtgattcccatcctggtcatcgcctgtgaccgcagcactgttcggcgcgatctagacaagctgctgcattatcggccctcggctg
agctcttccccatcatcgttagccaggactgcgggcacgaggagacggcccaggccatcgcctcctacggcagcgcggtcacgcac
atccggcagcccgacctgagcagcattgcggtgccgccggaccaccgcaagttccagggctactacaagatcgcgcgccactacc
gctgggcgctgggccaggtcttccggcagtttcgcttccccgcggccgtggtggtggaggatgacctggaggtggccccggacttct
tcgagtactttcgggccacctatccgctgctgaaggccgacccctccctgtggtgcgtctcggcctggaatgacaacggcaaggagc
agatggtggacgccagcaggcctgagctgctctaccgcaccgactttttccctggcctgggctggctgctgttggccgagctctgggc
tgagctggagcccaagtggccaaaggccttctgggacgactggatgcggcggccggagcagcggcaggggcgggcctgcatac
gccctgagatctcaagaacgatgacctttggccgcaagggtgtgagccacgggcagttctttgaccagcacctcaagtttatcaagctg
aaccagcagtttgtgcacttcacccagctggacctgtcttacctgcagcgggaggcctatgaccgagatttcctcgcccgcgtctacgg
tgctccccagctgcaggtggagaaagtgaggaccaatgaccggaaggagctgggggaggtgcgggtgcagtatacgggcaggga
cagcttcaaggctttcgccaaggctctgggtgtcatggatgaccttaagtcgggggttccgagagctggctaccggggtattgtcacctt
ccagttcccgggccgccgtgtccacctggcgcccccaccgacgtgggagggctatgatcctagctggaattag

FIG. 8

GnT1 Cys121Thr avipilviacdrstvrrtldkllhyrpsaelfpiivsqdcgheetaqaiasygsavthirqpdlssiavppdhrkfqgyykiarhyrwal
gqvfrqfrfpaavvveddlevapdffeyfratypllkadpslwcvsawndngkeqmvdasrpellyrtdffpglgwllllaelwael
epkwpkafwddwmrrpeqrqgracirpeisrtmtfgrkgvshgqffdqhlkfikInqqfvhftqldlsylqreaydrdflarvyg
apqlqvekvrtndrkelgevrvqytgrdsfkafakalgvmddllksgvpragyrgivtfqfpgrrvhlappptwegydpswn*

Gcggtgattccatcctgtcatcgcctgtgaccgcagcactgttccggcgactctagacaagctgctgcattatcggccctcggctg
agctcttcccatcatcgttagccaggactgcggcacgaggagacgggccaggccatcgcctcctacgcagccggtcacgcac
atccggcagcccgacctgagcagcagcattgcgatccgcgccgaccaccgcaagttccaggtactacaagatcgcgccactacc
gctgggcgctggaggtcttccgccagttccgccactatcgcctgctgagctgctcgactgcccgctgaaggccgaccctcctgtgaaggccgaccctccctgaaggcctgtgctgagctgtctaccgacgactttcctgggactgcctgcctggctgctgggccgagctctgggc
tcgagtactttcgggccactatcgcctgctgagctgctctaccgacgactttcctgggactgcctgcctggctgctgggccgagctctgggc
agatggtggacgccagcctgcaaggccttggccgcaaggtgtgagccagggccagcagggccaggggccaggggcctgcatac
tgagctgaagccaagtgccaaagcccaagaacgatgacctttggccgcaaggtgtgagccacgggcagtcttgaccagcagattcctgcccgctacgg
gccctgagatctcaagaacgatgacctttggccgcaaggtgtgagccacgggcagtcttgaccagcagattcctgcccgctacgg
aaccagcagttgtgcacttcaccagctggaccgtcttacctgcagcggaaggagccctatgaccggagggtgcggttgcagtacgggcaggga
tgtccccagtcgagtgaagaaagtgaggaccaatgaccggaaggagctggggggaggtgcggtgcagtacgggcaggga
cagcttcaaggctttcgccaaggctgtgggtgtcatgatgatgaccttaagtcgggaaggttccgagagctggctacccggggtattgtcaccttccagttcccggcccgccgtgccacctggccgccccccaccgacgtgggaggctatgatcctagctggaattag

FIG. 9

GnT1 Cys121Ala avipilviacdrstvrraldkllhyrpsaelfpiivsqdcgheetaqaiasygsavthirqpdlssiavppdhrkfqgyykiarhyrwa
lgqvfrqfrfpaavvveddlevapdffeyfratypllkadpslwcvsawndngkeqmvdasrpellyrtdffpglgwlllaelwae
lepkwpkafwddwmrrpeqrqgracirpeisrtmtfgrkgvshgqffdqhlkfiklnqqfvhftqldlsylqreaydrdflarvyg
apqlqvekvrtndrkelgevrvqytgrdsfkafakalgvmddlksgvpragyrgivtfqfpgrrvhlappptwegydpswn*

Gcggtgattcccatcctggtcatcgcctgtgaccgcagcactgttcggcgcgccctagacaagctgctgcattatcggccctcggctg
agctcttccccatcatcgttagccaggactgcgggcacgaggagacggcccaggccatcgcctcctacggcagcgcggtcacgcac
atccggcagcccgacctgagcagcattgcggtgccgccggaccaccgcaagttccagggctactacaagatcgcgcgccactacc
gctgggcgctgggccaggtcttccggcagtttcgcttccccgcggccgtggtggtggaggatgacctggaggtggccccggacttct
tcgagtactttcgggccacctatccgctgctgaaggccgacccctccctgtggtgcgtctcggcctggaatgacaacggcaaggagc
agatggtggacgccagcaggcctgagctgctctaccgcaccgactttttccctggcctgggctggctgctgttggccgagctctgggc
tgagctggagcccaagtggccaaaggccttctgggacgactggatgcggcggccggagcagcggcaggggcgggcctgcatac
gccctgagatctcaagaacgatgacctttggccgcaagggtgtgagccacgggcagttctttgaccagcacctcaagtttatcaagctg
aaccagcagtttgtgcacttcacccagctggacctgtcttacctgcagcgggaggcctatgaccgagatttcctcgcccgcgtctacgg
tgctccccagctgcaggtggagaaagtgaggaccaatgaccggaaggagctgggggaggtgcgggtgcagtatacgggcaggga
cagcttcaaggctttcgccaaggctctgggtgtcatggatgaccttaagtcgggggttccgagagctggctaccggggtattgtcacctt
ccagttcccgggccgccgtgtccacctggcgcccccaccgacgtgggagggctatgatcctagctggaattag

FIG. 10

GnT1 Arg120Ala, Cys121H avipilviacdrstvrahldkilhyrpsaelfpiivsqdcgheetaqaiasygsavthirqpdlssiavppdhrkfqgyykiarhyrw
algqvfrqfrfpaavvveddlevapdffeyfratypllkadpslwcvsawndngkeqmvdasrpellyrtdffpglgwlllaelwa
elepkwpkafwddwmrpeqrqgracirpeisrtmfgrkgvshgqffdqhlkfiklnqqfvhftqldlsylqreaydrdflarvy
gapqlqvekvrtndrkelgevrvqytgrdsfkafakalgvmddllksgvpragyrgivtfqfpgrrvhlappptwegydpswn*

Gcggtgattccatcctgtcatcgcctgtgaccgcagcactgttccgggccactagacaagctgctgcattatcggccctcggctg
agctcttcccatcatcgttagccaggactgcggccacgaggagacggccaggccatcgcctcctacggccgcagcggtcacgcac
atccggcagcccgacctgagcagcagcattgcgggccgaccaccgaagttccaggctactacaagatcgcgccactacc
gctggggcgctggcaggtcttccggcagttcgcttccggagatgacctgaggtggccccgactct
tcgagtactttcgggccacctatccgctgctgaaggccgactcctccggctgaaggccgtctcgtgctgtttggccgagctcgggc
agatggtggacgccagcaggcctctaccgacctcctgggacgactgatgcgccgagcagcggcaggagcgcgggcctgcatac
tgagctggagccccaagtgccaaaggcctctggggacctttggccgcaaggtgagccacggcagttcttgaccagcaccagttatcaagctg
gcctgagatctcaagaacagtttgtgcacttcacccagctgacctgtcttacctgaccatgaccaggaaggccgagattcctcgcccgtcacgg
aaccagcagttgtgcactgcagagaaagtgaggaccaatgaccggaaagagctggggagggtgcgggtgcagtatacggcaggga
tgctcccagctgcagtgccaaggctctggggtcatggatgaccttaagtcggggttccgagagctggctggctaccggggtattgtcacctt
ccagtcccgggccgccgtccacctggccgcccccaccgactgtggaggaggctatgatcctagctgaattag

FIG. 11

Rat Liver ST3Gal III amino acid sequence:

MGLLVFVRNLLLALCLFLVLGFLYYSAWKLHLLQWEDSNSLILSLDSAGQTLGTEYDRL
GFLLKLDSKLPAELATKYANFSEGACKPGYASAMMTAIFPRFSKPAPMFLDDSFRKW
ARIREFVPPFGIKGQDNLIKAILSVTKEYRLTPALDSLHCRRCIIVGNGGVLANKSLGS
RIDDYDIVIRLNSAPVKGFEKDVGSKTTLRITYPEGAMQRPEQYERDSLFVLAGFKW
QDFKWLKYIVYKERVSASDGFWKSVATRVPKEPPEIRILNPYFIQEAAFTLIGLPFNN
GLMGRGNIPTLGSVAVTMALDGCDEVAVAGFGYDMNTPNAPLHYYETVRMAAIKE
SWTHNIQREKEFLRKLVKARVITDLSSGI

FIG. 12

Full length UDP-N-acetylgalactosaminyltransferase 2 (GalNAcT2) nucleic acid and amino acid sequences

Amino acid sequence

```
Met Arg Arg Arg Ser Arg Met Leu Leu Cys Phe Ala Phe Leu Trp Val
1               5                   10                  15
Leu Gly Ile Ala Tyr Tyr Met Tyr Ser Gly Gly Gly Ser Ala Leu Ala
            20              25                  30
Gly Gly Ala Gly Gly Gly Ala Gly Arg Lys Glu Asp Trp Asn Glu Ile
            35              40                  45
Asp Pro Ile Lys Lys Lys Asp Leu His His Ser Asn Gly Glu Glu Lys
    50              55                  60
Ala Gln Ser Met Glu Thr Leu Pro Pro Gly Lys Val Arg Trp Pro Asp
65              70                  75                  80
Phe Asn Gln Glu Ala Tyr Val Gly Gly Thr Met Val Arg Ser Gly Gln
                85                  90                  95
Asp Pro Tyr Ala Arg Asn Lys Phe Asn Gln Val Glu Ser Asp Lys Leu
            100             105                 110
Arg Met Asp Arg Ala Ile Pro Asp Thr Arg His Asp Gln Cys Gln Arg
        115             120                 125
Lys Gln Trp Arg Val Asp Leu Pro Ala Thr Ser Val Val Ile Thr Phe
    130             135                 140
His Asn Glu Ala Arg Ser Ala Leu Leu Arg Thr Val Val Ser Val Leu
145             150                 155                 160
Lys Lys Ser Pro Pro His Leu Ile Lys Glu Ile Ile Leu Val Asp Asp
            165                 170                 175
Tyr Ser Asn Asp Pro Glu Asp Gly Ala Leu Leu Gly Lys Ile Glu Lys
            180                 185                 190
Val Arg Val Leu Arg Asn Asp Arg Arg Glu Gly Leu Met Arg Ser Arg
        195                 200                 205
Val Arg Gly Ala Asp Ala Ala Gln Ala Lys Val Leu Thr Phe Leu Asp
    210                 215                 220
Ser His Cys Glu Cys Asn Glu His Trp Leu Glu Pro Leu Leu Glu Arg
225                 230                 235                 240
Val Ala Glu Asp Arg Thr Arg Val Val Ser Pro Ile Ile Asp Val Ile
                245                 250                 255
Asn Met Asp Asn Phe Gln Tyr Val Gly Ala Ser Ala Asp Leu Lys Gly
            260                 265                 270
Gly Phe Asp Trp Asn Leu Val Phe Lys Trp Asp Tyr Met Thr Pro Glu
        275                 280                 285
```

FIG. 13A

Gln Arg Arg Ser Arg Gln Gly Asn Pro Val Ala Pro Ile Lys Thr Pro
    290             295             300
Met Ile Ala Gly Gly Leu Phe Val Met Asp Lys Phe Tyr Phe Glu Glu
305             310              315                 320
Leu Gly Lys Tyr Asp Met Met Met Asp Val Trp Gly Gly Glu Asn Leu
            325             330                 335
Glu Ile Ser Phe Arg Val Trp Gln Cys Gly Gly Ser Leu Glu Ile Ile
            340             345             350
Pro Cys Ser Arg Val Gly His Val Phe Arg Lys Gln His Pro Tyr Thr
        355             360             365
Phe Pro Gly Gly Ser Gly Thr Val Phe Ala Arg Asn Thr Arg Arg Ala
    370             375             380
Ala Glu Val Trp Met Asp Glu Tyr Lys Asn Phe Tyr Tyr Ala Ala Val
385             390             395                 400
Pro Ser Ala Arg Asn Val Pro Tyr Gly Asn Ile Gln Ser Arg Leu Glu
            405             410             415
Leu Arg Lys Lys Leu Ser Cys Lys Pro Phe Lys Trp Tyr Leu Glu Asn
            420             425             430
Val Tyr Pro Glu Leu Arg Val Pro Asp His Gln Asp Ile Ala Phe Gly
        435             440             445
Ala Leu Gln Gln Gly Thr Asn Cys Leu Asp Thr Leu Gly His Phe Ala
    450             455             460
Asp Gly Val Val Gly Val Tyr Glu Cys His Asn Ala Gly Gly Asn Gln
465             470             475                 480
Glu Trp Ala Leu Thr Lys Glu Lys Ser Val Lys His Met Asp Leu Cys
            485             490             495
Leu Thr Val Val Asp Arg Ala Pro Gly Ser Leu Ile Lys Leu Gln Gly
            500             505             510
Cys Arg Glu Asn Asp Ser Arg Gln Lys Trp Glu Gln Ile Glu Gly Asn
        515             520             525
Ser Lys Leu Arg His Val Gly Ser Asn Leu Cys Leu Asp Ser Arg Thr
    530             535             540
Ala Lys Ser Gly Gly Leu Ser Val Glu Val Cys Gly Pro Ala Leu Ser
545             550             555                 560
Gln Gln Trp Lys Phe Thr Leu Asn Leu Gln Gln
            565             570

FIG. 13A (CONT.)

Nucleic acid sequence

```
atgcggcggc gctgcggat gctgctctgc ttcgccttcc tgtgggtgct gggcatcgcc      60
tactacatgt actcggggg cggctctgcg ctggccgggg gcgcgggcgg cggagccggc     120
aggaaggagg actggaatga aattgacccc attaaaaaga aagaccttca tcacagcaat    180
ggagaagaga aagcacaaag catggagacc ctccctccag ggaaagtacg gtggccagac    240
tttaaccagg aagcttatgt tggagggacg atggtccgct ccgggcagga cccttacgcc    300
cgcaacaagt tcaaccaggt ggagagtgat aagcttcgaa tggacagagc catccctgac    360
acccggcatg accagtgtca ggggaagcag tggcggtgg atctgccggc caccagcgtg    420
gtgatcacgt ttcacaatga agccaggtcg gccctactca ggaccgtggt cagcgtgctt    480
aagaaaagcc cgccccatct cataaaagaa atcatcttgg tggatgacta cagcaatgat    540
cctgaggacg gggctctctt ggggaaaatt gagaaagtgc gagttcttag aaatgatcga    600
cgagaaggcc tcatgcgctc acggggttcgg ggggccgatg ctgcccaagc caaggtcctg    660
aacttcctgg acagtcactg cgagtgtaat gagcactggc tggagcccct cctggaaagg    720
gtggcggagg acaggactcg ggttgtgtca cccatcatcg atgtcattaa tatggacaac    780
tttcagtatg tggggcatc tgctgacttg aagggcggtt ttgattggaa cttggtattc    840
aagtgggatt acatgacgcc tgagcagaga aggtcccggc aggggaaccc agtcgcccct    900
ataaaaaccc ccatgattgc tgtgtgggctg tttgtgatgg ataagttcta ttttgaagaa    960
ctggggaagt acgacatgat gatggatgtg tggggagagag aaacctaga gatctcgttc   1020
cgcgtgtggc agtgtggtgg cagcctggag atcatccgt gcagccgtgt gggacacgtg   1080
ttccggaagc agcacccta caagttcccg ggtggcagtg gcactgtctt tgcccgaaac    1140
acccgccggg cagcagaggt ctggatggat gaatacaaaa atttctatta tgcagcagtg    1200
ccttctgcta gaaacgttcc ttatggaaat attcagagca gattggagct taggaagaaa    1260
ctcagctgca agccttttcaa atggtaacctt gaaaatgtct atccagagtt aagggttcca    1320
gaccatcagg atatagcttt tggggccttg cagcagggaa ctaactgcct cgacactttg    1380
ggacactttg ctgatggtgt ggttggagtt tatgaatgtc acaatgctgg gggaaaccag    1440
gaatgggcct tgacgaagga gaagtcggtg aagcacatgg atttgtgcct tactgtggtg    1500
gacccgggcac ccggctctct tataaagctg caggggctgcc gagaaaatga cagcagacag    1560
aaatgggaac agatcgaggg caactccaag ctgaggcacg tgggcagcaa cctgtgcctg    1620
gacagtcgca cggccaagag cggggggccta agcgtggagg tgtgtggccc ggcccttttcg    1680
cagcagtgga agttcacgct caacctgcag cag                                  1713
```

FIG. 13B

Δ51 UDP-N-acetylgalactosaminyltransferase 2, GalNAcT2, nucleic acid and amino acid sequences Amino acid sequence Lys Lys Lys Asp Leu His His Ser Asn Gly Glu Glu Lys Ala Gln Ser
1              5                  10                 15

Met Glu Thr Leu Pro Pro Gly Lys Val Arg Trp Pro Asp Phe Asn Gln
         20              25                 30

Glu Ala Tyr Val Gly Gly Thr Met Val Arg Ser Gly Gln Asp Pro Tyr
         35              40                 45

Ala Arg Asn Lys Phe Asn Gln Val Glu Ser Asp Lys Leu Arg Met Asp
    50              55              60

Arg Ala Ile Pro Asp Thr Arg His Asp Gln Cys Gln Arg Lys Gln Trp
65              70              75                  80

Arg Val Asp Leu Pro Ala Thr Ser Val Val Ile Thr Phe His Asn Glu
             85              90              95

Ala Arg Ser Ala Leu Leu Arg Thr Val Val Ser Val Leu Lys Lys Ser
            100             105             110

Pro Pro His Leu Ile Lys Glu Ile Ile Leu Val Asp Asp Tyr Ser Asn
        115             120             125

Asp Pro Glu Asp Gly Ala Leu Leu Gly Lys Ile Glu Lys Val Arg Val
    130             135             140

Leu Arg Asn Asp Arg Arg Glu Gly Leu Met Arg Ser Arg Val Arg Gly
145             150             155             160

Ala Asp Ala Ala Gln Ala Lys Val Leu Thr Phe Leu Asp Ser His Cys
                165             170             175

Glu Cys Asn Glu His Trp Leu Glu Pro Leu Leu Glu Arg Val Ala Glu
            180             185             190

Asp Arg Thr Arg Val Val Ser Pro Ile Ile Asp Val Ile Asn Met Asp
        195             200             205

Asn Phe Gln Tyr Val Gly Ala Ser Ala Asp Leu Lys Gly Gly Phe Asp
    210             215             220

Trp Asn Leu Val Phe Lys Trp Asp Tyr Met Thr Pro Glu Gln Arg Arg
225             230             235             240

Ser Arg Gln Gly Asn Pro Val Ala Pro Ile Lys Thr Pro Met Ile Ala
            245             250             255

Gly Gly Leu Phe Val Met Asp Lys Phe Tyr Phe Glu Glu Leu Gly Lys
        260             265             270

Tyr Asp Met Met Met Asp Val Trp Gly Gly Glu Asn Leu Glu Ile Ser
    275             280             285

Phe Arg Val Trp Gln Cys Gly Gly Ser Leu Glu Ile Ile Pro Cys Ser

FIG. 14A

```
                    290                    295                    300
Arg Val Gly His Val Phe Arg Lys Gln His Pro Tyr Thr Phe Pro Gly
305                 310                 315                 320
Gly Ser Gly Thr Val Phe Ala Arg Asn Thr Arg Arg Ala Ala Glu Val
                325                 330                 335
Trp Met Asp Glu Tyr Lys Asn Phe Tyr Tyr Ala Ala Val Pro Ser Ala
            340                 345                 350
Arg Asn Val Pro Tyr Gly Asn Ile Gln Ser Arg Leu Glu Leu Arg Lys
        355                 360                 365
Lys Leu Ser Cys Lys Pro Phe Lys Trp Tyr Leu Glu Asn Val Tyr Pro
370                 375                 380
Glu Leu Arg Val Pro Asp His Gln Asp Ile Ala Phe Gly Ala Leu Gln
385                 390                 395                 400
Gln Gly Thr Asn Cys Leu Asp Thr Leu Gly His Phe Ala Asp Gly Val
                405                 410                 415
Val Gly Val Tyr Glu Cys His Asn Ala Gly Gly Asn Gln Glu Trp Ala
            420                 425                 430
Leu Thr Lys Glu Lys Ser Val Lys His Met Asp Leu Cys Leu Thr Val
        435                 440                 445
Val Asp Arg Ala Pro Gly Ser Leu Ile Lys Leu Gln Gly Cys Arg Glu
450                 455                 460
Asn Asp Ser Arg Gln Lys Trp Glu Gln Ile Glu Gly Asn Ser Lys Leu
465                 470                 475                 480
Arg His Val Gly Ser Asn Leu Cys Leu Asp Ser Arg Thr Ala Lys Ser
                485                 490                 495
Gly Gly Leu Ser Val Glu Val Cys Gly Pro Ala Leu Ser Gln Gln Trp
            500                 505                 510
Lys Phe Thr Leu Asn Leu Gln Gln
        515                 520
```

FIG. 14A (CONT.)

Nucleic acid sequence

| | | | | | |
|---|---|---|---|---|---|
| aaaaagaaag | accttcatca | cagcaatgga | gaagagaaag | cacaaagcat | ggagaccctc | 60 |
| cctccaggga | aagtacggtg | gccagacttt | aaccaggaag | cttatgttgg | agggacgatg | 120 |
| gtccgctccg | ggcaggaccc | ttacgcccgc | aacaagttca | accaggtgga | gagtgataag | 180 |
| cttcgaatgg | acagagccat | ccctgacacc | cggcatgacc | agtgtcagcg | gaagcagtgg | 240 |
| cgggtggatc | tgccggccac | cagcgtggtg | atcacgtttc | acaatgaagc | caggtcggcc | 300 |
| ctactcagga | ccgtggtcag | cgtgcttaag | aaaagcccgc | cccatctcat | aaaagaaatc | 360 |
| atcttggtgg | atgactacag | caatgatcct | gaggacgggg | ctctcttggg | gaaaattgag | 420 |
| aaagtgcgag | ttcttagaaa | tgatcgacga | gaaggcctca | tgcgctcacg | ggttcggggg | 480 |
| gccgatgctg | cccaagccaa | ggtcctgacc | ttcctggaca | gtcactgcga | gtgtaatgag | 540 |
| cactggctgg | agcccctcct | ggaagggtg | gcggaggaca | ggactcgggt | tgtgtcaccc | 600 |
| atcatcgatg | tcattaatat | ggacaacttt | cagtatgtgg | gggcatctgc | tgacttgaag | 660 |
| ggcggttttg | attggaactt | ggtattcaag | tgggattaca | tgacgcctga | gcagagaagg | 720 |
| tcccggcagg | ggaacccagt | cgccccctata | aaaacccca | tgattgctgg | tgggctgttt | 780 |
| gtgatggata | agttctatt | tgaagaactg | gggaagtacg | acatgatgat | ggatgtgtgg | 840 |
| ggaggagaga | acctagagat | ctggttccgc | gtgtggcagt | gtggtggcag | cctggagatc | 900 |
| atcccgtgca | gccgtgtggg | acacgtgttc | cggaagcagc | accoctacac | gttcccgggt | 960 |
| ggcagtggca | ctgtctttgc | ccgaaacacc | cgccgggcag | cagaggtctg | gatggatgaa | 1020 |
| tacaaaaatt | tctattatgc | agcagtgcct | tctgctagaa | acgttcctta | tggaaatatt | 1080 |
| cagagcagat | tgggagcttag | gaagaaactc | agctgcaagc | cttttcaaatg | gtaccttgaa | 1140 |
| aatgtctatc | cagagttaag | ggttccagac | catcaggata | tagcttttgg | ggccttgcag | 1200 |
| cagggaacta | actgcctcga | cactttggga | cactttgctg | atggtgtggt | tggagtttat | 1260 |
| gaatgtcaca | atgctggggg | aaaacaggaa | tgggcttga | cgaaggagaa | gtcggtgaag | 1320 |
| cacatggatt | tgtgccttac | tgtggtggac | cgggcacgg | gctctcttat | aaagctgcag | 1380 |
| ggctgccgag | aaaatgacag | cagacagaaa | tgggaacaga | tcgagggcaa | ctccaagctg | 1440 |
| aggcacgtgg | gcagcaacct | gtgctggac | agtcgcacgg | ccaagagcgg | gggcctaagc | 1500 |
| gtggaggtgt | gtggcccggc | cctttcgcag | cagtggaagt | tcacgctcaa | cctgcagcag | 1560 |

FIG. 14B

|  | Volume (mL) | Activity (U/L) | A280 |
|---|---|---|---|
| Load | 890 | 1.5 | 0.110 |
| FT$_{A4-C4}$ | 670 | 9.2 | NA |
| FT$_{C5-C7}$ | 120 | 1.0 | 0 |
| Wash | 138 | 3.6 | 0.100 |
| D6 | 45 | 4.5 | 0 |
| D5 | 45 | 2.4 | 0.026 |
| D4 | 45 | 2.0 | 0.108 |
| D3/2 | 90 | 1.1 | 0.179 |
| E6 |  | 0.0 | 0.017 |

FIG. 20

Pooled A4-C4 and adjusted pH to 7.0 using 1mM HCl 670mL
load pH 7.0 16mS/cm

|  | Volume (mL) | Activity (U/L) pre-dialysis | Activity (U/L) post-dialysis | A280 | A280/ 1.51 (mg/mL) | Activity (U) | Mass (mg) | Specific Activity (U/mg) |
|---|---|---|---|---|---|---|---|---|
| Load | 670 | 9.2 | NA | NA |  |  |  |  |
| FT | 670 | 0.0 | NA | 0.122 |  |  |  |  |
| Wash | 9 | 2.9 | NA | -0.013 |  |  |  |  |
| A5/6 | 6 | 1.1 | NA | -0.005 |  |  |  |  |
| A7 | 3 | 0.1 | 19.3 (13mL) | 0.180 | 0.119 | 0.25 | 1.55 | 0.16 |
| A8 | 3 | 1.3 |  |  |  |  |  |  |
| A9 | 3 | 4.6 |  |  |  |  |  |  |
| A10 | 3 | 2.4 |  |  |  |  |  |  |
| A11 | 3 | 0.4 |  |  |  |  |  |  |

FIG. 22

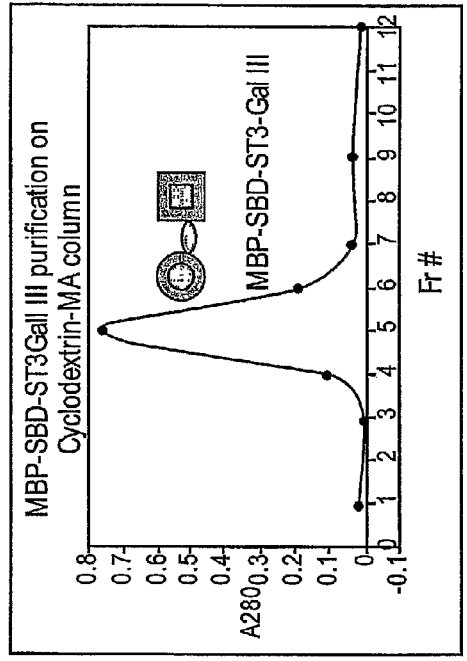
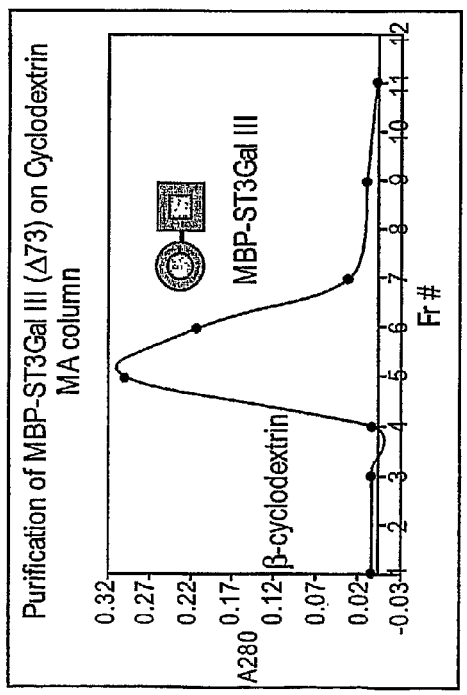
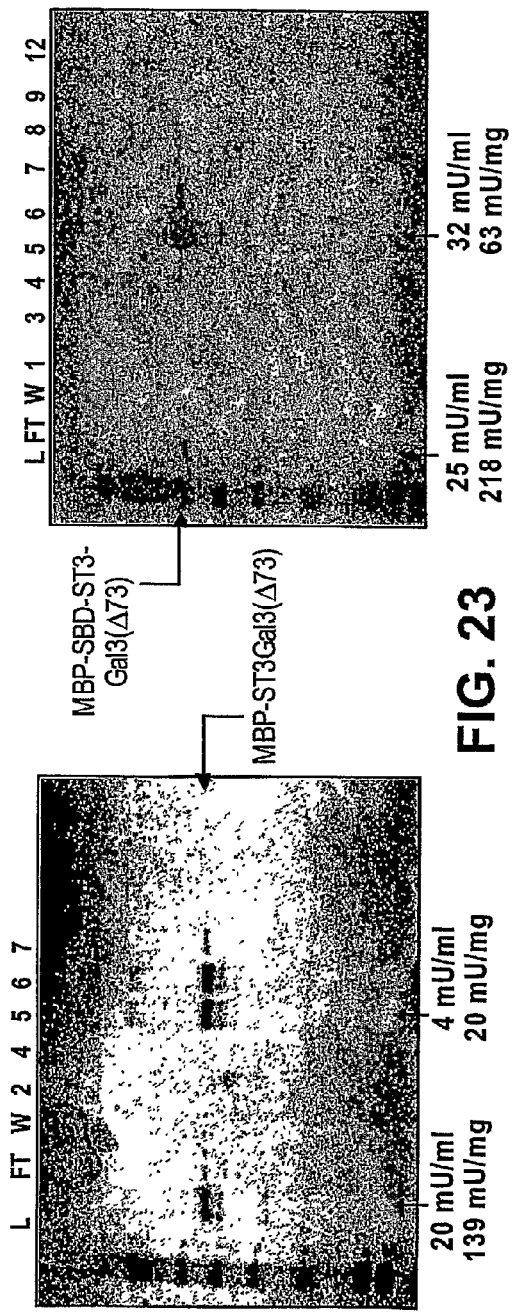
FIG. 23

MBP-pST3Gal1 fusion protein

MKIEEGKLVIWINGDKGYNGLAEVGKKFEKDTGIKVTVEHPDKLEEKFPQVAATGDGPDIIFWAHDRF
GGYAQSGLLAEITPDKAFQDKLYPFTWDAVRYNGKLIAYPIAVEALSLIYNKDLLPNPPKTWEEIPALD
KELKAKGKSALMFNLQEPYFTWPLIAADGGYAFKYENGKYDIKDVGVDNAGAKAGLTFLVDLIKNKH
MNADTDYSIAEAAFNKGETAMTINGPWAWSNIDTSKVNYGVTVLPTFKGQPSKPFVGVLSAGINAASP
NKELAKEFLENYLLTDEGLEAVNKDKPLGAVALKSYEEELAKDPRIAATMENAQKGEIMPNIPQMSAF
WYAVRTAVINAASGRQTVDEALKDAQTNSSSNNNNNNNLGIEGRISEFGSELSENFKKLMKYPYR
PCTCTRCIEEQRVSAWFDERFNRSMQPLLTAKNAHLEEDTYKWWLRLQREKQPNNLNDTIRELFQVVP
GNVDPLLEKRLVSCRRCAVVGNSGNLKESYYGPQIDSHDFVLRMNKAPTEGFEADVGSKTTHHFVYPE
SFRELAQEVSMILVPFKTTDLEWVISATTGRISHTYVPVPAKIKYVKKEKILYHPAFIKYVFDRWLQGH
GRYPSTGILSVIFSLHICDEVDLYGFGADSKGNWHHYWENNPSAGAFRKTGVHDGDFESNVTTILASIN
KIRIFKGR

FIG. 24A

MBPSBD-pST3Gal1 fusion protein

MKIEEGKLVIWINGDKGYNGLAEVGKKFEKDTGIKVTVEHPDKLEEKFPQVAATGDGPDIIFWAHDRF
GGYAQSGLLAEITPDKAFQDKLYPFTWDAVRYNGKLIAYPIAVEALSLIYNKDLLPNPPKTWEEIPALD
KELKAKGKSALMFNLQEPYFTWPLIAADGGYAFKYENGKYDIKDVGVDNAGAKAGLTFLVDLIKNKH
MNADTDYSIAEAAFNKGETAMTINGPWAWSNIDTSKVNYGVTVLPTFKGQPSKPFVGVLSAGINAASP
NKELAKEFLENYLLTDEGLEAVNKDKPLGAVALKSYEEELAKDPRIAATMENAQKGEIMPNIPQMSAF
WYAVRTAVINAASGRQTVDEALKDAQTNSSSNNNNNNNLGIEGRISEFGSIVATGGTTTTATPTG
SGSVTSTSKTTATASKTSTSTSCTTPTAVAVTFDLTATTTYGENIYLVGSISQLGDWETSDGIALSAD
KYTSSDPLWYVTVTLPAGESFEYKFIRIESDDSVEWESDPNREYTVPQACGTSTATVTDTWRGSELSEN
FKKLMKYPYRPCTCTRCIEEQRVSAWFDERFNRSMQPLLTAKNAHLEEDTYKWWLRLQREKQPNNLN
DTIRELFQVVPGNVDPLLEKRLVSCRRCAVVGNSGNLKESYYGPQDSHDFVLRMNKAPTEGFEADVG
SKTTHHFVYPESFRELAQEVSMILVPFKTTDLEWVISATTGRISHTYVPPAKIKVKKEKILYHPAFIK
YVFDRWLQGHGRYPSTGILSVIFSLHICDEVDLYGFGADSKGNWHHYWENNPSAGAFRKTGVHDGDF
ESNVTTILASINKIRIFKGR

FIG. 24B

MKIEEGKLVIWINGDKGYNGLAEVGKKFEKDTGIKVTVEHPDKLEEKFPQVAATGDGPDIIFWAHDRF
GGYAQSGLLAEITPDKAFQDKLYPFTWDAVRYNGKLIAYPIAVEALSLIYNKDLLPNPPKTWEEIPALD
KELKAKGKSALMFNLQEPYFTWPLIAADGGYAFKYENGKYDIDKVGVDNAGAKAGLTFLVDLIKNKH
MNADTDYSIAEAAFNKGETAMTINGPWAWSNIDTSKVNYGVTVLPTFKGQPSKPFVGVLSAGINAASP
NKELAKEFLENYLLTDEGLEAVNKDKPLGAVALKSYEEELAKDPRIAATMENAQKGEIMPNIPQMSAF
WYAVRTAVINAASGRQTVDEALKDAQTNSSSNNNNNNNLGIEGRISEFGSSEHLDKVPRTPGAL
STRKTPMATGAVPAKKKVVQAITKSPASSPHPTTRRRQRLKASEFKSEPRWDFEEEYSLDMSSLQT
NCSASVKIKASKSPVLQNIFLPNITLFLDSGRFTQSEWNRLEHFAPPFGFMELNQSLVQKVVTRFP
PVRQQQLLLASLPTGYSKCITCAVVGNGGILNDSRVGREIDSHDYVFRLSGAVIKGYEQDVGTRT
SFYGFTAFSLTQSILILGRRGFQHVPLGKDVRYLHFLEGTRNYEWLEAMFLNQTLAKTHLSWFR
HRPQEAFRNALDLDRYLLHPDFLRYMKNRFLRSKTLDTAXWRIYRPTTGALLLTALHLCDKV
SAYGFITEGHERFSDHYYDTSWKRLIFYINHDFRLERMVWKRLHDEGHWLYQRPQSDKAKN

FIG. 26A

MKIEEGKLVIWINGDKGYNGLAEVGKKFEKDTGIKVTVEHPDKLEEKFPQVAATGDGPDIIFWAHDRF
GGYAQSGLLAEITPDKAFQDKLYPFTWDAVRYNGKLIAYPIAVEALSLIYNKDLLPNPPKTWEEIPALD
KELKAKGKSALMFNLQEPYFTWPLIAADGGYAFKYENGKYDIDKVGVDNAGAKAGLTFLVDLIKNKH
MNADTDYSIAEAAFNKGETAMTINGPWAWSNIDTSKVNYGVTVLPTFKGQPSKPFVGVLSAGINAASP
NKELAKEFLENYLLTDEGLEAVNKDKPLGAVALKSYEEELAKDPRIAATMENAQKGEIMPNIPQMSAF
WYAVRTAVINAASGRQTVDEALKDAQTNSSSNNNNNNNNLGIEGRISEFGSKEPQTKPSRHQRTE
NIKERSLQSLAKPKSQAPTRARRTTIYAEPYPENNALNTQTQPKAHTTGDRGKEANQAPPEEQDK
VPHTAQRAAWKSPEKEKTMVNTLSPRGQDAGMASGRITEAQSWKSQDTKTTQGNGGQTRKLTA
SRTVSEKHQGKAATTAKTILPKSQHRMLAPTGAVSTRKITRQKGVTTAVIPPKEKKPQATPPPAPFQ
SPTTQRNQRLKAANFKSEPRWDFEEKYSFEIGGLQTTCPDSVKIKASKSLWLQKLFLPNLTLFLDS
RHFNQSEWDRLEHFAPPFGFMELNYSLVQKVVTRFPPVPQQQLLLASLPAGSLRCITCAVVGNG
GILNNSHMGQEIDSHDYVFRLSGALIKGYEQDVGTRISFYGFTAFSLTQSLLILGNRGFKNVPLGK
DVRYLHFLEGTRDYEWLEALLMNQTVMSKNLFWFRHRPQEAFREALHMDRYLLHPDFLRYM
KNIRFLRSKTLDGAHWRIYRPTTGALLLTALQLCDQVSAYGFITEGHERFSDHYYDTSWKRLIFY
INHDFKLEREVWKRLHDEGHIRLYQRPGPGTAKAKN

FIG. 26B

```
  1 mkfrepllgg saampgaslq racrllvavc alhlgvtlvy ylagrdlrrl pqlvgvhppl
 61 qgsshgaaai gqpsgelrlr gvappplqn sskprsraps nldayshpgp gpgpgsnlts
121 apvpstttrs ltacpeespl lvgpmliefn ipvdlklieq qnpkvklggr ytpmdcisph
181 kvaiiilfrn rqehlkywly ylhpmvqrqq ldygiyving agesmfnrak llnvgfkeal
241 kdydyncfvf sdvdlipmnd hntyrcfsqp rhisvamdkf gfslpyvqyf ggvsalskqq
301 flsingfpnn ywgwgeddd iynrlafrgm svsrpnavig kcrmirhsrd kknepnpqrf
361 driahtketm lsdglnslty mvlevqrypl ytkitvdigt ps
```

FIG. 30

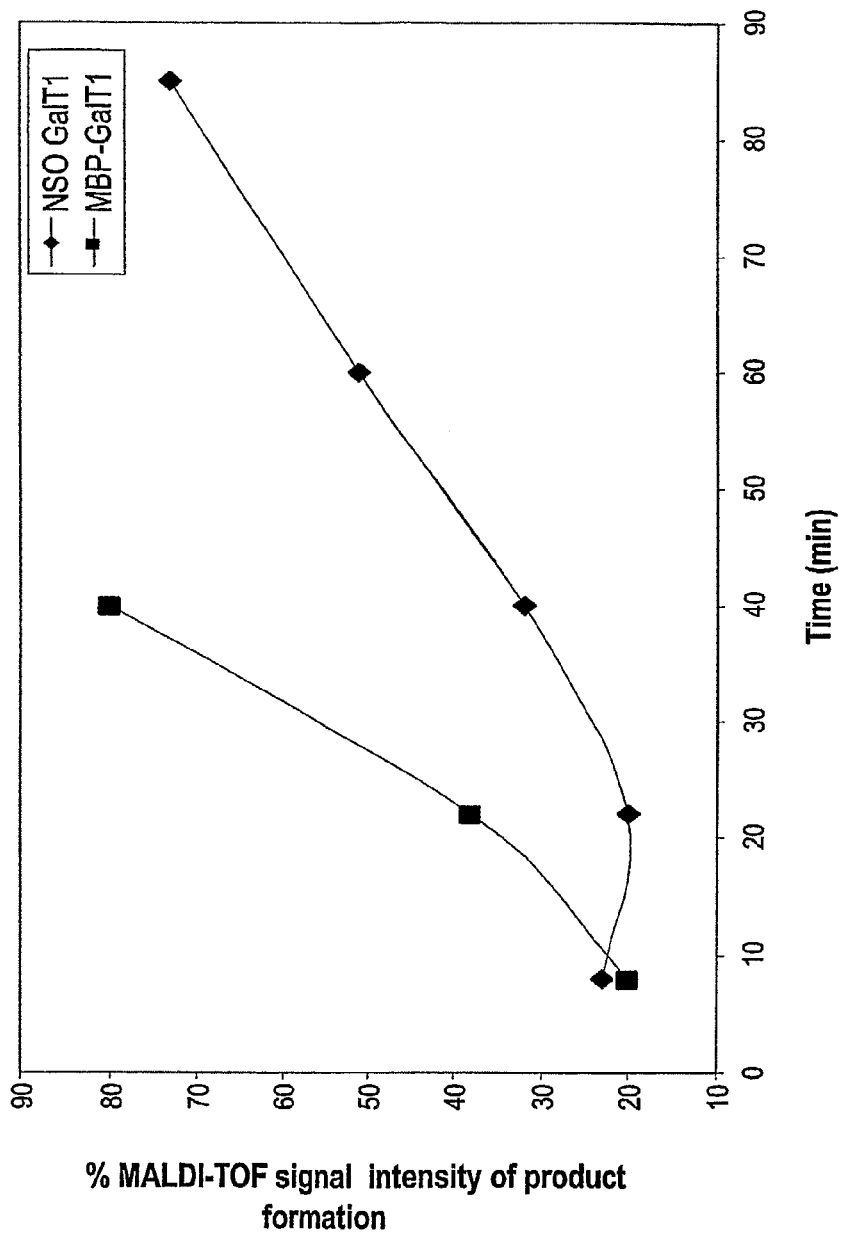

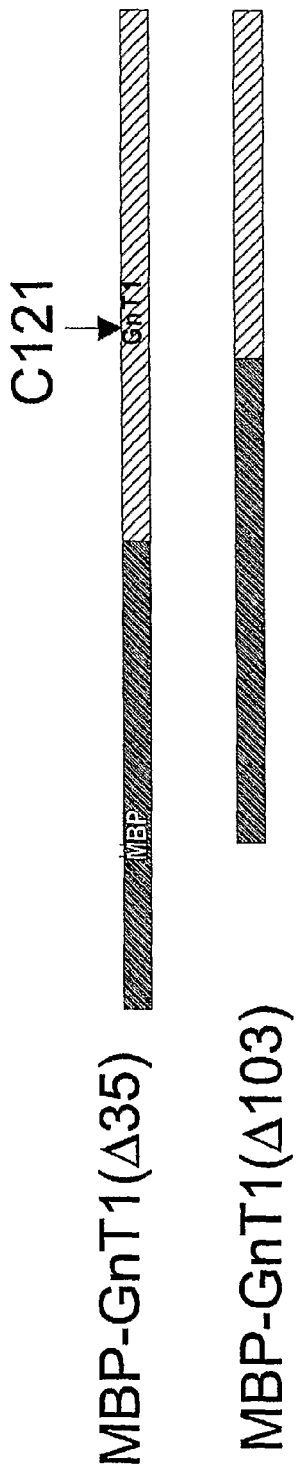

FIG. 35

GnT1 constructs

MBP-GnT1(Δ35)
MBP-GnT1(Δ103)

```
  1  mlkkqsaglv lwgailfvaw nallllffwt rpapgrppsv saldgdpasl trevirlaqd
 61  aevelerqrg llqqigdals sqrgrvptaa ppaqprvpvt papavipilv iacdrstvrr
121  cldkllhyrp saelfpiivs qdcgheetaq aiasygsavt hirqpdlssi avppdhrkfq
181  gyykiarhyr walgqvfrqf rfpaavvved dlevapdffe yfratypllk adpslwcvsa
241  wndngkeqmv dasrpellyr tdffpglgwl llaelwaele pkwpkafwdd wmrrpeqrgg
301  racirpeisr tmtfgrkgvs hggqffdqhlk fiklnqqfvh ftqldlsylq reaydrdfla
361  rvygapqlqv ekvrtndrke lgevrvqytg rdsfkafaka lgvmddlksg vpragyrgiv 421  tfqfrgrrvh lappptwegy dpswn
```

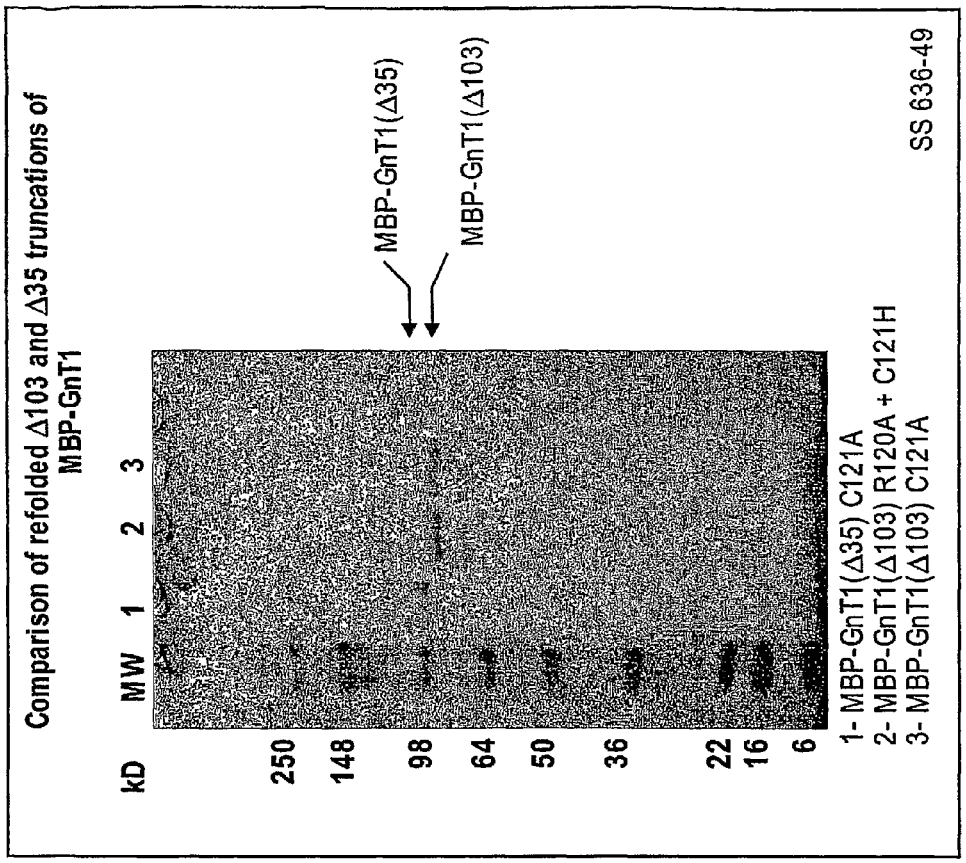
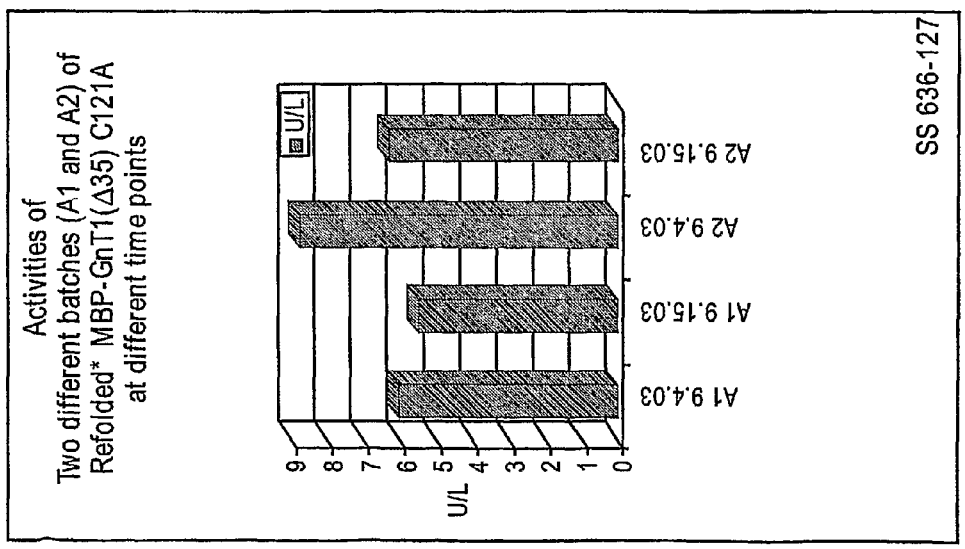
FIG. 36

```
  1 mapmrkkstl klltllvlfi fltsfflnys htvvttawfp kqmvielsen fkklmkypyr
 61 pctctrciee qrvsawfder fnrsmqpllt aknahleedt ykwwlrlqre kqpnnlndti
121 relfqvvpgn vdpllekrlv scrrcavvgn sgnlkesyyg pqidshdfvl rmnkaptegf
181 eadvgsktth hfvypesfre laqevsmilv pfkttdlewv isatttgtis htyvpvpaki
241 kvkkekiliy hpafikyvfd rwlqghgryp stgilsvifs lhicdevdly gfgadskgnw
301 hhywennpsa gafrktgvhd gdfesnvtti lasinkirif kgr
```

FIG. 37

Human ST6GalNAcI
MRSCLWRCRHLSQGVQWSLLLAVLVFFLFALPSFIKEPQTKPSRHQRTENIKERSLQS
LAKPKSQAPTRARRTTIYAEPVPENNALNTQTQPKAHTTGDRGKEANQAPPEEQDK
VPHTAQRAAWKSPEKEKTMVNTLSPRGQDAGMASGRTEAQSWKSQDTKTTQGNG
GQTRKLTASRTVSEKHQGKAATTAKTLIPKSQHRMLAPTGAVSTRTRQKGVTTAVIP
PKEKKPQATPPPAPFQSPTTQRNQRLKAANFKSEPRWDFEEKYSFEIGGLQTTCPDSV
KIKASKSLWLQKLFLPNLTLFLDSRHFNQSEWDRLEHFAPPFGFMELNYSLVQKVVT
RFPPVPQQQLLLASLPAGSLRCITCAVVGNGGILNNSHMGQEIDSHDYVFRLSGALIK
GYEQDVGTRTSFYGFTAFSLTQSLLILGNRGFKNVPLGKDVRYLHFLEGTRDYEWLE
ALLMNQTVMSKNLFWFRHRPQEAFREALHMDRYLLLHPDFLRYMKNRFLRSKTLD
GAHWRIYRPTTGALLLLTALQLCDQVSAYGFITEGHERFSDHYYDTSWKRLIFYINH
DFKLEREVWKRLHDEGIIRLYQRPGPGTAKAKN

FIG. 38A

Chicken ST6GalNAcI
MGFLIRRLPKDSRIFRWLLILTVFSFIITSFSALFGMEKSIFRQLKIYQSIAHMLQVDTQ
DQQGSNYSANGRISKVGLERDIAWLELNTAVSTPSGEGKEEQKKTVKPVAKVEEAK
EKVTVKPFPEVMGITNTTASTASVVERTKEKTTARPVPGVGEADGKRTTIALPSMKE
DKEKATVKPSFGMKVAHANSTSKDKPKAEEPPASVKAIRPVTQAATVTEKKKLRAA
DFKTEPQWDFDDEYILDSSSPVSTCSESVRAKAAKSDWLRDLFLPNITLFIDKSYFNV
SEWDRLEHFAPPYGFMELNYSLVEEVMSRLPPNPHQQLLLANSSSNVSTCISCAVVG
NGGILNNSGMGQEIDSHDYVFRVSGAVIKGYEKDVGTKTSFYGFTAYSLVSSLQNLG
HKGFKKIPQGKHIRYIHFLEAVRDYEWLKALLLDKDIRKGFLNYYGRRPRERFDEDF
TMNKYLVAHPDFLRYLKNRFLKSKNLQKPYWRLYRPTTGALLLLTALHLCDRVSAY
GYITEGHQKYSDHYYDKEWKRLVFYVNHDFNLEKQVWKRLHDENIMKLYQRS

FIG. 38B

Mouse ST6GalNAcI protein beginning at residue 32 of the native mouse protein
DPRAKDSRCQFIWKNDASAQENQQKAEPQVPIMTLSPRVHNKESTSVSSKDLKKQER
EAVQGEQAEGKEKRKLETIRPAPENPQSKAEPAAKTPVSEHLDKLPRTPGALSTRKTP
MATGAVPAKKKVVQATKSPASSPHPTTRRRQRLKASEFKSEPRWDFEEEYSLDMSSL
QTNCSASVKIKASKSPWLQNIFLPNITLFLDSGRFTQSEWNRLEHFAPPFGFMELNQSL
VQKVVTRFPPVRQQQLLLASLPTGYSKCITCAVVGNGGILNDSRVGREIDSHDYVFR
LSGAVIKGYEQDVGTRTSFYGFTAFSLTQSILILGRRGFQHVPLGKDVRYLHFLEGTR
NYEWLEAMFLNQTLAKTHLSWFRHRPQEAFRNALDLDRYLLLHPDFLRYMKNRFL
RSKTLDTAHWRIYRPTTGALLLLTALHLCDKVSAYGFITEGHQRFSDHYYDTSWKRL
IFYINHDFRLERMVWKRLHDEGIIWLYQRPQSDKAKN

FIG. 38C

Hum (h)ST6GalNAcI truncations

| | | |
|---|---|---|
| Δ35 | K36 — 565 aa — N600 | |
| Δ72 | T73 — 528 aa | |
| Δ109 | E110 — 491 aa | |
| Δ133 | M134 — 467 aa | |
| Δ170 | T171 — 430 aa | |
| Δ232 | A233 — 368 aa | |
| Δ272 | G273 — 327 aa | |

FIG. 39

MASKSWLNFLTFLCGSAIGFLLCSQLFSILLGEKVDTQPNVLHNDPHARHSDDNGQN
HLEGQMNFNADSSQHKDENTDIAENLYQKVRILCWVMTGPQNLEKKAKHVKATW
AQRCNKVLFMSSEENKDFPAVGLKTKEGRDQLYWKTIKAFQYVHEHYLEDADWFL
KADDDTYVILDNLRWLLSKYDPEEPIYFGRRFKPYVKQGYMSGGAGYVLSKEALKR
FVDAFKTDKCTHSSSIEDLALGRCMEIMNVEAGDSRDTIGKETFHPFVPEHHLIKGYL
PRTFWYWNYNYYPPVEGPGCCSDLAVSFHYVDSTTMYELEYLVYHLRPYGYLYRY
QPTLPERILKEISQANKNEDTKVKLGNP

FIG. 41

| Sequence | Size | Range | Mode |
|---|---|---|---|
| SC1GALT1.AMI | 342 | 1- | 342 Normal |
| SPTS122.AMI | 342 | 1- | 342 Normal |

| | 10 | 20 | 30 | 40 | 50 | |
|---|---|---|---|---|---|---|
| SC1GALT1.AMI | EFMPYDGHRH | GDVNDAHHSH | DMMEMSGPEQ | DVGGHEHVHE | NSTIAERLYS | 50 |
| SPTS122.AMI | EFMPYDGHRH | GDVNDAHHSH | DMMEMSGPEQ | DVGGHEHVHE | NSTIAERLYS | 50 |

| | 60 | 70 | 80 | 90 | 100 | |
|---|---|---|---|---|---|---|
| SC1GALT1.AMI | EVRVLCWIMT | NPSNHQKKAR | HVKRTWGKRC | NKLIFMSSAK | DDELDAVALP | 100 |
| SPTS122.AMI | EVRVLCWIMT | NPSNHQKKAR | HVKRTWGKRC | NKLIFMSSAK | DDELDAVALP | 100 |

| | 110 | 120 | 130 | 140 | 150 | |
|---|---|---|---|---|---|---|
| SC1GALT1.AMI | VGEGRNNLWG | KTKEAYKYIY | EHHINDADWF | LKADDDTYTI | VENMRYMLYP | 150 |
| SPTS122.AMI | VGEGRNNLWG | KTKEAYKYIY | EHHINDADWF | LKADDDTYTI | VENMRYMLYP | 150 |

| | 160 | 170 | 180 | 190 | 200 | |
|---|---|---|---|---|---|---|
| SC1GALT1.AMI | YSPETPVYFG | CKFKPYVKQG | YMSGGAGYVL | SREAVRRFVV | EALPNPKLCK | 200 |
| SPTS122.AMI | YSPETPVYFG | CKFKPYVKQG | YMSGGAGYVL | SREAVRRFVV | EALPNPKLCK | 200 |

| | 210 | 220 | 230 | 240 | 250 | |
|---|---|---|---|---|---|---|
| SC1GALT1.AMI | SDNSGAEDVE | IGKCLQNVNV | LAGDSRDSNG | RGRFFPFVPE | HHLIPSHTDK | 250 |
| SPTS122.AMI | SDNSGAEDVE | IGKCLQNVNV | LAGDSRDSNG | RGRFFPFVPE | HHLIPSHTDK | 250 |

| | 260 | 270 | 280 | 290 | 300 | |
|---|---|---|---|---|---|---|
| SC1GALT1.AMI | KFWYWQYIFY | KTDEGLDCCS | DNAISFHYVS | PNQMYVLDYL | IYHLRPYGII | 300 |
| SPTS122.AMI | KFWYWQYIFY | KTDEGLDCCS | DNAISFHYVS | PNQMYVLDYL | IYHLRPYGII | 300 |

| | 310 | 320 | 330 | 340 | 350 | |
|---|---|---|---|---|---|---|
| SC1GALT1.AMI | NTPDALPNKL | AVGELMPEIK | EQATESTSDG | VSKRSAETKT | Q*........ | 350 |
| SPTS122.AMI | NTPDALPNKL | AVGELMPEIK | EQATESTSDG | VSKRSTETKT | Q*........ | 350 |

FIG. 42

*Yersinia* MBP
```
MKIEEGKLVI WINGDKGYNG LAEVGKKFEK DTGIKVTIEH PDKLEEKFPQ
VAATGDGPDI IFWAHDRFGG YAQSGLLAEL TPSKAFQEKL FPFTWDAVRF
NGKLIGYPVA VEALSLIYNK DLVKEAPKTW EEIPALDKTL RANGKSAIMW
NLQEPYFTWP VIAADGGYAF KFENGVYDAK NVGVNNAGAQ AGLQFIVDLV
KNKHINADTD YSIAEAAFNK GETAMTINGP WAWSNIDKSK INYGVTLLPT
FHGQPSKPFV GVLTAGINAA SPNKELATEF LENYLITDQG LAEVNKDKPL
GAVALKSFQE QLAKDPRIAA TMDNATNGEI MPNIPQMAAF WYATRSAVLN
AITGRQTVEA ALNDAATRIT K
```

FIG. 43A

*E. coli* MBP
```
MKIEEGKLVI WINGDKGYNG LAEVGKKFEK DTGIKVTVEH PDKLEEKFPQ
VAATGDGPDI IFWAHDRFGG YAQSGLLAEI TPDKAFQDKL YPFTWDAVRY
NGKLIAYPIA VEALSLIYNK DLLPNPPKTW EEIPALDKEL KAKGKSALMF
NLQEPYFTWP LIAADGGYAF KYENGKYDIK DVGVDNAGAK AGLTFLVDLI
KNKHMNADTD YSIAEAAFNK GETAMTINGP WAWSNIDTSK VNYGVTVLPT
FKGQPSKPFV GVLSAGINAA SPNKELAKEF LENYLLTDEG LEAVNKDKPL
GAVALKSYEE ELAKDPRIAA TMENAQKGEI MPNIPQMSAF WYAVRTAVIN
AASGRQTVDE ALKDAQTNS
```

FIG. 43B

*Pyrococcus furiosus* MBP
```
MKIEEGKVVI WHAMQPNELE VFQSLAEEYM ALSPEVEIVF EQKPNLEDAL
KAAIPTGQGP DLFIWAHDWI GKFAEAGLLE PIDEYVTEDL LNEFAPMAQD
AMQYKGHYYA LPFAAETVAI IYNKEMVSEP PKTFDEMKAI MEKYYDPANE
KYGIAWPINA YFISAIAQAF GGYYFDDKTE QPGLDKPETI EGFKFFFTEI
WPYMAPTGDY NTQQSIFLEG RAPMMVNGPW SINDVKKAGI NFGVVPLPPI
IKDGKEYWPR PYGGVKLIYF AAGIKNKDAA WKFAKWLTTS EESIKTLALE
LGYIPVLTKV LDDPEIKNDP VIYGFGQAVQ HAYLMPKSPK MSAVWGGVDG
AINEILQDPQ NADIEGILKK YQQEILNNMQ G
```

FIG. 43C

*Thermococcus litoralis* MBP
```
MKIEEGKIVF AVGGAPNEIE YWKGVIAEFE KKYPGVTVEL KRQATDTEQR
RLDLVNALRG KSSDPDVFLM DVAWLGQFIA SGWLEPLDDY VQKDNYDLSV
FFQSVINLAD KQGGKLYALP VYIDAGLLYY RKDLLEKYGY SKPPETWQEL
VEMAQKIQSG ERETNPNFWG FVWQGKQYEG LVCDFVEYVY SNGGSLGEFK
DGKWVPTLNK PENVEALQFM VDLIHKYKIS PPNTYTEMTE EPVRLMFQQG
NAAFERNWPY AWGLHNADDS PVKGKVGVAP LPHFPGHKSA ATLGGWHIGI
SKYSDNKALA WEFVKFVESY SVQKGFAMNL GWNPGRVDVY DDPAVVSKSP
HLKELRAVFE NAVPRPIVPY YPQLSEIIQK YVNSALAGKI SPQEALDKAQ
KEAEELVKQY SK
```

FIG. 43D

*Thermatoga maritime* MBP
```
MKIEQTKLTI WSSEKQVDIL QKLGEEFKAK YGIPVEVQYV DFGSIKSKFL
TAAPQGQGAD IIVGAHDWVG ELAVNGLIEP IPNFSDLKNF YDTALKAFSY
GGKLYGVPYA MEAVALIYNK DYVDSVPKTM DELIEKAKQI DEEYGGEVRG
FIYDVANFYF SAPFILGYGG YVFKETPQGL DVTDIGLANE GAVKGAKLIK
RMIDEGVLTP GDNYGTMDSM FKEGLAAMII NGLWAIKSYK DAGINYGVAP
IPELEPGVPA KPFVGVQGFM INAKSPNKVI AMEFLTNFIA RKETMYKIYL
ADPRLPARKD VLELVKDNPD VVAFTQSASM GTPMPNVPEM APVWSAMGDA
LSIIINGQAS VEDALKEAVD KIKAQIEK
```

FIG. 43E

*Vibrio cholerae* MBP

```
MKIEEGQLTI WINGDKGYNG LAEVGKKFEA DTGIKVTVAH PDALQDKFPQ
TAATGDGPDI VFWAHDRFGG YAEAGLLVEI KPSAKIQEGI VDFAWDAVKY
NGKIIGYPIA VESLSLIYNK DLVPNPPKSW EEVAELDAKL KKEGKSAIMW
NLKEPYFTWP LMAADGGYAF KYGVDGYDVK DAGINNKGVK DAMNFVKGLV
DKGVISPDMD YSVSESAFNQ GNTAMTINGP WSWGNIEKSG INYGVTTLPK
FNGQASKPFV GVLTAGISTA SPNKDLAVEF IENYLLTNDG LRMVNNDKPL
GAVALNSFQR ELDADARIAA TMDNAMNGEI MPNIPQMNAF WSSAKNAIIN
IVDGRQTV

```
                    1                                                50
HSGALNAT1.pep   (1)MRKFAYCKVVLATSLIWVLLDMFLLLYFS------------------ECNKC
HSGALNAT2.pep   (1)MRRRS---RMLLCFAFLWVLGIAYYMYSGGGSALAGGAGGGAGRKEDWNEI
Consensus       (1)MRK A  KMLL A IWVL  F L                          D N
                    51                                              100
HSGALNAT1.pep  (35)DEKKERGLPAGDVLEPVQKPHEGP-G-----EMGKPVVIPKEDQEKMKEM
HSGALNAT2.pep  (49)DPIKKKDLHHSNGEEKAQSMETLPPGKVRWPDFNQEAYVGGTMVRSGQDP
Consensus      (51)D KK L       E  Q   P G     D          I        D
                    101                                             150
HSGALNAT1.pep  (79)FKINQFNLMASEMIALNRSLPDVRLEGCKTKVYPDNLPTTSVVIVFHNEA
HSGALNAT2.pep  (99)YARNKFNQVESDKLRMDRAIPDTRHDCQRKQWRVDLPATSVVITFHNEA
Consensus     (101)F  N FN M SD I LRAIPD R D C   K W  LP TSVVI FHNEA
                    151                                             200
HSGALNAT1.pep (129)WSTLLRTVHSVINRSPRHMIEEIVLVDDASERDFLKRPLESYVKKLKVPV
HSGALNAT2.pep (149)RSALLRTVVSVLKKSPPHLIKEIILVDDYSN------DPEDGALLGKIEKV
Consensus     (151)  S LLRTV SVI KSP HLI EIILVDD S          PD L     V
                    201                                             250
HSGALNAT1.pep (179)HVIRMEQRSGLIRARLKGAAVSKGQVITFLDAHCECTVGWLEPLLARIKH
HSGALNAT2.pep (194)RVLRNDRREGLMRSRVRGADAAQAKVLTFLDSHCECNEHWLEPLLERVAE
Consensus     (201)  VIR D R GLIRARLKGA  A A VITFLDAHCEC   WLEPLL RI
                    251                                             300
HSGALNAT1.pep (229)DRRTVVCPIIDVISDDTFEYMAGSDMTYGGFNWKLNFRWYPVPQREMDRR
HSGALNAT2.pep (244)DRTRVVSPIIDVINMDNFQYVGASADLKGGFDWNLVFKWDYMTPEQRRSR
Consensus     (251)DR  VV PIIDVI D F YMAAS    GGF W L FKW M      R
                    301                                             350
HSGALNAT1.pep (279)KGDRTLPVRTPTMAGGLFSIDRDYFQEIGTYDAGMDIWGGENLEISFRIW
HSGALNAT2.pep (294)QGNPVAPIKTPMIAGGLFVMDKFYFEELGKYDMMMDVWGGENLEISFRVW
Consensus     (301) G    PIKTP IAGGLF IDK YF EIG YD  MDIWGGENLEISFRIW
                    351                                             400
HSGALNAT1.pep (329)QCGGTLEIVICSHVGHVFRKATPYTFPGGTGQIINKNNRRLAEVWMDEFK
HSGALNAT2.pep (344)QCGGSLEIIPCSRVGHVFRKQHPYTFPGGSGIVFARNTRRAAEVWMDEYK
Consensus     (351)QCGGSLEII CS VGHVFRK  PYTFPGGSG I  KN RR AEVWMDEFK
                    401                                             450
HSGALNAT1.pep (379)NFFYIISPGVTKVDYGDISSRVGLRHKLQCKPFSWYLENIYPDSQIPRHY
HSGALNAT2.pep (394)NFYYAAVPSARNVPYGNIQSRLELRKKLSCKPFKWYLENVYPELRVPDHQ
Consensus     (401)NFFY    P   V YG I SRL LR KL CKPF WYLENIYPD  IP H
                    451                                             500
HSGALNAT1.pep (429)FSLGEIRNVETNQCLDNMARKENEKVGIFNCHGMGGNQVFSYTANKEIRT
HSGALNAT2.pep (444)DIAFGALQQGTN-CLDTLGHFADGVVGVYECHNAGGNQEWALTKEKSVKH
Consensus     (451)        N TN CLD  A        VGIF CH  GGNQ FA T K IK
                    501                                             550
HSGALNAT1.pep (479)DDLCLDVSKLN--GPVTMLKCHHLKGNQLWEYDPVKLTLQHVNSNQCLDK
HSGALNAT2.pep (493)MDLCLTVVDRAPGSLIKLQGCRENDSRQKWEQIEGNSKLRHVGSNLCLDS
Consensus     (501) DLCL V        I L   C      Q WE         L HV SN CLD
                    551                                584
HSGALNAT1.pep (527)ATEEDSQVPSIRDCNGSRSQQWLLRNVTLPEIF-
HSGALNAT2.pep (543)RTAK-SGGLSVEVCGPALSQQWKFTLNLQQ----
Consensus     (551)  T    S      SI C    A SQQW
```

FIG. 44

METHODS OF REFOLDING MAMMALIAN GLYCOSYLTRANSFERASES

CROSS REFERENCE TO RELATED APPLICATIONS

This application claims the benefit of U.S. Provisional Application No. 60/542,210, filed Feb. 4, 2004, and of U.S. Provisional Application No. 60/599,406, filed Aug. 6, 2004, and of U.S. Provisional Application No. 60/627,406, filed Nov. 12, 2004; each of which are herein incorporated by reference for all purposes.

FIELD OF INVENTION

The present invention provides methods of refolding mammalian glycosyltransferases that have been produced in bacterial cells, including glycosyltransferase mutants that have enhanced ability to be refolded, and methods to use such refolded glycosyltransferases. The invention also provides methods of refolding more than one glycosyltransferase in a single vessel, methods to use such refolded glycosyltransferases, and reaction mixtures comprising the refolded glycosyltransferases.

BACKGROUND OF THE INVENTION

Eukaryotic organisms synthesize oligosaccharide structures or glycoconjugates, such as glycolipids or glycoproteins, that are commercially and therapeutically useful. In vitro synthesis of oligosaccharides or glycoconjugates can be carried out using recombinant eukaryotic glycosyltransferases. The most efficient method to produce recombinant eukaryotic glycosyltransferases for oligosaccharide synthesis is to express the protein in bacteria. However, in bacteria, many eukaryotic glycosyltransferases are expressed as insoluble proteins in bacterial inclusion bodies, and yields of active protein from the inclusion bodies can be very low. Thus, there is a need for improved methods to produce eukaryotic glycosyltransferases in bacteria. The present invention solves this and other needs.

BRIEF SUMMARY OF THE INVENTION

The present invention provides a method of refolding an insoluble, recombinant, eukaryotic glycosyltransferase that comprises a maltose binding protein domain (MBD). The insoluble, recombinant, eukaryotic glycosyltransferase is solubilized in a solubilization buffer and then contacted with a refolding buffer comprising a redox couple, such that the refolded eukaryotic glycosyltransferase catalyzes the transfer of a sugar from a donor substrate to an acceptor substrate. In one embodiment, the eukaryotic glycosyltransferase is truncated to remove all or a portion of a stem region of the protein. In another embodiment, an unpaired cysteine in the eukaryotic glycosyltransferase is removed by substitution with a non-cysteine amino acid. In a further embodiment an unpaired cysteine in the eukaryotic glycosyltransferase is removed by substitution with a non-cysteine amino acid and the eukaryotic glycosyltransferase is also truncated to remove all or a portion of a stem region of the protein.

In one embodiment, the eukaryotic glycosyltransferase is selected from the group consisting of GnT1, GalT1, StIII Gal3, St3GalI, St6 GalNAcTI, Core GalITI, GalNAcT2.

In one embodiment, the eukaryotic glycosyltransferase further comprises a purification domain, for example, a starch binding domain (SBD), a thioredoxin domain, a SUMO domain, a poly-His domain, a myc epitope domain, and a glutathione-S-transferase domain.

In one embodiment, the eukaryotic glycosyltransferase further comprises a self cleaving domain.

In one embodiment, the eukaryotic glycosyltransferase is expressed in a bacterial host cell as an insoluble inclusion body.

In one embodiment, a second insoluble, recombinant eukaryotic glycosyltransferase is refolded with the first eukaryotic glycosyltransferase. In a further embodiment, a third insoluble, recombinant eukaryotic glycosyltransferase is refolded with the first eukaryotic glycosyltransferase and the second eukaryotic glycosyltransferase. Additional insoluble, recombinant eukaryotic glycosyltransferase can be added and refolded together depending on the needs of the user, e.g., refolding of 4, 5, 6, 7, 8, 9, or 10 glycosyltransferases together.

In one embodiment, the redox couple is selected from the group consisting of reduced glutathione/oxidized glutathione (GSH/GSSG) and cysteine/cystamine.

In one embodiment, the acceptor substrate is selected from a protein, a peptide, a glycoprotein, and a glycopeptide.

In one embodiment, the eukaryotic glycosyltransferase is a sialyltransferase. Sialyltransferases can include, e.g., StIII Gal3, St3GalI, St6 GalNAcTI. In a further aspect, the donor substrate is a CMP-sialic acid PEG molecule and the acceptor substrate is selected from a protein, a peptide, a glycoprotein, and a glycopeptide.

The present invention also provides a recombinant, eukaryotic glycosyltransferase, in which a stem anchor region and a transmembrane domain have been deleted from the protein, and wherein the glycosyltransferase is fused in frame to a maltose binding protein (MBP) domain. In one embodiment, the fusion of the recombinant, eukaryotic glycosyltransferase and the MBP domain is expressed as an insoluble inclusion body in bacteria, e.g., E. coli.

In one embodiment, all or a portion of the stem region is deleted from the recombinant, eukaryotic glycosyltransferase. In another embodiment, an unpaired cysteine in the recombinant, eukaryotic glycosyltransferase is removed by substitution with a non-cysteine amino acid.

In a further embodiment, the recombinant, eukaryotic glycosyltransferase is one of the following: a GnT1 protein, a GalT1 protein, an StIII Gal3 protein, an St3GalI protein, an St6 GalNAcTI protein, a Core GalITI protein, or a GalNAcT2 protein.

In one embodiment, the recombinant, eukaryotic glycosyltransferase is a GnT1 protein. In one aspect, the GnT1 protein is a truncated human GnT1 protein selected from GnT1 Δ35 and GnT1Δ103. In another aspect, the GnT1 protein is a human GnT1 protein comprising an unpaired cysteine substitution selected from the group consisting of CYS121ALA, CYS121ASP, and ARG120ALA, CYS121HIS. In a further aspect, the GnT1 protein is both truncated and has had an unpaired cysteine residue removed by a substitution mutation.

In one embodiment, the recombinant, eukaryotic glycosyltransferase is a GalT1 protein. In one aspect, the GalT1 protein is a truncated bovine GalT1 protein selected from GalT1 Δ70 and GalT1 Δ129. In another aspect, the GalT1 protein is a bovine GalT1 protein comprising an unpaired cysteine substitution of CYS342THR. In a further aspect, the GalT1 protein is both truncated and has had an unpaired cysteine residue removed by a substitution mutation.

In one embodiment, the recombinant, eukaryotic glycosyltransferase is an ST3GalIII protein. In one aspect, the ST3GalIII protein is a truncated rat ST3GalIII protein selected from ST3GalIII Δ28, ST3GalIII Δ73, ST3GalIII Δ85 and ST3GalIII Δ86. In another aspect, the ST3GalIII protein comprises an amino acid substitution for an unpaired cysteine residue. In a further aspect, the ST3GalIII protein is both truncated and has had an unpaired cysteine residue removed by a substitution mutation.

In one embodiment, the recombinant, eukaryotic glycosyltransferase of claim 15, wherein the glycosyltransferase is a Corel GalT1 protein. In one aspect, the Corel GalT1 protein is a truncated *Drosophila* protein or a truncated human protein. In another aspect, a *Drosophila* or human Corel GalT1 protein comprises an amino acid substitution for an unpaired cysteine residue. In a further aspect, a *Drosophila* or human Corel GalT1 protein is both truncated and has had an unpaired cysteine residue removed by a substitution mutation.

In one embodiment, the recombinant, eukaryotic glycosyltransferase is an ST3Gal1 protein. In one aspect, the ST3Gal1 protein is a truncated human protein selected from ST3Gal1 Δ29, ST3Gal1 Δ45, and ST3Gal1 Δ56. In another aspect, the ST3Gal1 protein comprises an amino acid substitution for an unpaired cysteine residue. In a further aspect, the ST3 Gal1 protein is both truncated and has had an unpaired cysteine residue removed by a substitution mutation.

In one embodiment, the recombinant, eukaryotic glycosyltransferase is an ST6GalNAc1 protein. In one aspect, the ST6GalNAc1 protein is a truncated mouse protein, a truncated chicken protein or a truncated human protein, e.g. one of the truncation listed in Table 14. In another aspect, a mouse, chicken, or human ST6GalNAc1 protein comprises an amino acid substitution for an unpaired cysteine residue. In a further aspect, a mouse, chicken, or human ST6GalNAc1 protein is both truncated and has had an unpaired cysteine residue removed by a substitution mutation.

In one embodiment, the recombinant, eukaryotic glycosyltransferase of claim 15, wherein the glycosyltransferase is an GalNAcT2 protein. In one aspect, the GalNAcT2 protein is a truncated human protein selected from GalNAcT2 Δ40, GalNAcT2 Δ51, GalNAcT2 Δ74 and GalNAcT2 Δ95. In another aspect, the human GalNAcT2 protein comprises an amino acid substitution for an unpaired cysteine residue. In a further aspect, the human GalNAcT2 protein is both truncated and has had an unpaired cysteine residue removed by a substitution mutation.

The present invention also provides a method of remodeling a protein, a peptide, a glycoprotein, or a glycopeptide using the recombinant, eukaryotic glycosyltransferases listed above, after the proteins have been refolded and have enzymatic activity.

The present invention provides improved methods to refold insoluble eukaryotic glycosyltransferases in an active form and also provides glycosyltransferases, e.g., N-acetylglucosaminyltransferase I (GnTI) enzymes that have enhanced refolding properties.

In one aspect, the invention provides a recombinant eukaryotic N-acetylglucosaminyltransferase I (GnTI) enzyme, that has been mutated to replace an unpaired cysteine residue with an amino acid that enhances refolding of the enzyme from an insoluble precipitate, e.g., bacterial inclusion bodies. The GnT1 enzyme includes at least the catalytic domain of the GnT1 enzyme. The GnT1 enzyme is biologically active, i.e., able to catalyze the transfer of a donor substrate to an acceptor substrate.

In one embodiment, the GnTI enzyme is a human protein. Some mutations of the CYS121 residue in human GnT1 enhance refolding. Those mutants include e.g., CYS121SER mutation, a CYS121ALA mutation, CYS121ASP mutation, and a double mutant, ARG120ALA, CYS121HIS. Representative sequences of GnT1 mutants are shown in FIGS. 7-11. In other eukaryotes, e.g., similar mutations of an unpaired cysteine residue, CYS123, enhance refolding of the GnT1 enzyme.

In another embodiment, the GnTI enzyme also includes an amino acid tag, e.g., a maltose binding protein (MBP), a polyhistidine tag, a glutathione S transferase (GST), a starch binding protein (SBP), and a myc epitope.

In another aspect, the invention provides nucleic acids encoding a recombinant eukaryotic GnTI enzyme, that has been mutated to replace an unpaired cysteine residue with an amino acid that enhances refolding of the enzyme from an insoluble precipitate, e.g., bacterial inclusion bodies. As above, the encoded GnT1 enzyme includes at least the catalytic domain of the GnT1 enzyme, and is biologically active, i.e., able to catalyze the transfer of a donor substrate to an acceptor substrate.

In one embodiment, the nucleic acids encode a human GnTI enzyme. Some mutations of the CYS121 residue in human GnT1 enhance refolding. Those mutants include e.g., CYS121SER mutation, a CYS121ALA mutation, CYS121ASP mutation, and a double mutant, ARG120ALA, CYS121HIS. Representative nucleic acids sequences of GnT1 mutant proteins and nucleic acids are shown in FIGS. 7-11. In other eukaryotes, e.g., similar mutations of an unpaired cysteine residue, CYS123, enhance refolding of the GnT1 enzyme.

In a further embodiment, the encoded GnTI enzyme also includes an amino acid tag, e.g., a maltose binding protein (MBP), a polyhistidine tag, a glutathione S transferase (GST), a starch binding protein (SBP), and a myc epitope.

The invention also includes expression vectors that include the mutated GnT1 nucleic acids, host cells that include the GnT1 expression vectors, and methods of producing the mutated GnT1 enzymes using the host/expression vector system.

In another embodiment, the invention provides a method of adding N-acetylglucosamine residues to an acceptor molecule with a terminal mannose residue, by contacting the acceptor molecule with an activated N-acetylglucosamine molecule and a eukaryotic GnTI enzyme that has been mutated to enhance refolding. The acceptor molecule can be e.g., a polysaccharide, an oligosaccharide, a glycolipid, or a glycoprotein.

In another aspect, the invention provides a method of refolding at least two insoluble, recombinant eukaryotic glycosyltransferase proteins in a single vessel, by contacting the glycosyltransferases with a refolding buffer that includes a redox couple. After refolding, at least two of the refolded glycosyltransferases have biological activity, e.g., are able to catalyze the transfer of a donor substrate to an acceptor substrate.

The refolding buffer can also include a detergent, or a chaotropic agent, or arginine, or PEG. In some embodiments the pH of the refolding buffer is between 6.0 and 10.0. In one embodiment, the pH of the refolding buffer is between 6.5 and 8.0. In another embodiment, the pH of the refolding buffer is between 8.0 and 9.0.

In another embodiment, the glycosyltransferases include an amino acid tag, e.g., a maltose binding protein (MBP), a polyhistidine tag, a glutathione S transferase (GST), a starch binding protein (SBP), and a myc epitope In one embodiment, more than one glycosyltransferase from an N-linked glycan biosynthetic pathway are refolded together.

In one embodiment, a sialyltransferase is refolded with another glycosyltransferase using the methods of the invention.

In one embodiment, an N-acetylglucosaminyltransferase is refolded with another glycosyltransferase using the methods of the invention.

In one embodiment, a galactosyltransferase is refolded with another glycosyltransferase using the methods of the invention.

In another embodiment, a sialyltransferase, an N-acetylglucosaminyltransferase, and a galactosyltransferase are refolded together in a single vessel using the methods of the invention.

In one embodiment, more than one glycosyltransferase from an O-linked glycan biosynthetic pathway are refolded together. In a further embodiment, a first enzyme is an N-acetylgalactosaminyltransferase. In a preferred embodiment, a first enzyme is an N-acetylglucosaminyltransferase 2 (GalNAcT2).

The present invention also provides a reaction mixture including a recombinant eukaryotic GnTI enzyme, that has been mutated to replace an unpaired cysteine residue with an amino acid that enhances refolding of the enzyme from an insoluble precipitate, e.g., bacterial inclusion bodies and at least one other glycosyltransferase that have been refolded in the same vessel. The second glycosyltransferase can be e.g., a sialyltransferase or a galactosyltransferase. In one embodiment, the reaction mixture includes the mutated eukaryotic GnT1 enzyme, a sialyltransferase, and a galactosyltransferase. The reaction mixtures can be used with an acceptor molecule with a donor sugar, to produce e.g., a polysaccharide, an oligosaccharide, a glycolipid, or a glycoprotein.

In another aspect, the invention provides a method of refolding an insoluble recombinant eukaryotic sialyltransferase, by (a) solubilizing the sialyltransferase; and then (b) contacting the soluble sialyltransferase with a refolding buffer including a redox couple. The refolded sialyltransferase is biologically active and catalyzes the transfer of sialic acid from a donor substrate to an acceptor substrate. In one embodiment, the refolded sialytransferase is dialyzed or diafiltered.

The refolding buffer can also include a detergent, or a chaotropic agent, or arginine. In some embodiments the pH of the refolding buffer is between 6.0 and 10.0. In one embodiment, the pH of the refolding buffer is between 6.5 and 8.0. In another embodiment, the pH of the refolding buffer is between 8.0 and 9.0. In another embodiment, the pH of the refolding buffer is between 7.5 and 8.5.

In one embodiment, the redox couple in the refolding buffer is reduced glutathione/oxidized glutathione (GSH/GSSG). In a further embodiment, the molar ratio of GSH/GSSG is between 100:1 and 1:10. In a preferred embodiment, the molar ratio of GSH/GSSG is 10:1. In a still further embodiment, the refolding buffer comprises about 0.02-10 mM GSH, 0.005-10 mM GSSG, 0.005-10 mM lauryl maltoside, 50-250 mM NaCl, 2-10 mM KCl, 0.01-0.05% PEG 3350, and 150-550 mM L-arginine.

In another embodiment, the sialyltransferase includes an amino acid tag e.g., maltose binding protein (MBP), a polyhistidine tag, a glutathione S transferase (GST), a starch binding protein (SBP), and a myc epitope. In a further embodiment, the sialyltransferase is purified using a tag binding molecule that binds to the amino acid tag. For example, the amino acid tag can be MBP and the tag binding molecule can be amylose, maltose, or a cyclodextrin.

In another embodiment, the refolded sialyltransferase catalyzes the transfer of sialic acid from CMP-sialic acid to a glycoprotein.

In a further embodiment, the refolded sialyltransferase catalyzes the transfer of 10 KPEG or 20 K PEG from CMP-SA-PEG (10 kDa) or CMP-SA-PEG (20 kDa) to a glycoprotein.

In another embodiment, the sialyltransferase is rat liver ST3GalIII.

In another aspect, the invention provides a method of adding a sialyl moiety to a glycoprotein, by contacting the glycoprotein with CMP-sialic acid with a refolded mammalian sialyltransferase that was refolded using the methods disclosed herein.

In another aspect, the invention provides a method of adding a PEG moiety to a glycoprotein, the method comprising by contacting the glycoprotein with CMP-SA-PEG (10 kDa) or CMP-SA-PEG (20 kDa) and a refolded mammalian sialyltransferase that was refolded using the methods disclosed herein.

In a further aspect the invention provides a method of refolding an insoluble recombinant eukaryotic N-acetylgalactosaminyltransferase 2 (GalNAcT2) by solubilizing the GalNAcT2 in a solubilization buffer; and then contacting the soluble GalNAcT2 with a refolding buffer that includes a redox couple to refold the GalNAcT2. After refolding, the refolded GalNAcT2 catalyzes the transfer of N-acetylgalactosamine from a donor substrate to an acceptor substrate. The method can optionally include steps of dialyzing or diafiltering the refolded GalNAcT2 or further purification of the refolded GalNAcT2.

In some embodiments the redox couple of the refolding buffer is reduced glutathione/oxidized glutathione (GSH/GSSG) or cysteine/cystamine. The refolding buffer can also include the following: a detergent, a choatropic agent, or arginine. In some embodiments, the pH of the refolding buffer is between 6.0 and 10.0. In one preferred embodiment, the pH of the refolding buffer is about 8.0.

In preferred embodiments, the solubilization buffer pH is between 6.0 and 10.0. In a more preferred embodiment, the solubilization buffer pH is about 8.0.

The recombinantly expressed GalNAcT2 can include an amino acid tag. The amino acid tag can be, e.g., a maltose binding protein (MBP), a polyhistidine tag, a glutathione S transferase (GST), a starch binding protein (SBP), or a myc epitope. A tag binding molecule can be used to purify the refolded GalNAcT2. When the amino acid tag is MBP and the tag binding molecule is generally one of the following: amylose, maltose, or a cyclodextrin.

In a preferred embodiment, the refolded GalNAcT2 catalyzes the transfer of N-acetylgalactosamine from a donor substrate to a peptide, protein, glycopeptide or glycoprotein.

BRIEF DESCRIPTION OF THE DRAWINGS

FIG. 1 provides the buffer conditions tested in refolding MBP-ST3GalIII from bacterial inclusion bodies. The activity of the refolded enzymes is also provided.

FIG. 6 provides an alignment of a human GnT1 amino acid sequence (top line, NP_002397) and a rabbit GnT1 amino acid sequence (bottom line, P27115). The conserved unpaired cysteines are underlined and in bold text.

FIG. 7 provides the amino acid sequence of a GnT1 Cys121Ser mutant and a nucleic acid sequence that encodes the mutant GnT1 protein. The amino acid sequence depicted begins with amino acid residue 104 of the full length human protein and is representative of mammalian GnT1 proteins with the following unpaired cysteine mutation: . . . stvrrsdldkllh . . . , where the bold residue is mutated from the wild-type cysteine.

FIG. 8 provides the amino acid sequence of a GnT1 Cys121Asp mutant and a nucleic acid sequence that encodes the mutant GnT1 protein. The amino acid sequence depicted begins with amino acid residue 104 of the full length human protein and is representative of mammalian GnT1 proteins with the following unpaired cysteine mutation: . . . stvrrtldkllh . . . , where the bold residue is mutated from the wild-type cysteine.

FIG. 9 provides the amino acid sequence of a GnT1 Cys121Thr mutant and a nucleic acid sequence that encodes the mutant GnT1 protein. The amino acid sequence depicted begins with amino acid residue 104 of the full length human protein and is representative of mammalian GnT1 proteins with the following unpaired cysteine mutation: . . . stvrrtldkllh . . . , where the bold residue is mutated from the wild-type cysteine.

FIG. 10 provides the amino acid sequence of a GnT1 Cys121Ala mutant and a nucleic acid sequence that encodes the mutant GnT1 protein. The amino acid sequence depicted begins with amino acid residue 104 of the full length human protein and is representative of mammalian GnT1 proteins with the following unpaired cysteine mutation: . . . stvrraldkllh . . . , where the bold residue is mutated from the wild-type cysteine.

FIG. 11 provides the amino acid sequence of a GnT1 Arg120Ala, Cys121His mutant and a nucleic acid sequence that encodes the mutant GnT1 protein. The amino acid sequence depicted begins with amino acid residue 104 of the full length human protein and is representative of mammalian GnT1 proteins with the following double mutation: . . . stvrahldkllh . . . , where the bold residue is mutated from the wild-type cysteine.

FIG. 12 provides the amino acid sequence of rat liver ST3GalIII. The underlined and italicized sequence was deleted to make the Δ28 deletion.

FIGS. 13A and 13B provide full length nucleic acid and amino acid sequences of UDP-N-acetylgalactosaminyltransferase 2 (GalNAcT2). The accession number of the nucleic acid and protein is NM_004481.

FIGS. 14A and 14B provide nucleic acid and amino acid sequences of a Δ51GalNAcT2. The numbering is based on the full length amino acid and nucleic acid sequences shown in FIGS. 13A and B.

FIG. 18A shows the results using a control purified MBP-GalNAcT2 (D51), or a negative control that lacked a substrate, or bacterially expressed MBP-GalNAcT2(D51) that was solubilized at pH 6.5 and refolded at pH 6.5. FIG. 18B shows the experimental results.

FIG. 20 provides the GalNAcT2 activity of specific column fractions from the QXL column shown in FIG. 19. The most active fractions were applied to a Hydroxyapatite Type I (80 μm) (BioRad, Hercules, Calif.) column.

FIG. 22 provides the GalNAcT2 activity of HA type I eluted fractions.

FIG. 23 provides a comparison of purification and activity of ST3Gal3 proteins fused to either an MBP tag or to an MBP-SBD tag.

FIG. 24 provides the amino acid sequences of the MBP-ST3Gal1 fusion protein (A) and the MBP-SBD-ST3Gal1 fusion protein (B).

FIG. 26 provides the amino acid sequence of mouse and human ST6GalNAcI proteins fused to MBP. Part A shows the sequence of a mouse truncation fusion: MBP-mST6GalNAcI S127. Part B shows the sequence of a human truncation fusion: MBP-hST6GalNAcI K36.

FIG. 30 provides the amino acid sequence of the full length bovine GalT1 protein.

FIG. 34 provides kinetics of glycosylation of RNAse B using the refolded and purified MBP-GalT1 (D70) protein or NSO GalT1, a soluble form of the bovine GalT1 protein that was expressed in a mammalian cell system.

FIG. 35 provides a schematic of the MBP-GnT1 fusion proteins, and depicts the truncations, e.g., Δ103 or Δ35, and the Cys121Ser mutation (top). The bottom of the figure provides the full length human GnT1 protein.

FIG. 36 provides an SDS-PAGE gel showing in the right panel the refolded MBP-GnT1 fusion proteins: MBP-GnT1 (D35) C121A, MBP-GnT1(D103) R120A+C121H, and MBP-GnT1(D103) C121A. The left panel shows GnT1 activities of two different batches (A1 and A2) of refolded MBP-GnT1(D35) C121A at different time points.

FIG. 37 provides a full length sequence of porcine ST3Gal1.

FIG. 38 provides full length amino acid sequences for A) human ST6GalNAcI and for B) chicken ST6GalNAcI, and C) a sequence of the mouse ST6GalNAcI protein beginning at residue 32 of the native mouse protein.

FIG. 39 provides a schematic of a number of preferred human ST6GalNAcI truncation mutants.

FIG. 41 provides the full length sequence of human Core 1 GalT1 protein.

FIG. 42 provides the sequences of two *Drosophila* Core 1 GalT1 proteins.

FIG. 43 provides the sequences of exemplary bacterial MBP proteins that can be fused to glycosyltransferases to enhance refolding. A. *Yersinia* MBP; B. *E. coli* MBP; C. *Pyrococcus furiosus* MBP; D. *Thermococcus litoralis* MBP; E. *Thermatoga maritime* MBP; and F. *Vibrio cholerae* MBP.

FIG. 44 provides an alignment of human GalNAcT1 and GalNAcT2 proteins. Because the alignment programs account for sequence insertions or deletions, the numbering of cysteine residues is not the same as mentioned text and published sequences. In the case of hGalNAc-T2 cysteine 227 (published) corresponds to position 235 in the alignment and cysteine 229 (published) is 237 in the alignment. The hGalNAc-T1 cysteines are 212 (published), which corresponds to cysteine 235 (alignment) and 214 (published), which corresponds to cysteine 237 (alignment). The relevant cysteine residues are indicated by larger font size.

DEFINITIONS

Figure 2:
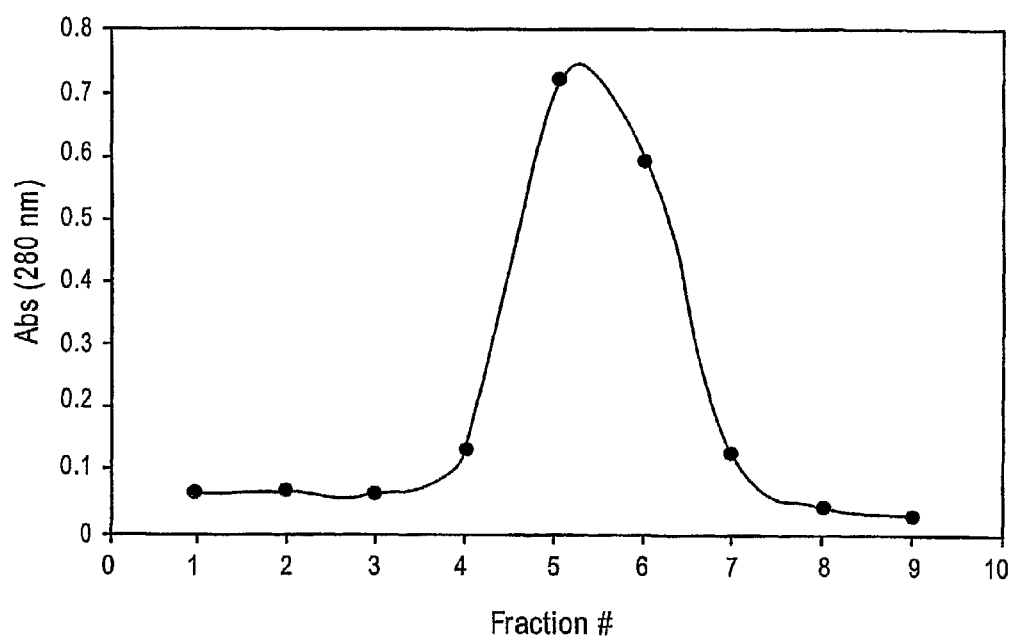
FIG. 2 provides an elution profile of refolded and dialyzed MBP-ST3GalIII from an amylose column.

The recombinant glycosyltransferase proteins of the invention are useful for transferring a saccharide from a donor substrate to an acceptor substrate. The addition generally takes place at the non-reducing end of an oligosaccharide or carbohydrate moiety on a biomolecule. Biomolecules as defined here include but are not limited to biologically significant molecules such as carbohydrates, proteins (e.g., glycoproteins), and lipids (e.g., glycolipids, phospholipids, sphingolipids and gangliosides).

The following abbreviations are used herein:
Ara=arabinosyl;
Fru=fructosyl;
Fuc=fucosyl;
Gal=galactosyl;
GalNAc=N-acetylgalactosylamino;
Glc=glucosyl;
GlcNAc=N-acetylglucosylamino;
Man=mannosyl; and
NeuAc=sialyl (N-acetylneuraminyl)
FT or FucT=fucosyltransferase*
ST=sialyltransferase*
GalT=galactosyltransferase*

Arabic or Roman numerals are used interchangeably herein according to the naming convention used in the art to indicate the identity of a specific glycosyltransferase (e.g., FTVII and FT7 refer to the same fucosyltransferase).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN)

(Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

An "acceptor substrate" for a glycosyltransferase is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate will often vary for different types of a particular glycosyltransferase. For example, the acceptor substrate for a mammalian galactoside 2-L-fucosyltransferase ($\alpha$1,2-fucosyltransferase) will include a Gal$\beta$1,4-GlcNAc-R at a non-reducing terminus of an oligosaccharide; this fucosyltransferase attaches a fucose residue to the Gal via an $\alpha$1,2 linkage. Terminal Gal$\beta$1,4-GlcNAc-R and Gal$\beta$1,3-GlcNAc-R and sialylated analogs thereof are acceptor substrates for $\alpha$1,3 and $\alpha$1,4-fucosyltransferases, respectively. These enzymes, however, attach the fucose residue to the GlcNAc residue of the acceptor substrate. Accordingly, the term "acceptor substrate" is taken in context with the particular glycosyltransferase of interest for a particular application. Acceptor substrates for additional glycosyltransferases, are described herein. Acceptor substrates also include e.g., peptides, proteins, glycopeptides, and glycoproteins.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrates for sialyltransferases, for example, are activated sugar nucleotides comprising the desired sialic acid. For instance, in the case of NeuAc, the activated sugar is CMP-NeuAc. Other donor substrates include e.g., GDP mannose, UDP-galactose, UDP-N-acetylgalactosamine, CMP-NeuAc-PEG (also referred to as CMP-sialic acid-PEG), UDP-N-acetylglucosamine, UDP-glucose, UDP-glucorionic acid, and UDP-xylose. Sugars include, e.g., NeuAc, mannose, galactose, N-acetylgalactosamine, N-acetylglucosamine, glucose, glucorionic acid, and xylose. Bacterial, plant, and fungal systems can sometimes use other activated nucleotide sugars.

A "method of remodeling a protein, a peptide, a glycoprotein, or a glycopeptide" as used herein, refers to addition of a sugar residue to a protein, a peptide, a glycoprotein, or a glycopeptide using a glycosyltransferase. In a preferred embodiment, the sugar residue is covalently attached to a PEG molecule.

A "eukaryotic glycosyltransferase" as used herein refers to an enzyme that is derived from a eukaryotic organism and that catalyzes transfer of a sugar reside from a donor substrate, i.e., an activated nucleotide sugar to an acceptor substrate, e.g., an oligosaccharide, a glycolipid, a peptide, a protein, a glycopeptide, or a glycoprotein. In preferred embodiments, a eukaryotic glycosyltransferase transfers a sugar from a donor substrate to a peptide, a protein, a glycopeptide, or a glycoprotein. In another preferred embodiment, a eukaryotic glycosyltransferase is a type II transmembrane glycosyltransferase. A eukaryotic glycosyltransferase can be derived from an eukaryotic organism, e.g., a multicellular eukaryotic organism, a plant, an invertebrate animal, such as *Drosophila* or *C. elegans*, a vertebrate animal, an amphibian or reptile, a mammal, a rodent, a primate, a human, a rabbit, a rat, a mouse, a cow, or a pig and so on.

A "eukaryotic N-acetylglucosaminyltransferase I (GnTI or GNTI)" as used herein, refers to a $\beta$-1,2-N-acetylglucosaminyltransferase I isolated from a eukaryotic organism. The enzyme catalyzes the transfer of N-acetylglucosamine (GlcNAc) from a UDP-GlcNAc donor to an acceptor molecule comprising a mannose sugar. Like other eukaryotic glycosyltransferases, GnTI has a transmembrane domain, a stem region, and a catalytic domain. Eukaryotic GnT1 proteins include, e.g., human, accession number NP_002397; Chinese hamster, accession number AAK61868; rabbit, accession number AAA31493; rat, accession number NP_110488; golden hamster, accession number AAD04130; mouse, accession number P27808; zebrafish, accession number AAH58297; *Xenopus*, accession number CAC51119; *Drosophila*, accession number NP 525117; *Anopheles*, accession number XP_315359; *C. elegans*, accession number NP_497719; *Physcomitrella patens*, accession number CAD22107; *Solanum tuberosum*, accession number CAC80697; *Nicotiana tabacum*, accession number CAC80702; *Oryza sativa*, accession number CAD30022; *Nicotiana benthamiana*, accession number CAC82507; and *Arabidopsis thaliana*, accession number NP_195537, each of which are herein incorporated by reference.

A "eukaryotic N-acetylgalactosaminyltransferase (GalNAcT)" as used herein, refers to an N-acetylgalactosaminyltransferase isolated from a eukaryotic organism. The enzyme catalyzes the transfer of N-acetylgalactosamine (GalNAc) from a UDP-GalNAc donor to an acceptor molecule. Like other eukaryotic glycosyltransferases, GalNAcT enzymes have a transmembrane domain, a stem region, and a catalytic domain. A number of GalNAcT enzymes have been isolated and characterized, e.g., GalNAcT1, accession number X85018; GalNAcT2, accession number X85019 (both described in White et al., *J. Biol. Chem.* 270:24156-24165 (1995)); and GalNAcT3, accession number X92689 (described in Bennett et al., *J. Biol. Chem.* 271:17006-17012 (1996), each of which are herein incorporated by reference).

A "eukaryotic $\beta$-1,4-galactosyltransferase (GalT1) as used herein, refers to a $\beta$-1,4-galactosyltransferase isolated from a eukaryotic organism. The enzyme catalyzes the transfer of galactose from a UDP-Gal donor to an acceptor molecule. Like other eukaryotic glycosyltransferases, GalT1 enzymes have a transmembrane domain, a stem region, and a catalytic domain. A number of GalT1 enzymes have been isolated and characterized, e.g., the full length bovine sequence, D'Agostaro et al., *Eur. J. Biochem.* 183:211-217 (1989) and accession number CAA32695, each of which are herein incorporated by reference.

A "eukaryotic $\alpha$(2,3)sialyltransferase (ST3Gal3)" as used herein, refers to an $\alpha$(2,3)sialyltransferase isolated from a eukaryotic organism. This enzyme catalyzes the transfer of sialic acid to the Gal of a Gal$\beta$1,3GlcNAc, Gal$\beta$1,3GalNAc or Gal$\beta$1,4GlcNAc glycoside (see, e.g., Wen et al. (1992) *J. Biol. Chem.* 267: 21011; Van den Eijnden et al. (1991) *J. Biol. Chem.* 256: 3159). The sialic acid is linked to a Gal with the formation of an $\alpha$-linkage between the two saccharides. Bonding (linkage) between the saccharides is between the 2-position of NeuAc and the 3-position of Gal. Like other eukaryotic glycosyltransferases, ST3GalIII enzymes have a transmembrane domain, a stem region, and a catalytic domain. This particular enzyme can be isolated from rat liver (Weinstein et al. (1982) *J. Biol. Chem.* 257: 13845); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. Rat ST3GalIII has been cloned and the sequence is known. See, e.g., Wen et al., *J. Biol. Chem.* 267:21011-21019 (1992) and Accession number M97754, each of which are herein incorporated by reference.

A "eukaryotic α-N-acetylgalactosaminide α-2,6-sialyltransferase I (ST6GalNAcT1) as used herein, refers to an α(2,6)sialyltransferase isolated from a eukaryotic organism. The enzyme catalyzes the transfer of sialic acid from a CMP-sialic acid donor to an acceptor molecule. The transfer is an α2,6-linkage to N-acetylgalactosamine-O-Thr/Ser. Like other eukaryotic glycosyltransferases, ST6GalNAcT1 enzymes have a transmembrane domain, a stem region, and a catalytic domain. A number of ST6GalNAcT1 enzymes have been isolated and characterized, e.g., the full length mouse sequence, Kurosawa et al., *J. Biochem.* 127:845-854 (2000) and accession number JC7248, each of which are herein incorporated by reference. Other exemplary ST6GalNAcT1 amino acid sequences are found in FIG. 38.

A "eukaryotic gal β1,3GalNAc α2,3-sialyltransferase (ST3GalI)" as used herein, refers to a gal β1,3GalNAc α2,3-sialyltransferase isolated from a eukaryotic organism. The enzyme catalyzes the transfer of sialic acid from a CMP-sialic acid donor to an acceptor molecule. The transfer is an α2,3-linkage to N-acetylgalactosamine-O-Thr/Ser. Like other eukaryotic glycosyltransferases, ST3 GalI enzymes have a transmembrane domain, a stem region, and a catalytic domain. A number of ST3GalI enzymes have been isolated and characterized, e.g., the full length porcine sequence, Gillespie et al., *J. Biol. Chem.* 267:21004-21010 (1992) and accession number A45073, each of which are herein incorporated by reference.

A "eukaryotic core I galactosyltransferase (Core 1 GalT1)" as used herein refers to a protein with Core 1 β1,3-Galactosyltransferase activity. Like other eukaryotic glycosyltransferases, Core 1 GalT1 enzymes have a transmembrane domain, a stem region, and a catalytic domain. A number of Core 1 GalT1 enzymes have been isolated and characterized, e.g., the *Drosophila* and human sequences of FIGS. 41 and 42. The human protein is characterized in Ju et al., *J. Biol. Chem.* 277 (1), 178-186 (2002), which is herein incorporated by reference for all purposes.

An "unpaired cysteine residue" as used herein, refers to a cysteine residue, which in a correctly folded protein (i.e., a protein with biological activity), does not form a disulfide bind with another cysteine residue.

An "insoluble glycosyltransferase" refers to a glycosyltransferase that is expressed in bacterial inclusion bodies. Insoluble glycosyltransferases are typically solubilized or denatured using e.g., detergents or chaotropic agents or some combination. "Refolding" refers to a process of restoring the structure of a biologically active glycosyltransferase to a glycosyltransferase that has been solubilized or denatured. Thus, a refolding buffer, refers to a buffer that enhances or accelerates refolding of a glycosyltransferase.

A "redox couple" refers to mixtures of reduced and oxidized thiol reagents and include reduced and oxidized glutathione (GSH/GSSG), cysteine/cystine, cysteamine/cystaime, DTT/GSSG, and DTE/GSSG. (See, e.g., Clark, *Cur. Op. Biotech.* 12:202-207 (2001)).

The term "contacting" is used herein interchangeably with the following: combined with, added to, mixed with, passed over, incubated with, flowed over, etc.

The term "PEG" refers to poly(ethylene glycol). PEG is an exemplary polymer that has been conjugated to peptides. The use of PEG to derivatize peptide therapeutics has been demonstrated to reduce the immunogenicity of the peptides and prolong the clearance time from the circulation. For example, U.S. Pat. No. 4,179,337 (Davis et al.) concerns non-immunogenic peptides, such as enzymes and peptide hormones coupled to polyethylene glycol (PEG) or polypropylene glycol. Between 10 and 100 moles of polymer are used per mole peptide and at least 15% of the physiological activity is maintained.

The term "specific activity" as used herein refers to the catalytic activity of an enzyme, e.g., a recombinant glycosyltransferase fusion protein of the present invention, and may be expressed in activity units. As used herein, one activity unit catalyzes the formation of 1 μmol of product per minute at a given temperature (e.g., at 37° C.) and pH value (e.g., at pH 7.5). Thus, 10 units of an enzyme is a catalytic amount of that enzyme where 10 μmol of substrate are converted to 10 μmol of product in one minute at a temperature of, e.g., 37° C. and a pH value of, e.g., 7.5.

"N-linked" oligosaccharides are those oligosaccharides that are linked to a peptide backbone through asparagine, by way of an asparagine-N-acetylglucosamine linkage. N-linked oligosaccharides are also called "N-glycans." All N-linked oligosaccharides have a common pentasaccharide core of $Man_3GlcNAc_2$. They differ in the presence of, and in the number of branches (also called antennae) of peripheral sugars such as N-acetylglucosamine, galactose, N-acetylgalactosamine, fucose and sialic acid. Optionally, this structure may also contain a core fucose molecule and/or a xylose molecule.

"O-linked" oligosaccharides are those oligosaccharides that are linked to a peptide backbone through threonine, serine, hydroxyproline, tyrosine, or other hydroxy-containing amino acids.

A "substantially uniform glycoform" or a "substantially uniform glycosylation pattern," when referring to a glycoprotein species, refers to the percentage of acceptor substrates that are glycosylated by the glycosyltransferase of interest (e.g., fucosyltransferase). It will be understood by one of skill in the art, that the starting material may contain glycosylated acceptor substrates. Thus, the calculated amount of glycosylation will include acceptor substrates that are glycosylated by the methods of the invention, as well as those acceptor substrates already glycosylated in the starting material.

The term "biological activity" refers to an enzymatic activity of a protein. For example, biological activity of a sialyltransferase refers to the activity of transferring a sialic acid moiety from a donor molecule to an acceptor molecule. Biological activity of a GalNAcT2 refers to the activity of transferring an N-acetylgalactosamine moiety from a donor molecule to an acceptor molecule. For GalNAcT2 proteins, an acceptor molecule can be a protein, a peptide, a glycoprotein, or a glycopeptide. Biological activity of a GnT1 protein refers to the activity of transferring a N-acetylglucosamine moiety from a donor molecule to an acceptor molecule. Biological activity of a galactosyltransferase refers to the activity of transferring a galactose moiety from a donor molecule to an acceptor molecule.

"Commercial scale" refers to gram scale production of a product saccharide in a single reaction. In preferred embodiments, commercial scale refers to production of greater than about 50, 75, 80, 90 or 100, 125, 150, 175, or 200 grams.

The term "substantially" in the above definitions of "substantially uniform" generally means at least about 60%, at least about 70%, at least about 80%, or more preferably at least about 90%, and still more preferably at least about 95% of the acceptor substrates for a particular glycosyltransferase are glycosylated.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Protein", "polypeptide", or "peptide" refer to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell. In preferred embodiments, a recombinant eukaryotic glycosyltransferase is produced by a recombinant bacterial cell.

A "fusion protein" refers to a protein comprising amino acid sequences that are in addition to, in place of, less than, and/or different from the amino acid sequences encoding the original or native full-length protein or subsequences thereof. Components of fusion proteins include "accessory enzymes" and/or "purification tags." An "accessory enzyme" as referred to herein, is an enzyme that is involved in catalyzing a reaction that, for example, forms a substrate for a glycosyltransferase. An accessory enzyme can, for example, catalyze the formation of a nucleotide sugar that is used as a donor moiety by a glycosyltransferase. An accessory enzyme can also be one that is used in the generation of a nucleotide triphosphate required for formation of a nucleotide sugar, or in the generation of the sugar which is incorporated into the nucleotide sugar. The recombinant fusion protein of the invention can be constructed and expressed as a fusion protein with a molecular "purification tag" at one end, which facilitates purification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence AspTyrLysAspAspAsp AspLys or a substantially identical variant thereof. Other suitable tags are known to those of skill in the art, and include, for example, an affinity tag such as a hexahistidine peptide, which will bind to metal ions such as nickel or cobalt ions. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, E. coli thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Maltose binding domains are preferably used for their ability to enhance refolding of insoluble eukaryotic glycosyltransferases, but can also be used to assist in purification of a fusion protein. Purification of maltose binding domain proteins is known to those of skill in the art. Starch binding domains are described in WO 99/15636, herein incorporated by reference. Affinity purification of a fusion protein comprising a starch binding domain using a betacyclodextrin (BCD)-derivatized resin is described in U.S. Ser. No. 60/468,374, filed May 5, 2003, herein incorporated by reference in its entirety.

The term "functional domain" with reference to glycosyltransferases, refers to a domain of the glycosyltransferase that confers or modulates an activity of the enzyme, e.g., acceptor substrate specificity, catalytic activity, binding affinity, localization within the Golgi apparatus, anchoring to a cell membrane, or other biological or biochemical activity. Examples of functional domains of glycosyltransferases include, but are not limited to, the catalytic domain, stem region, and signal-anchor domain.

The terms "expression level" or "level of expression" with reference to a protein refers to the amount of a protein produced by a cell. The amount of protein produced by a cell can be measured by the assays and activity units described herein or known to one skilled in the art. One skilled in the art would know how to measure and describe the amount of protein produced by a cell using a variety of assays and units, respectively. Thus, the quantitation and quantitative description of the level of expression of a protein, e.g., a glycosyltransferase, is not limited to the assays used to measure the activity or the units used to describe the activity, respectively. The amount of protein produced by a cell can be determined by standard known assays, for example, the protein assay by Bradford (1976), the bicinchoninic acid protein assay kit from Pierce (Rockford, Ill.), or as described in U.S. Pat. No. 5,641,668.

The term "enzymatic activity" refers to an activity of an enzyme and may be measured by the assays and units described herein or known to one skilled in the art. Examples of an activity of a glycosyltransferase include, but are not limited to, those associated with the functional domains of the enzyme, e.g., acceptor substrate specificity, catalytic activity, binding affinity, localization within the Golgi apparatus, anchoring to a cell membrane, or other biological or biochemical activity.

A "stem region" with reference to glycosyltransferases refers to a protein domain, or a subsequence thereof, which in the native glycosyltransferases is located adjacent to the trans-membrane domain, and has been reported to function as a retention signal to maintain the glycosyltransferase in the Golgi apparatus and as a site of proteolytic cleavage. Stem regions generally start with the first hydrophilic amino acid following the hydrophobic transmembrane domain and end at the catalytic domain, or in some cases the first cysteine residue following the transmembrane domain. Exemplary stem regions include, but is not limited to, the stem region of fucosyltransferase VI, amino acid residues 40-54; the stem region of mammalian GnT1, amino acid residues from about 36 to about 103 (see, e.g., the human enzyme); the stem region of mammalian GalT1, amino acid residues from about 71 to about 129 (see e.g., the bovine enzyme); the stem region of mammalian ST3GalIII, amino acid residues from about 29 to about 84 (see, e.g., the rat enzyme); the stem region of invertebrate Core 1 GalT1, amino acid residues from about 36 to about 102 (see e.g., the *Drosophila* enzyme); the stem region of mammalian Core 1 GalT1, amino acid residues from about 32 to about 90 (see e.g., the human enzyme); the stem region of mammalian ST3Gal1, amino acid residues from about 28 to about 61 (see e.g., the porcine enzyme) or for the human enzyme amino acid residues from about 18 to about 58; the stem region of mammalian ST6GalNAcI, amino acid residues from about 30 to about 207 (see e.g., the murine enzyme), amino acids 35-278 for the human enzyme or amino acids 37-253 for the chicken enzyme; the stem region of mammalian GalNAcT2, amino acid residues from about 71 to about 129 (see e.g., the rat enzyme).

A "catalytic domain" refers to a protein domain, or a subsequence thereof, that catalyzes an enzymatic reaction performed by the enzyme. For example, a catalytic domain of a sialyltransferase will include a subsequence of the sialyltransferase sufficient to transfer a sialic acid residue from a donor to an acceptor saccharide. A catalytic domain can include an entire enzyme, a subsequence thereof, or can include additional amino acid sequences that are not attached to the enzyme, or a subsequence thereof, as found in nature. An exemplary catalytic region is, but is not limited to, the catalytic domain of fucosyltransferase VII, amino acid residues 39-342; the catalytic domain of mammalian GnT1, amino acid residues from about 104 to about 445 (see, e.g., the human enzyme); the catalytic domain of mammalian GalT1, amino acid residues from about 130 to about 402 (see e.g., the bovine enzyme); and the catalytic domain of mammalian ST3GalIII, amino acid residues from about 85 to about 374 (see, e.g., the rat enzyme). Catalytic domains and truncation mutants of GalNAcT2 proteins are described in U.S. Ser. No. 60/576,530 filed Jun. 3, 2004; and U.S. provisional patent application 60/598,584, filed Aug. 3, 2004; both of which are herein incorporated by reference for all purposes. Catalytic domains can also be identified by alignment with known glycosyltransferases.

A "subsequence" refers to a sequence of nucleic acids or amino acids that comprise a part of a longer sequence of nucleic acids or amino acids (e.g., protein) respectively.

A "glycosyltransferase truncation" or a "truncated glycosyltransferase" or grammatical variants, refer to a glycosyltransferase that has fewer amino acid residues than a naturally occurring glycosyltransferase, but that retains enzymatic activity. Truncated glycosyltransferases include, e.g., truncated GnT1 enzymes, truncated GalT1 enzymes, truncated ST3GalIII enzymes, truncated GalNAcT2 enzymes, truncated Core 1 GalT1 enzymes, amino acid residues from about 32 to about 90 (see e.g., the human enzyme); truncated ST3Gal1 enzymes, truncated ST6GalNAcI enzymes, and truncated GalNAcT2 enzymes. Any number of amino acid residues can be deleted so long as the enzyme retains activity. In some embodiments, domains or portions of domains can be deleted, e.g., a signal-anchor domain can be deleted leaving a truncation comprising a stem region and a catalytic domain; a signal-anchor domain and a portion of a stem region can be deleted leaving a truncation comprising the remaining stem region and a catalytic domain; or a signal-anchor domain and a stem region can be deleted leaving a truncation comprising a catalytic domain.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. In preferred embodiments, a recombinant expression cassette encoding an amino acid sequence comprising a eukaryotic glycosyltransferase is expressed in a bacterial host cell.

A "heterologous sequence" or a "heterologous nucleic acid", as used herein, is one that originates from a source foreign to the particular host cell, or, if from the same source, is modified from its original form. Thus, a heterologous glycoprotein gene in a eukaryotic host cell includes a glycoprotein-encoding gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, and preferably at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and HPLC or a similar means for purification, for example, may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or proteins, refers to two or more sequences or subsequences that have at least greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances.

Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every polynucleotide sequence described herein which encodes a protein also describes every possible silent variation, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of proteins, e.g., glycosyltransferases, and nucleic acid which encode proteins yield essentially identical products. For example, due to the degeneracy of the genetic code, "silent substitutions" (i.e., substitutions of a nucleic acid sequence which do not result in an alteration in an encoded protein) are an implied feature of every nucleic acid sequence which encodes an amino acid. As described herein, sequences are preferably optimized for expression in a particular host cell used to produce the chimeric glycosyltransferases (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

The practice of this invention can involve the construction of recombinant nucleic acids and the expression of genes in host cells, preferably bacterial host cells. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, prokaryotic cells, such as *E. coli*, and eukaryotic cells including insect, mammalian and fungal cells (e.g., *Aspergillus niger*)

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

DETAILED DESCRIPTION OF THE INVENTION

I. Introduction

The present invention provides conditions for refolding eukaryotic glycosyltransferases that are expressed as insoluble proteins in bacterial inclusion bodies. Refolding buffers comprising redox couples are used to enhance refolding of insoluble eukaryotic glycosyltransferases. Refolding can also be enhanced by fusing a maltose binding domain to the insoluble eukaryotic glycosyltransferase. For some insoluble eukaryotic glycosyltransferases, refolding can also be enhanced by site directed mutagenesis to remove unpaired cysteines. Additional refolding enhancement can be provided be truncating a eukaryotic glycosyltransferase to remove, e.g., a signal-anchor domain, a transmemebrane domain, and/or all or a portion of a stem region of the protein. The invention also provides methods to refold more than one glycosyltransferase in a single vessel, thereby enhancing refolding of the proteins and increasing efficiency of protein production. The refolded eukaryotic glycosyltransferases can be used to produce or to remodel polysaccharides, oligosaccharides, glycolipids, proteins, peptides, glycopeptides, and glycoproteins. The refolded eukaryotic glycosyltransferases can also be used to glycoPEGylate proteins, peptides, glycopeptides, or glycoproteins as described in PCT/US02/32263, which is herein incorporated by reference for all purposes.

II. Refolding Insoluble Glycosyltransferases

Many recombinant proteins expressed in bacteria are expressed as insoluble aggregates in bacterial inclusion bodies. Inclusion bodies are protein deposits found in both the cytoplasmic and periplasmic space of bacteria. (See, e.g., Clark, *Cur. Op. Biotech.* 12:202-207 (2001)). Eukaryotic glycosyltransferases are frequently expressed in bacterial inclusion bodies. Some eukaryotic glycosyltransferases are soluble in bacteria, i.e., not produced in inclusion bodies, when only the catalytic domain of the protein is expressed. However, many eukaryotic glycosyltransferases remain insoluble and are expressed in bacterial inclusion bodies, even if only the catalytic domain is expressed, and methods for refolding these proteins to produce active glycosyltransferases are provided herein.

A. Conditions for Refolding Active Glycosyltransferases

To produce active eukaryotic glycosyltranferases from bacterial cells, eukaryotic glycosyltranferases are expressed in bacterial inclusion bodies, the bacteria are harvested, disrupted and the inclusion bodies are isolated and washed. The proteins within the inclusion bodies are then solubilized. Solubilization can be performed using denaturants, e.g., guanidinium chloride or urea; extremes of pH, such as acidic or alkaline conditions; or detergents.

After solubilization, denaturants are removed from the glycosyltransferase mixture. Denaturant removal can be done by a variety of methods, including dilution into a refolding buffer or buffer exchange methods. Buffer exchange methods include dialysis, diafiltration, gel filtration, and immobilization of the protein onto a solid support. (See, e.g., Clark, *Cur. Op. Biotech.* 12:202-207 (2001)). Any of the above methods can be combined to remove denaturants.

Disulfide bond formation in the eukaryotic glycosyltransferase is promoted by addition of a refolding buffer comprising a redox couple. Redox couples include reduced and oxidized glutathione (GSH/GSSG), cysteine/cystine, cysteamine/cystamine, DTT/GSSG, and DTE/GSSG. (See, e.g., Clark, *Cur. Op. Biotech.* 12:202-207 (2001), which is herein incorporated by reference for all purposes). In some embodiments, redox couples are added at an particular ratio of reduced to oxidized component, e.g., 1/20, 20/1, 1/4, 4/1, 1/10, 10/1, 1/2, 2/1, 1/5, 5/1, or 5/5.

Refolding can be performed in buffers at pH's ranging from, for example, 6.0 to 10.0. Refolding buffers can include other additives to enhance refolding, e.g., L-arginine (0.4-1M); PEG; low concentrations of denaturants, such as urea (1-2M) and guanidinium chloride (0.5-1.5 M); and detergents (e.g., Chaps, SDS, CTAB, lauryl maltoside, and Triton X-100).

Refolding can be over a given period of time, e.g., for 1-48 hours, or overnight. Refolding can be done from about 4° C. to about 40° C., including ambient temperatures.

A eukaryotic glycosyltransferase protein comprising a catalytic domain is expressed in bacterial inclusion bodies and then refolded using the above methods. Eukaryotic glycosyltransferases that comprise all or a portion of a stem region and a catalytic domain can also be used in the a methods described herein, as can eukaryotic glycosyltransferases comprising a catalytic domain fused to an MBP protein.

Those of skill will recognize that a protein has been refolded correctly when the refolded protein has detectable biological activity. For a glycosyltransferase biological activity is the ability to catalyze transfer of a donor substrate to an acceptor substrate, e.g., a refolded ST3GalIII is able to transfer sialic acid to an acceptor substrate. Biological activity includes e.g., specific activities of at least 1, 2, 5, 7, or 10 units of activity. Unit is defined as follows: one activity unit catalyzes the formation of 1 μmol of product per minute at a given temperature (e.g., at 37° C.) and pH value (e.g., at pH 7.5). Thus, 10 units of an enzyme is a catalytic amount of that enzyme where 10 μmol of substrate are converted to 10 μmol of product in one minute at a temperature of, e.g., 37° C. and a pH value of, e.g., 7.5.

In one embodiment, eukaryotic ST3GalIII is expressed in bacterial inclusion bodies, solubilized, and refolded in a buffer comprising a redox couple, e.g., GSH/GSSG or cystamine/cysteine.

In one embodiment, eukaryotic GnT1 is expressed in bacterial inclusion bodies, solubilized, and refolded in a buffer comprising a redox couple, e.g., GSH/GSSG or cystamine/cysteine.

In one embodiment, eukaryotic GalT1 is expressed in bacterial inclusion bodies, solubilized, and refolded in a buffer comprising a redox couple, e.g., GSH/GSSG or cystamine/cysteine.

In one embodiment, eukaryotic St3GalI is expressed in bacterial inclusion bodies, solubilized, and refolded in a buffer comprising a redox couple, e.g., GSH/GSSG or cystamine/cysteine.

In one embodiment, eukaryotic St6 GalNAcTI is expressed in bacterial inclusion bodies, solubilized, and refolded in a buffer comprising a redox couple, e.g., GSH/GSSG or cystamine/cysteine.

In one embodiment, eukaryotic Core GalITI is expressed in bacterial inclusion bodies, solubilized, and refolded in a buffer comprising a redox couple, e.g., GSH/GSSG or cystamine/cysteine.

In one embodiment, eukaryotic GalNAcT2 is expressed in bacterial inclusion bodies, solubilized, and refolded in a buffer comprising a redox couple, e.g., GSH/GSSG or cystamine/cysteine.

B. Fusion of Eukaryotic Glycosyltransferases to Maltose Binding Protein Domains to Enhance Refolding Maltose binding protein (MBP) domains are typically fused to proteins to enhance solubility of a the protein with a cell. See, e.g., Kapust and Waugh *Pro. Sci.* 8:1668-1674 (1999). However, many eukaryotic glycosyltransferases, including truncated eukaryotic glycosyltransferases, remain insoluble when expressed in bacteria, even after fusion to a MBP domain. However, this application discloses that MBP domains can enhance refolding of insoluble eukaryotic glycosyltransferases after solubilization of the proteins from e.g., an inclusion body. MBP domains from a variety of bacterial sources can be used in the invention, for example *Yersinia E. coli, Pyrococcus furiosus, Thermococcus litoralis, Thermatoga maritime*, and *Vibrio cholerae*, see, e.g., FIG. 43. In a preferred embodiment an *E. coli* MBP protein is fused to a eukaryotic glycosyltransferase. Amino acid linkers can be placed between the MBP domain and the glycosyltransferase. In another preferred embodiment, the MBP domain is fused to the amino terminus of the glycosyltransferase protein. The methods described above can be used to refold the MBP glycosyltransferase fusion proteins.

In one embodiment, a eukaryotic ST3GalIII protein is fused to an MBP domain, expressed in bacterial inclusion bodies, solubilized, and refolded in a buffer comprising a redox couple, e.g., GSH/GSSG or cystamine/cysteine.

In one embodiment, a eukaryotic GnT1 protein is fused to an MBP domain, expressed in bacterial inclusion bodies, solubilized, and refolded in a buffer comprising a redox couple, e.g., GSH/GSSG or cystamine/cysteine.

In one embodiment, a eukaryotic GalT1 protein is fused to an MBP domain, expressed in bacterial inclusion bodies, solubilized, and refolded in a buffer comprising a redox couple, e.g., GSH/GSSG or cystamine/cysteine.

In one embodiment, a eukaryotic St3GalI protein is fused to an MBP domain, expressed in bacterial inclusion bodies, solubilized, and refolded in a buffer comprising a redox couple, e.g., GSH/GSSG or cystamine/cysteine.

In one embodiment, a eukaryotic St6 GalNAcTI protein is fused to an MBP domain, expressed in bacterial inclusion bodies, solubilized, and refolded in a buffer comprising a redox couple, e.g., GSH/GSSG or cystamine/cysteine.

In one embodiment, a eukaryotic Core GalITI protein is fused to an MBP domain, expressed in bacterial inclusion bodies, solubilized, and refolded in a buffer comprising a redox couple, e.g., GSH/GSSG or cystamine/cysteine.

In one embodiment, a eukaryotic GalNAcT2 protein is fused to an MBP domain, expressed in bacterial inclusion bodies, solubilized, and refolded in a buffer comprising a redox couple, e.g., GSH/GSSG or cystamine/cysteine.

Additional amino acid tags can be added to an MBP-glycosyltransferase fusion. For example, purification tags can be added to enhance purification of the refolded protein. Purification tags include, e.g., a polyhistidine tag, a glutathione S transferase (GST), a starch binding protein (SBP), an *E. coli* thioredoxin domain, a carboxy-terminal half of the SUMO protein, a FLAG epitope, and a myc epitope. Refolded glycosyltransferases can be further purified using a binding partner that binds to the purification tag. In a preferred embodiment, an MBP tag is fused to the eukaryotic glycosyltransferase to enhance refolding. Purification tags can be fused to MBP glycosyltransferase fusion protein including e.g., GnT1, GalT1, StIII Gal3, St3GalI, St6 GalNAcTI, Core GalITI, or GalNAcT2.

In another embodiment, addition of an MBP domain to a protein can increase the expression of the protein. See, e.g., example 12 where fusion of the SiaA protein to an MBP domain increased the expression of the protein. Other proteins with enhanced expression on fusion to MBP include e.g., GnT1, GalT1, StIII Gal3, St3GalI, St6 GalNAcTI, Core GalITI, or GalNAcT2.

In another embodiment a self-cleaving protein tag, such as an intein, is included between the MPB domain and the glycosyltransferase to facilitate removal of the MBP domain after the fusion protein has been refolded. Inteins and kits for their use are commercially available, e.g., from New England Biolabs.

C. Mutagenesis of Glycosyltransferases to Enhance Refolding

Refolding of glycosyltransferases can also be enhanced by mutagenesis of the glycosyltransferase amino acid sequence. In one embodiment an unpaired cysteine residue is identified and mutated to enhance refolding of a glyscosyltransferase. In another embodiment, the amino terminus of the glycosyltransferase is truncated to remove a transmembrane domain, or to remove a transmembrane domain and all or a portion of the stem region of the protein. In a further embodiment, a glycosyltransferase is mutated to remove at least one unpaired cysteine residue and to truncate the amino terminus of the protein, e.g., to remove a transmembrane domain, or to remove a transmembrane domain and all or a portion of the stem region of the protein. Once a glycosyltransferase nucleic acid sequence has been isolated, standard molecular biology methods can be used to change the nucleic acid sequence and thus the encoded amino acid sequence in a manner described herein.

1. Mutagenesis of Unpaired Cysteines in Glycosyltransferases to Enhance Refolding As refolding occurs, cysteine residues in a denatured protein form disulfide bonds that help to reproduce the structure of the active protein. Incorrect pairing of cysteine residues can lead to protein misfolding. Proteins with unpaired cysteine residues are susceptible to misfolding because a normally unpaired cysteine can form a disulfide bond with normally paired cysteine making correct cysteine pairing and protein refolding impossible. Thus, one method to enhance refolding of a particular glycosyltransferase is to identify unpaired cysteine residues and remove them.

Unpaired cysteine residues can be identified by determining the structure of the glycosyltransferase of interest. Protein structure can be determined based on actual data for the glycosyltransferase of interest, e.g., circular dichroism, NMR, and X-ray crystallography. Protein structure can also be determined using computer modeling. Computer modeling is a technique that can be used to model related structures based on known three-dimensional structures of homologous molecules. Standard software is commercially available. (See e.g., www.accelrys.com for the multitude of software available to do computer modeling.) Once an unpaired cysteine residue is identified, the DNA encoding the glycosyltransferase of interest can be mutated using standard molecular biology techniques to remove the unpaired cysteine, by deletion or by substitution with another amino acid residue. Computer modeling is used again to select an amino acid of appropriate size, shape, and charge for substitution. Unpaired cysteines can also be determined by peptide mapping. Once the glycosyltransferase of interest is mutated, the protein is expressed in bacterial inclusion bodies and refolding ability is determined. A correctly refolded glycosyltransferase will have biological activity.

In preferred embodiments, the following amino acid residues are substituted for an unpaired cysteine residue in a eukaryotic glycosyltransferase to enhance refolding: Ala, Ser, Thr, Asp, Ile, or Val. Gly can also be used if the unpaired cysteine is not in a helical structure.

Human N-acetylglucosaminyltransferase I (GnTI, accession number NP_002397) is an example of a glycosyltransferase that exhibited enhanced refolding after mutagenesis of an unpaired cysteine. (See, e.g., Example 2, below.) Human GNTI is closely related to a number of eukaryotic GNTI proteins, e.g., Chinese hamster, accession number AAK61868; rabbit accession number AAA31493; rat accession number NP_110488; golden hamster, accession number AAD04130; mouse, accession number P27808; zebrafish, accession number AAH58297; *Xenopus*, accession number CAC51119; *Drosophila*, accession number NP_525117; *Anopheles*, accession number XP_315359; *C. elegans*, accession number NP_497719; *Physcomitrella patens*, accession number CAD22107; *Solanum tuberosum*, accession number CAC80697; *Nicotiana tabacum*, accession number CAC80702; *Oryza sativa*, accession number CAD30022; *Nicotiana benthamiana*, accession number CAC82507; and *Arabidopsis thaliana*, accession number NP_195537.

The structure of the rabbit N-acetylglucosaminyltransferase I (GnTI) protein had been determined and showed that CYS123 was unpaired. (Amino acid residue numbers refer to the full length protein sequence even when a GNTI protein has been truncated.) Computer modeling based on the rabbit GnTI was used to determine the structure of the human GnTI protein. An alignment is shown in FIG. 6. In the human GnTI protein, CYS121 was unpaired. Substitutions for CYS121 were made in human GnTI. A CYS121 SER mutant and a CYS121ALA mutant were active. In contrast, a CYS121THR mutant had no detectable activity and a CYS121ASP mutant had low activity. A double mutant, ARG120ALA, CYS121HIS, was constructed based on the predicted structure of the *C. elegans* GNT1 protein, and had activity.

The amino acid sequences of the eukaryotic GnTI proteins listed above can be used to determine protein structure based on computer modeling and the conserved function of CYS123 from rabbit and CYS121 from human. Based on that analysis, residue 123 is an unpaired cysteine in the following proteins: Chinese hamster GnTI, the rabbit GnTI, the rat GnTI, the golden hamster GnTI, and the mouse GnTI. Thus, CYS123 can be mutated in each of the GnTI enzymes to serine, alanine, or arginine to produce an active protein with enhanced refolding activity. The following double mutant in the above proteins, ARG122ALA CYS123HIS, will also exhibit enhanced refolding.

In one embodiment, any of the eukaryotic GnT1 proteins listed above is mutated to remove an unpaired cysteine residue, e.g., CYS121SER, CYS121ALA, CYS121ASP, or the double mutant ARG120ALA CYS121HIS, expressed in bacterial inclusion bodies, solubilized, and refolded in a buffer comprising a redox couple, e.g., GSH/GSSG or cystamine/cysteine.

Another glycosyltransferase that exhibits enhanced refolding on mutation of an unpaired cysteines is Gal T1. Cysteine 342 was mutated to a threonine residue in the bovine Gal T1 and the mutated enzyme exhibited enhanced refolding after solubilization. See, e.g., Ramakrishnan et al. *J. Biol. Chem.* 276:37666-37671 (2001). Of interest, mutation of an unpaired cysteine to threonine in the GnTI enzyme, abolished activity.

In one embodiment, a Gal T1 protein is mutated to remove an unpaired cysteine residue, e.g., CYS342THR, expressed in bacterial inclusion bodies, solubilized, and refolded in a buffer comprising a redox couple, e.g., GSH/GSSG or cystamine/cysteine.

Another glycosyltransferase that exhibits enhanced refolding on mutation of an unpaired cysteines is GalNAc T2. Many amino acids residues are shared between the GalNAc T2 protein and the GalNAc T1 protein. After mutation of two cysteines residues, CYS212 and CYS214, the human GalNAc T1 protein remained active when expressed from COS cells. See, e.g., Tenno et al., *Eur. J. Biochem.* 269:4308-4316 (2002). The active mutations included CYS212ALA, CYS214ALA, CYS212SER, CYS214SER, and a double mutant CYS212SER CYS214SER. Cysteine residues corresponding to human GalNAc T1 CYS212 and CYS214 residues are conserved in the human GalNAc T2 protein, i.e., residues CYS227 and CYS229. See, e.g., FIG. 44. Thus, a GalNAc T2 protein comprising one of the following mutations can be used to enhance refolding of the insoluble protein: CYS227ALA, CYS229ALA, CYS227SER, CYS229SER, and a double mutant CYS227SER CYS229SER. The numbering of residues refers to human GalNAc T2 proteins, but conserved cysteines residues that correspond to CYS227 and CYS229 can be identified in other eukaryotic GalNAc T2 proteins, e.g., mouse, rat, rabbit, pig, and mutated to enhance refolding.

In one embodiment, a GalNAc T2 protein is mutated to remove an unpaired cysteine residue, e.g., CYS227ALA, CYS229ALA, CYS227SER, CYS229SER, or a double mutant CYS227SER CYS229SER, expressed in bacterial inclusion bodies, solubilized, and refolded in a buffer comprising a redox couple, e.g., GSH/GSSG or cystamine/cysteine.

Another glycosyltransferase that exhibits enhanced refolding on mutation of an unpaired cysteines is Core 1 Gal T1. In one embodiment, the *drosophila* Core 1 Gal T1 is mutated. In another embodiment, the human Core 1 Gal T1 is mutated. The *drosophila* Core 1 Gal T1 protein has seven cysteine residues. Each cysteine residue is mutated individually to either serine or alanine. The mutated *drosophila* Core 1 Gal T1 proteins are expressed in *E. coli* inclusion bodies, solubilized, and refolded. Enzymatic activity of the refolded mutant *drosophila* Core 1 Gal T1 is assayed and compared to wild type refolded *drosophila* Core 1 Gal T1 activity. Enhanced refolding is indicated by an increase in enzymatic activity in a mutant *drosophila* Core 1 Gal T1 as compared to the wild type protein.

In one embodiment, a Core 1 Gal T1 protein is mutated to remove an unpaired cysteine residue, e.g., either the *drosophila* protein or the human protein, expressed in bacterial inclusion bodies, solubilized, and refolded in a buffer comprising a redox couple, e.g., GSH/GSSG or cystamine/cysteine. Preferred cysteine residues for substitution in the *drosophila* Core 1 Gal T1 are C103, C127, C208, C246, C261, C315 and C316.

2. Truncation of Glycosyltransferases to Enhance Refolding

Eukaryotic glycosyltransferases generally include the following domains: a catalytic domain, a stem region, a transmembrane domain, and a signal-anchor domain. When expressed in bacteria, the signal anchor domain, and transmembrane domains are typically deleted. Eukaryotic glycosyltransferases used in the methods of the invention can include all or a portion of the stem region and the catalytic domain. In some embodiments, the eukaryotic glycosyltransferases comprise only the catalytic domain.

Glycosyltransferase domains can be identified for deletion mutagenesis. For example, those of skill in the art can identify a stem region in a eukaryotic glycosyltransferase and delete stem region amino acids one by one to identify truncated eukaryotic glycosyltransferase proteins with high activity on refolding.

The deletion mutants in this application are referenced in two ways: Δ or D followed by the number of residues deleted from the amino terminus of the native full length amino acid sequence, or by the symbol and residue number of the first amino acid residue translated from the native full length amino acid sequence. For example, ST6GalNAcI Δ or D35 and ST6GalNAcI K36, both refer to the same truncation of the human ST6GalNAcI protein.

For example, the rat ST3GalIII protein includes a stem region from about amino acid residues 29-84. The catalytic domain of the protein comprises amino acids from about residue 85-374. Thus, a truncated rat ST3GalIII protein can have deletions at the amino terminus of about e.g., 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, or 85 residues.

Deletion mutations can also be made in a GnT1 protein. For example, the human GnT1 protein includes a stem region from about amino acid residues 31-112. Thus, a truncated human GnT1 protein can have deletions at the amino terminus of about e.g., 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 98, 99, 100, 101, 102, 103, 104, 105, 106, 107, 108, 109, 110, or 111 residues.

Deletion mutations can also be made in a Gal T1 protein. For example, the bovine GalT1 protein includes a stem region from about amino acid residues 71-129. Thus, a truncated bovine GalT1 protein can have deletions at the amino terminus of about e.g., 70, 71, 72, 73, 74, 75, 76, 77, 78, 79, 80, 81, 82, 83, 84, 85, 86, 87, 88, 89, 90, 91, 92, 93, 94, 95, 96, 97 98, 99, 100, 101, 102, 103, 104, 105, 106, 017, 108, 109, 110, 111, 112, 113, 114, 115, 116, 117, 118, 119, 120, 121, 122, 123, 124, 125, 126, 127, or 128 residues.

Deletion mutations can also be made in a Corel GalT1 protein. For example, the *Drosophila* Corel GalT1 protein includes a stem region from about amino acid residues 36-102. Thus, a truncated *Drosophila* Corel GalT1 protein can have deletions at the amino terminus of about e.g., 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 98, 99, 100, 101, or 102 residues. As another example, the human Corel GalT1 protein includes a stem region from about amino acid residues 32-90. Thus, a truncated human Corel GalT1 protein can have deletions at the amino terminus of about e.g., 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 residues.

Deletion mutations can also be made in an ST3Gal1 protein. For example, the human ST3Gal1 protein includes a stem region from about amino acid residues 18-58. Thus, a truncated human ST3Gal1 protein can have deletions at the amino terminus of about e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, or 58 residues. As another example, the porcine ST3Gal1 protein includes a stem region from about amino acid residues 28-61. Thus, a truncated porcine ST3Gal1 protein can have deletions at the amino terminus of about e.g., 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, or 61 residues.

Deletion mutations can also be made in a GalNAcT2 protein. For example, the rat GalNAcT2 protein includes a stem region from about amino acid residues 40-95. Thus, a truncated rat GalNAcT2 protein can have deletions at the amino terminus of about e.g., 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95 residues.

Deletion mutations can also be made in an ST6GalNAcI protein. For example, the mouse ST6GalNAcI protein includes a stem region from about amino acid residues 30-207. Thus, a truncated mouse ST6GalNAcI protein can have deletions at the amino terminus of about e.g., 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 98, 99, 100, 101, 102, 103, 104, 105, 106, 017, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204, 205, 206, or 207 residues. As another example, the human ST6GalNAcI protein includes a stem region from about amino acid residues 35-278. Thus, a truncated human ST6GalNAcI protein can have deletions at the amino terminus of about e.g., 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 98, 99, 100, 101, 102, 103, 104, 105, 106, 017, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 256, 257, 258, 259, 260, 261, 262, 263, 264, 265, 266, 267, 268, 269, 270, 271, 272, 273, 274, 275, 276, 277, or 278 residues. As still another example, chicken ST6GalNAcI protein includes a stem region from about amino acid residues 37-253. Thus, a truncated chicken ST6GalNAcI protein can have deletions at the amino terminus of about e.g., 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 98, 99, 100, 101, 102, 103, 104, 105, 106, 017, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, or 253 residues.

D. One Pot Refolding of Glycosyltransferases

These embodiments of the invention are based on the surprising observation that multiple eukaryotic glycosyltransferases expressed in bacterial inclusion bodies can be refolded in a single vessel, i.e., a one pot method. Using this method at least two glycosyltransferases can be refolded together resulting in savings of time and materials. Refolding conditions are described above. The refolding conditions are optimized for the mixture of glycosyltransferases, thus, conditions may not be optimal for any particular enzyme in the mixture. However, because refolding is optimized for the combination of glycosyltransferases, each of the refolded glycosyltransferases in the end product has detectable biological activity. Biological activity refers to enzymatic activity of the refolded enzymes and can be expressed as specific activity. Biological activity includes e.g., specific activities of at least 0.1, 0.5, 1, 2, 5, 7, or 10 units of activity. Unit is defined as follows: one activity unit catalyzes the formation of 1 μmol of product per minute at a given temperature (e.g., at 37° C.) and pH value (e.g., at pH 7.5). Thus, 10 units of an enzyme is a catalytic amount of that enzyme where 10 μmol of substrate are converted to 10 μmol of product in one minute at a temperature of, e.g., 37° C. and a pH value of, e.g., 7.5. The reaction mixture comprising refolded glycosyltransferases can then be used e.g., to synthesize oligosaccharides, to synthesize glycolipids, to remodel glycoproteins, and to glycoPEGlyate glycoproteins.

In some embodiments, the glycosyltransferases can be solubilized individually from inclusion bodies and then combined under conditions appropriate for refolding. In other embodiments, inclusion bodies containing glycosyltransferases are combined, solubilized, and then refolded under appropriate conditions.

Refolding buffers typically include a redox couple. Refolding can be performed at pH's ranging from, for example, 6.0 to 10.0. Refolding buffers can include other additives to enhance refolding, e.g., L-arginine (0.4-1M); PEG; low concentrations of denaturants, such as urea (1-2M) and guanidinium chloride (0.5-1.5 M); and detergents (e.g., Chaps, SDS, CTAB, and Triton X-100).

In some embodiments, refolding is performed in a stationary vessel, i.e., without mixing, stirring, shaking or otherwise moving the reaction mixture.

The combination of refolded enzymes can include enzymes to construct a particular oligosaccharide structure. Those of skill will be able to identify appropriate glycosyltransferases for inclusion in the mixture once a desired end product is identified.

The reaction mixtures of refolded enzymes can include glycosyltransferases that have been mutated to enhance refolding, e.g., the GnTI enzymes described above.

In a preferred embodiment, enzymes that perform N-linked glycosylation steps are refolded together in a single vessel. For example, N-acetylglucosaminyltransferase I (GnTI), β-1,4 galactosyltransferase I (Gal TI), and N-acetyllactosaminide α-2,3-sialyltransferase (ST3GalIII) can be expressed in bacterial inclusion bodies, solubilized, and refolded together in a single vessel. The end product exhibited activity of all three proteins, indicating they were all correctly refolded. Refolding also occurred when GnTI and Gal TI were refolded together without ST3GalIII. The experiments are described in detail in Example 3.

In another preferred embodiment, O-linked glycosylation of a peptide or protein is accomplished using the bacterially expressed and refolded glycosyltransferases of this disclosure. For example, a refolded MBP-GalNAcT2(D51) enzyme can be used to add GalNAc to polypeptides. E.g., example 4 provides a demonstration that refolded MBP-GalNAcT2 (D51) can be used to add GalNAc to the GCSF protein. Combinations of O-linked glycosyltransferases can be used to remodel e.g., proteins, peptides, glycoproteins or glycopeptides. Those combinations include e.g., GalNAc-T2 and ST6GalNAc1; or GalNAc-T2, core 1 GalT1 and ST3Gal1 or ST3GalT2

III. Glycosyltransferases

The glycosyltransferases of use in practicing the present invention are eukaryotic glycosyltransferases. Examples of such glycosyltransferases include those described in Staudacher, E. (1996) *Trends in Glycoscience and Glycotechnology*, 8: 391-408, afmb.cnrs-mrs.fr/~pedro/CAZY/gtfhtml and www.vei.co.uk/TGN/gt_guide.htm, but are not limited thereto.

Eukaryotic Glycosyltransferases

Some eukaryotic glycosyltransferases have topological domains at their amino terminus that are not required for catalytic activity (see, U.S. Pat. No. 5,032,519). Of the glycosyltransferases characterized to date, the "cytoplasmic domain," is most commonly between about 1 and about 10 amino acids in length, and is the most amino-terminal domain; the adjacent domain, termed the "signal-anchor domain," is generally between about 10-26 amino acids in length; adjacent to the signal-anchor domain is a "stem region," which is generally between about 20 and about 60 amino acids in length, and known to function as a retention signal to maintain the glycosyltransferase in the Golgi apparatus; and at the carboxyl side of the stem region is the catalytic domain.

Many mammalian glycosyltransferases have been cloned and expressed and the recombinant proteins have been characterized in terms of donor and acceptor substrate specificity and they have also been investigated through site directed mutagenesis in attempts to define residues or domains involved in either donor or acceptor substrate specificity (Aoki et al. (1990) *EMBO. J.* 9: 3171-3178; Harduin-Lepers et al. (1995) *Glycobiology* 5(8): 741-758; Natsuka and Lowe (1994) *Current Opinion in Structural Biology* 4: 683-691; Zu et al. (1995) *Biochem. Biophys. Res. Comm.* 206(1): 362-369; Seto et al. (1995) *Eur. J. Biochem.* 234: 323-328; Seto et al. (1997) *J. Biol. Chem.* 272: 14133-141388).

In one group of embodiments, a functional domain of the recombinant glycosyltransferase proteins of the present invention is obtained from a known sialyltransferase. Examples of sialyltransferases that are suitable for use in the present invention include, but are not limited to, ST3GalIII, ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al. (1996) *Glycobiology* 6: v-xiv). An exemplary α2,3-sialyltransferase (EC 2.4.99.6) transfers sialic acid to the non-reducing terminal Gal of a Galβ1→4GlcNAc disaccharide or glycoside. See, Van den Eijnden et al., *J. Biol. Chem.*, 256:3159 (1981), Weinstein et al., *J. Biol. Chem.*, 257:13845 (1982) and Wen et al., *J. Biol. Chem.*, 267:21011 (1992). Another exemplary α2,3-sialyltransferase (EC 2.4.99.4) transfers sialic acid to the non-reducing terminal Gal of a Galβ1→3GalNAc disaccharide or glycoside. See, Rearick et al., *J. Biol. Chem.*, 254: 4444 (1979) and Gillespie et al., *J. Biol. Chem.*, 267:21004 (1992). Further exemplary enzymes include Gal-β-1,4-GlcNAc α-2,6 sialyltransferase (See, Kurosawa et al. *Eur. J. Biochem.* 219: 375-381 (1994)). Sialyltransferase nomenclature is described in Tsuji, S. et al. (1996) *Glycobiology* 6:v-vii.

An example of a sialyltransferase that is useful in the claimed methods is ST3GalIII, which is also referred to as α(2,3)sialyltransferase (EC 2.4.99.6). This enzyme catalyzes the transfer of sialic acid to the Gal of a Galβ1,3GlcNAc, Galβ1,3GalNAc or Galβ1,4GlcNAc glycoside (see, e.g., Wen et al. (1992) *J. Biol. Chem.* 267: 21011; Van den Eijnden et al. (1991) *J. Biol. Chem.* 256: 3159). The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al. (1982) *J. Biol. Chem.* 257: 13845); the human cDNA (Sasaki et al. (1993) *J. Biol. Chem.* 268: 22782-22787; Kitagawa & Paulson (1994) *J. Biol Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3GalIII. Rat ST3GalIII has been cloned and the sequence is known. See, e.g., Wen et al., *J. Biol. Chem.* 267:21011-21019 (1992) and Accession number M97754.

In another group of embodiments, a functional domain of the recombinant glycosyltransferase proteins of the present inventions is obtained from a fucosyltransferase. A number of fucosyltransferases are known to those of skill in the art. Briefly, fucosyltransferases include any of those enzymes which transfer L-fucose from GDP-fucose to a hydroxy position of an acceptor sugar. In some embodiments, for example, the acceptor sugar is a GlcNAc in a Galβ(1→4)GlcNAc group in an oligosaccharide glycoside. Suitable fucosyltransferases for this reaction include the known Galβ (1→3,4) GlcNAc α(1→3,4)fucosyltransferase (FTIII, E.C. No. 2.4.1.65) which is obtained from human milk (see, Palcic, et al., *Carbohydrate Res.* 190:1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAc α(1→3)fucosyltransferases (FTIV, FTV, and FTVI, E.C. No. 2.4.1.65) and NeuAcα(2,3)βGal(1→4)βGlcNAc α(1→3)fucosyltransferases (FTVII) which are found in human serum. Also, available is the α1,3 fucosyltransferase IX (nucleotide sequences of human and mouse FTIX) as described in Kaneko et al. (1999) *FEBS Lett.* 452: 237-242. In addition, a recombinant form of Galβ (1→3,4)GlcNAc α(1→3,4)fucosyltransferase is available (see, Dumas, et al., *Bioorg. Med. Letters* 1:425-428 (1991) and Kukowska-Latallo, et al., *Genes and Development* 4:1288-1303 (1990)). Other exemplary fucosyltransferases include α1,2 fucosyltransferase (E.C. No. 2.4.1.69). Enzymatic fucosylation can be carried out by the methods described in Mollicone, et al., *Eur. J. Biochem.* 191:169-176 (1990) or U.S. Pat. No. 5,374,655.

In another group of embodiments, a functional domain of the recombinant glycosyltransferase proteins of the present inventions is obtained from known galactosyltransferases. Exemplary galactosyltransferases include β-1,4 galactosyltransferase I, α1,3-galactosyltransferases (E.C. No. 2.4.1.151, see, e.g., Dabkowski et al., *Transplant Proc.* 25:2921 (1993) and Yamamoto et al. *Nature* 345:229-233 (1990), bovine (GenBank j04989, Joziasse et al. (1989) *J. Biol. Chem.* 264:14290-14297), murine (GenBank m26925; Larsen et al. (1989) *Proc. Nat'l. Acad. Sci. USA* 86:8227-8231), porcine (GenBank L36152; Strahan et al (1995) *Immunogenetics* 41:101-105)). Another suitable α1,3-galactosyltransferase is that which is involved in synthesis of the blood group B antigen (EC 2.4.1.37, Yamamoto et al. (1990) *J. Biol. Chem.* 265:1146-1151 (human)). Also suitable for use in the fusion proteins of the invention are α1,4-galactosyltransferases, which include, for example, EC 2.4.1.90 (LacNAc synthetase) and EC 2.4.1.22 (lactose synthetase) (bovine (D'Agostaro et al (1989) Eur. J. Biochem. 183:211-217), human (Masri et al. (1988) *Biochem. Biophys. Res. Commun.* 157:657-663), murine (Nakazawa et al (1988) *J. Biochem.* 104:165-168), as well as E.C. 2.4.1.38 and the ceramide galactosyltransferase (EC 2.4.1.45, Stahl et al. (1994) *J. Neurosci. Res.* 38:234-242). Other suitable galactosyltransferases include, for example, α1,2-galactosyltransferases (from e.g., *Schizosaccharomyces pombe*, Chapell et al (1994) *Mol. Biol. Cell* 5:519-528).

Other glycosyltransferases that are useful in the recombinant fusion proteins of the present invention have been described in detail, as for the sialyltransferases, galactosyltransferases, and fucosyltransferases. In particular, the glycosyltransferase can also be, for instance, a glucosyltransferase, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, β(1,3)-N-acetylgalactosaminyltransferase, β(1,4)-N-acetylgalactosaminyltransferases (U.S. Pat. No. 5,691,180, Nagata et al. *J. Biol. Chem.* 267:12082-12089 (1992), and Smith et al. *J. Biol. Chem.* 269:15162 (1994)) and protein N-acetylgalactosaminyltransferase (Homa et al. *J. Biol. Chem.* 268:12609 (1993)). Suitable N-acetylglucosaminyltransferases include GnTI (2.4.1.101, Hull et al., *BBRC* 176: 608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Also of interest are enzymes involved in proteoglycan synthesis, such as, for example, N-acetylgalactosaminyltransferase I (EC 2.4.1.174), and enzymes involved in chondroitin sulfate synthesis, such as N-acetylgalactosaminyltransferase II (EC 2.4.1.175). Suitable mannosyltransferases include α(1,2) mannosyltransferase, α(1,3) mannosyltransferase, β(1,4) mannosyltransferase, Dol-P-Man synthase, OCh1, and Pmt1. Xylosyltransferases include, for example, protein xylosyltransferase (EC 2.4.2.26).

In some embodiments, eukaryotic N-acetylgalactosaminyltransferases are expressed in bacteria and refolded using the methods of this disclosure. A number of GalNAcT enzymes have been isolated and characterized, e.g., GalNAcT1, accession number X85018; GalNAcT2, accession number X85019 (both described in White et al., *J. Biol.*

Chem. 270:24156-24165 (1995)); and GalNAcT3, accession number X92689 (described in Bennett et al., J. Biol. Chem. 271:17006-17012 (1996)).

IV. Nucleic Acids

Nucleic acids that encode glycosyltransferases, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), or the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

A DNA that encodes a glycosyltransferase, or a subsequences thereof, can be prepared by any suitable method described above, including, for example, cloning and restriction of appropriate sequences with restriction enzymes. In one preferred embodiment, nucleic acids encoding glycosyltransferases are isolated by routine cloning methods. A nucleotide sequence of a glycosyltransferase as provided in, for example, GenBank or other sequence database (see above) can be used to provide probes that specifically hybridize to a glycosyltransferase gene in a genomic DNA sample, or to an mRNA, encoding a glucosyltransferase, in a total RNA sample (e.g., in a Southern or Northern blot). Once the target nucleic acid encoding a glycosyltransferase is identified, it can be isolated according to standard methods known to those of skill in the art (see, e.g., Sambrook et al. (1989) *Molecular Cloning: A Laboratory Manual,* 2nd Ed., Vols. 1-3, Cold Spring Harbor Laboratory; Berger and Kimmel (1987) *Methods in Enzymology, Vol.* 152: *Guide to Molecular Cloning Techniques*, San Diego: Academic Press, Inc.; or Ausubel et al. (1987) *Current Protocols in Molecular Biology*, Greene Publishing and Wiley-Interscience, New York). Further, the isolated nucleic acids can be cleaved with restriction enzymes to create nucleic acids encoding the full-length glycosyltransferse, or subsequences thereof, e.g., containing subsequences encoding at least a subsequence of a stem region or catalytic domain of a glycosyltransferase. These restriction enzyme fragments, encoding a glycosyltransferase or subsequences thereof, may then be ligated, for example, to produce a nucleic acid encoding a recombinant glycosyltransferase fusion protein.

A nucleic acid encoding a glycosyltransferase, or a subsequence thereof, can be characterized by assaying for the expressed product. Assays based on the detection of the physical, chemical, or immunological properties of the expressed protein can be used. For example, one can identify a cloned glycosyltransferase, including a glycosyltransferase fusion protein, by the ability of a protein encoded by the nucleic acid to catalyze the transfer of a saccharide from a donor substrate to an acceptor substrate. In a preferred method, capillary electrophoresis is employed to detect the reaction products. This highly sensitive assay involves using either saccharide or disaccharide aminophenyl derivatives which are labeled with fluorescein as described in Wakarchuk et al. (1996) *J. Biol. Chem.* 271 (45): 28271-276. For example, to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Id.).

Also, a nucleic acid encoding a glycosyltransferase, or a subsequence thereof, can be chemically synthesized. Suitable methods include the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill recognizes that while chemical synthesis of DNA is often limited to sequences of about 100 bases, longer sequences may be obtained by the ligation of shorter sequences.

Nucleic acids encoding glycosyltransferases, or subsequences thereof, can be cloned using DNA amplification methods such as polymerase chain reaction (PCR). Thus, for example, the nucleic acid sequence or subsequence is PCR amplified, using a sense primer containing one restriction enzyme site (e.g., NdeI) and an antisense primer containing another restriction enzyme site (e.g., HindIII). This will produce a nucleic acid encoding the desired glycosyltransferase or subsequence and having terminal restriction enzyme sites. This nucleic acid can then be easily ligated into a vector containing a nucleic acid encoding the second molecule and having the appropriate corresponding restriction enzyme sites. Suitable PCR primers can be determined by one of skill in the art using the sequence information provided in GenBank or other sources. Appropriate restriction enzyme sites can also be added to the nucleic acid encoding the glycosyltransferase protein or protein subsequence by site-directed mutagenesis. The plasmid containing the glycosyltransferase-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683, 202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Other physical properties of a cloned glycosyltransferase protein, including glycosyltransferase fusion protein, expressed from a particular nucleic acid, can be compared to properties of known glycosyltransferases to provide another method of identifying suitable sequences or domains of the glycosyltransferase that are determinants of acceptor substrate specificity and/or catalytic activity. Alternatively, a putative glycosyltransferase gene or recombinant glycosyltransferase gene can be mutated, and its role as glycosyltransferase, its ability to be refolded, or the role of particular sequences or domains established by detecting a variation in the structure of a carbohydrate normally produced by the unmutated, naturally-occurring, or control glycosyltransferase.

Functional domains of cloned glycosyltransferases can be identified by using standard methods for mutating or modifying the glycosyltransferases and testing the modified or mutated proteins for activities such as acceptor substrate activity and/or catalytic activity, as described herein. The functional domains of the various glycosyltransferases can be used to construct nucleic acids encoding recombinant glycosyltransferase fusion proteins comprising the functional domains of one or more glycosyltransferases. These fusion proteins can then be tested for the desired acceptor substrate or catalytic activity.

In an exemplary approach to cloning recombinant glycosyltransferase fusion proteins, the known nucleic acid or amino acid sequences of cloned glycosyltransferases are aligned and compared to determine the amount of sequence identity between various glycosyltransferases. This information can be used to identify and select protein domains that confer or modulate glycosyltransferase activities, e.g., acceptor substrate activity and/or catalytic activity based on the amount of sequence identity between the glycosyltransferases of interest. For example, domains having sequence identity between the glycosyltransferases of interest, and that are associated with a known activity, can be used to construct recombinant glycosyltransferase fusion proteins containing that domain, and having the activity associated with that domain (e.g., acceptor substrate specificity and/or catalytic activity).

V. Expression of Recombinant Glycosyltransferases

Recombinant eukaryotic glycosyltransferases can be expressed in a variety of host cells, including *E. coli*, other bacterial hosts, yeast, and various higher eukaryotic cells such as the COS, CHO and HeLa cells lines and myeloma cell lines. The host cells can be mammalian cells, plant cells, or microorganisms, such as, for example, yeast cells, bacterial cells, or filamentous fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. The cells can be of any of several genera, including *Saccharomyces* (e.g., *S. cerevisiae*), *Candida* (e.g., *C. utilis, C. parapsilosis, C. krusei, C. versatilis, C. lipolytica, C. zeylanoides, C. guilliermondii, C. albicans,* and *C. humicola*), *Pichia* (e.g., *P. farinosa* and *P. ohmeri*), *Torulopsis* (e.g., *T. candida, T. sphaerica, T. xylinus, T. famata,* and *T. versatilis*), *Debaryomyces* (e.g., *D. subglobosus, D. cantarellii, D. globosus, D. hansenii,* and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia, Enterobacter, Azotobacter, Erwinia, Klebsielia.*

Typically, the polynucleotide that encodes the fusion protein is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of recombinant eukaryotic glycosyltransferases in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

For expression of the recombinant eukaryotic glycosyltransferases in yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (EMBO J. (1982) 6:675-680), and MFα (Herskowitz and Oshima (1982) in *The Molecular Biology of the Yeast Sacczaromyces* (eds. Strathern, Jones, and Broach) Cold Spring Harbor Lab., Cold Spring Harbor, N.Y., pp. 181-209). Another suitable promoter for use in yeast is the ADH2/GAPDH hybrid promoter as described in Cousens et al., *Gene* 61:265-275 (1987). For filamentous fingi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Suitable constitutive promoters for use in plants include, for example, the cauliflower mosaic virus (CaMV) 35S transcription initiation region and region VI promoters, the 1'- or 2'-promoter derived from T-DNA of *Agrobacterium tumefaciens*, and other promoters active in plant cells that are known to those of skill in the art. Other suitable promoters include the full-length transcript promoter from Figwort mosaic virus, actin promoters, histone promoters, tubulin promoters, or the mannopine synthase promoter (MAS). Other constitutive plant promoters include various ubiquitin or polyubiquitin promoters derived from, inter alia, *Arabidopsis* (Sun and Callis, *Plant J.*, 11 (5): 1017-1027 (1997)), the mas, Mac or DoubleMac promoters (described in U.S. Pat. No. 5,106,739 and by Comai et al., *Plant Mol. Biol.* 15:373-381 (1990)) and other transcription initiation regions from various plant genes known to those of skill in the art. Useful promoters for plants also include those obtained from Ti- or Ri-plasmids, from plant cells, plant viruses or other hosts where the promoters are found to be functional in plants. Bacterial promoters that function in plants, and thus are suitable for use in the methods of the invention include the octopine synthetase promoter, the nopaline synthase promoter, and the manopine synthetase promoter. Suitable endogenous plant promoters include the ribulose-1,6-biphosphate (RUBP) carboxylase small subunit (ssu) promoter, the ($\alpha$-conglycinin promoter, the phaseolin promoter, the ADH promoter, and heat-shock promoters.

Either constitutive or regulated promoters can be used in the present invention. Regulated promoters can be advantageous because the host cells can be grown to high densities before expression of the fusion proteins is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l Acad. Sci. USA* 80: 21), and the bacteriophage T7 promoter (Studier et al. (1986) *J. Mol. Biol.*; Tabor et al. (1985) *Proc. Nat'l Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO 98/20111, provides a level of expression that is greater than that provided by either promoter alone.

Inducible promoters for use in plants are known to those of skill in the art (see, e.g., references cited in Kuhlemeier et al (1987) *Ann. Rev. Plant Physiol.* 38:221), and include those of the 1,5-ribulose bisphosphate carboxylase small subunit genes of *Arabidopsis thaliana* (the "ssu" promoter), which are light-inducible and active only in photosynthetic tissue.

Inducible promoters for other organisms are also well known to those of skill in the art. These include, for example, the arabinose promoter, the lacZ promoter, the metallothionein promoter, and the heat shock promoter, as well as many others.

A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. N0. WO 98/20111.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA $\alpha$-amylase promoter, *Aspergillus niger* glucoamylase promoter, and *Aspergillus oryzae* glucoamylase promoter may be used as regulatory sequences.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra. A preferred selectable marker for use in bacterial cells is a kanamycin resistance marker (Vieira and Messing, *Gene* 19: 259 (1982)). Use of kanamycin selection is advantageous over, for example, ampicillin selection because ampicillin is quickly degraded by $\beta$-lactamase in culture medium, thus removing selective pressure and allowing the culture to become overgrown with cells that do not contain the vector.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The recombinant eukaryotic glycosyltransferases of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant eukaryotic glycosyltransferase may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

VI. Proteins and Protein Purification

The recombinant eukaryotic glycosyltransferase proteins can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, *Methods in Enzymology Vol. 182: Guide to Protein Purification.*, Academic Press, Inc. N.Y. (1990)). In preferred embodiments, purification of the recombinant eukaryotic glycosyltransferase proteins occurs after refolding of the protein. Substantially pure compositions of at least about 70 to 90%, homogeneity are preferred; more preferably at least 91%, 92%, 93%, 94%, 95%, 96%, or 97%; and 98 to 99% or more homogeneity are most preferred. The purified proteins may also be used, e.g., as immunogens for antibody production.

To facilitate purification of the recombinant eukaryotic glycosyltransferase proteins of the invention, the nucleic acids that encode the recombinant eukaryotic glycosyltransferase proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Purification tags also include maltose binding domains and starch binding domains. Purification of maltose binding domain proteins is known to those of skill in the art. Starch binding domains are described in WO 99/15636, herein incorporated by reference. Affinity purification of a fusion protein comprising a starch binding domain using a betacylodextrin (BCD)-derivatized resin is described in U.S. Ser. No. 60/468, 374, filed May 5, 2003, herein incorporated by reference in its entirety.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the glycosyltransferase catalytic or functional domains and/or accessory enzyme catalytic domains without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

VII. Uses of Refolded Glycosyltransferases

The invention provides recombinant eukaryotic glycosyltransferase proteins and methods of using the recombinant eukaryotic glycosyltransferase proteins to enzymatically synthesize glycoproteins, glycolipids, and oligosaccharide moieties, and to glycoPEGylate glycoproteins. The glycosyltransferase reactions of the invention take place in a reaction medium comprising at least one glycosyltransferase, acceptor substrate, and donor substrate, and typically a soluble divalent metal cation. In some embodiments, accessory enzymes and substrates for the accessory enzyme catalytic moiety are also present, so that the accessory enzymes can synthesize the donor substrate for the glycosyltransferase. The recombinant eukaryotic glycosyltransferase proteins and methods of the present invention rely on the use the recombinant eukaryotic glycosyltransferase proteins to catalyze the addition of a saccharide to an acceptor substrate.

A number of methods of using glycosyltransferases to synthesize glycoproteins and glycolipids having desired oligosaccharide moieties are known. Exemplary methods are described, for instance, WO 96/32491, Ito et al. (1993) *Pure Appl. Chem.* 65: 753, and U.S. Pat. Nos. 5,352,670, 5,374, 541, and 5,545,553.

The recombinant eukaryotic glycosyltransferase proteins prepared as described herein can be used in combination with additional glycosyltransferases, that may or may not have required refolding for activity. For example, one can use a combination of refolded recombinant eukaryotic glycosyltransferase protein and a bacterial glycosyltranferase, which may or may not have been refolded after isolation from a host cell. Similarly, the recombinant eukaryotic glycosyltransferase can be used with recombinant accessory enzymes, which may or may not be part of the fusion protein.

The products produced by the above processes can be used without purification. In some embodiments, oligosaccharides are produced. Standard, well known techniques, for example, thin or thick layer chromatography, ion exchange chromatography, or membrane filtration can be used for recovery of glycosylated saccharides. Also, for example, membrane filtration, utilizing a nanofiltration or reverse osmotic membrane as described in commonly assigned AU Patent No. 735695 may be used. As a further example, membrane filtration wherein the membranes have a molecular weight cutoff of about 1000 to about 10,000 can be used to remove proteins. As another example, nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, for example, the oligosaccharides produced by the compositions and methods of the present invention can be retained in the membrane and contaminating salts will pass through.

VIII. Donor Substrate/Acceptor Substrates

Suitable donor substrates used by the recombinant glycosyltransferase fusion proteins and methods of the invention include, but are not limited to, UDP-Glc, UDP-GlcNAc, UDP-Gal, UDP-GalNAc, GDP-Man, GDP-Fuc, UDP-GlcUA, and CMP-sialic acid. Guo et al., *Applied Biochem. and Biotech.* 68: 1-20 (1997)

Suitable acceptor substrates used by the recombinant glycosyltransferase fusion proteins and methods of the invention include, but are not limited to, polysaccharides, oligosaccharides, proteins, lipids, gangliosides and other biological structures (e.g., whole cells) that can be modified by the methods of the invention. Exemplary structures, which can be modified by the methods of the invention include any a of a number glycolipids, glycoproteins and carbohydrate structures on cells known to those skilled in the art as set forth is Table 1.

TABLE 1

| Hormones and Growth Factors |
|---|
| G-CSF |
| GM-CSF |
| TPO |
| EPO |
| EPO variants |
| α-TNF |
| Leptin |
| Enzymes and Inhibitors |
| t-PA |
| t-PA variants |
| Urokinase |
| Factors VII, VIII, IX, X |
| DNase |
| Glucocerebrosidase |
| Hirudin |
| α1 antitrypsin |
| Antithrombin III |
| Cytokines and Chimeric Cytokines |
| Interleukin-1 (IL-1), 1B, 2,3,4 |
| Interferon-α (IFN-α) |
| IFN-α-2b |
| IFN-β |
| IFN-γ |
| Chimeric diptheria toxin- |
| IL-2 |
| Receptors and Chimeric Receptors |
| CD4 |
| Tumor Necrosis Factor (TNF) receptor |
| Alpha-CD20 |
| MAb-CD20 |

TABLE 1-continued

MAb-alpha-CD3
MAb-TNF receptor
MAb-CD4
PSGL-1
MAb-PSGL-1
Complement
GlyCAM or its chimera
N-CAM or its chimera
LFA-3
CTLA-IV
Monoclonal Antibodies (Immunoglobulins)

MAb-anti-RSV
MAb-anti-IL-2 receptor
MAb-anti-CEA
MAb-anti-platelet IIb/IIIa receptor
MAb-anti-EGF
MAb-anti-Her-2 receptor
Cells Red blood cells
White blood cells (e.g., T cells, B cells, dendritic cells, macrophages, NK cells, neutrophils, monocytes and the like
Stem cells Examples of suitable acceptor substrates used in fucosyltransferase-catalyzed reactions, and examples of suitable acceptor substrates used in sialyltransferase-catalyzed reactions are described in Guo et al., *Applied Biochem. and Biotech.* 68: 1-20 (1997), but are not limited thereto.

IX. Glycosyltransferase Reactions

The recombinant eukaryotic glycosyltransferase proteins, acceptor substrates, donor substrates and other reaction mixture ingredients are combined by admixture in an aqueous reaction medium. The medium generally has a pH value of about 5 to about 8.5. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For fucosyltransferases, the pH range is preferably maintained from about 6.0 to 8.0. For sialyltransferases, the range is preferably from about 5.5 to about 7.5.

Enzyme amounts or concentrations are expressed in activity units, which is a measure of the initial rate of catalysis. One activity unit catalyzes the formation of 1 µmol of product per minute at a given temperature (typically 37° C.) and pH value (typically 7.5). Thus, 10 units of an enzyme is a catalytic amount of that enzyme where 10 µmol of substrate are converted to 10 µmol of product in one minute at a temperature of 37° C. and a pH value of 7.5.

The reaction mixture may include divalent metal cations ($Mg^{2+}$, $Mn^{2+}$). The reaction medium may also comprise solubilizing detergents (e.g., Triton or SDS) and organic solvents such as methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about 0° C. to about 45° C., and more preferably at about 20° C. to about 37° C.

The reaction mixture so formed is maintained for a period of time sufficient to obtain the desired high yield of desired oligosaccharide determinants present on oligosaccharide groups attached to the glycoprotein to be glycosylated. For large-scale preparations, the reaction will often be allowed to proceed for between about 0.5-240 hours, and more typically between about 1-18 hours.

One or more of the glycosyltransferase reactions can be carried out as part of a glycosyltransferase cycle. Preferred conditions and descriptions of glycosyltransferase cycles have been described. A number of glycosyltransferase cycles (for example, sialyltransferase cycles, galactosyltransferase cycles, and fucosyltransferase cycles) are described in U.S. Pat. No. 5,374,541 and WO 9425615 A. Other glycosyltransferase cycles are described in Ichikawa et al. *J. Am. Chem. Soc.* 114:9283 (1992), Wong et al. *J. Org. Chem.* 57: 4343 (1992), DeLuca, et al., *J. Am. Chem. Soc.* 117:5869-5870 (1995), and Ichikawa et al. In *Carbohydrates and Carbohydrate Polymers*. Yaltami, ed. (ATL Press, 1993).

Other glycosyltransferases can be substituted into similar transferase cycles as have been described in detail for the fucosyltransferases and sialyltransferases. In particular, the glycosyltransferase can also be, for instance, glucosyltransferases, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, α(1,3) N-acetylgalactosaininyltransferase, β(1,4) N-acetylgalactosaminyltransferases (Nagata et al. *J. Biol. Chem.* 267:12082-12089 (1992) and Smith et al. *J. Biol. Chem.* 269:15162 (1994)) and polypeptide N-acetylgalactosaminyltransferase (Homa et al. *J. Biol. Chem.* 268:12609 (1993)). Suitable N-acetylglucosaminyltransferases include GnTI (2.4.1.101, Hull et al., *BBRC* 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Suitable mannosyltransferases include α(1,2) mannosyltransferase, α(1,3) mannosyltransferase, β(1,4) mannosyltransferase, Dol-P-Man synthase, OCh1, and Pmt1.

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed. The considerations discussed below, while in the context of a sialyltransferase, are generally applicable to other glycosyltransferase cycles.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

X. Multienzyme Oligosaccharide Synthesis

As discussed above, in some embodiments, two or more enzymes may be used to form a desired oligosaccharide determinant on a glycoprotein or glycolipid. For example, a particular oligosaccharide determinant might require addition of a galactose, a sialic acid, and a fucose in order to exhibit a desired activity. Accordingly, the invention provides methods in which two or more enzymes, e.g., glycosyltransferases, trans-sialidases, or sulfotransferases, are used to obtain high-yield synthesis of a desired oligosaccharide determinant.

In a particularly preferred embodiment, one of the enzymes used is a sulfotransferase which sulfonates the saccharide or the peptide. Even more preferred is the use of a sulfotransferase to prepare a ligand for a selectin (Kimura et al., *Proc Natl Acad Sci USA* 96(8):4530-5 (1999)).

In some cases, a glycoprotein- or glycolipid linked oligosaccharide will include an acceptor substrate for the particular glycosyltransferase of interest upon in vivo biosynthesis of the glycoprotein or glycolipid. Such glycoproteins or glycolipids can be glycosylated using the recombinant glycosyltransferase fusion proteins and methods of the invention without prior modification of the glycosylation pattern of the glycoprotein or glycolipid, respectively. In other cases, however, a glycoprotein or glycolipid of interest will lack a suitable acceptor substrate. In such cases, the methods of the invention can be used to alter the glycosylation pattern of the glycoprotein or glycolipid so that the glycoprotein- or glycolipid-linked oligosaccharides then include an acceptor substrate for the glycosyltransferase-catalyzed attachment of a preselected saccharide unit of interest to form a desired oligosaccharide moiety.

Glycoprotein- or glycolipid linked oligosaccharides optionally can be first "trimmed," either in whole or in part, to expose either an acceptor substrate for the glycosyltransferase or a moiety to which one or more appropriate residues can be added to obtain a suitable acceptor substrate. Enzymes such as glycosyltransferases and endoglycosidases are useful for the attaching and trimming reactions. For example, a glycoprotein that displays "high mannose"-type oligosaccharides can be subjected to trimming by a mannosidase to obtain an acceptor substrate that, upon attachment of one or more preselected saccharide units, forms the desired oligosaccharide determinant.

The methods are also useful for synthesizing a desired oligosaccharide moiety on a protein or lipid that is unglycosylated in its native form. A suitable acceptor substrate for the corresponding glycosyltransferase can be attached to such proteins or lipids prior to glycosylation using the methods of the present invention. See, e.g., U.S. Pat. No. 5,272,066 for methods of obtaining polypeptides having suitable acceptors for glycosylation.

Thus, in some embodiments, the invention provides methods for in vitro sialylation of saccharide groups present on a glycoconjugate that first involves modifying the glycoconjugate to create a suitable acceptor.

XI. Conjugation of Modified Sugars to Peptides

The modified sugars are conjugated to a glycosylated or non-glycosylated peptide or protein using an appropriate enzyme to mediate the conjugation. Preferably, the concentrations of the modified donor sugar(s), enzyme(s) and acceptor peptide(s) or protein(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), and U.S. Pat. Nos. 5,352, 670, 5,374,541, and 5,545,553.

In a some embodiments, an endoglycosidase is used in the reaction in combination with glycosyltransferases. The enzymes are used to alter a saccharide structure on the peptide at any point either before or after the addition of the modified sugar to the peptide.

In another embodiment, the method makes use of one or more exo- or endoglycosidase. The glycosidase is typically a mutant, which is engineered to form glycosyl bonds rather than rupture them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g., enzyme concentration, donor concentration, acceptor concentration, temperature, solvent volume), which are optimized for a selected system.

The present invention also provides for the industrial-scale production of modified peptides. As used herein, an industrial scale generally produces at least one gram of finished, purified conjugate.

In the discussion that follows, the invention is exemplified by the conjugation of modified sialic acid moieties to a glycosylated peptide. The exemplary modified sialic acid is labeled with PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other water-soluble polymers, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GlcNAc. The method includes incubating the peptide to be modified with a reaction mixture that contains a suitable amount of a galactosyltransferase (e.g., galβ1,3 or galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

Methods for conjugation of modified sugars to peptides or proteins are found e.g., in U.S. Ser. No. 60/328,523 filed Oct. 10, 2001; U.S. Ser. No. 60/387,292, filed Jun. 7, 2002; U.S. Ser. No. 60/391,777 filed Jun. 25, 2002; U.S. Ser. No. 60/404, 249 filed Aug. 16, 2002; and PCT/US02/32263; each of which are herein incorporated by reference for all purposes.

EXAMPLES

Example 1

Refolding Rat Liver ST3 GalIII Expressed in Bacteria

Refolding Rat Liver GST-ST3GalIII Fusion Protein

Rat liver N-acetyllactosaminide α-2,3-sialyltransferase (ST3GalIII) was cloned into pGEX-KT-Ext vector and expressed as GST-ST3-Gal III inclusion bodies in *E. coli* BL21 cells. Inclusion bodies were refolded using a GSH/GSSG redox system. The refolded enzyme, GST-ST3-GalIII, was active and transferred sialic acid to an LNnT sugar substrate and to asialylated glycoproteins, for example, transferrin and Factor IX.

Cloning ST3GalIII into pGEX-XT-KT Vector

Rat liver ST3-GalIII gene was cloned into BamH1 and EcoR1 sites of the pGEX-KT-Ext vector after PCR Amplification using the following primers:

```
Sense
Sial 5'Tm      5'-TTTGGATCCAAGCTACACTTACTCCAATGG

Antisense:
Sial 3' Whole  5'-TTTGAATTCTCAGATACCACTGCTTAAGTC
```

Expression of GST-ST3GalIII in *E. coli* BL21 Cells pGEX-ST3GalIII, an expression vector comprising the ST3GalIII GST fusion, was transformed into chemically competent *E. coli* BL21 cells. Single colonies were picked, inoculated into five ml LB media with 100 µg/ml carbenicillin, and grown overnight at 37° C. with shaking. The next day, one ml of overnight culture was transferred into one liter of LB media with 100 µg/ml carbenicillin. Bacteria were grown until to an $OD_{620}$ of 0.7, then 150 µM IPTG (final) was added to the medium. Bacteria were grown at 37° C. for one to two hours more, then shifted to room temperature and grown overnight with shaking. Cells were harvested by centrifugation; bacterial pellets were resuspended in PBS buffer and lysed using a French Press. Soluble and insoluble fractions were separated by centrifugation for thirty minutes at 10,000 RPM in a Sorvall, SS 34 rotor at 4° C.

Purification of the Inclusion Bodies

Fifty ml of Novagen's Wash buffer (20 mM Tris.HCl, pH 7.5, 10 mM EDTA, 1% Triton X-100) was added to the insoluble fraction, i.e., the inclusion bodies (IB's). The insoluble fraction was vortexed to resuspend the pellet. The suspended IB's were centrifuged and washed at least twice by resuspending in Wash Buffer as above. Clean precipitates (IB's) were recovered and were stored at −20° C. until use.

Refolding Inclusion Bodies

The IB's were weighed (144 mg) and dissolved in Genotech IBS buffer (1.44 ml). The resuspended IB's were incubated at 4° C. for one hour in an Eppendorf centrifuge tube. Insoluble material was removed by centrifugation at maximum speed in an Eppendorf centrifuge. Solubilized IB's were diluted to 4 ml final volume. Refolding of GST-ST3GalIII was tested in refolding buffer solutions containing cyclodextrin, polyethylene glycol (PEG), ND SB-201, or a GSH/GSSG redox system. One ml of solubilized IB's were diluted rapidly by pipetting into the refolding solution, vigorously mixed for 30-40 seconds, and then gently stirred for two hours at 4° C. Three ml aliquots of the refolded GST-ST3GalIII solutions were dialyzed against cold PBS buffer or a buffer containing 50 mM Tris.HCL, pH 7.0; 100 mM NaCl; and 1% glycerol using Pierce Slide-A-lyzers (MWCO:3.5 kDa). After dialysis, the GST-ST3GalIII solutions were concentrated 3, 6 and 12 fold using Vivaspin 5 K (VivaScience) concentrators in Jouan centrifuge at 4,000 rpm at 4° C.

After refolding and dialysis, the refolded GST-ST3GalIII proteins were analyzed by SDS-polyacrylamide gel electrophoresis. The GST-ST3GalIII fusion, with a molecular weight of about 63-64 kDa, was present under all refolding conditions. (Data not shown).

Sialylation of Oligosaccharides Using Refolded GST-ST3 Gal III

Enzymatic assays using oligosaccharide substrates were carried out using CE-LIF (Capillary Electrophoresis-Laser Induced Fluorescence). Refolded ST3 Gal III enzymes were assayed for ability to transfer of sialic acid from CMP-NAN (cytidine 5-Monophosphate-β-D-sialic acid) to LNnT-APTS (Lacto-N-Neotetraose-9-aminopyrene 1-4, 6 trisulfonic acid) to form LSTd-APTS (Lactosialic-Tetrasaccharide-d-APTS). Reactions were performed in 96 well microtiter plates in 100 μl of a buffer containing 20 mM MOPS, pH 6.5; 0.8 mM CMP-NAN; 22.1 mM LNnT; 25 μM LNnT-APTS; 2.5 mM $MnCl_2$. Reactions were started by addition of 20 μl of refolded ST3 Gal III at 30° C. for thirty minutes. Reactions were quenched with a 1 to 25 dilution with water. The diluted reaction was analyzed by CE-LIF using an N—CHO coated capillary according to manufacturer's guide. Activities were calculated as the ratio of the normalized peak areas of LNnT-APTS to LSTd-APTS. Results comparing different refolding conditions are shown in Table 2. Two additional experiments using the GSH/GSSG system are shown in Table 3.

TABLE 2

GST-ST3-Gal III activities after screening different folding systems. The proteins were assayed directly without concentration.

| Cyclodextrin | PEG | ND SB-201 | GSH/GSSG |
|---|---|---|---|
| 0 | 0 | 0 | 7.8 U/L* |

*Activities reported here are Units per L refolded enzyme.

TABLE 3

GST-ST3GalIII activities after two separate folding experiments using GSH/GSSG system.

| GSH/GSSG | Conc | Activity |
|---|---|---|
| Refolding Trial 1 | 12x | 182 U/L* |
| Refolding Trial 2 | 40x | 531 U/L* |

*Activities reported here are Units per L refolded enzyme

Sialylation of Glycoproteins Using Refolded GST-ST3 Gal III

Twenty μL of asialylated Transferrin (2 μg/μL) or asialylated Factor IX (2 μg/μL), was added to fifty μL of a buffer containing 50 mM Tris, pH 8.0; and 150 mM NaCl, with 10 μL of 100 mM $MnCl_2$; 10 μL of 200 mM CMP-NAN; and 0.05% sodium azide. The reaction mixture was incubated with 30 μL refolded GST-ST3GalIII at 30° C. overnight or longer with shaking at 250 rpm. After the reactions were stopped, the sialylated proteins were separated on pH 7-3 IEF (Isoelectric focusing gel, Invitrogen) and stained with Comassie Blue according to manufacturer's guideline. Both Transferrin and Factor IX were sialylated by GST-ST3GalIII. (Data not shown).

Refolding a Rat Liver ST3GalIII Fused to an MBP Tag.

Rat liver ST3GalIII was cloned into pMAL-c2x vector and expressed as a maltose binding protein (MBP) fusion, MBP-ST3GalIII, in inclusion bodies of *E. coli* TB1 cells. The refolded MBP-ST3GalIII was active and transferred sialic acid to LNnT, a sugar substrate, and to asialylated glycoproteins, for example asialo-transferrin.

Cloning ST3GalIII into pMAL-c2x Vector

The rat liver ST3-GalIII nucleic acid was cloned into BamH1 and XbaI sites of the pMAL-c2x vector after PCR Amplification using the following primers:

```
Sense
ST3BAMH1      5'-TAATGGATTCAAGCTACACTTACTCCAATGG

Antisense:
ST3XBA1       5'-GCGCTCTAGATCAGATACCACTGCTTAAGT
```

Nucleotides encoding amino acids 28-374, e.g., the stem region and catalytic domain of ST3GalIII, were fused to the MBP amino acid tag.

Three other truncations of ST3GalIII were constructed and fused to MBP. The three ST3Gal III (Δ73, Δ85, Δ86) inserts were isolated by PCR using the following 5' primers (ST3 BamH1 Δ73) TGTATCGGATCCCTGGCCACCAAG-TACGCTAACTT; (ST3 BamH1 Δ85) TGTATCGGATCCT-GCAAACCCGGCTACGCTTCAGCCAT; and (ST3 BamH1 Δ86) TGTATCGGATCCAAACCCGGCTACGCT-TCAGCCAT) respectively, in pairs with the common 3' primer (ST3-Xho1-GGTCTCCTCGAGTCAGATACCACT-GCTTAA). Each PCR product was digested with BamHI and Xho1, subcloned into BamHI-XhoI digested pCWin2-MBP Kanr vector, transformed into TB1 cells, and screened for the correct construct.

PCR reactions were carried out under the following conditions. One cycle at 95° C. for 1 minute. One μl vent polymerase was added. Ten of the following cycles were performed: 94° C. for 1 minute; 65° C. for 1 minute; and 72° C. for 1 minute. After a final ten minutes at 72° C., the reaction was cooled to 4° C.

All of the ST3GalIII truncations had activity after refolding. The experiments described below were performed using the MBP Δ73ST3GalIII truncation.

Expression of MBP-ST3GalIII in *E. coli* TB1 Cells

The pMAL-ST3GalIII plasmid was transformed into chemically competent *E. coli* TB1 cells. Three isolated colonies containing TB1/pMAL-ST3 GalIII construct were picked from the LB agar plates. The colonies were grown in five ml of LB media supplemented with 60 μg/ml carbenicillin at 37° C. with shaking until the liquid cultures reached an $OD_{620}$ of 0.7. Two one ml aliquots were withdrawn from each culture and used to inoculate fresh media with or without 500 μM IPTG (final). The cultures were grown at 37° C. for two hours. Bacterial cells were harvested by centrifugation. Total cell lysates were prepared heating the cell pellets in the presence of SDS and DTT. IPTG induced expression of MBP-ST3GalIII. (Data not Shown).

Expression of MBP-ST3GalIII and Purification of the Inclusion Bodies:

A one ml aliquot of TB1/pMAL-ST3GalIII overnight culture was inoculated into 0.5 liter of LB media with 50 μg/ml carbenicillin and grown to an $OD_{620}$ of 0.7. Expression of MBP-ST3GalIII was induced by addition of 0.5 mM IPTG, followed by overnight incubation at room temperature. The next day bacterial cells were harvested by centrifugation. Cell pellets were resuspended in a buffer containing 75 mM Tris HCl, pH 7.4; 100 mM NaCl; and 1% glycerol. Bacterial cells were lyzed using a French Press. Soluble and insoluble fractions were separated by centrifugation for thirty minutes, 4° C., 10,000 rpm, Sorvall, SS 34 rotor). Soluble and insoluble fractions were separated by centrifugation for thirty minutes at 10,000 RPM in a Sorvall, SS 34 rotor at 4° C.

Purification of the Inclusion Bodies and Refolding of MBP-ST3GalIII Using GSH/GSSG The MBP-ST3GalIII inclusion bodies were purified and suspended using the same methods and buffers used for the GST-ST3GalIII fusion proteins described above. The MBP-ST3GalIII were refolded using the GSH/GSSG system described above. The refolded MBP-ST3GalIII enzymes were dialyzed against cold 65 mM Tris.HCL pH 7.5, 100 mM NaCl, 1% glycerol using Pierce SnakeSkin Dialysis bag (MWCO:7 kDa). The refolded and dialyzed MBP-ST3GalIII were concentrated from 3-14 fold using Vivaspin 5 K (Viva-Science) concentrators in Jouan centrifuge at 4,000 rpm at 4° C. The refolded MBP-ST3GalIII proteins were analyzed by SDS-Polyacrylamide gel electrophoresis. An 81 kDa MBP-ST3GalIII was detected. (Data not shown).

MBP-ST3 Gal III Enzymatic Activity Assays

Refolded MBP-ST3 Gal III enzymes were assayed for ability to transfer sialic acid from CMP-NAN to LNnT-APTS to form LSTd-APTS, as described above. The refolded MBP-ST3 Gal III enzymes were active and transferred sialic acid to LNnT-APTS to form LSTd-APTS. (Data not shown).

Refolded MBP-ST3 Gal III enzymes were assayed for ability to transfer sialic acid from CMP-NAN to glycoproteins. Transfer of sialic acid to asialo-Transferrin was assayed as described above, for GST-ST3-GalIII enzymes. The refolded MBP-ST3 Gal III enzymes were active and transferred sialic acid to asialo-Transferrin. (Data not shown). Although refolded GST-ST3 Gal III and MBP-ST3 Gal III enzymes had similar activities for transfer of sialic acid to a soluble oligosaccharide acceptor molecule, refolded MBP-ST3 Gal III enzymes were more active in transfer of sialic acid to a glycoprotein acceptor molecule.

Additional Assays of Conditions for Refolding MBP-ST3GalIII

MBP-ST3GalIII was refolded using the conditions shown in FIG. 1. The buffer, redox couple and detergent (if used) were mixed before addition of solubilized IB's to start the refolding reaction. IB's were diluted 1/20. MBP-ST3GalIII refolding was also successful using with different redox couples, for example Cystamine2HCl/Cysteine at molar ratios of 1/4, 4/1, 1/10, or 5/5. (Data not shown).

ST3 Gal III Enzymatic Activity Assays

Refolded MBP-ST3 Gal III enzymes were assayed for ability to transfer sialic acid from CMP-NAN to LNnT-APTS to form LSTd-APTS, as described above. Results are shown in FIG. 1. The highest refolded MBP-ST3 Gal III activities were seen using conditions, 8, 11, 13 and 16. When refolding was scaled up to five ml, MBP-ST3 Gal III proteins refolded using conditions 8 and 16 had the highest activity. (See, e.g., Table 4).

TABLE 4

| Condition | U/L folded protein | U/g IB's |
|---|---|---|
| 8 | 70 | 37.0 |
| 6 | 50 | 40.5 |

Purification of MBP-ST3GalIII on Amylose Column

Figure 3:
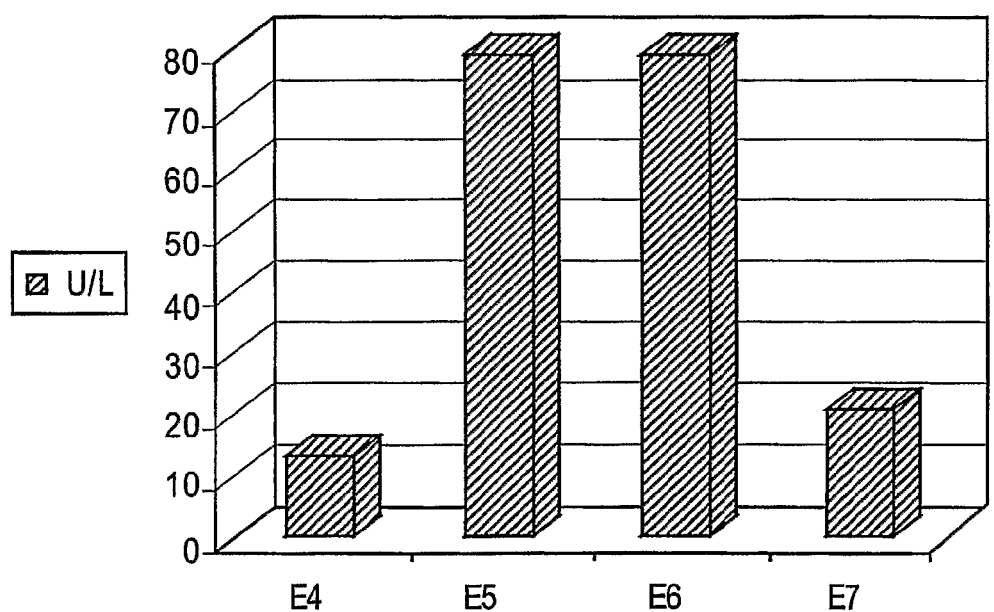
FIG. 3 provides the ST3GalIII activities of the elution fractions from the amylose column.

Refolded MBP-ST3GalIII proteins from the 5 ml refolding preperation were combined and dialyzed against 100 mM Tris HCl pH 7.4, 100 mM NaCl and 1% glycerol. The refolded MBP-ST3GalIII proteins were applied to an amylose column. Most of the refolded MBP-ST3GalIII protein was bound to the amylose column and eluted with 10 mM maltose. An elution profile is shown in FIG. 2. Enzymatic activity of the MBP-ST3GalIII fractions was determined using the LnNT assay and is shown in FIG. 3.

Figure 4:
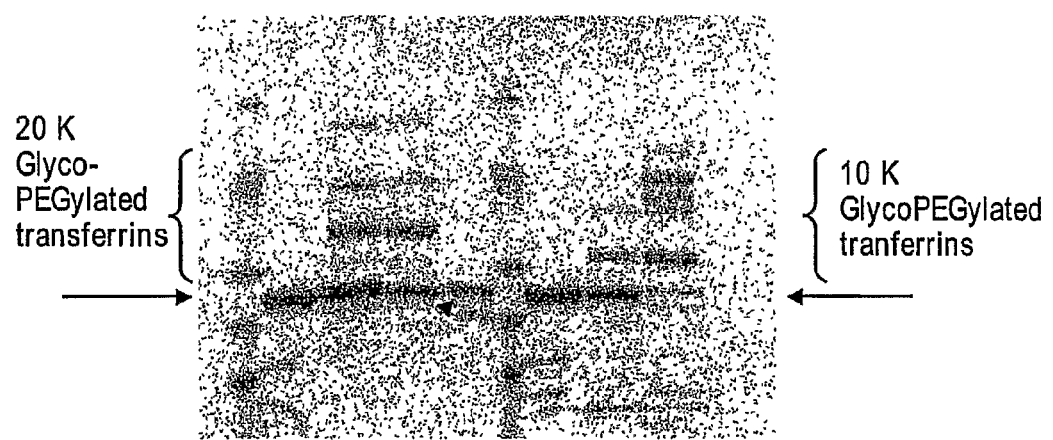
FIG. 4 provides the results of an assay of glycoPEGylation of transferrin using purified refolded MBP-ST3GalIII. Lanes are as follows: (1) MW markers [250, 148, 98, 64, 50 kD]; (2) Control asioalotransferrin with no enzyme, indicated by solid arrow; (3) transferrin-SA-PEG (20 kDa) production with Fraction #5, products indicated by arrowhead; (4) transferrin-SA-PEG (20 kDa) production with Fraction #6, products indicated by arrowhead; (5) Purified, refolded MBP-ST3GalIII Fr #6, indicated by dotted arrow; (6) MW markers; (7) same as 2; (8) transferrin-SA-PEG (10 kDa) production with Fr #4, products indicated by brackets; and (9) transferrin-SA-PEG (10 kDa) production with Fr #5, products indicated by brackets.

GlycoPEGYlation of Asialotransferrin with Refolded MBP-ST3GalIII:

Asialo-transferrin (2 mg/ml) was incubated with purified fractions of refolded 100 µl of MBP-ST3GalIII in the presence of CMP-SA-PEG (10 kDa, 1.6 mM) or CMP-SA-PEG (20 kDa, 1.06 mM) in 230 µl reaction. GlycoPEgylation reactions were carried out at 30° C. overnight or for three days. Aliquots were withdrawn from the reactions and analyzed on 4-20% SDS-polyacrylamide gel. Results are shown in FIG. 4. Purified, refolded MBP-ST3 GalIII transfers 10 or 20 K PEGylated sialic acids to asialo-transferrin.

Large Scale MBP-ST3GalIII Refolding

The following method was used to make large scale refolded MBP-ST3GalIII.

Wet IB's (470 mg) were dissolved IB solubilization Buffer (13 ml) in 15 ml culture tube. IB solubilization buffer includes the following: 4 M Guanidine HCl; 100 mM Tris HCl, pH 9; and 100 mM NaCl. IB's were incubated in IB solubilization buffer at 4° C. for about 1 hour with gentle shaking. Any insoluble material was removed by centrifugation in 1.5 mL Eppendorf tubes, at 4° C. at max speed, for 30 minutes. The solubilized IB's were transferred to clean tubes and protein concentration was determined using absorbance at 280 nm.

The following refolding solution was prepared and kept at 4° C.: 55 mM MES buffer, pH 6.5; 264 mM NaCl; 11 mM KCl; 0.055% PEG 550; 550 mM Arginine. The buffer was supplemented with 0.3 mM Lauryl maltoside (LM); 0.1 mM oxidized glutathione (GSSG); 1 mM reduced glutathione (GSH) immediately before the addition of solubilized IB's. Two ml of solubilized IB's were added into 43 ml of refolding buffer in 50 ml sterile culture tube. The tube was placed on a rocker-shaker and gently shaken for 24 hours at 4° C. The refolded protein was dialyzed in dialysis tubing (MWCO: 7 kD) against Dialysis Buffer (100 mM Tris HCl, pH 7.5; 100 mM NaCl; and 5% glycerol) twice (in 10-20 volume excess buffer).

The large scale dialyzed, refolded MBP-Gal III was analyzed for ST3GalIII activity, and exhibited about 53.6 U/g IB.

Example 2

Site Directed Mutagenesis of Human GnTI to Enhance Refolding

A truncated human N-acetylglucosaminyltransferase I (103 amino terminal amino acids deleted) was expressed in *E. coli* as a maltose binding fusion protein (GnTI/MBP). The fusion protein was insoluble and was expressed in inclusion bodies. After solubilization and refolding, the GnTI/MBP fusion protein had low activity. The crystal structure of a truncated form of rabbit GnTI (105 amino terminal amino acids deleted) shows an unpaired cysteine residue (CYS123) near the active site. (See, e.g., Unligil et al., *EMBO J.* 19:5269-5280 (2000)). The corresponding unpaired cysteine in the human GnTI was identified as CYS121 and was replaced with a series of amino acids that are similar in size and chemical characteristics. The amino acids used include serine (Ser), threonine (Thr), alanine (Ala) and aspartic acid (Asp). In addition, a double mutant, ARG120ALA, CYS121HIS, was also made. The mutant GnTI/MBP fusion proteins were expressed in *E. coli*, refolded and assayed for GnTI activity towards glycoproteins.

Mutagenesis was done using a Quick Change Site-Directed Mutagenesis Kit from Stratagene. Additional restriction sites were introduced with some of the GnT1 mutations. For example an ApaI site (underlined, GGGCCCAC) was introduced into the GnT1 ARG120ALA, CYS121HIS mutant, i.e., CGC CTG→GCC CAC (changes in bold). The following mutagenic oligonucleotides were used to make the double mutant: GnT1 R120A, C121H+, 5'CCGCAGCACT-GTTCGGGCCCACCTGGACAAGCTGCTG 3'; and GnT1 R120A, C121H-5'CAGCAGCTTGTCCAGGTGGGC-CCGAACAGTGCTGCGG 3' (changes shown in bold). An AscI site (underlined, GGCGCGCC) was introduced into the GnT1 CYS121ALA mutant, i.e., CTG→GCC (changes in bold). The following mutagenic oligonucleotides were used to make the GnT1 CYS121ALA mutant: GnT1C123A+ 5'AGCACTGTTCGGCGCGCCCTGGACAAGCTGCTG 3; and GnT1C123A-5'CAGCAGCTTGTC-CAGGGCGCGCCAACAGTGCT 3'

The activity of the mutant proteins expressed in *E. coli* was compared to the activity of wild type GnT1 expressed in baculovirus. A CYS121SER GNTI mutant was active in a TLC based assay. In contrast, a CYS121THR mutant had no detectable activity and a CYS121ASP mutant had low activity. A CYS121ALA mutant was very active, and a double mutant, ARG120ALA, CYS121HIS, based on the amino acid sequence of the *C. elegans* GnT1 protein (Gly14), also exhibited activity, including transfer of GlcNAc to glycoproteins. Amino acid and encoding nucleic acid sequences of the GnT1 mutants are provided in FIGS. 7-11.

A second GnT1 truncation was made and fused to MBP: MBP-GnT1(D35). FIG. 35 provides a schematic of the MBP-GnT1 fusion proteins, and depicts the truncations, e.g., Δ103 or Δ35, and the Cys121 Ser mutation (top). The bottom of the figure provides the full length human GnT1 protein. Mutations of Cys121 were also made in the MBP-GnT1(D35) protein.

Both fusion proteins were expressed in *E. coli* and both had activity for remodeling of the RNAse B glycoprotein. FIG. 36 provides an SDS-PAGE gel showing in the right panel the refolded MBP-GnT1 fusion proteins: MBP-GnT1(D35) C121A, MBP-GnT1(D103) R120A+C121H, and MBP-GnT1(D103) C121A. The left panel shows the activities for remodeling the RNAse B glycoprotein of two different batches (A1 and A2) of refolded MBP-GnT1(D35) C121A at different time points. The MBP-GnT1 (D103) C121A also remodeled the RNAse B glycoprotein. Data not shown.

Example 3

MPB Fusions to GalT1

Figure 31:
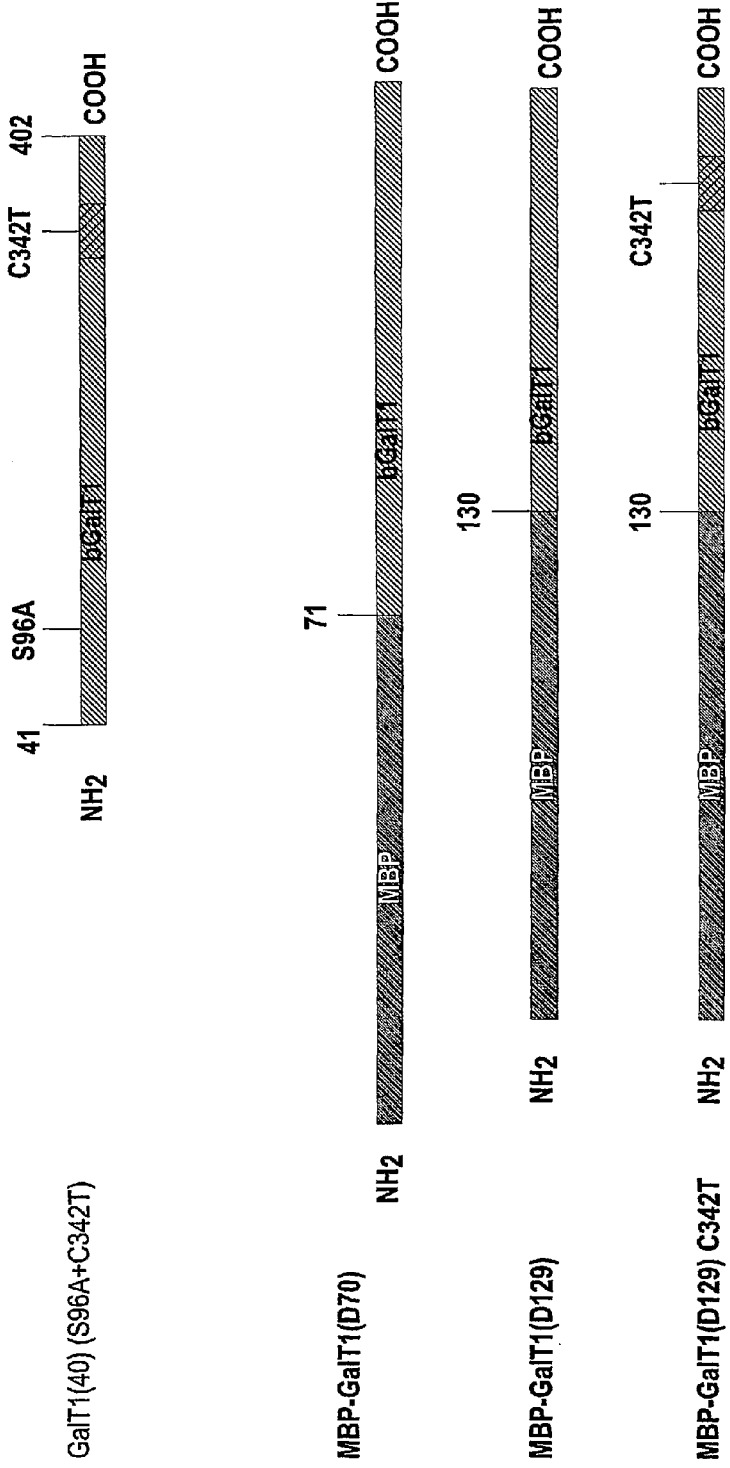
FIG. 31 depicts GalT1 mutants schematically, as well as a control protein GalT1(40) (S96A+C342T).

The following fusions between truncated bovine GalT1 and MBP were constructed: MBP-GalT1 (D129) wt, (D70) wt or (D129 C342T). (For the full length bovine sequence, see, e.g., D'Agostaro et al., *Eur. J. Biochem.* 183:211-217 (1989) and accession number CAA32695.) Each construct had activity after refolding. The amino acid sequence of the full length bovine GalT1 protein is provided in FIG. 30. The mutants are depicted schematically in FIG. 31 with a control protein GalT1 (40) (S96A+C342T). See, e.g., Ramakrishnan et al., *J. Biol. Chem.* 276:37666-37671 (2001).

MBP-GalT1 (D70) was expressed in *E. coli* strain JM109. After overnight induction with IPTG, inclusion bodies were isolated from the insoluble pellet after cells were lysed using a French Press. IB's were washed twice and then solubilized in 4 M GndHCl, 100 mM NaCl, 0.1 M Tris HCl pH 9.0. Refolding was done at pH 6.5 with GSSH/GSH (10/1) by dilution into refolding buffer (1/20, 0.1-0.2 mg/ml protein), followed by overnight incubation at 4° C., without shaking. Refolded proteins were dialyzed against 50 mM Tris HCl pH 8.0 twice (MWCO: 7 kD). The dialyzed MBP-GalT1 (D70) proteins were loaded onto an amylose column; washed; and then eluted with 10 mM Maltose.

GalT1 activity was assayed using oligosaccharides as an acceptor. The enzymatic assays were carried out using HPLC/PAD (High Performance Liquid Chromatography with Pulsed Amperometric Detection). The conversion of LNT2 (Lacto-N-Triose-2) into LNnT (Lacto-N-Neotetraose) using UDP-Gal (Uridine 5'-Diphosphogalactose) by GalTI enzyme was performed as follows: The reaction was carried out in 100 μl of 50 mM Hepes, pH 7 buffer containing 6 mM UDP-Gal, 5 mM LNT-2, 5 mM MnCl2 and 100 ul of refolded enzyme at 37° C. for 60 minutes. The reaction was quenched (1 to 10 dilution) with water and centrifuged through a 10,000 MWCO spin filter. The filtrate was then diluted 1 to 10. This diluted reaction was analyzed by HPLC using a Dionex DX-500 system and a CarboPac PA1 column with sodium hydroxide buffer. The sample product peak area was compared to an LNnT calibration curve, and the activity was calculated based on the amount of LNnT produced per min per μl of enzyme in the reaction.

Figure 32:
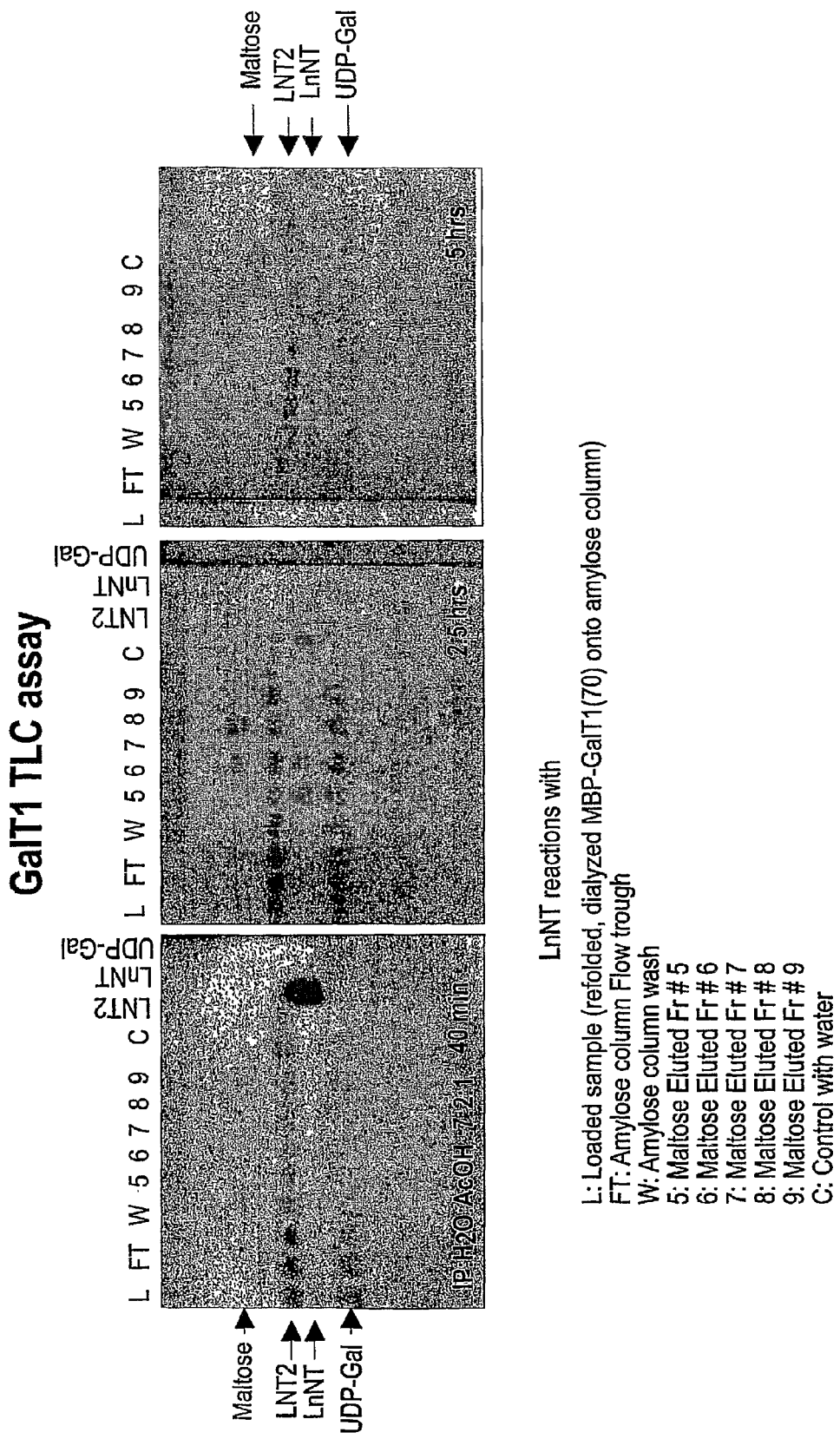
FIG. 32 provides the results of enzymatic assays of the refolded and purified MBP-GalT1 (D70) protein. The assay measured conversion of LNT2 (Lacto-N-Triose-2) into LNnT (Lacto-N-Neotetraose) using UDP-Gal (Uridine 5'-Diphosphogalactose) as a donor substrate.
Figure 33:
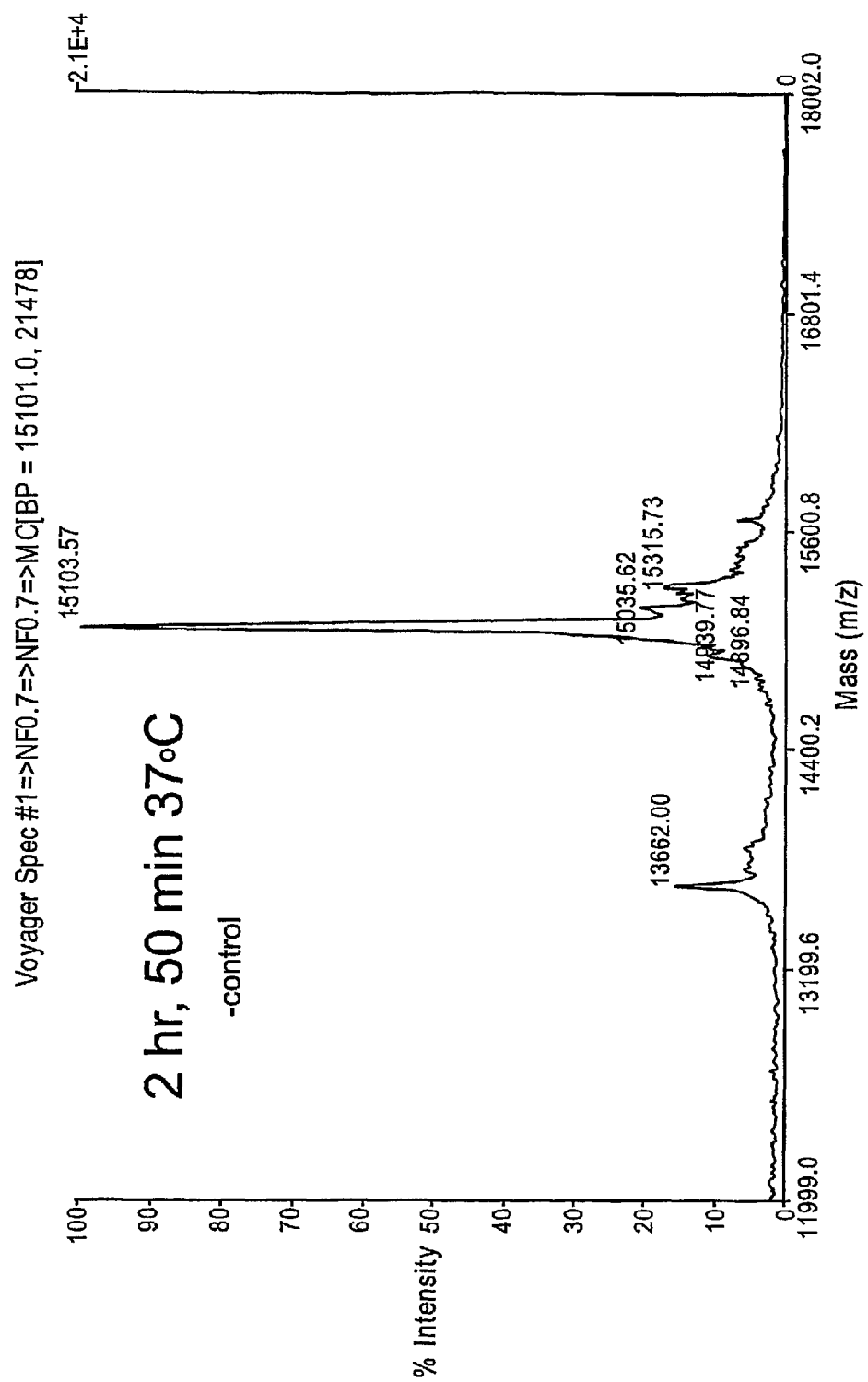
FIG. 33 provides an RNAse B remodeling assay of MBP-GalT1 (D70) and a control protein GalT1(40) (S96A+C342T), also referred to as Qasba's GalT1.
Figure 33:
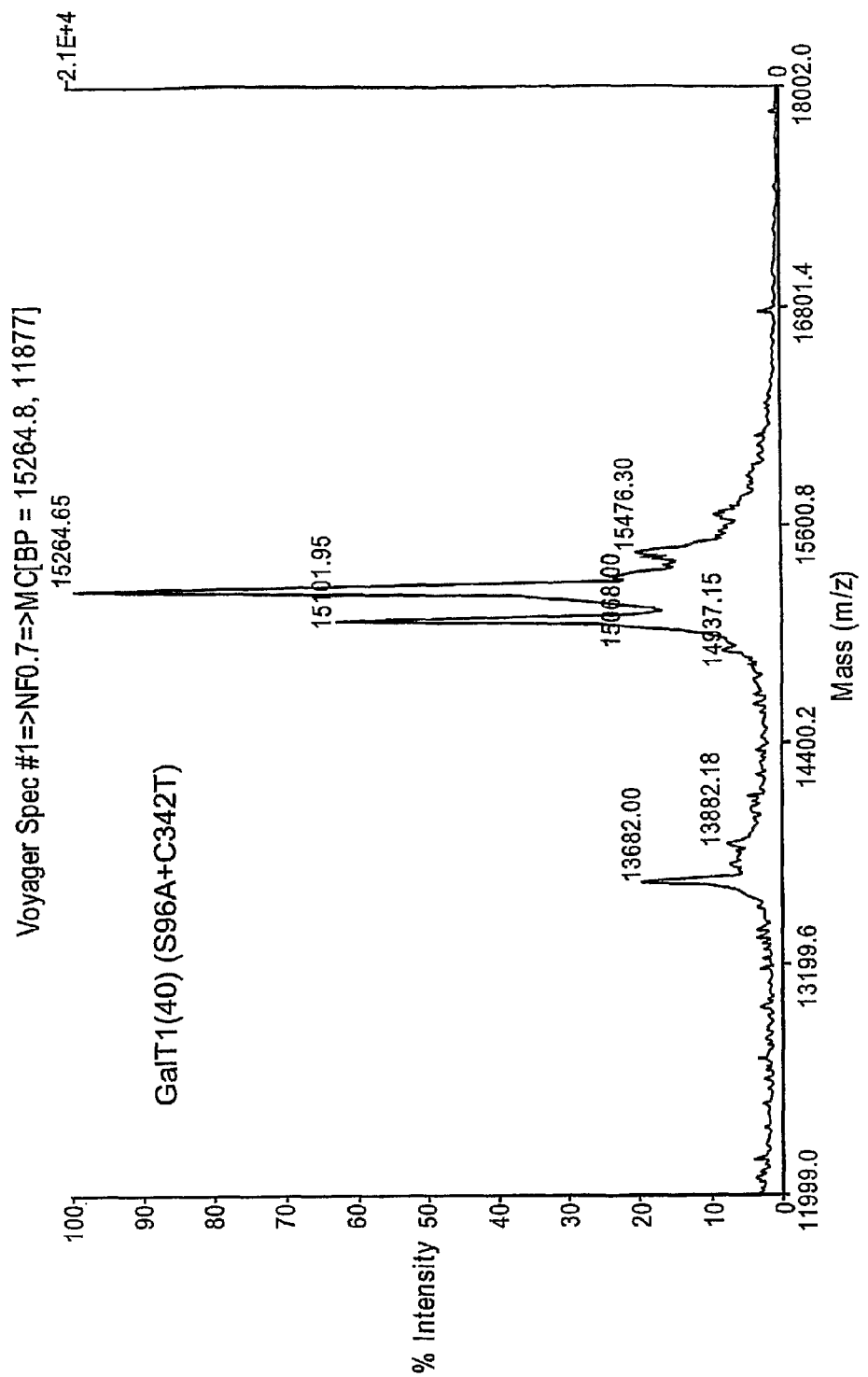
Figure 33:
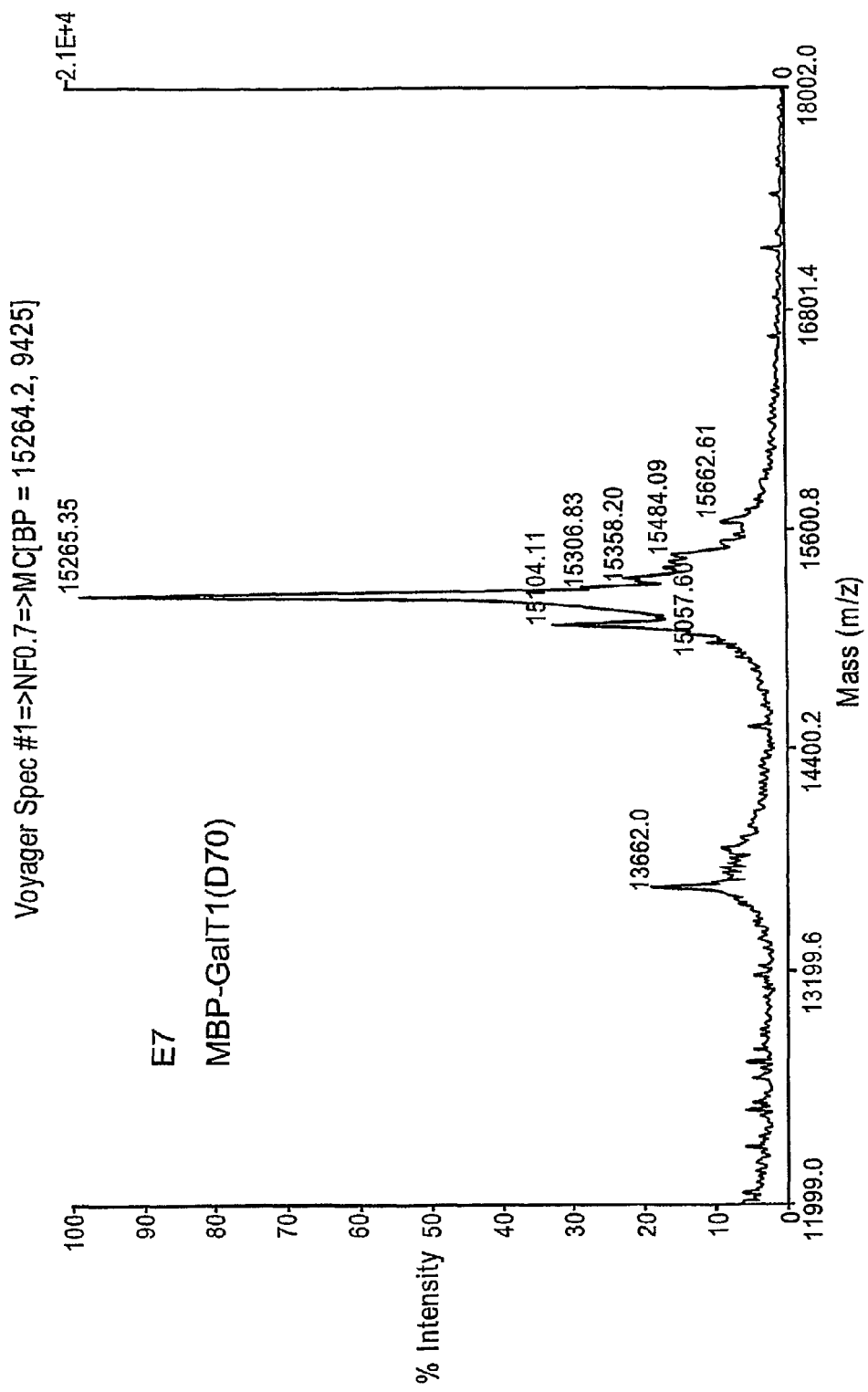
Figure 33:
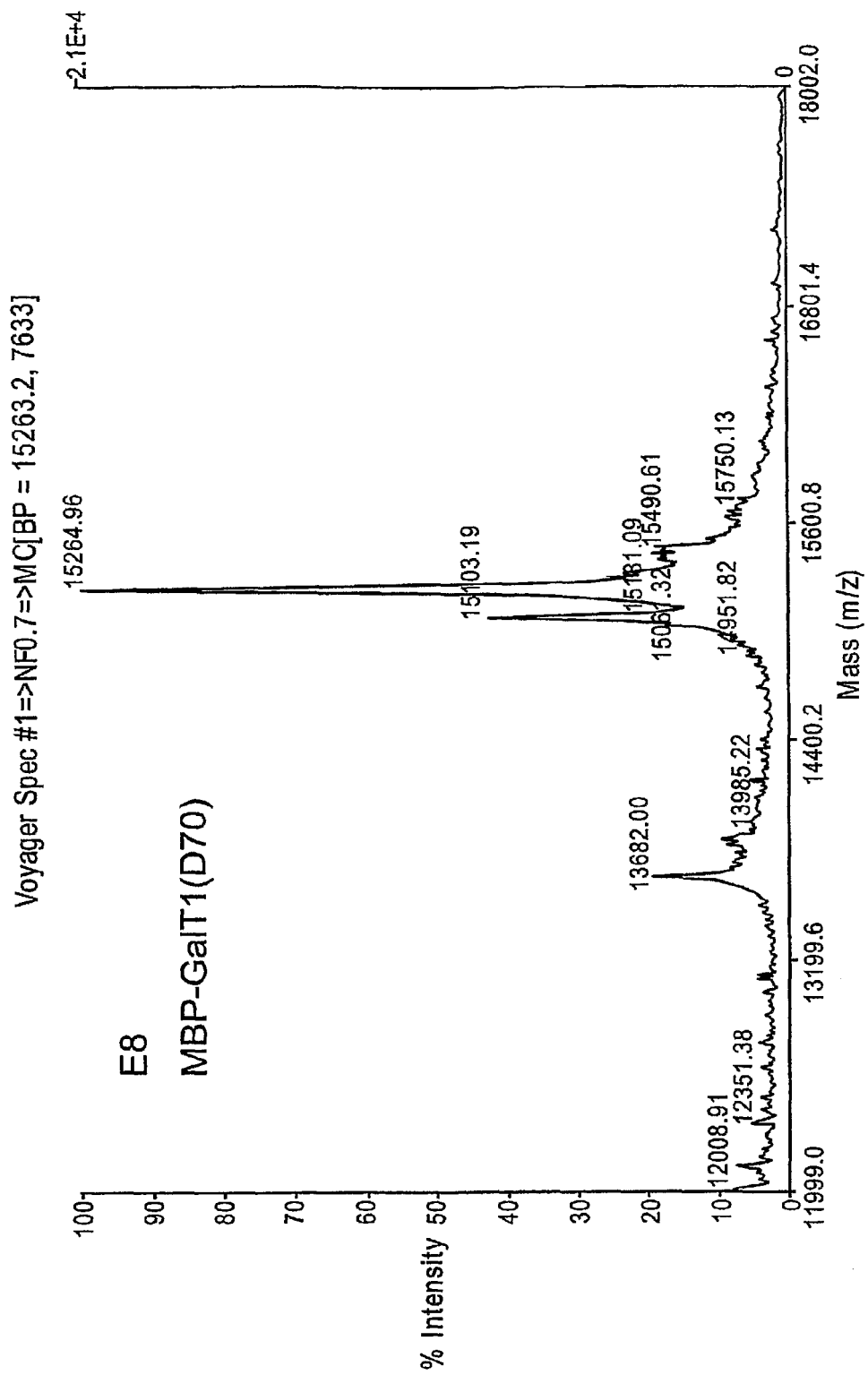

The purified MBP-GalT1 (D70) proteins had activity using both soluble oligosaccharides and glycoproteins (e.g., RNAseB) as acceptor molecules. Results are shown in FIGS. 32 and 33. In the RNAse B remodeling assay, MBP-GalT1 (D70) was compared to a control protein GalT1(40) (S96A+C342T), which is an unfused truncation of the bovine GalT1 protein that was also expressed in *E. coli* and refolded. The MBP-GalT1 (D70) protein had more activity toward the RNAse B glycoprotein than did the GalT1 (40) (S96A+C342T). The MBP-GalT1 (D129) truncation also had more activity toward the RNAse B glycoprotein than did the GalT1 (40) (S96A+C342T) protein. (Data not shown).

Kinetics of the refolded and purified MBP-GalT1 (D70) protein for glycosylation of RNAse B were determined and compared to NSO GalT1, a soluble form of the bovine GalT1 protein that was expressed in a mammalian cell system. As shown in FIG. 34, the refolded and purified MBP-GalT1 (D70) had improved kinetics compared to the NSO GalT1 protein.

Example 4

One Pot Method of Refolding Multiple Glycosyltransferases

Eukaryotic ST3GalIII, GalT1, and GnT1 enzymes build N-glycan chains on glycoproteins. Additional modifications, for example GlycoPEGylation, can be performed using CMP-NAN-PEG as a donor substrate. Eukaryotic ST3GalIII, GalT1, and GnT1 enzymes are typically expressed in eukaryotic expression systems, for example fungal or mammalian cells.

Eukaryotic ST3GalIII, GalT1, and GnT1 enzymes each fused to a maltose binding protein (MBP) domain were solubilized, combined, and refolded together in a single vessel. The MBP fused and refolded enzymes were active and were used to add N-glycans to glycoproteins or to glycoPEGylate glycoproteins. The refolding buffer included a redox couple, for example, glutathione oxidized/reduced (GSH/GSSG). Refolding was enhanced by addition of arginine and polyethylene glycol 3350 (PEG). The IB's can be solubilized individually and added to refolding buffer in different proportions or solubilized together from IB's and added to the refolding buffer directly. The one step purification or immobilization of these enzymes can also be done using the MBP fusion tag.

Preparation of a Refolded Glycosyltransferase Mixture (SuperGlycoMix)

Preparation of the Glycosyltransferases IB's

Bacterial strains used to produce eukaryotic ST3GalIII, GalT1, and GnT1 enzymes are shown in Table 5. The table also shows the estimated molecular weight of the MBP fusion proteins. (MW based on amino acid composition, Vector NTI software.) All nucleic acids encoding the eukaryotic enzymes were expressed from IPTG inducible expression vectors.

TABLE 5

| Strain/Construct | Protein expressed (IBS's) | MW (kD) |
| --- | --- | --- |
| JM109/pCWori-MBP-GaT1 (Δ129) C342T | MBP-GalT1(Δ129) C342T | 74.2 |
| JM109/pCWIN2-MBP-GnT1 (Δ103) C121A | MBP-GnT1(Δ103) C121A | 82.4 |
| TB1/pMAL-ST3GalIII | MBP-ST3GalIII | 82 |

Following IPTG induction of *E. coli* cultures, IB's containing GnT1, GalT1 and ST3GalIII enzymes isolated by lysing the cells using a French Press or detergent lysis (Novagen's Bugbuster Reagent). Pellets were recovered after centrifugation and processed to obtain IB's, as described previously. IB's were washed at least two times using Novagen's IB wash buffer. Washed IB's were stored at −20° C. until they are ready to use in refolding experiments IB's containing ST3GalIII, GalT1, or GnT1 were separately dissolved in a buffer containing 6 M Guanidine HCl, 50 mM Tris HCl pH 8.0, 5 mM EDTA, 10 mM DTT at 4° C. for one hour. Cleared supernatants were obtained after centrifugation (Max speed at Eppendorf Micro-centrifuge). The protein content of the solubilized IB's was determined by measuring absorbance at 280 nm. The protein contents in Table 6 were determined based on the extinction coefficients of each MBP-Glycosyltransferase. The extinction coefficients were calculated using Vector NTi software (See Table 5)

TABLE 6

Protein concentrations in solubilized IB's.

| Protein | A280 at 1 mg/ml | mg/ml |
| --- | --- | --- |
| MBP-ST3GalIII | 1.49 | 4.23 |
| MBP-GalT1(Δ129) C342T | 1.39 | 6.80 |
| MBP-GnT1(Δ103) C121A | 1.7 | 3.29 |

One Pot Refolding of Glycosyltyransferases

Solubilized IB's were mixed at equal amounts, as shown in Table 7.

TABLE 7

Solubilized IB's were mixed at following amounts before refolding.

| Protein | V(mL) | mg | % of total protein |
| --- | --- | --- | --- |
| MBP-ST3GalIII | 0.8 | 3.4 | 36 |
| MBP-GalT1(Δ129) C342T | 0.5 | 3.4 | 36 |
| MBP-GnT1(Δ103) C121A | 0.8 | 2.6 | 28 |
| Total | 2.1 | 9.4 | 100 |

The protein concentration of the total solubilized IB mixture was 4.5 mg/ml. The mixture was diluted approximately 1/20 in refolding buffer making the final concentration of the total protein mixture 0.22 mg/mL. Refolding buffer containing 55 mM MES, pH 6.5; 550 mM Arginine; 0.055% PEG3350; 264 mM NaCl; 11 mM KCl; 1 mM GSH; and 0.1 mM GSSG. Refolding can also be performed in a buffer with Tris HCl, pH 8.2 and a Cysteine/Cystamine redox couple can be substituted for GSH/GSSG. The IB mixture was diluted into the refolding buffer and incubated at 4° C. overnight (16-18 hours). Estimated concentrations of the glycosyltransferases in refolding reaction:

| MBP-ST3GalIII | 0.081 mg/mL |
| --- | --- |
| MBP-GalT1 (Δ129) C342T | 0.081 mg/mL |
| MBP-GnT1 (Δ103) C121A | 0.062 mg/mL |

After overnight refolding, the refolded glycosyltransferase mix was dialyzed to remove chaotropic agent (i.e. Guanidine HCl). Dialysis was carried out twice against 50 mM Tris HCl pH 8.0 at 4° C. (20 fold per dialysis) in a dialysis bag (Snake-Skin, MWCO: 7 kD, Pierce). The dialyzed refolded glycosyltransferase mix (Superglycomix, SGM) was concentrated six fold using VivaSpin 6 mL (MWCO: 10 kD) centrifugal concentrators. After concentration, all three glycoproteins were present in the mixture, as determined by SDS-PAGE analysis. (Data not shown). After concentrating the SGM, enzymatic activities of GnT1, GalT1, and ST3GalIII were determined.

Enzymatic Activities of SuperGlycoMix

Superglycomix (SGM), the one pot refolded glycosyltransferase mix contains three glycosyltransferases: ST3GalIII, GalT1 and GnT1. These enzymes were individually assayed for their enzymatic activities and analyzed using the methods indicated below. The enzymatic activities are listed in Table 8.

ST3 Gal III Enzymatic Activity Assays

ST3GalIII assays were carried out using HPLC/UV (High Performance Liquid Chromatography with Ultraviolet Detection). The conversion of LNnT (Lacto-N-Neotetraose) into LSTd (Lactosialic-Tetrasaccharide-d) using CMP-NAN (cytidine 5'-Monophosphate-β-D-sialic acid) by ST3GalIII enzyme was performed as follows. The reaction was carried out in a 96 well microtiter plate in 100 μl of 20 mM MOPS, pH 6.5 buffer containing 2 mM CMP-NAN, 30 mM LNnT, 10 mM MnCl$_2$ and 20 ul of refolded enzyme at 30° C. for 120 minutes. The reaction was quenched by heating to 98° C. for 1 min. The microtiter plate was centrifuged at 3600 rpm for 10 min to pellet any precipitate. 75 μl of supernatant was diluted 1:1 with 75 μl of water. The diluted reaction was analyzed by LC/UV using a YMC-Pack Polyamine II column with a sodium phosphate buffer/acetonitrile gradient and detection at 200 nm. The sample product peak area was compared to an LSTd calibration curve, and the activity was calculated based on the amount of LSTd produced per min per μl of enzyme in the reaction.

GalTI Enzymatic Activity Assays:

The enzymatic assays were carried out using HPLC/PAD (High Performance Liquid Chromatography with Pulsed Amperometric Detection). The conversion of LNT2 (Lacto-N-Triose-2) into LNnT (Lacto-N-Neotetraose) using UDP-Gal (Uridine 5'-Diphosphogalactose) by GalTI enzyme was performed as follows. The reaction was carried out in 100 ul of 50 mM Hepes, pH 7 buffer containing 6 mM UDP-Gal, 5 mM LNT-2, 5 mM MnCl$_2$ and 100 μl of refolded enzyme at 37° C. for 60 minutes. The reaction was quenched (1 to 10 dilution) with water and centrifuged through a 10,000 MWCO spin filter. The filtrate was then diluted 1 to 10. This diluted reaction was analyzed by HPLC using a Dionex DX-500 system and a CarboPac PA1 column with sodium hydroxide buffer. The sample product peak area was compared to an LNnT calibration curve, and the activity was calculated based on the amount of LNnT produced per min per μl of enzyme in the reaction.

GnTI Enzymatic Activity Assays:

The activity of GnTI is determined by measuring the transfer of a tritiated sugar from UDP-$^3$H-GlcNAc (Uridine diphosphate N-acetyl-D-glucosamine [6-$^3$H(N)]) to n-octyl 3,6-Di-O-(α-mannopyranosyl) β-D-mannopyranoside (OM3), a trimannosyl core with an octyl tail. The reaction was carried out in 20 μl of 100 mM MES, pH 6.0 buffer containing 3 mM UDP-GlcNAc, 0.1 mM UDP-$^3$H-GlcNAc, 0.5 mM OM3, 20 mM MnCl$_2$ and 10 μl of refolded enzyme at 37° C. for 60 minutes. The reaction was quenched (1 to 6 dilution) with water and applied to a polymeric reversed-phase resin in a 96 well format that was previously conditioned according to the manufacturer's recommendations. The resin was washed twice with 200 ul of water and the product was eluted with 50 μl of 100% MeOH into a capture plate. Scintillation fluid (200 μL) was added to each well and the plate was mixed and counted using a PerkinElmer Top-Count NXT microplate scintillation counter. The activity was calculated based on the amount of $^3$H-GlcNAc incorporated into the product per min per μl of enzyme in the reaction.

TABLE 8

Enzymatic activities of refolded Glycosyltransferases in SGM

| Enzymatic activity | mU/mL |
|---|---|
| GnT1 | 1 |
| GalT1 | 165 |
| ST3GalIII | 10 |

The activities reported in the table above are close or in the range when these enzymes were refolded separately. GnT1 and GalT1 activities are close to those obtained using mammalian or baculovirus expression systems. ST3GalIII activities are somewhat lower than in ST3GalIII preparation obtained after fungal expression system. The ST3GalIII assay used here is modified from the procedure and values reported here approximately 4-5 fold lower than those obtained a method based on CE-LIF (Capillary electrophoresis-Laser induced Fluorescence).

Remodeling RNAseB-Man$_5$ Using Superglycomix

A small glycoprotein, RNAseB with one N linked Man5 sugar, was remodeled by SGM in the presence of UDP-sugars (UDP-GlcNAc and UDP-Gal). The remodeling reaction was carried out either using UDP-GlcNAc or both UDP-GlcNAc and UDP-Gal to test the both GnT1 and GalT1 activities. Eight μl of SGM was added to 10 mM MES buffer pH 6.5 containing 5 mM UDP-GlcNAc, or/and 5 mM UDP-Gal, 9 μg RNAseBMan$_5$, 5 mM MnCl$_2$ in 25 μl assay incubated at 33° C. for overnight to 48 hours. At the end of the reaction, ten μl aliquots were dialyzed against H$_2$O and 1.5 μl samples were spotted on MALDI-TOF plates. Samples were analyzed on MALDI-TOF after being treated with TFA and cinnapinic acid.

The remodeling of RNAseBman5 was done by transferring GlcNAc and Gal on Man5 of the RNaseB. After 48 hrs incubation at 33° C., majority of the GlcNAc and Gal transfer onto RNAseB was accomplished as indicated in MALDI-TOF spectra of the remodeled RNAseBMan$_5$. Results are summarized in Table 9.

TABLE 9

MALDI-TOF Spectra of the species after SGM reactions.

| | m/z RNAseB | | |
|---|---|---|---|
| Reaction | Man$_5$ | Man$_5$-GlcNAc | Man$_5$GlcNAc-Gal |
| No Enzyme | 14983 | — | — |
| SGM + UDP-GlcNAc | 14973 | 15177 | — |
| SGM + UDP-GlcNAc + UDP-Gal | 14982 | 15170 | 15348 |

GlycoPEGylation EPO Remodeling Using SGM

Figure 5:
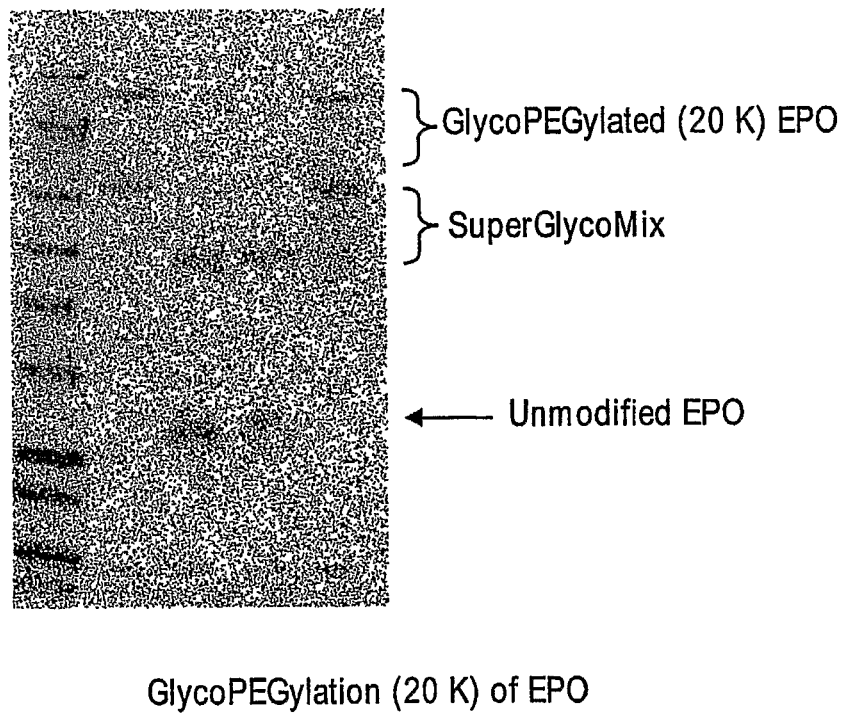
FIG. 5 provides the results of an assay of GlycoPEGylation of EPO using the refolded SuperGlycoMix. Lanes are as follows: (1) MW markers, SeeBlue2 Invitrogen, (250, 148, 98, 64, 50, 36, 22, 16, 6 kD); (2) Positive control with EPO, +NSO expressed GalT1, BV GnT1, *Aspergillus* ST3GalIII and sugar nucleotides; (3) Negative control, Same as 2 without UDP-GlcNAc; (4) EPO, Purified and separately refolded MBP-GalT1(Δ129) C342T, Refolded MBP-GnT1 (Δ103), and *Aspergillus niger* expressed ST3GalIII; (5) EPO, SuperGlycoMix (mixture of MBP-ST3GalIII, MBP-GalT1(Δ129) C342T, MBP-GnT1(Δ103)C123A and sugar nucleotides.

GlycoPEGylation (20 K) was carried out in one pot reaction composed of the following components: 10 mM MES pH 6.5, 5 mM MgCl$_2$, 5 mM UDP-GlcNAc, 5 mM UDP-GalNAc, 0.5 mM CMP-SA-PEG (20 kDa), 24 μg EPO, 8 μL concentrated SGM. In control reactions, SGM was replaced by individual enzymes either refolded or expressed in mammalian cells or insect cells or Aspergillus. After overnight incubations, the reactions were analyzed on SDS-polyacrylamide gel. Results are shown in FIG. 5. SGM added 20 K PEG to EPO.

Assessment of One Pot Refolding Conditions for Multiple Glycosyltransferases

Conditions for refolding multiple glycosyltranferases were assessed, including pH and refolding two or three enzymes at once.

Preparation of Glycosyltransferase Inclusion Bodies

E. coli strains transformed with glycosyltransferase expression plasmids were described previously, with one exception. MBP-ST3GalIII was expressed in JM109 cells from a pCWori-ST3GalIII plasmid. The inclusion bodies were isolated and solubilized as described above. Protein contents were assessed as described above and are shown in Table 10.

TABLE 10

Solubilized IB's were mixed at following amounts before refolding.

| Protein | A280 | A280 (at 1 mg/ml) | mg | % (of sol. protein) |
|---|---|---|---|---|
| MBP-ST3GalIII | 32.3 | 1.49 | 21.7 | 13.6 |
| MBP-GalT1(Δ129) C342T | 35.7 | 1.39 | 25.7 | 13.7 |
| MBP-GnT1(Δ103) C121S | 42.8 | 1.7 | 25.2 | 9.7 |

One Pot Refolding of Glycosyltyransferase IB Mixtures

After determining their protein contents, solubilized IB's were mixed at amounts shown before diluted in the refolding buffers (Table 11). Refolding experiments of the GT's were carried out in 44 ml volume at 4° C. at stationary phase using buffer A or B (below) and 0.1 mM GSSG and 1 mM GSH. Buffer A: 55 mM MES pH 6.5, 550 mM Arginine, 0.055% PEG3350, 264 mM NaCl, 11 mM KCl, supplemented with 1 mM GSH, 0.1 mM GSSG. Buffer B: 55 mM Tris HCl pH 8, 550 mM Arginine, 0.055% PEG3350, 264 mM NaCl, 11 mM KCl, supplemented with 1 mM GSH, 0.1 mM GSSG.

TABLE 11

Mixing amounts of solubilized GT IB's in 2 mL IBSB

| | Conc(mg/mL) | V (mL) | mg |
|---|---|---|---|
| Refolding in Buffer A | | | |
| Refold 1 (A-2x) | | | |
| MBP-GnT1 (Δ103) C121S | 25.2 | 0.2 | 5 |
| MBP-GalT1 (Δ129) C342T | 25.7 | 0.2 | 5 |
| IBSB | — | 1.6 | — |

TABLE 11-continued

Mixing amounts of solubilized GT IB's in 2 mL IBSB

|  | Conc(mg/mL) | V (mL) | mg |
|---|---|---|---|
| Refold 2 (A-3x) | | | |
| MBP-GnT1 (Δ103) C121S | 25.2 | 0.2 | 5 |
| MBP-GalT1 (Δ129) C342T | 25.7 | 0.2 | 5 |
| MBP-ST3GalIII | 21.7 | 0.4 | 8.7 |
| IBSB | — | 1.2 | — |
| Refolding in Buffer B | | | |
| Refold 3 (B-2x) | | | |
| MBP-GnT1 (Δ103) C121S | 25.2 | 0.2 | 5 |
| MBP-GalT1 (Δ129) C342T | 25.7 | 0.2 | 5 |
| IBSB | — | 1.4 | — |
| Refold 4 (B-3x) | | | |
| MBP-GnT1 (Δ103) C121S | 25.2 | 0.2 | 5 |
| MBP-GalT1 (Δ129) C342T | 25.7 | 0.2 | 5 |
| MBP-ST3GalIII | 21.7 | 0.4 | 8.7 |
| IBSB | — | 1.2 | — |

For double refolding (2×, two glycosyltranferases) 10 mg total protein in 2 ml was added into 41 mL refolding buffer (above) 0.45 mL 100 mM GSH, 0.45 mL 10 mM GSSG, after dilution total protein was 0.44 mg/ml. For triple refolding (3×, three glycosyltransferases) 18.7 mg total protein in 2 ml was added into 41 mL refolding buffer (above), 0.45 mL 100 mM GSH, 0.45 mL 10 mM GSSG. After dilution total protein was 0.83 mg/ml. The protein concentrations were higher than previous triple refolding experiment (0.22 mg/ml in SGM). Estimated concentrations of the glycosyltransferases in refolding reaction follow:

| MBP-ST3GalIII | 0.39 mg/mL |
| MBP-GalT1 (Δ129) C342T | 0.23 mg/mL |
| MBP-GnT1 (Δ103) C121S | 0.23 mg/mL |

After overnight refolding, the refolded glycosyltransferase mix was dialyzed. Dialysis was carried out twice against 50 mM Tris HCl pH 8.0 at 4° C. in a dialysis bag (SnakeSkin, MWCO: 7 kD, Pierce). After dialysis, the glycosyltransferase mix was concentrated 9-12 fold using 6 mL VIVA-Spin (MWCO: 10 K) centrifugal concentrators.

SDS-PAGE analysis demonstrated that the proteins were present after refolding, dialysis, and concentration.

Enzymatic Assays of Refolded Glycosyltransferase Mixtures

Enzymatic assays were performed as described above. Results are shown in Table 12.

TABLE 12

Enzymatic activities of refolded Glycosyltransferases after double and triple refolding experiments.

| Folding | Fold conc | Enzymatic activity | mU/mL |
|---|---|---|---|
| Buffer A (A-2x) | | GnT1 | 0.84 |
| | | GalT1 | 598 |
| Buffer A (A-3x) | | GnT1 | 0.16 |
| | | GalT1 | 306 |
| | | ST3GalIII | 4 |
| Buffer B (B-2x) | | GnT1 | 3.32 |
| | | GalT1 | 747 |
| Buffer B (B-3x) | | GnT1 | 0.47 |
| | | GalT1 | 425 |
| | | ST3GalIII | 11 |

The highest activity was seen on mixing MBP fused GnT1 and GalT1 in equal amounts and refolded in buffer B. Adding non-equivalent amount of MBP-fused ST3GalIII affected refolding efficiency due to total high protein. Nevertheless, two different refolding buffer using either two GT's or three GT's, can be used to obtain active soluble proteins.

Example 5

Refolding Eukaryotic GalNAcT2

A truncated human GalNAcT2 enzyme was expressed in *E. coli* and used to determine optimal conditions for solubilization and refolding using the methods described above. The full length human GalNAcT2 nucleic acid and amino acid sequences are provided in FIGS. 13A and B. The sequences of the mutant protein, GalNAcT2(D51), are shown in FIGS. 14A and B. The mutant was expressed in *E. coli* as an MBP fusion protein, MBP-GalNAcT2(D51). Other GalNAcT2 mutants were made, expressed in *E. coli* and were able to be refolded: MBP-GalNAcT2(D40), MBP-GalNAcT2(D73), and MBP-GalNAcT2(D94). Data not shown. Details of the construction of the additional deletion mutants is found in U.S. Ser. No. 60/576,530, filed Jun. 3, 2004 and U.S. Ser. No. 60/598,584, Aug. 3, 2004, both of which are herein incorporated by reference for all purposes.

Figure 15:
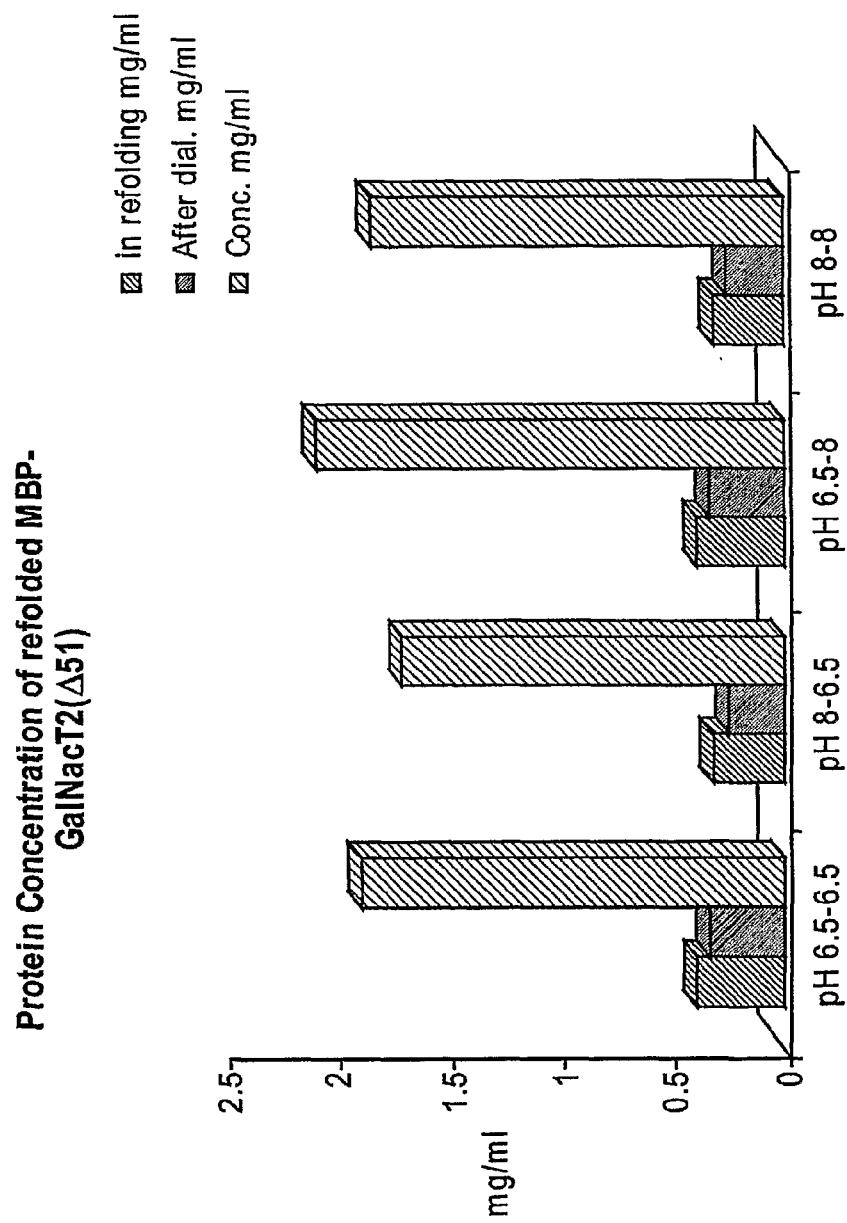
FIG. 15 provides a demonstration of the protein concentration of refolded MBP-GalNAcT2(D51) after solubilization at pH 6.5 or pH 8.0 and refolding at pH 6.5 or pH 8.0. The pH values tested are expressed as solubilization pH-refolding pH. Protein concentrations were measured immediately after refolding (light gray bars), after dialysis (dark gray bars), and after concentration (white bars).

Cultures of bacteria expressing MBP-GalNAcT2(D51) were grown and harvested as described above. Inclusion bodies were purified from bacteria as described above. Solubilization of the inclusion bodies was performed at pH 6.5 or at pH 8.0. After solubilization, MBP-GalNAcT2(D51) protein was refolded at either pH 6.5 or pH 8.0 using buffers A and B, i.e., Buffer A: 55 mM MES pH 6.5, 550 mM Arginine, 0.055% PEG3350, 264 mM NaCl, 11 mM KCl, supplemented with 1 mM GSH, 0.1 mM GSSG; and Buffer B: 55 mM Tris HCl pH 8, 550 mM Arginine, 0.055% PEG3350, 264 mM NaCl, 11 mM KCl, supplemented with 1 mM GSH, 0.1 mM GSSG. After refolding, MBP-GalNAcT2(D51) protein was dialyzed and then concentrated. FIG. 15 provides a demonstration of the protein concentration of refolded MBP-GalNAcT2(D51) after solubilization at pH 6.5 or pH 8.0 and refolding at pH 6.5 or pH 8.0.

Figure 16:
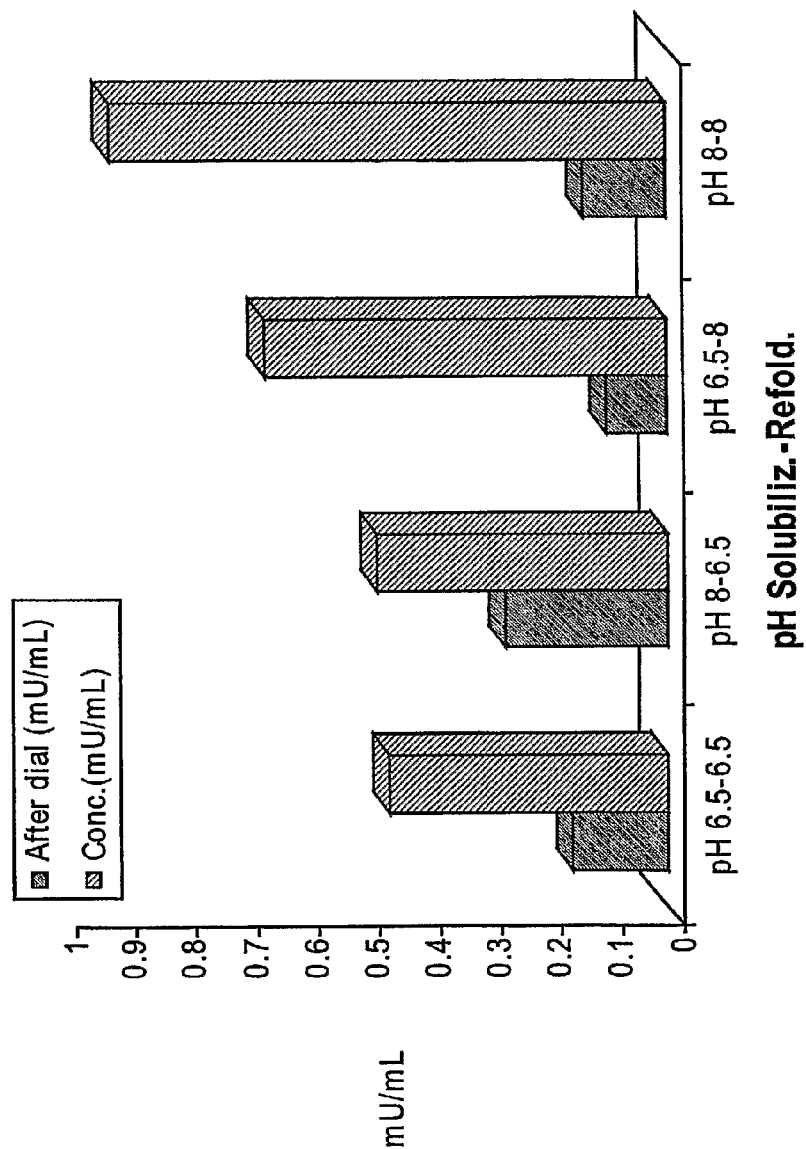
FIG. 16 provides a demonstration of the enzymatic activity of refolded MBP-GalNAcT2(D51) after solubilization at pH 6.5 or pH 8.0 and refolding at pH 6.5 or pH 8.0. The pH values tested are expressed as solubilization pH-refolding pH. Activity was measured after dialysis (light gray bars) and after concentration (dark gray bars).
Figure 17:
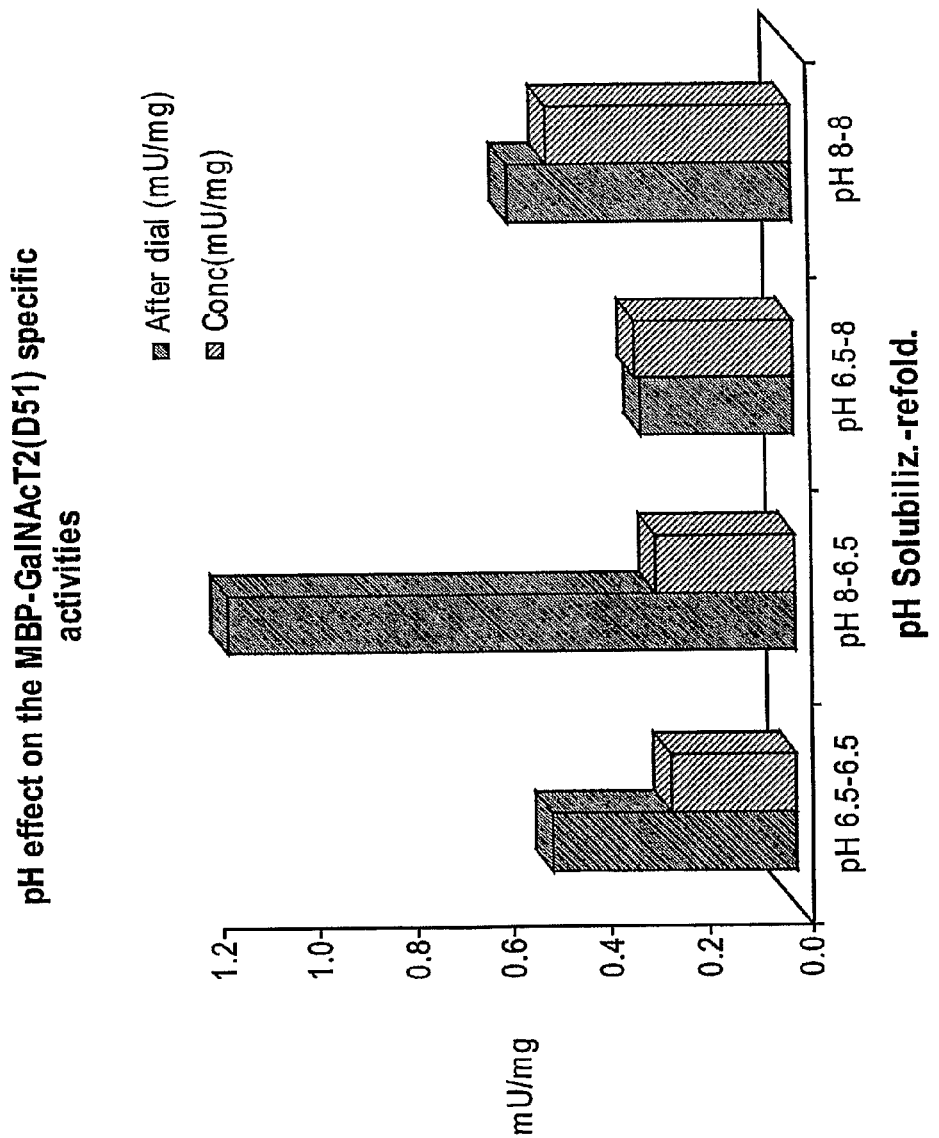
FIG. 17 provides a demonstration of the specific activity of refolded MBP-GalNAcT2(D51) after solubilization at pH 6.5 or pH 8.0 and refolding at pH 6.5 or pH 8.0. The pH values tested are expressed as solubilization pH-refolding pH. Specific activity was measured after dialysis (white bars) and after concentration (dark gray bars).

A radiolabeled [$^3$H]-UDP-GalNAc assay was performed to determine the activity of the *E. coli*-expressed refolded MBP-GalNAcT2(D51) by monitoring the addition of radiolabeled GalNAc to a peptide acceptor. The acceptor was a MuC-2-like peptide having the sequence MVTPTPTPTC). The peptide was dissolved in 1M Tris-HCl pH=8.0. See, e.g., U.S. Ser. No. 60/576,530 filed Jun. 3, 2004; and U.S. provisional patent application 60/598,584, filed Aug. 3, 2004; both of which are herein incorporated by reference for all purposes. FIG. 16 provides a demonstration of the enzymatic activity of refolded MBP-GalNAcT2(D51) after solubilization at pH 6.5 or pH 8.0 and refolding at pH 6.5 or pH 8.0. FIG. 17 provides a demonstration of the specific activity of refolded MBP-GalNAcT2(D51) after solubilization at pH 6.5 or pH 8.0 and refolding at pH 6.5 or pH 8.0. The highest activity levels were observed with MBP-GalNAcT2(D51) that had been solubilized at pH 8.0 and refolded at pH 8.0. The highest specific activity levels were also observed with solubilization at pH 8.0 and refolding at pH 8.0.

Solubilized and refolded MBP-GalNAcT2(D51) was assayed for its ability to add GalNAc to the G-CSF protein. The assay consisted of an aliquot of enzyme and a reaction buffer (27 mM MES, pH=7, 200 mM NaCl, 20 mM MgCl2, 20 mM MnCl2, and 0.1% Tween 80), G-CSF Protein (2 mg/ml in H$_2$O), and 100 mM UDP-GalNAc. For each refold sample, 4.4 μL of sample were added to 15 μL of reaction solution. For the positive control, 1 μL of standard GalNAcT2 Baculovirus was added along with 3.4 μL of H$_2$O to one tube. Reactions were incubated at 32° C. on a rotary shaker for several days, during which time an overnight time point and a 5 day time point were assayed by MALDI. See, e.g., U.S. Ser. No. 60/576,530 filed Jun. 3, 2004; and U.S. provisional patent application 60/598,584, filed Aug. 3, 2004; both of which are herein incorporated by reference for all purposes.

Figure 18A:
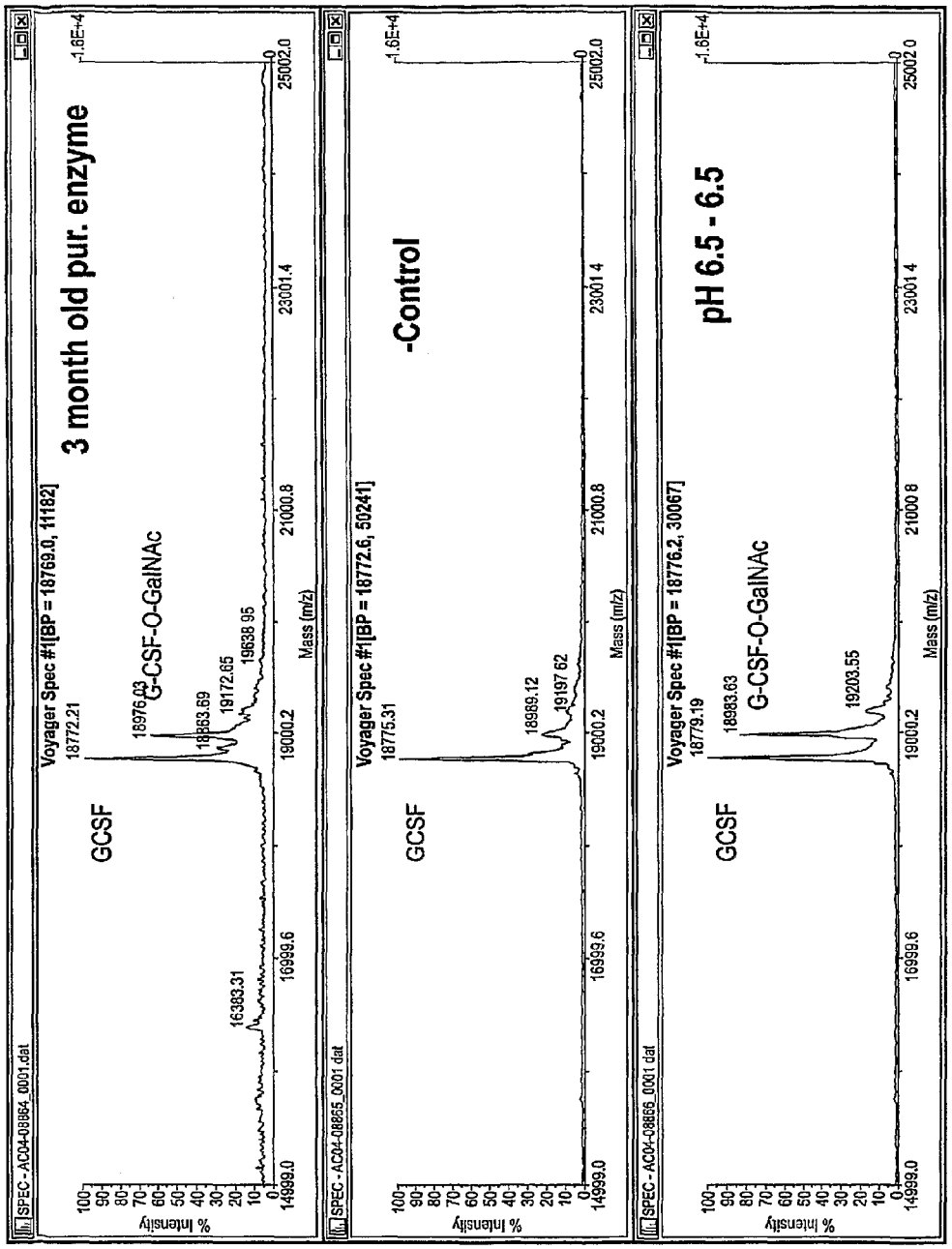
FIGS. 18A and 18B provide results of remodeling of recombinant granulocyte colony stimulating factor (GCSF) using refolded MBP-GalNAcT2(D51) after solubilization at pH 6.5 or pH 8.0 and refolding at pH 6.5 or pH 8.0.
Figure 18B:
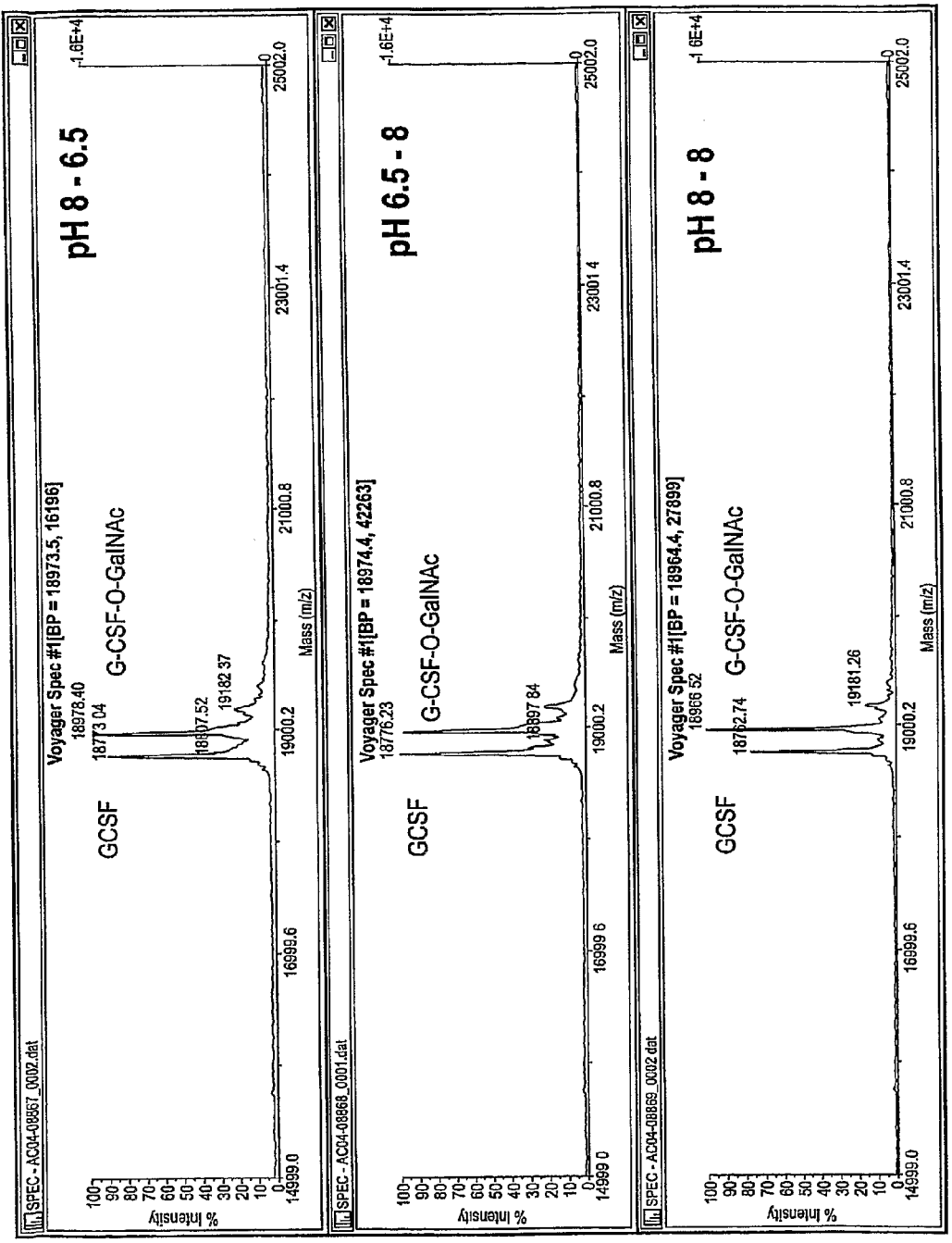

FIGS. 18A and 18B provide results of remodeling of recombinant granulocyte colony stimulating factor (GCSF) using refolded MBP-GalNAcT2(D51) after solubilization at pH 6.5 or pH 8.0 and refolding at pH 6.5 or pH 8.0. A positive control, i.e., purified MBP-GalNAcT2(D51) that had been expressed in baculovirus, and a negative control, i.e., reaction mixture lacking a substrate were included. The highest levels of GCSF remodeling activity were seen using MBP-GalNAcT2(D51) that had been solubilized at pH 8.0 and refolded at pH 8.0.

Example 6

Refolding and Purification of Eukaryotic GalNAcT2

Four liters of bacteria that express recombinant MBP-GalNAcT2(D51) were grown and harvested. Inclusion bodies were isolated, washed, and two grams dry weight of inclusion bodies were solubilized at 4° C. in 200 mL of solubilization buffer (7M urea/50 mM Tris/10 mM DTT/5 mM EDTA at pH 8.0). After solubilization, the mixture was then diluted in to 4 L of refolding buffer (50 mM Tris/550 mM L-Arginine/250 mM NaCl/10 mM KCl/0.05% PEG 3350/4 mM L-cysteine/1 mM cystamine dihydrochloride at pH 8.0). Refolding was carried out at 4-10° C. for about 20 hours, with stirring. The mixture was then filtered using a 10 SP CUNO filter, concentrated 5 fold on 4 ft 2 membrane, diafiltered 4 times with 10 mM Tris/5 mM NaCl at pH 8.0. The conductivity of the final refolded MBP-GalNAcT2(D51) solution was 1.4 mS/cm. The refolded protein was stored at 4° C. for several days.

Figure 19:
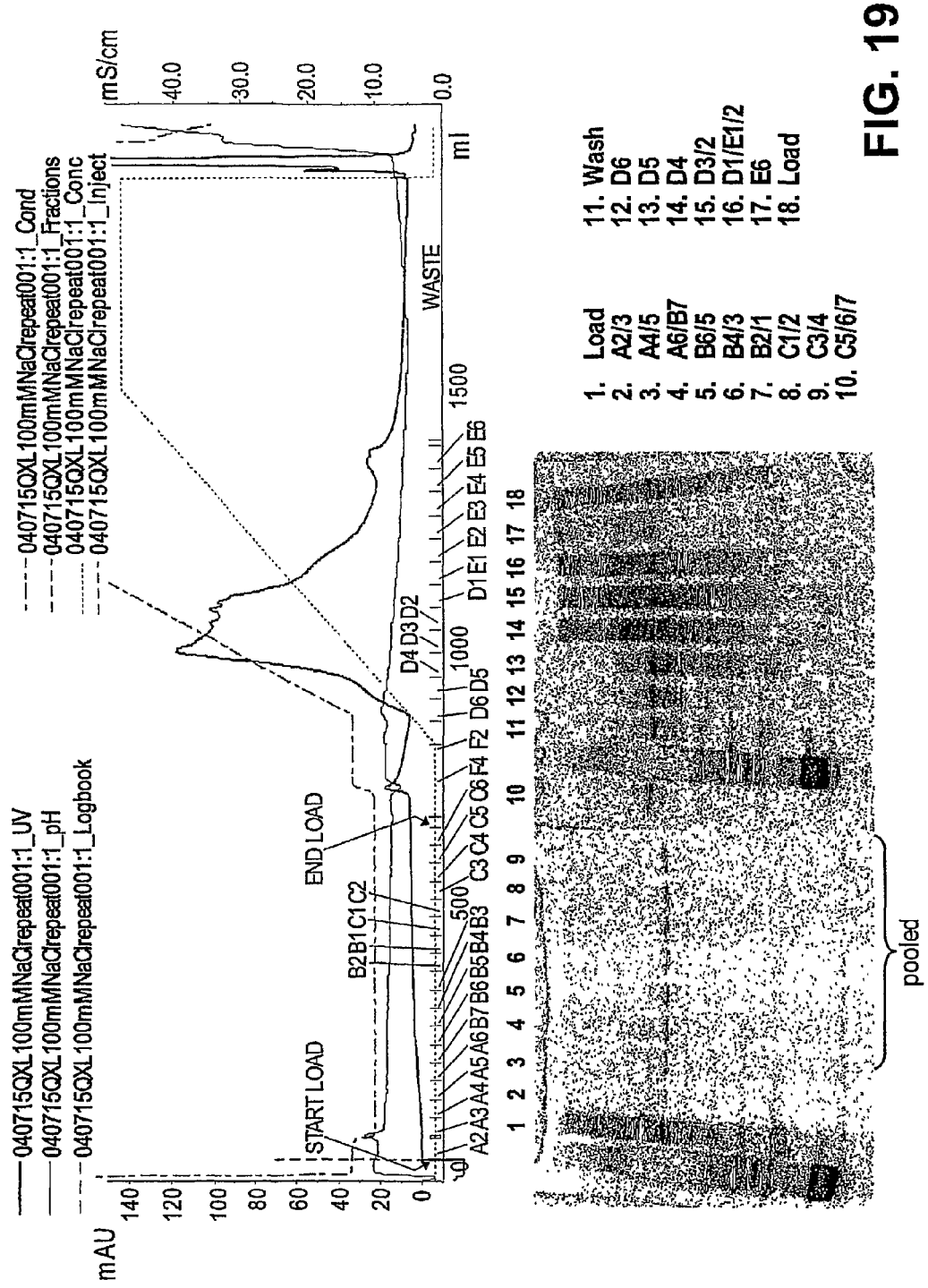
FIG. 19 provides a profile of refolded MBP-GalNAcT2 (D51) proteins after elution from a Q Sepharose XL (QXL) column (Amersham Biosciences, Piscataway, N.J.). The top of the figure shows a chromatogram illustrating the elution of MBP-GalNAcT2(D51) from the QXL column. Fraction numbers are indicated on the X-axis and the relative absorbance of each fraction is indicated on the Y-axis. The bottom shows an image of two electrophoretic gels used to visualize the eluted fractions. The contents of each lane on the gel are described in the figure.
Figure 21:
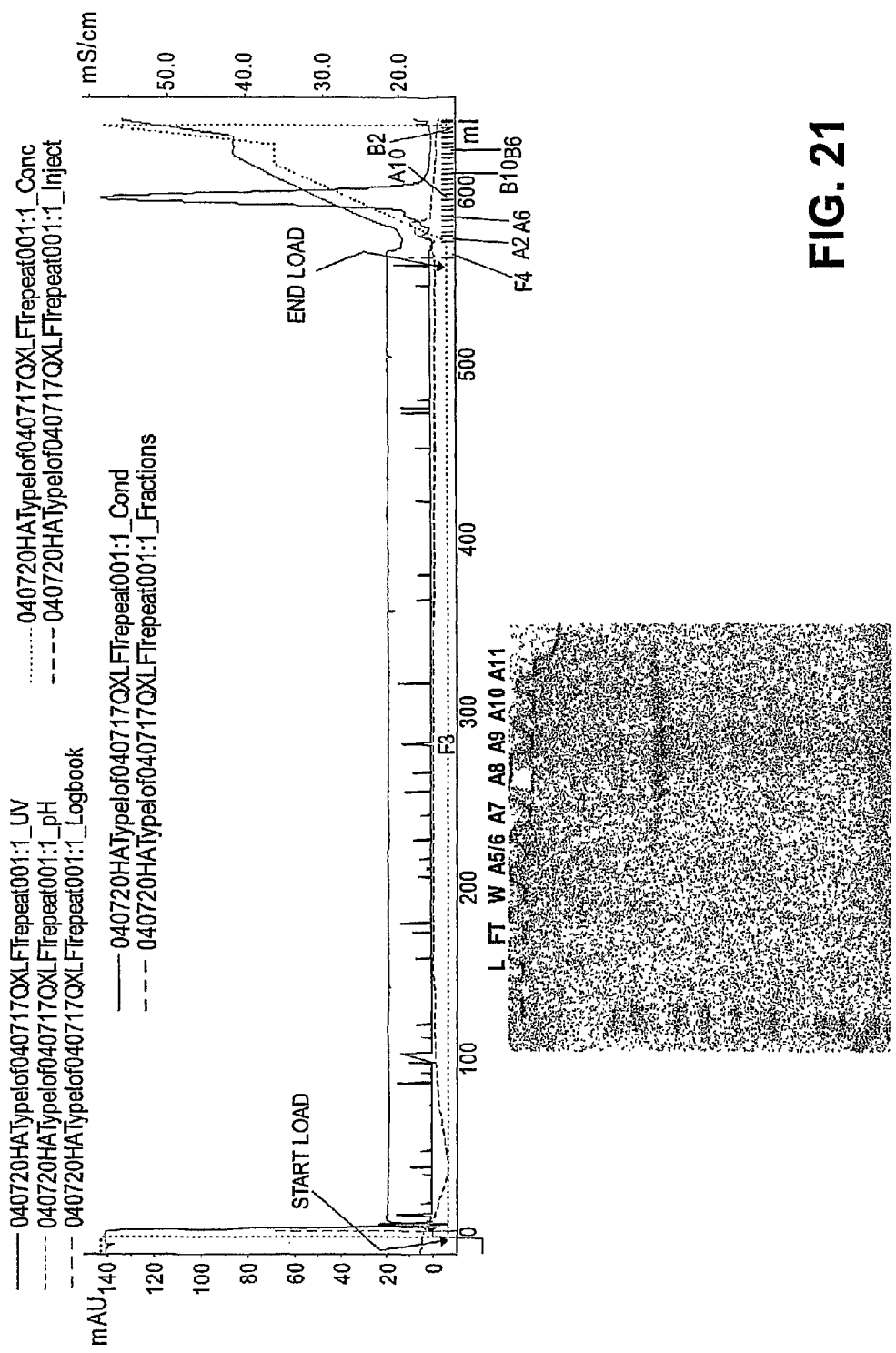
FIG. 21 provides a profile of refolded MBP-GalNAcT2 (D51) proteins after elution from the HA type I column. The top of the figure shows a chromatogram illustrating the elution of MBP-GalNAcT2(D51) from the HA type I column. Fraction numbers are indicated on the X-axis and the relative absorbance of each fraction is indicated on the Y-axis. The bottom shows an image of an electrophoretic gel used to visualize the eluted fractions. The contents of each lane on the gel are described in the figure.

The refolded proteins were applied to a Q Sepharose XL (QXL) column (Amersham Biosciences, Piscataway, N.J.). An elution profile is shown in FIG. 19 and the enzymatic activity of specific column fractions are shown in FIG. 20. The active fractions were combined and applied to an Hydroxyapatite Type I (80 μm) (BioRad, Hercules, Calif.) column. An elution profile is shown in FIG. 21 and activity of HA type I eluted fractions is shown in FIG. 22. The combination of QXL and HA type I chromatography resulted in active, highly purified MBP-GalNAcT2(D51).

Example 7

Purification of Eukaryotic MBP-SBD ST3Gal3

The Δ73 ST3GalIII truncation was fused in frame to the maltose binding protein and a starch binding domain to form a doubly tagged protein: MBP-SBD-ST3Gal3 (Δ73). The MBP was at the amino terminus, followed by the SBD, and then the truncated ST3GalIII protein. Refolding and purification of the MBP-SBD-ST3Gal3 (Δ73) protein was compared to a single tag protein: MBP-ST3GalIII (Δ73). Both proteins were expressed in E. coli as insoluble inclusion bodies, and were solubilized and refolded as described herein. The proteins were then dialyzed and subjected to affinity purification using a cyclodextrin column that binds to both the MBP and SBD tags. Results are shown in FIG. 23. The MBP-SBD-ST3Gal3 (Δ73) protein had higher specific activity after dialysis and retained more specific activity after elution from the column with cyclodextrin.

Example 8

Refolding of MBP-ST3Gal1 and MBPSBD-ST3Gal1 Proteins

Eukaryotic ST3 Gal1 was fused to MPB or MBP and SBD. The DNA sequence of the porcine ST3Gal1 gene was used as a template for the design of the pcWINMBP-pST3Gal1 and pcWINMBP/SBD-pST3Gal1 constructs described herein. The full length porcine ST3 Gal1 sequence is provided in FIG. 37. For expression in E. Coli, a codon optimized and truncated version of pST3Gal1 was used, i.e., pST3 Gal1 Δ45. The encoded amino acid sequences are provided in FIG. 24. The ST3Gal1 gene coding sequence was next digested and transferred to pcWIN2-MBP and pcWINMBP/SBD vectors using the BamHI and XhoI cloning sites. These constructs were confirmed to be correct by restriction and sequence analysis and then were used to transform the E. Coli strain JM109 using 50 ug/ml Kanamycin selection. An individual colony from each was used to inoculate a 2 ml culture of Maritone-10 ug/ml Kanamycin that was incubated for 16 hrs at 37° C. Each culture was mixed separately 1:1 with 50% glycerol and frozen at −80° C. and referred as the stock vial. A small amount of each stock vial was used to streak a Maritone-Kan plate. After 16 hr incubation at 37° C., a single colony from each was used to inoculate a 25 ml culture of Maritone-10 ug/ml Kanamycin that was incubated for 16 hrs at 37° C. The 25 ml culture was then used to inoculate a 1 L culture of Maritone-10 ug/ml Kanamycin that was incubated at 37° C. and monitored for OD600. When the OD600 reached 0.8, IPTG was added to 1 mM and the cells were incubated for an additional 16 hrs. Cells were then harvested by centrifugation at 7000×G for 15 mins.

Inclusion bodies were then isolated, the ST3Gal1 fusion proteins were solubilized, and refolded. Bacterial cells pellets were resuspended at a ratio of 1 g wet cell pellet per 10 mL of 20 mM Tris pH 8, 5 mM EDTA and lysed by mechanical disruption with two passes through a microfluidizer. Insoluble material, i.e., the inclusion bodies or IB's, was pelleted by centrifugation at 7000×g at 4° C. in the Sorvall RC3 for 30 minutes, and the supernatant discarded. A typical wash cycle consisted of completely resuspending the pellet in the wash buffer, and repeating the centrifugation for 15 minutes. The pellet was washed once in an excess volume (at least 10 mL (up to 20) per g original cell pellet) of high salt buffer (wash I: 10 mM Tris pH 7.4, 1 M NaCl, 5 mM EDTA), once in detergent buffer (wash II: 25 mM Tris pH 8, 100 mM NaCl, 1% Triton X100, 1% Na-deoxycholate, 5 mM EDTA), and (to remove traces of detergent in addition to washing the IBs) three times in wash buffer (wash III: 10 mM Tris pH 8, 5 mM EDTA).

Washed IB's were resuspended in solubilization buffer (8M Urea, 50 mM BisTris pH 6.5, 5 mM EDTA, 10 mM DTT) and adjusted to 2 mg/ml protein concentration. Refolding was performed as a rapid 20 fold dilution into refold buffer (55 mM Tris pH 8.2, 10.56 mM NaCl, 0.44 mM KCl, 2.2 mM MgCl2, 2.2 mM CaCl2, 0.055% Peg3350, 550 mM L-Arginine, 1 mM GSH, 100 mcM GSSG) and stirred for 16 hrs at 4° C. The buffer was then exchanged by desalting using G50 Sephadex to 50 mM BisTris pH 6.5, 75 mM NaCl, 0.05% Tween 80.

To determine if the refolded enzymes were active, a sialyltransferase assay was performed. Transfer of sialic acid to the donor (asialo-bovine submaxillary mucin) was monitored using radiolabeled CMP-NAN. Chicken ST6GalNac1 expressed in a baculovirus system was used as a positive control.

Briefly, 40 μL of the reaction mix was added to 10 μL of enzyme sample and incubated at 37° C. for 1 hour. The glycoprotein was precipitated by adding 100 μL of phosphotungstic acid/15% TCA to the reaction with mixing. After centrifugation, supernatants were aspirated and discarded. Five hundred μL of 5% TCA was added to wash unincorporated CMP-$^{14}$C-sialic acid from the pellet. Reactions were centrifuged again and supernatants were aspirated and discarded. Pellets were resuspended using 100 μL of 10 N NaOH. One mL of 1 M Tris Buffer, pH 7.5 was added to the resuspended pellet and then the mixture was transferred to a scintillation vial. Five mL of scintillation fluid (Ecolume, ICN Biomedicals) was added and mixed well. The total counts added to a reaction was determined by adding 40 μL of reaction mix into a scintillation vial and adding 100 μL of 10 N NaOH, 1 mL of water, and 5 mL of scintillation fluid, and mixing well. Vials were counted for 1 minute. The reaction conditions are provided in Table 13.

TABLE 13

| Reagent | Manufacturer | Cat. No. | Amount per Assay Tube | Final Concentration in the Assay |
|---|---|---|---|---|
| CMP [$^{14}$C] Sialic Acid | Amersham | CFB-165 | 4 uL | 100,000 CPM |
| 7 mM CMP-Sialic Acid | Neose | AES 533pg.42 | 1.4 uL | 0.2 mM |
| 25 mg/mL Asialo-Bovine Submaxillary Mucin | Sigma, Hydrolyzed at Neose | M-3895 | 20 uL | 250-500 ug |
| 1 M Bis/Tris Buffer pH 6.5 | Sigma | B-9754 | 2.5 uL | 50 mM |
| 5 M NaCl | Sigma | S-7653 | 1 uL | 100 mM |
| dH2O | N/A | N/A | 11.1 uL | |

Total Reaction Mix Volume per Assay Tube: 40 uL

Figure 25:
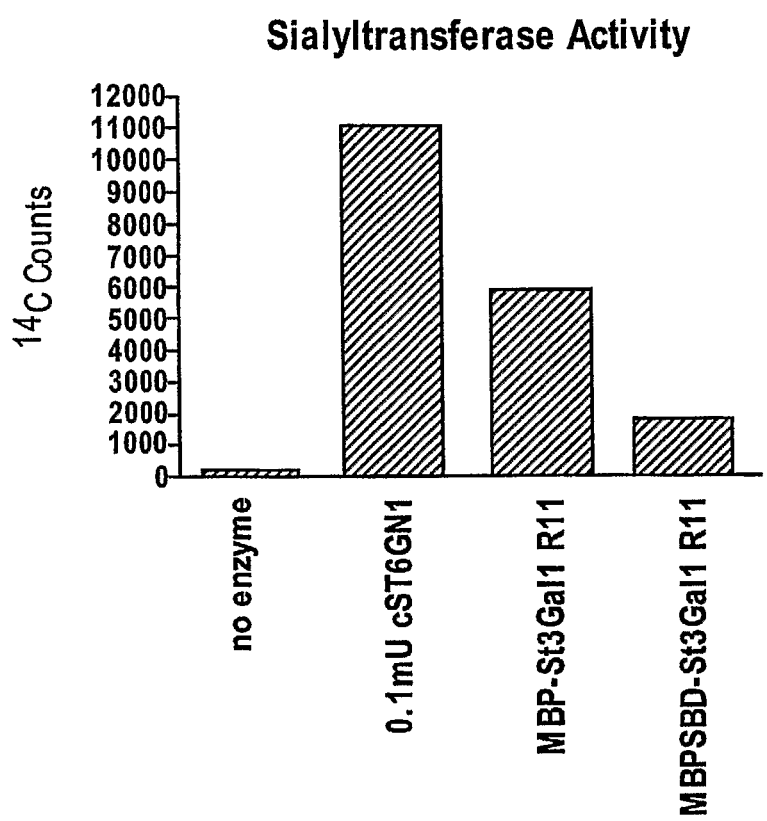
FIG. 25 provides the sialyltransferase activity of the MBP-ST3Gal3 fusion protein) and the MBP-SBD-ST3Gal3 fusion protein. positive and negative controls are also shown.

Results are shown in FIG. 25. Both refolded fusion proteins, MBP-pST3Gal1 and MBP-SBD-pST3Gal1 had detectable sialyltransferase activity.

Example 9

Refolding of MBP-ST6GalNAc1 Proteins

Eukaryotic ST6GalNAc I was fused to MPB. Briefly, five mouse ST6GalNAc I constructs were generated: D32, E52, S127, S186, and S201. Each construct was expressed behind the MBP-tag from the vector pcWin2-MBP, and differ in the extent of the 'stem' region included in the construct. D32 is the longest form, starting immediately downstream of the predicted amino-terminal transmembrane domain. S201 is the shortest, beginning shortly before the predicted start of the conserved catalytic domain.

In addition to the mouse constructs, human ST6GalNAc I K36 was also expressed as a fusion with MBP. The human construct begins just after the transmembrane domain. DNA encoding human ST6GalNAc1 from K36 to its c-terminus was isolated by PCR using the existing baculovirus expression vector as template, and cloned into the BamHI-XhoI sites within pcWin2-MBP.

For reference, the sequences for MBP-mST6GalNAcI S127 and MBP-hST6GalNAcI K36 are included in FIG. 26. In addition, FIG. 38 provides full length amino acid sequences for human ST6GalNAcI and for chicken ST6GalNAcI, and a sequence of the mouse ST6GalNAcI protein beginning at residue 32 of the native mouse protein.

Figure 40:
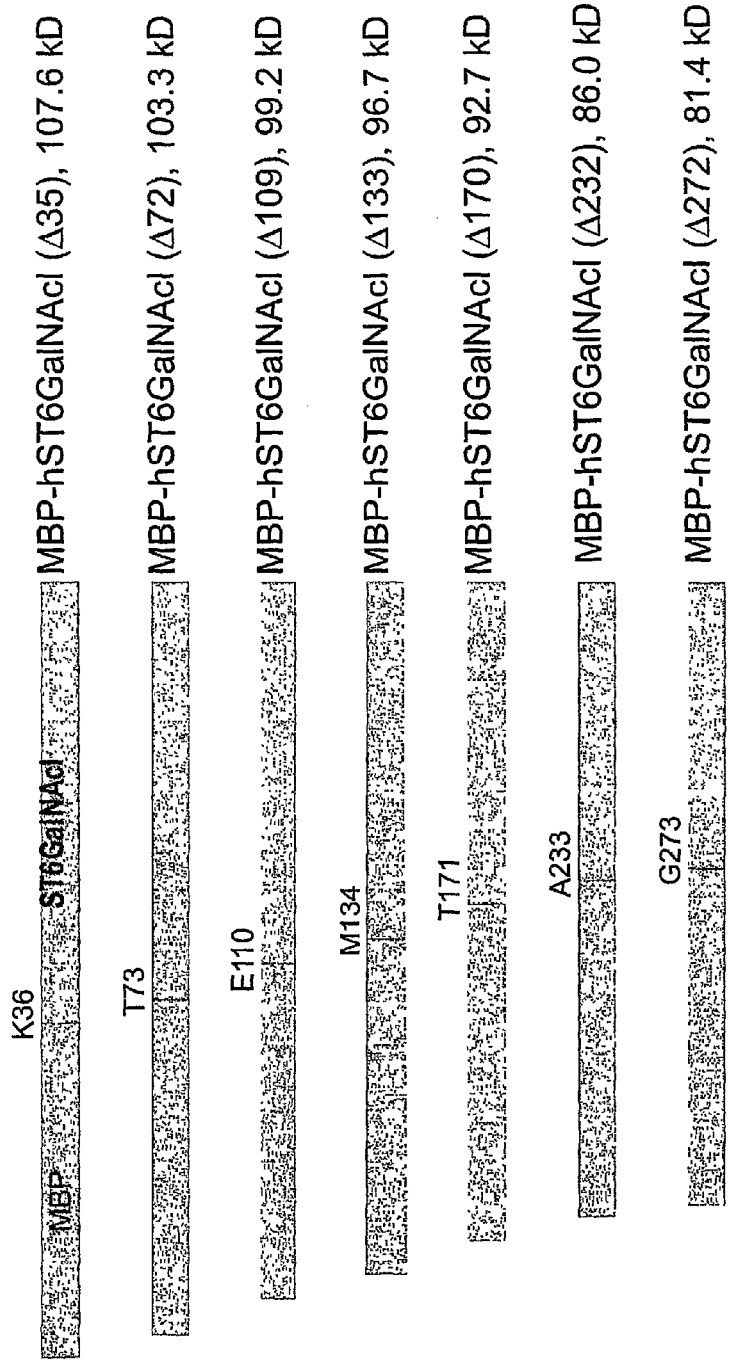
FIG. 40 shows a schematic of MBP fusion proteins including the human ST6GalNAcI truncation mutants.

Deletion mutants additional to those described above have been made and a complete list of preferred ST6GalNAcI for use in the invention is found is Table 14. FIG. 39 provides a schematic of a number of preferred human ST6GalNAcI truncation mutants. FIG. 40 shows a schematic of MBP fusion proteins including the human ST6GalNAcI truncation mutants.

TABLE 14

ST6GalNAcI Mutants

| | Truncation Site | Mutation |
|---|---|---|
| HUMAN | Δ35 | K36 |
| | Δ124 | K125 |
| | Δ257 | S258 |
| | Δ35 | K36 |
| | Δ72 | T73 |
| | Δ109 | E110 |
| | Δ133 | M134 |
| | Δ170 | T171 |
| | Δ232 | A233 |
| | Δ272 | G273 |

TABLE 14-continued

ST6GalNAcI Mutants

| | Truncation Site | Mutation |
|---|---|---|
| CHICKEN | Δ48 | Q49 |
| | Δ152 | V153 |
| | Δ225 | L226 |
| | Δ232 | T233 |
| MOUSE | Δ31 | D32 |
| | Δ51 | E52 |
| | Δ126 | S127 |
| | Δ185 | S186 |
| | Δ200 | S201 |

Figure 45:
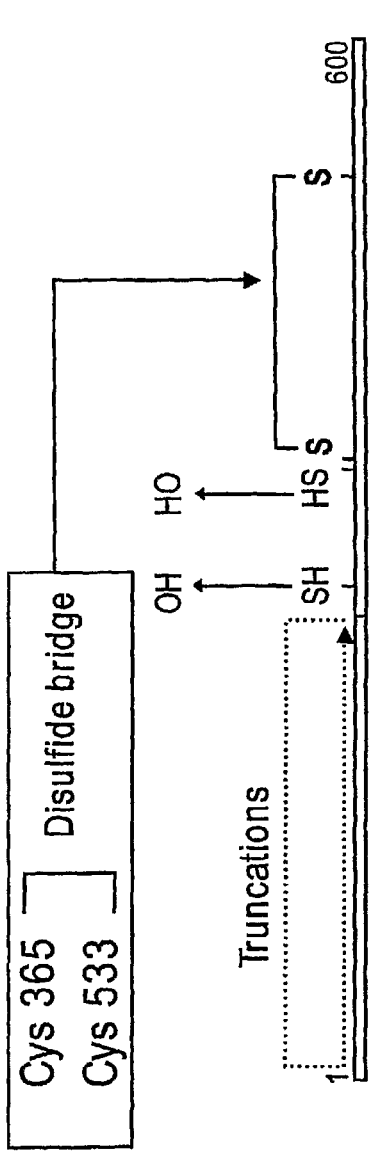
FIG. 45 shows the position of paired and unpaired cysteine residues in the human ST6GalNAcI protein. Single and double cysteine substitution are also shown, e.g., C280S, C362S, C362T, (C280S+C362S), and (C280S+C362T).

FIG. 45 shows the position of paired and unpaired cysteine residues in the human ST6GalNAcI protein. Single and double cysteine substitution are also shown, e.g., C280S, C362S, C362T, (C280S+C362S), and (C280S+C362T).

Initial expression studies showed that the ST6GalNAcI fusion proteins were expressed as insoluble proteins. To recover active recombinant enzyme, the inactive, insoluble proteins were isolated and refolded as described:

Logarithmically growing 0.5 L cultures of JM109 cells bearing either pcWin2-MBP-mST6GalNAcI D32, E52, S127, S186, or pcWin2-MBP-hST6GalNAcI K36 were induced with 1 mM IPTG overnight at 37° C. Cells were collected by centrifugation, and lysed by mechanical disruption in a microfluidizer in 100 mL of 20 mM Tris pH8, 5 mM EDTA. Insoluble matter was collected by centrifugation at 7000×g for 20 minutes. The supernatants were discarded, and the pellets were washed with a high salt buffer (20 mM Tris pH 7.4, 1M NaCl, 5 mM EDTA), detergent buffer (25 mM Tris pH 8, 1% Na-deoxycholate, 1% Triton x100, 100 mM NaCl, 5 mM EDTA), and TE (10 mM Tris pH 8, 1 mM EDTA). Each wash was in 100 mL, and the pellet was collected by centrifugation as described above. Following the washing, the inclusion body pellets were aliquoted and stored at −80° C.

To screen for conditions that allow proper refolding and thus recovery of ST6GalNAc I activity, aliquots of the mouse and human ST6GalNAcI fusion protein inclusion bodies were solubilized in 6M guanidine, 10 mM DTT, 1×TBS. Protein concentration was normalized by Bradford assay, and the solubilized proteins were transferred to a series of commercially-available protein refolding buffers. Refolds were carried out in 0.25 mL at 0.2 mg/mL overnight at 4° C. in a 96-well plate with shaking. The refolds were transferred to a 96-well dialysis plate (25000 MWCO) and dialyzed against 1×TBS, 0.05% Tween-80 for four hours at 4° C., followed by overnight dialysis against 10 mM BisTris pH 7.1, 100 mM NaCl, 0.05% Tween-80 at 4° C.

Refolded recombinant ST6GalNAcI fusion proteins were tested for activity in a 384-well solid phase activity assay. Briefly, the activity assay detects the ST6GalNAcI-mediated transfer of a biotinylated sialic acid from biotinylated CMP-NAN to the surface of an asialo-bovine submaxillary mucin-coated well in a 384-well plate. Each reaction (13.5 μL refold+1.5 μL 10× reaction buffer) was performed in quadruplicate. 10× reaction buffer was 0.2M BisTris ph 6.7, 25 mM MgCl2, 25 mM MnCl2, 0.5% Tween-80, and 1 mM donor. After overnight incubation at 37° C., the plate was washed with excess 1×TBS, 0.05% Tween-20, and biotin detected with europium-labeled streptavidin as per manufacturer's instructions (Perkin Elmer). Europium fluorescence levels retained on the plate, indicative of ST6GalNAcI activity, were documented with a Perkin Elmer Victor3V plate reader, and expression and activity results are summarized in Table 15. Three of the refolded ST6GalNAcI fusion proteins had detectable activity.

TABLE 15

Summary of refolded ST6GalNAcI fusion proteins tested for activity by solid phase assay.

| Construct | Refolded protein detected by SDS-PAGE | Refolded protein activity detected by solid phase assay |
|---|---|---|
| MBP-mST6GalNAcI D32 | + | − |
| MBP-mST6GalNAcI E52 | ++ | − |
| MBP-mST6GalNAcI S127 | +++ | + |
| MBP-mST6GalNAcI S186 | +/− | +/− |
| MBP-hST6GalNAcI K36 | +/− | + |

Example 10

Refolding of Core 1 GalT1 Proteins

Eukaryotic Core 1 GalT1 is fused to MPB or to the double tag, MBPSPD. The *drosophila* and human Core 1 GalT1 proteins are used. FIG. 41 provides the full length sequence of human Core 1 GalT1 protein. FIG. 42 provides the sequences of two *drosophila* Core 1 GalT1 proteins. Truncations of each enzyme are made throughout the stem region, i.e., starting with the full length stem region and deleting one amino acid at a time such that the smallest truncation comprises only a Core 1 GalT1 catalytic domain. Cysteine residues throughout the proteins' catalytic domain are also mutated one at a time to either serine or alanine residues. MBP fusions are made using the truncated proteins, the cysteine mutants or combinations of the two. Proteins are expressed in *E. coli* as inclusion bodies, are solubilized, and are then refolded using the methods described herein. Refolding is determined by measuring enzymatic activity. Active enzymes have been correctly refolded. Enzymatic activity of Core 1 GalT1 is measured as disclosed in Ju et al., *J. Biol. Chem.* 277:178-186 (2002), which is herein incorporated by reference for all purposes.

Example 11

One Pot Refolding of O-linked Glycosyltransferases

The O-linked Glycosyltransferases GalNAcT2, Core1 and ST3Gal1 can be collectively used to add a core 1 structure including a terminal sialic acid or sialic acid-PEG onto a serine or threonine residues of selected proteins including therapeutic proteins. The expression of these enzymes in *E. coli* and recovery of active enzymes from refolding inclusion bodies is useful for developing a cost effective scaleable process. Here we describe co-refolding two of these enzymes (MBP-GalNAcT2 and MBP-ST3Gal1) from *E. coli* inclusion bodies. The advantages of co-refolding include decreased reagent use and increased refolding efficiency.

Two strains of JM109 were selected for kanamycin resistance and determined to be carrying the appropriate expression plasmids that accumulate inclusion bodies of MBP-GalNAcT2 and MBP-ST3Gal1 upon induction with IPTG.

After separate overnight inductions with 1 mM IPTG, bacterial cells pellets were resuspended at a ratio of 1 g wet cell pellet per 10 mL of 20 mM Tris pH 8, 5 mM EDTA and lysed by mechanical disruption with two passes through a microfluidizer. Insoluble material, i.e., the inclusion bodies or IB's, was pelleted by centrifugation at 7000×G at 4° C. in the Sorvall RC3 for 30 minutes, and the supernatant discarded. A typical wash cycle consisted of completely resuspending the pellet in the wash buffer, and repeating the centrifugation for 15 minutes. The pellet was washed once in an excess volume (at least 10 mL (up to 20) per g original cell pellet) of high salt buffer (wash I: 10 mM Tris pH 7.4, 1 M NaCl, 5 mM EDTA), once in detergent buffer (wash II: 25 mM Tris pH 8, 100 mM NaCl, 1% Triton X100, 1% Na-deoxycholate, 5 mM EDTA), and (to remove traces of detergent in addition to washing the IBs) three times in wash buffer (wash III: 10 mM Tris pH 8, 5 mM EDTA).

Washed IB's were resuspended in solubilization buffer (8M Urea, 50 mM BisTris pH 6.5, 5 mM EDTA, 10 mM DTT) and adjusted to 4 mg/ml protein concentration. The urea protein solution was clarified by centrifugation at 14000×G for 5 minutes. Refolding was performed as a rapid dilution to 0.1 mg/ml in refold buffer (55 mM Tris pH 8.2, 10.56 mM NaCl, 0.44 mM KCl, 2.2 mM $MgCl_2$, 2.2 mM $CaCl_2$, 0.055% Peg3350, 550 mM L-Arginine, 1 mM GSH, 100 mcM GSSG) and stirred for 16 hrs at 4° C.

The experimental system was set up as follows: Refolding conditions were held constant while refolding either MBP-GalNAcT2 and MBP-ST3Gal1 separately or co-refolding in the same vessel. Following refold, the mixtures were desalted by low speed centrifugation using G50 Sephadex equilibrated in 50 mM BisTris pH 6.5, 75 mM NaCl, 0.05% Tween 80. Soluble material was recovered after centrifugation at top speed in a microfuge.

Figure 27A:
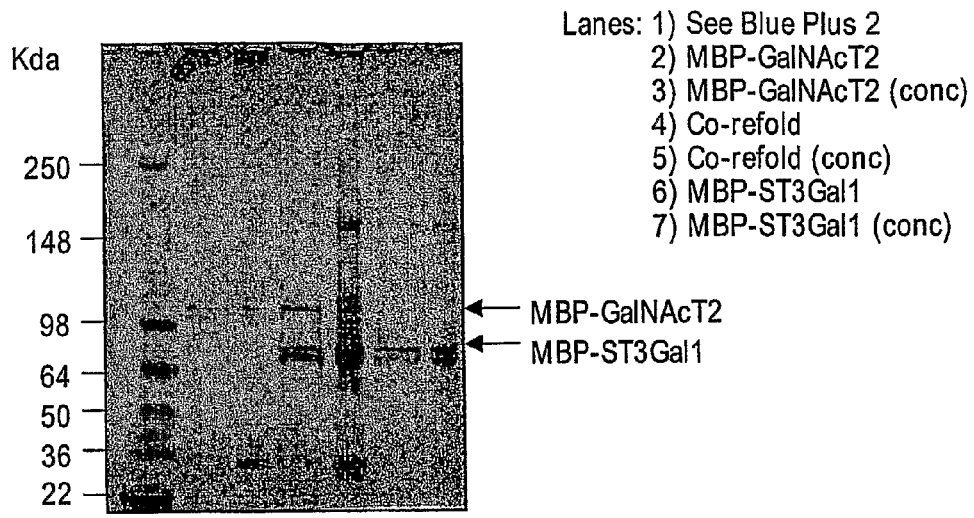
FIG. 27 provides SDS-PAGE gels of O-linked glycosyltransferase enzyme (A) concentrations after co-refolding and the (B) results of an enzyme assay after co-refolding. MBP-GalNAcT2 and MBP-ST3GalI were co-refolded together. Enzyme activity was tested after addition of Core I Gal T1 enzyme. The substrates were IFα-2b and 20K-Peg-CMP-NAN.

To determine the yield of soluble enzyme following the refolding, each reaction was subjected to SDS-PAGE analysis followed by staining with coomassie blue to visualize the polypeptides (FIG. 27A). Results show that co-refolding increases the yield of soluble enzymes (lanes for co-refold vs separate).

Figure 27B:
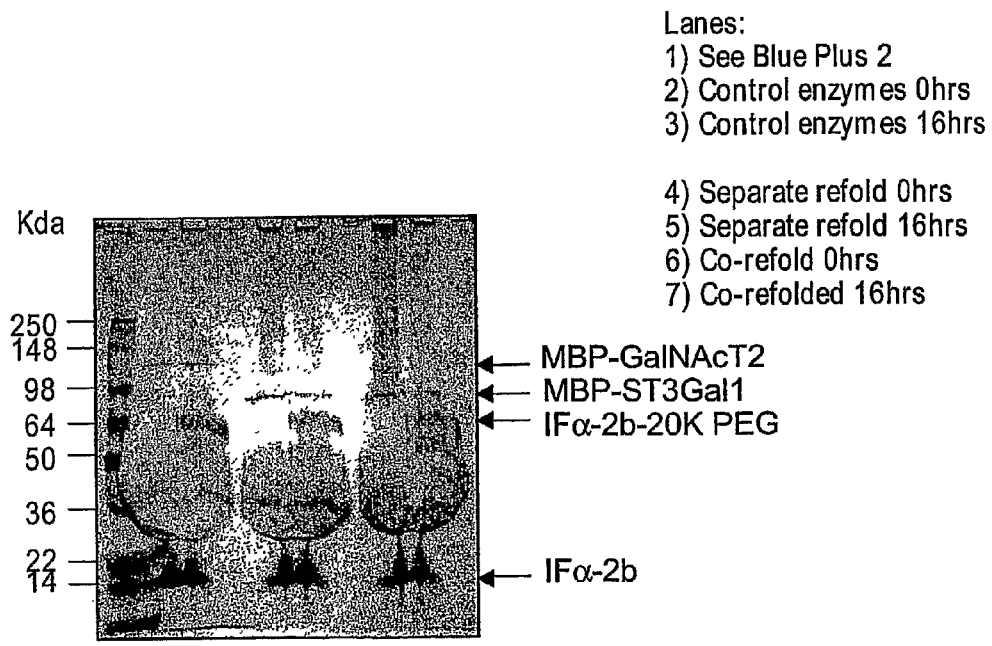
Figure 28:
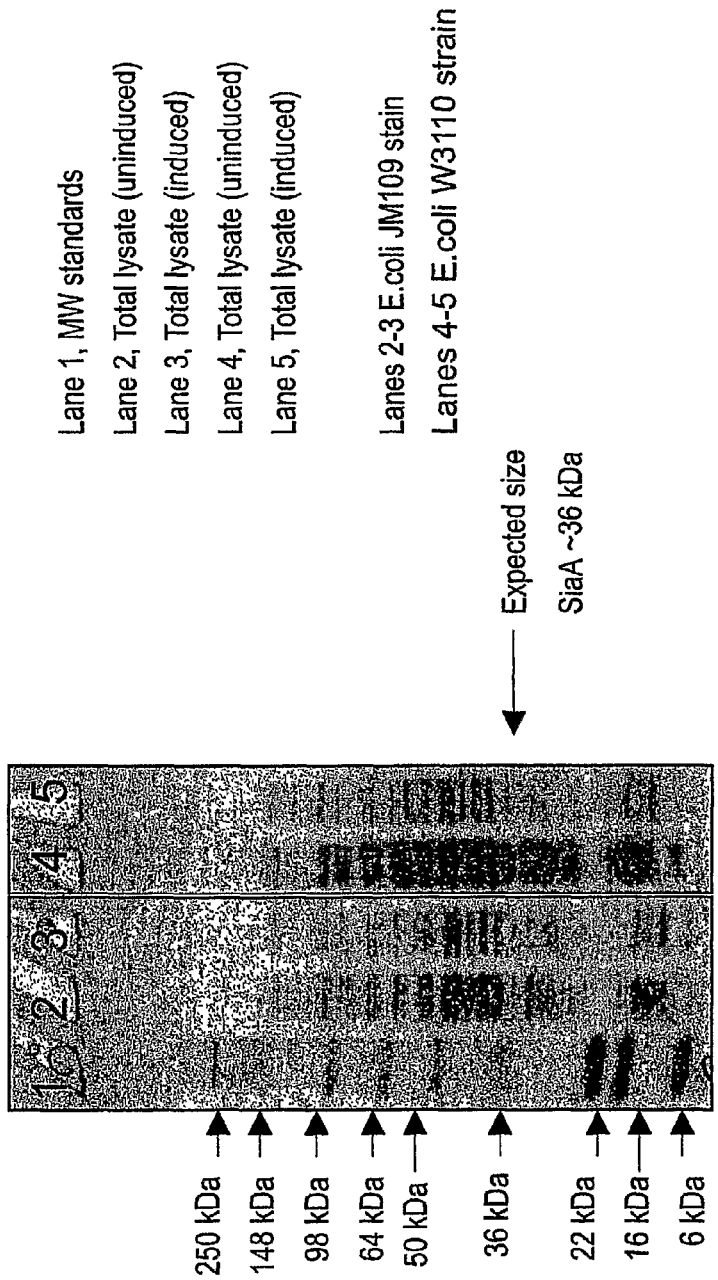
FIG. 28 provides an SDS-PAGE gel showing expression of the native SiaA protein in *E. coli* before and after induction with IPTG.
Figure 29:
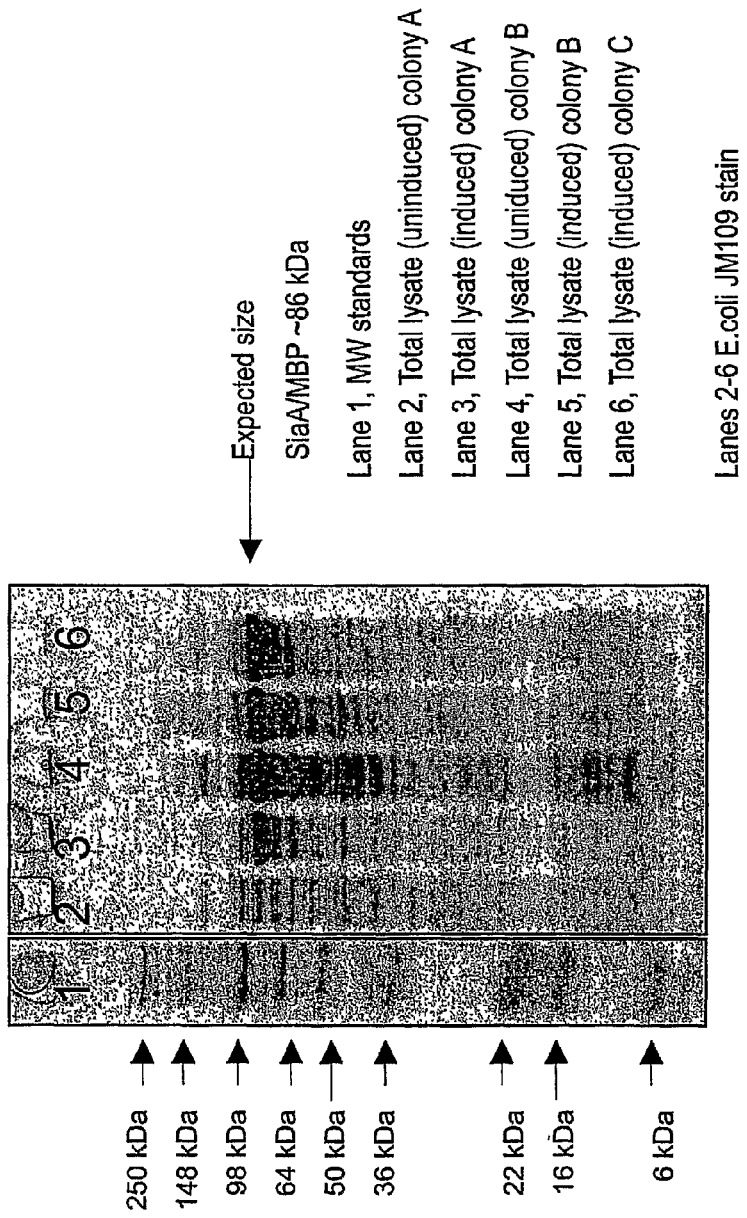
FIG. 29 provides an SDS-PAGE gel showing expression of an MBP-SiaA fusion protein in *E. coli* before and after induction with IPTG.

In the second experiment, 6 µg of the therapeutic protein IFα-2b was subjected to a one pot three enzyme pegylation reaction. The concentration of enzymes used for this reaction are 1.4 ug MBP-GalNAcT2, 0.5 mu BV Core1, and 1.4 ug MBP-ST3Gal1, the sugars used are 1.2 ug UDP-GalNac and 1.2 ug UDP-Gal and 125 ug 20K-Peg-CMP-NAN in a 20 ul reaction for either 0 hrs or 16 hrs using the following reaction buffer (50 mM MES pH 6.2, 150 mM NaCl, 10 mM MnCl2). The extent of pegylation of IFα-2b in half of the reaction was visualized by coomassie blue staining following SDS-PAGE (FIG. 27B). The experiment was designed to directly compare the one pot pegylation using either the combination of individually refolded enzymes to the co-refolded enzymes holding all other components and concentrations constant. Results demonstrate an increase in pegylated product in the reaction where the enzymes were co-refolded compared to being refolded separately (lane 5 vs 7).

Example 12

Enhanced Expression of MBP-SiaA Fusion Protein

The SiaA gene from non-typeable *Haemophilus influenzae* was codon optimized for expression in *E. coli*. The gene was digested with NdeI and EcoRI, agarose gel purified and ligated into NdeI/EcoRI digested pcWin2, prior to transformation into *E. coli* strain JM109 or W3110. Plasmid DNA was isolated from the recombinants and screened with NdeI and EcoRI. One JM109 and one W3110 colony each containing the correct construct was seeded into 2 ml of animal free LB containing 10 µg/ml kanamycin sulfate and grown for 6 h at 37° C. at 250 RPM of agitation. A 100 µl aliquot was removed, centrifuged 2 minutes at 10,000×g and the supernatant discarded. This pellet was frozen at −20° C. and represents the uninduced cell. IPTG was added to the remainder of the culture at a final concentration of 1 mM IPTG and incubated for 2 h at 37° C. and 250 RPM of agitation. A 100 µl aliquot was removed and processed as described (represents induced cell).

The restriction sites at the ends of the SiaA gene were changed to 5'BamHI and the 3' end maintained as EcoRI using PCR. The PCR product was digested with BamHI and EcoRI, purified by agarose gel electrophoresis and ligated into BamHI/EcoRI digested pcWin2 MBP. JM109 cells transformed with this ligation reaction were cultured and plasmid DNA was isolated. The plasmid DNA was screened using BamHI and EcoRI. Three colonies containing the correct structure were seeded into 2 ml of animal free LB containing 10 µg/ml kanamycin sulfate and grown for 6 h at 37° C. at 250 RPM of agitation. A 100 µl aliquot was removed, centrifuged 2 minutes at 10,000×g and the supernatant discarded. This pellet was frozen at −20° C. and represents the uninduced cell. IPTG was added to the remainder of the culture at a final concentration of 1 mM IPTG and incubated for 2 h at 37° C. and 250 RPM of agitation. A 100 µl aliquot was removed and processed as described (represents induced cell).

Each 100 µl aliquot was boiled 5 minutes in 100 µl of SDS-PAGE sample buffer containing 50 mM DTT. The samples were loaded on 4-20% acrylamide Tris-glycine gel (Invitrogen) and electrophoresed for ~2 h, stained with Invitrogen Simply Blue Safestain, destained with water and scanned. Figure X shows undetectable levels of expression of native SiaA upon induction, whereas Figure Y shows high levels of expression of SiaA fused to MBP upon IPTG induction. This result demonstrates that MBP supplied from the pcWin2 MBP vector drives high level protein expression.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

```
<160> NUMBER OF SEQ ID NOS: 80

<210> SEQ ID NO 1
<211> LENGTH: 445
<212> TYPE: PRT
<213> ORGANISM: Homo sapiens
<220> FEATURE:
<223> OTHER INFORMATION: human beta-1,2-N-acetylglucosaminyltransferase
      I (GnTI, GnT1)

<400> SEQUENCE: 1

Met Leu Lys Lys Gln Ser Ala Gly Leu Val Leu Trp Gly Ala Ile Leu
  1               5                  10                  15

Phe Val Ala Trp Asn Ala Leu Leu Leu Phe Phe Trp Thr Arg Pro
                 20                  25                  30

Ala Pro Gly Arg Pro Pro Ser Val Ser Ala Leu Asp Gly Asp Pro Ala
             35                  40                  45

Ser Leu Thr Arg Glu Val Ile Arg Leu Ala Gln Asp Ala Glu Val Glu
         50                  55                  60

Leu Glu Arg Gln Arg Gly Leu Leu Gln Gln Ile Gly Asp Ala Leu Ser
```

| | | | | | | | | | | | | | | | |
|---|---|---|---|---|---|---|---|---|---|---|---|---|---|---|---|

Ser Gln Arg Gly Arg Val Pro Thr Ala Ala Pro Pro Ala Gln Pro Arg
    65                  70                  75                  80

Val Pro Val Thr Pro Ala Pro Val Ile Pro Ile Leu Val Ile Ala
            85                  90                  95

Cys Asp Arg Ser Thr Val Arg Arg Cys Leu Asp Lys Leu Leu His Tyr
            100                 105                 110

115                 120                 125

Arg Pro Ser Ala Glu Leu Phe Pro Ile Ile Val Ser Gln Asp Cys Gly
            130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
            165                 170                 175

Arg Lys Phe Gln Gly Tyr Tyr Lys Ile Ala Arg His Tyr Arg Trp Ala
            180                 185                 190

Leu Gly Gln Val Phe Arg Gln Phe Arg Phe Pro Ala Ala Val Val Val
            195                 200                 205

Glu Asp Asp Leu Glu Val Ala Pro Asp Phe Phe Glu Tyr Phe Arg Ala
210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Arg Pro Glu
            245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
            275                 280                 285

Asp Asp Trp Met Arg Arg Pro Glu Gln Arg Gln Gly Arg Ala Cys Ile
            290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
            325                 330                 335

Gln Phe Val His Phe Thr Gln Leu Asp Leu Ser Tyr Leu Gln Arg Glu
            340                 345                 350

Ala Tyr Asp Arg Asp Phe Leu Ala Arg Val Tyr Gly Ala Pro Gln Leu
            355                 360                 365

Gln Val Glu Lys Val Arg Thr Asn Asp Arg Lys Glu Leu Gly Glu Val
            370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
            405                 410                 415

Arg Gly Ile Val Thr Phe Gln Phe Arg Gly Arg Val His Leu Ala
            420                 425                 430

Pro Pro Pro Thr Trp Glu Gly Tyr Asp Pro Ser Trp Asn
            435                 440                 445

<210> SEQ ID NO 2
<211> LENGTH: 447
<212> TYPE: PRT
<213> ORGANISM: Oryctolagus cuniculus
<220> FEATURE:
<223> OTHER INFORMATION: rabbit beta-1,2-N-acetylglucosaminyl-
      transferase I (GnTI, GnT1)

<400> SEQUENCE: 2

```
Met Leu Lys Lys Gln Ser Ala Gly Leu Val Leu Trp Gly Ala Ile Leu
 1               5                  10                  15

Phe Val Ala Trp Asn Ala Leu Leu Leu Phe Phe Trp Thr Arg Pro
             20                  25                  30

Val Pro Ser Arg Leu Pro Ser Asp Asn Ala Leu Asp Asp Pro Ala
             35                  40                  45

Ser Leu Thr Arg Glu Val Ile Arg Leu Ala Gln Asp Ala Glu Val Glu
 50                  55                  60

Leu Glu Arg Gln Arg Gly Leu Leu Gln Gln Ile Arg Glu His His Ala
 65                  70                  75                  80

Leu Trp Ser Gln Arg Trp Lys Val Pro Thr Ala Ala Pro Pro Ala Gln
                 85                  90                  95

Pro His Val Pro Val Thr Pro Pro Ala Val Ile Pro Ile Leu Val
            100                 105                 110

Ile Ala Cys Asp Arg Ser Thr Val Arg Arg Cys Leu Asp Lys Leu Leu
            115                 120                 125

His Tyr Arg Pro Ser Ala Glu Leu Phe Pro Ile Ile Val Ser Gln Asp
130                 135                 140

Cys Gly His Glu Glu Thr Ala Gln Val Ile Ala Ser Tyr Gly Ser Ala
145                 150                 155                 160

Val Thr His Ile Arg Gln Pro Asp Leu Ser Asn Ile Ala Val Gln Pro
                165                 170                 175

Asp His Arg Lys Phe Gln Gly Tyr Tyr Lys Ile Ala Arg His Tyr Arg
            180                 185                 190

Trp Ala Leu Gly Gln Ile Phe His Asn Phe Asn Tyr Pro Ala Ala Val
            195                 200                 205

Val Val Glu Asp Asp Leu Glu Val Ala Pro Asp Phe Phe Glu Tyr Phe
210                 215                 220

Gln Ala Thr Tyr Pro Leu Leu Lys Ala Asp Pro Ser Leu Trp Cys Val
225                 230                 235                 240

Ser Ala Trp Asn Asp Asn Gly Lys Glu Gln Met Val Asp Ser Ser Lys
                245                 250                 255

Pro Glu Leu Leu Tyr Arg Thr Asp Phe Phe Pro Gly Leu Gly Trp Leu
            260                 265                 270

Leu Leu Ala Glu Leu Trp Ala Glu Leu Glu Pro Lys Trp Pro Lys Ala
            275                 280                 285

Phe Trp Asp Asp Trp Met Arg Arg Pro Glu Gln Arg Lys Gly Arg Ala
    290                 295                 300

Cys Val Arg Pro Glu Ile Ser Arg Thr Met Thr Phe Gly Arg Lys Gly
305                 310                 315                 320

Val Ser His Gly Gln Phe Phe Asp Gln His Leu Lys Phe Ile Lys Leu
                325                 330                 335

Asn Gln Gln Phe Val Pro Phe Thr Gln Leu Asp Leu Ser Tyr Leu Gln
            340                 345                 350

Gln Glu Ala Tyr Asp Arg Asp Phe Leu Ala Arg Val Tyr Gly Ala Pro
            355                 360                 365

Gln Leu Gln Val Glu Lys Val Arg Thr Asn Asp Arg Lys Glu Leu Gly
            370                 375                 380

Glu Val Arg Val Gln Tyr Thr Gly Arg Asp Ser Phe Lys Ala Phe Ala
385                 390                 395                 400

Lys Ala Leu Gly Val Met Asp Asp Leu Lys Ser Gly Val Pro Arg Ala
```

```
                    405                 410                 415
Gly Tyr Arg Gly Ile Val Thr Phe Leu Phe Arg Gly Arg Val His
            420                 425                 430

Leu Ala Pro Pro Gln Thr Trp Asp Gly Tyr Asp Pro Ser Trp Thr
            435                 440                 445

<210> SEQ ID NO 3
<211> LENGTH: 342
<212> TYPE: PRT
<213> ORGANISM: Artificial Sequence
<220> FEATURE:
<223> OTHER INFORMATION: Description of Artificial Sequence:
      beta-1,2-N-acetylglucosaminyltransferase I (GnTI,
      GnT1) Cys121Ser mutant

<400> SEQUENCE: 3

Ala Val Ile Pro Ile Leu Val Ile Ala Cys Asp Arg Ser Thr Val Arg
 1               5                  10                  15

Arg Ser Leu Asp Lys Leu Leu His Tyr Arg Pro Ser Ala Glu Leu Phe
            20                  25                  30

Pro Ile Ile Val Ser Gln Asp Cys Gly His Glu Glu Thr Ala Gln Ala
        35                  40                  45

Ile Ala Ser Tyr Gly Ser Ala Val Thr His Ile Arg Gln Pro Asp Leu
    50                  55                  60

Ser Ser Ile Ala Val Pro Pro Asp His Arg Lys Phe Gln Gly Tyr Tyr
65                  70                  75                  80

Lys Ile Ala Arg His Tyr Arg Trp Ala Leu Gly Gln Val Phe Arg Gln
                85                  90                  95

Phe Arg Phe Pro Ala Ala Val Val Glu Asp Asp Leu Glu Val Ala
            100                 105                 110

Pro Asp Phe Phe Glu Tyr Phe Arg Ala Thr Tyr Pro Leu Leu Lys Ala
        115                 120                 125

Asp Pro Ser Leu Trp Cys Val Ser Ala Trp Asn Asp Asn Gly Lys Glu
    130                 135                 140

Gln Met Val Asp Ala Ser Arg Pro Glu Leu Leu Tyr Arg Thr Asp Phe
145                 150                 155                 160

Phe Pro Gly Leu Gly Trp Leu Leu Leu Ala Glu Leu Trp Ala Glu Leu
                165                 170                 175

Glu Pro Lys Trp Pro Lys Ala Phe Trp Asp Asp Trp Met Arg Arg Pro
            180                 185                 190

Glu Gln Arg Gln Gly Arg Ala Cys Ile Arg Pro Glu Ile Ser Arg Thr
        195                 200                 205

Met Thr Phe Gly Arg Lys Gly Val Ser His Gly Gln Phe Phe Asp Gln
    210                 215                 220

His Leu Lys Phe Ile Lys Leu Asn Gln Gln Phe Val His Phe Thr Gln
225                 230                 235                 240

Leu Asp Leu Ser Tyr Leu Gln Arg Glu Ala Tyr Asp Arg Asp Phe Leu
                245                 250                 255

Ala Arg Val Tyr Gly Ala Pro Gln Leu Gln Val Glu Lys Val Arg Thr
            260                 265                 270

Asn Asp Arg Lys Glu Leu Gly Glu Val Arg Val Gln Tyr Thr Gly Arg
        275                 280                 285

Asp Ser Phe Lys Ala Phe Ala Lys Ala Leu Gly Val Met Asp Asp Leu
    290                 295                 300

Lys Ser Gly Val Pro Arg Ala Gly Tyr Arg Gly Ile Val Thr Phe Gln
305                 310                 315                 320
```

Phe Pro Gly Arg Arg Val His Leu Ala Pro Pro Pro Thr Trp Glu Gly
                325                 330                 335

Tyr Asp Pro Ser Trp Asn
            340

<210> SEQ ID NO 4
<211> LENGTH: 1029
<212> TYPE: DNA
<213> ORGANISM: Artificial Sequence
<220> FEATURE:
<223> OTHER INFORMATION: Description of Artificial Sequence:
      beta-1,2-N-acetylglucosaminyltransferase I (GnTI,
      GnT1) Cys121Ser mutant

<400> SEQUENCE: 4

| | |
|---|---|
| gcggtgattc ccatcctggt catcgcctgt gaccgcagca ctgttcggcg ctctctagac | 60 |
| aagctgctgc attatcggcc ctcggctgag ctcttcccca tcatcgttag ccaggactgc | 120 |
| gggcacgagg agacggccca ggccatcgcc tcctacggca gcgcggtcac gcacatccgg | 180 |
| cagcccgacc tgagcagcat tgcggtgccg ccggaccacc gcaagttcca gggctactac | 240 |
| aagatcgcgc ccactaccg ctgggcgctg ggccaggtct tccggcagtt tcgcttcccc | 300 |
| gcggccgtgg tggtggagga tgacctggag gtggccccgg acttcttcga gtactttcgg | 360 |
| gccacctatc cgctgctgaa ggccgacccc tccctgtggt gcgtctcggc ctggaatgac | 420 |
| aacggcaagg agcagatggt ggacgccagc aggcctgagc tgctctaccg caccgacttt | 480 |
| ttccctggcc tgggctggct gctgttggcc gagctctggg ctgagctgga gcccaagtgg | 540 |
| ccaaaggcct tctgggacga ctggatgcgg cggccggagc agcggcaggg gcgggcctgc | 600 |
| atacgccctg agatctcaag aacgatgacc tttggccgca agggtgtgag ccacgggcag | 660 |
| ttctttgacc agcacctcaa gtttatcaag ctgaaccagc agtttgtgca cttcacccag | 720 |
| ctggacctgt cttacctgca gcgggaggcc tatgaccgag atttcctcgc ccgcgtctac | 780 |
| ggtgctcccc agctgcaggt ggagaaagtg aggaccaatg accggaagga gctggggggag | 840 |
| gtgcgggtgc agtatacggg cagggacagc ttcaaggctt cgccaaggc tctgggtgtc | 900 |
| atggatgacc ttaagtcggg ggttccgaga gctggctacc ggggtattgt caccttccag | 960 |
| ttcccgggcc gccgtgtcca cctggcgccc caccgacgt gggagggcta tgatcctagc | 1020 |
| tggaattag | 1029 |

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence:unpaired
      cysteine mutation Cys121Ser mutant region

<400> SEQUENCE: 5

Ser Thr Val Arg Arg Ser Leu Asp Lys Leu Leu His
 1               5                  10

<210> SEQ ID NO 6
<211> LENGTH: 342
<212> TYPE: PRT
<213> ORGANISM: Artificial Sequence
<220> FEATURE:
<223> OTHER INFORMATION: Description of Artificial Sequence:
      beta-1,2-N-acetylglucosaminyltransferase I (GnTI,
      GnT1) Cys121Asp mutant

<400> SEQUENCE: 6

```
Ala Val Ile Pro Ile Leu Val Ile Ala Cys Asp Arg Ser Thr Val Arg
  1               5                  10                  15
Arg Asp Leu Asp Lys Leu Leu His Tyr Arg Pro Ser Ala Glu Leu Phe
             20                  25                  30
Pro Ile Ile Val Ser Gln Asp Cys Gly His Glu Thr Ala Gln Ala
         35                  40                  45
Ile Ala Ser Tyr Gly Ser Ala Val Thr His Ile Arg Gln Pro Asp Leu
 50                  55                  60
Ser Ser Ile Ala Val Pro Pro Asp His Arg Lys Phe Gln Gly Tyr Tyr
 65                  70                  75                  80
Lys Ile Ala Arg His Tyr Arg Trp Ala Leu Gly Val Phe Arg Gln
                 85                  90                  95
Phe Arg Phe Pro Ala Ala Val Val Glu Asp Leu Glu Val Ala
                100                 105                 110
Pro Asp Phe Phe Glu Tyr Phe Arg Ala Thr Tyr Pro Leu Leu Lys Ala
            115                 120                 125
Asp Pro Ser Leu Trp Cys Val Ser Ala Trp Asn Asp Asn Gly Lys Glu
130                 135                 140
Gln Met Val Asp Ala Ser Arg Pro Glu Leu Leu Tyr Arg Thr Asp Phe
145                 150                 155                 160
Phe Pro Gly Leu Gly Trp Leu Leu Ala Glu Leu Trp Ala Glu Leu
                165                 170                 175
Glu Pro Lys Trp Pro Lys Ala Phe Trp Asp Asp Trp Met Arg Arg Pro
            180                 185                 190
Glu Gln Arg Gln Gly Arg Ala Cys Ile Arg Pro Glu Ile Ser Arg Thr
        195                 200                 205
Met Thr Phe Gly Arg Lys Gly Val Ser His Gly Gln Phe Phe Asp Gln
            210                 215                 220
His Leu Lys Phe Ile Lys Leu Asn Gln Gln Phe Val His Phe Thr Gln
225                 230                 235                 240
Leu Asp Leu Ser Tyr Leu Gln Arg Glu Ala Tyr Asp Arg Asp Phe Leu
                245                 250                 255
Ala Arg Val Tyr Gly Ala Pro Gln Leu Gln Val Glu Lys Val Arg Thr
                260                 265                 270
Asn Asp Arg Lys Glu Leu Gly Glu Val Arg Val Gln Tyr Thr Gly Arg
            275                 280                 285
Asp Ser Phe Lys Ala Phe Ala Lys Ala Leu Gly Val Met Asp Asp Leu
290                 295                 300
Lys Ser Gly Val Pro Arg Ala Gly Tyr Arg Gly Ile Val Thr Phe Gln
305                 310                 315                 320
Phe Pro Gly Arg Arg Val His Leu Ala Pro Pro Thr Trp Glu Gly
                325                 330                 335
Tyr Asp Pro Ser Trp Asn
            340
```

<210> SEQ ID NO 7
<211> LENGTH: 1029
<212> TYPE: DNA
<213> ORGANISM: Artificial Sequence
<220> FEATURE:
<223> OTHER INFORMATION: Description of Artificial Sequence: beta-1,2-N-acetylglucosaminyltransferase I (GnTI, GnT1) Cys121Asp mutant

<400> SEQUENCE: 7

```
gcggtgattc ccatcctggt catcgcctgt gaccgcagca ctgttcggcg cgatctagac    60
aagctgctgc attatcggcc ctcggctgag ctcttcccca tcatcgttag ccaggactgc   120
gggcacgagg agacggccca ggccatcgcc tcctacggca gcgcggtcac gcacatccgg   180
cagcccgacc tgagcagcat tgcggtgccg ccggaccacc gcaagttcca gggctactac   240
aagatcgcgc gccactaccg ctgggcgctg gccaggtct tccggcagtt tcgcttcccc   300
gcggccgtgt ggtggagga tgacctggag gtggccccgg acttcttcga gtactttcgg   360
gccacctatc cgctgctgaa ggccgacccc tccctgtggt gcgtctcggc ctggaatgac   420
aacggcaagg agcagatggt ggacgccagc aggcctgagc tgctctaccg caccgacttt   480
ttccctggcc tgggctggct gctgttggcc gagctctggg ctgagctgga gcccaagtgg   540
ccaaaggcct tctgggacga ctggatgcgc cggccggagc agcggcaggg gcgggcctgc   600
atacgccctg agatctcaag aacgatgacc tttggccgca agggtgtgag ccacgggcag   660
ttctttgacc agcaccctcaa gtttatcaag ctgaaccagc agtttgtgca cttcacccag   720
ctggacctgt cttacctgca gcgggaggcc tatgaccgag atttcctcgc ccgcgtctac   780
ggtgctcccc agctgcaggt ggagaaagtg aggaccaatg accggaagga gctgggggag   840
gtgcgggtgc agtatacggg cagggacagc ttcaaggctt cgccaaggc tctgggtgtc   900 atggatgacc ttaagtcggg ggttccgaga gctggctacc ggggtattgt caccttccag   960
ttcccgggcc gccgtgtcca cctggcgccc ccaccgacgt gggagggcta tgatcctagc  1020
tggaattag                                                          1029
```

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:unpaired
cysteine mutation Cys121Asp mutant region

<400> SEQUENCE: 8

Ser Thr Val Arg Arg Asp Leu Asp Lys Leu Leu His
1               5                   10

<210> SEQ ID NO 9
<211> LENGTH: 342
<212> TYPE: PRT
<213> ORGANISM: Artificial Sequence
<220> FEATURE:
<223> OTHER INFORMATION: Description of Artificial Sequence:
beta-1,2-N-acetylglucosaminyltransferase I (GnTI,
GnT1) Cys121Thr mutant

<400> SEQUENCE: 9

Ala Val Ile Pro Ile Leu Val Ile Ala Cys Asp Arg Ser Thr Val Arg
1               5                   10                  15

Arg Thr Leu Asp Lys Leu Leu His Tyr Arg Pro Ser Ala Glu Leu Phe
                20                  25                  30

Pro Ile Ile Val Ser Gln Asp Cys Gly His Glu Glu Thr Ala Gln Ala
            35                  40                  45

Ile Ala Ser Tyr Gly Ser Ala Val Thr His Ile Arg Gln Pro Asp Leu
        50                  55                  60

Ser Ser Ile Ala Val Pro Pro Asp His Arg Lys Phe Gln Gly Tyr Tyr
65                  70                  75                  80

Lys Ile Ala Arg His Tyr Arg Trp Ala Leu Gly Gln Val Phe Arg Gln

```
                    85                  90                  95
Phe Arg Phe Pro Ala Val Val Glu Asp Asp Leu Glu Val Ala
            100                 105                 110
Pro Asp Phe Glu Tyr Phe Arg Ala Thr Tyr Pro Leu Leu Lys Ala
            115                 120                 125
Asp Pro Ser Leu Trp Cys Val Ser Ala Trp Asn Asp Asn Gly Lys Glu
            130                 135                 140
Gln Met Val Asp Ala Ser Arg Pro Glu Leu Leu Tyr Arg Thr Asp Phe
145                 150                 155                 160
Phe Pro Gly Leu Gly Trp Leu Leu Leu Ala Glu Leu Trp Ala Glu Leu
                165                 170                 175
Glu Pro Lys Trp Pro Lys Ala Phe Trp Asp Asp Trp Met Arg Arg Pro
            180                 185                 190
Glu Gln Arg Gln Gly Arg Ala Cys Ile Arg Pro Glu Ile Ser Arg Thr
            195                 200                 205
Met Thr Phe Gly Arg Lys Gly Val Ser His Gly Gln Phe Phe Asp Gln
            210                 215                 220
His Leu Lys Phe Ile Lys Leu Asn Gln Gln Phe Val His Phe Thr Gln
225                 230                 235                 240
Leu Asp Leu Ser Tyr Leu Gln Arg Glu Ala Tyr Asp Arg Asp Phe Leu
                245                 250                 255
Ala Arg Val Tyr Gly Ala Pro Gln Leu Gln Val Glu Lys Val Arg Thr
            260                 265                 270
Asn Asp Arg Lys Glu Leu Gly Glu Val Arg Val Gln Tyr Thr Gly Arg
            275                 280                 285
Asp Ser Phe Lys Ala Phe Ala Lys Ala Leu Gly Val Met Asp Asp Leu
            290                 295                 300
Lys Ser Gly Val Pro Arg Ala Gly Tyr Arg Gly Ile Val Thr Phe Gln
305                 310                 315                 320
Phe Pro Gly Arg Arg Val His Leu Ala Pro Pro Thr Trp Glu Gly
                325                 330                 335
Tyr Asp Pro Ser Trp Asn
            340

<210> SEQ ID NO 10
<211> LENGTH: 1029
<212> TYPE: DNA
<213> ORGANISM: Artificial Sequence
<220> FEATURE:
<223> OTHER INFORMATION: Description of Artificial Sequence:
      beta-1,2-N-acetylglucosaminyltransferase I (GnTI,
      GnT1) Cys121Thr mutant

<400> SEQUENCE: 10
gcggtgattc ccatcctggt catcgcctgt gaccgcagca ctgttcggcg cactctagac        60
aagctgctgc attatcggcc ctcggctgag ctcttcccca tcatcgttag ccaggactgc      120
gggcacgagg agacggccca ggccatcgcc tcctacggca gcgcggtcac gcacatccgg      180
cagcccgacc tgagcagcat gcggtgccgc ccggaccacc gcaagttcca gggctactac      240
aagatcgcgc gccactaccg ctgggcgctg gccaggtct ccggcagtt tcgcttcccc        300 gcggccgtgg tggtggagga tgacctggag gtggccccgg acttcttcga gtactttcgg      360
gccacctatc cgctgctgaa ggccgacccc tccctgtggt gcgtctcggc ctggaatgac      420
aacggcaagg agcagatggt ggacgccagc aggcctgagc tgctctaccg caccgacttt      480
ttccctggcc tgggctggct gctgttggcc gagctctggg ctgagctgga gcccaagtgg      540
```

```
ccaaaggcct tctgggacga ctggatgcgg cggccggagc agcggcaggg gcgggcctgc    600
atacgccctg agatctcaag aacgatgacc tttggccgca agggtgtgag ccacgggcag    660
ttctttgacc agcacctcaa gtttatcaag ctgaaccagc agtttgtgca cttcacccag    720
ctggacctgt cttacctgca gcggaggcc tatgaccgag atttcctcgc cgcgtctac     780 ggtgctcccc agctgcaggt ggagaaagtg aggaccaatg accggaagga gctgggggag    840
gtgcgggtgc agtatacggg cagggacagc ttcaaggctt cgccaaggc tctgggtgtc     900 atggatgacc ttaagtcggg ggttccgaga gctggctacc ggggtattgt caccttccag    960
ttcccgggcc gccgtgtcca cctggcgccc ccaccgacgt gggagggcta tgatcctagc   1020
tggaattag                                                          1029
```

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:unpaired
      cysteine mutation Cys121Thr mutant region

<400> SEQUENCE: 11

Ser Thr Val Arg Arg Thr Leu Asp Lys Leu Leu His
 1               5                  10

<210> SEQ ID NO 12
<211> LENGTH: 342
<212> TYPE: PRT
<213> ORGANISM: Artificial Sequence
<220> FEATURE:
<223> OTHER INFORMATION: Description of Artificial Sequence:
      beta-1,2-N-acetylglucosaminyltransferase I (GnTI,
      GnT1) Cys121Ala mutant

<400> SEQUENCE: 12

Ala Val Ile Pro Ile Leu Val Ile Ala Cys Asp Arg Ser Thr Val Arg
 1               5                  10                  15

Arg Ala Leu Asp Lys Leu Leu His Tyr Arg Pro Ser Ala Glu Leu Phe
                20                  25                  30

Pro Ile Ile Val Ser Gln Asp Cys Gly His Glu Glu Thr Ala Gln Ala
            35                  40                  45

Ile Ala Ser Tyr Gly Ser Ala Val Thr His Ile Arg Gln Pro Asp Leu
        50                  55                  60

Ser Ser Ile Ala Val Pro Pro Asp His Arg Lys Phe Gln Gly Tyr Tyr
    65                  70                  75                  80

Lys Ile Ala Arg His Tyr Arg Trp Ala Leu Gly Gln Val Phe Arg Gln
                85                  90                  95

Phe Arg Phe Pro Ala Ala Val Val Val Glu Asp Asp Leu Glu Val Ala
                100                 105                 110

Pro Asp Phe Phe Glu Tyr Phe Arg Ala Thr Tyr Pro Leu Leu Lys Ala
            115                 120                 125

Asp Pro Ser Leu Trp Cys Val Ser Ala Trp Asn Asp Asn Gly Lys Glu
        130                 135                 140

Gln Met Val Asp Ala Ser Arg Pro Glu Leu Leu Tyr Arg Thr Asp Phe
    145                 150                 155                 160

Phe Pro Gly Leu Gly Trp Leu Leu Leu Ala Glu Leu Trp Ala Glu Leu
                165                 170                 175

Glu Pro Lys Trp Pro Lys Ala Phe Trp Asp Asp Trp Met Arg Arg Pro

```
              180                 185                 190
Glu Gln Arg Gln Gly Arg Ala Cys Ile Arg Pro Glu Ile Ser Arg Thr
            195                 200                 205
Met Thr Phe Gly Arg Lys Gly Val Ser His Gly Gln Phe Phe Asp Gln
        210                 215                 220
His Leu Lys Phe Ile Lys Leu Asn Gln Gln Phe Val His Phe Thr Gln
225                 230                 235                 240
Leu Asp Leu Ser Tyr Leu Gln Arg Glu Ala Tyr Asp Arg Asp Phe Leu
                245                 250                 255
Ala Arg Val Tyr Gly Ala Pro Gln Leu Gln Val Glu Lys Val Arg Thr
            260                 265                 270
Asn Asp Arg Lys Glu Leu Gly Glu Val Arg Val Gln Tyr Thr Gly Arg
        275                 280                 285
Asp Ser Phe Lys Ala Phe Ala Lys Ala Leu Gly Val Met Asp Asp Leu
    290                 295                 300
Lys Ser Gly Val Pro Arg Ala Gly Tyr Arg Gly Ile Val Thr Phe Gln
305                 310                 315                 320
Phe Pro Gly Arg Arg Val His Leu Ala Pro Pro Thr Trp Glu Gly
                325                 330                 335
Tyr Asp Pro Ser Trp Asn
            340

<210> SEQ ID NO 13
<211> LENGTH: 1029
<212> TYPE: DNA
<213> ORGANISM: Artificial Sequence
<220> FEATURE:
<223> OTHER INFORMATION: Description of Artificial Sequence:
      beta-1,2-N-acetylglucosaminyltransferase I (GnTI,
      GnT1) Cys121Ala mutant

<400> SEQUENCE: 13
gcggtgattc ccatcctggt catcgcctgt gaccgcagca ctgttcggcg cgccctagac       60
aagctgctgc attatcggcc ctcggctgag ctcttcccca tcatcgttag ccaggactgc      120
gggcacgagg agacggccca ggccatcgcc tcctacggca gcgcggtcac gcacatccgg      180
cagcccgacc tgagcagcat gcggtgccg ccggaccacc gcaagttcca gggctactac      240
aagatcgcgc gccactaccg ctgggcgctg gccaggtct ccggcagtt tcgcttcccc       300
gcggccgtgg tggtggagga tgacctggag gtggccccgg acttcttcga gtactttcgg      360
gccacctatc cgctgctgaa ggccgacccc tccctgtggt gcgtctcggc ctggaatgac      420
aacggcaagg agcagatggt ggacgccagc aggcctgagc tgctctaccg caccgacttt     480
ttccctggcc tgggctggct gctgttggcc gagctctggg ctgagctgga gcccaagtgg      540
ccaaaggcct tctgggacga ctggatgcgg cggccggagc agcggcaggg gcgggcctgc      600
atacgccctg agatctcaag aacgatgacc tttggccgca agggtgtgag ccacgggcag      660
ttcttgacc agcacctcaa gtttatcaag ctgaaccagc agtttgtgca cttcacccag      720
ctggacctgt cttacctgca gcggggaggcc tatgaccgag atttcctcgc ccgcgtctac      780
ggtgctcccc agctgcaggt ggagaaagtg aggaccaatg accggaagga gctggggagag      840
gtgcgggtgc agtatacggg cagggacagc ttcaaggctt cgccaaggc tctggtgtc       900
atggatgacc ttaagtcggg ggttccgaga gctggctacc ggggtattgt caccttccag      960
ttcccgggcc gccgtgtcca cctggcgccc ccaccgacgt gggagggcta tgatcctagc    1020
tggaattag                                                            1029
```

```
<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence:unpaired
      cysteine mutation Cys121Ala mutant region

<400> SEQUENCE: 14

Ser Thr Val Arg Arg Ala Leu Asp Lys Leu Leu His
 1               5                  10

<210> SEQ ID NO 15
<211> LENGTH: 342
<212> TYPE: PRT
<213> ORGANISM: Artificial Sequence
<220> FEATURE:
<223> OTHER INFORMATION: Description of Artificial Sequence:
      beta-1,2-N-acetylglucosaminyltransferase I (GnTI,
      GnT1) Arg120Ala Cys121His double mutant

<400> SEQUENCE: 15

Ala Val Ile Pro Ile Leu Val Ile Ala Cys Asp Arg Ser Thr Val Arg
 1               5                  10                  15

Ala His Leu Asp Lys Leu Leu His Tyr Arg Pro Ser Ala Glu Leu Phe
            20                  25                  30

Pro Ile Ile Val Ser Gln Asp Cys Gly His Glu Glu Thr Ala Gln Ala
        35                  40                  45

Ile Ala Ser Tyr Gly Ser Ala Val Thr His Ile Arg Gln Pro Asp Leu
    50                  55                  60

Ser Ser Ile Ala Val Pro Pro Asp His Arg Lys Phe Gln Gly Tyr Tyr
65                  70                  75                  80

Lys Ile Ala Arg His Tyr Arg Trp Ala Leu Gly Gln Val Phe Arg Gln
                85                  90                  95

Phe Arg Phe Pro Ala Ala Val Val Val Glu Asp Asp Leu Glu Val Ala
            100                 105                 110

Pro Asp Phe Phe Glu Tyr Phe Arg Ala Thr Tyr Pro Leu Leu Lys Ala
        115                 120                 125

Asp Pro Ser Leu Trp Cys Val Ser Ala Trp Asn Asp Asn Gly Lys Glu
    130                 135                 140

Gln Met Val Asp Ala Ser Arg Pro Glu Leu Leu Tyr Arg Thr Asp Phe
145                 150                 155                 160

Phe Pro Gly Leu Gly Trp Leu Leu Leu Ala Glu Leu Trp Ala Glu Leu
                165                 170                 175

Glu Pro Lys Trp Pro Lys Ala Phe Trp Asp Asp Trp Met Arg Arg Pro
            180                 185                 190

Glu Gln Arg Gln Gly Arg Ala Cys Ile Arg Pro Glu Ile Ser Arg Thr
        195                 200                 205

Met Thr Phe Gly Arg Lys Gly Val Ser His Gly Gln Phe Phe Asp Gln
    210                 215                 220

His Leu Lys Phe Ile Lys Leu Asn Gln Gln Phe Val His Phe Thr Gln
225                 230                 235                 240

Leu Asp Leu Ser Tyr Leu Gln Arg Glu Ala Tyr Asp Arg Asp Phe Leu
                245                 250                 255

Ala Arg Val Tyr Gly Ala Pro Gln Leu Gln Val Glu Lys Val Arg Thr
            260                 265                 270

Asn Asp Arg Lys Glu Leu Gly Glu Val Arg Val Gln Tyr Thr Gly Arg
```

```
            275                 280                 285
Asp Ser Phe Lys Ala Phe Ala Lys Ala Leu Gly Val Met Asp Asp Leu
        290                 295                 300

Lys Ser Gly Val Pro Arg Ala Gly Tyr Arg Gly Ile Val Thr Phe Gln
305                 310                 315                 320

Phe Pro Gly Arg Arg Val His Leu Ala Pro Pro Thr Trp Glu Gly
                325                 330                 335

Tyr Asp Pro Ser Trp Asn
            340
```

<210> SEQ ID NO 16
<211> LENGTH: 1029
<212> TYPE: DNA
<213> ORGANISM: Artificial Sequence
<220> FEATURE:
<223> OTHER INFORMATION: Description of Artificial Sequence:
      beta-1,2-N-acetylglucosaminyltransferase I (GnTI,
      GnT1) Arg120Ala Cys121His double mutant

<400> SEQUENCE: 16

```
gcggtgattc ccatcctggt catcgcctgt gaccgcagca ctgttcgggc ccacctagac    60
aagctgctgc attatcggcc ctcggctgag ctcttcccca tcatcgttag ccaggactgc   120
gggcacgagg agacggccca ggccatcgcc tcctacggca gcgcggtcac gcacatccgg   180
cagcccgacc tgagcagcat tgcggtgccg ccggaccacc gcaagttcca gggctactac   240
aagatcgcgc gccactaccg ctgggcgctg ggccaggtct ccggcagtt tcgcttcccc    300
gcggccgtgg tggtggagga tgacctggag gtggccccgg acttcttcga gtactttcgg   360
gccacctatc cgctgctgaa ggccgacccc tccctgtggt gcgtctcggc ctggaatgac   420
aacggcaagg agcagatggt ggacgccagc aggcctgagc tgctctaccg caccgacttt   480
ttccctggcc tgggctggct gctgttggcc gagctctggg ctgagctgga gcccaagtgg   540
ccaaaggcct ctgggacga ctggatgcgc ggccggagc agcggcaggg gcgggcctgc    600
atacgccctg agatctcaag aacgatgacc tttggccgca agggtgtgag ccacgggcag   660
ttctttgacc agcaccctcaa gtttatcaag ctgaaccagc agtttgtgca cttcacccag   720
ctggacctgt cttacctgca gcgggaggcc tatgaccgag atttcctcgc ccgcgtctac   780
ggtgctcccc agctgcaggt ggagaaagtg aggaccaatg accggaagga ctggggggag   840
gtgcgggtgc agtatacggg cagggacagc ttcaaggctt cgccaaggc tctgggtgtc    900
atggatgacc ttaagtcggg ggttccgaga gctggctacc ggggtattgt caccttccag   960
ttcccgggcc gccgtgtcca cctggcgccc ccaccgacgt gggagggcta tgatcctagc  1020
tggaattag                                                          1029
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:unpaired
      cysteine mutation Arg120Ala Cys121His double
      mutant region

<400> SEQUENCE: 17

```
Ser Thr Val Arg Ala His Leu Asp Lys Leu Leu His
  1               5                   10
```

<210> SEQ ID NO 18

<211> LENGTH: 374
<212> TYPE: PRT
<213> ORGANISM: Rattus norvegicus
<220> FEATURE:
<223> OTHER INFORMATION: rat liver Gal beta-1,3-GalNAc
    alpha-2,3-sialyltransferase III (ST3GalIII)
<220> FEATURE:
<221> NAME/KEY: PEPTIDE
<222> LOCATION: (1)..(28)
<223> OTHER INFORMATION: delta28 deletion

<400> SEQUENCE: 18

```
Met Gly Leu Leu Val Phe Val Arg Asn Leu Leu Ala Leu Cys Leu
 1               5                  10                  15

Phe Leu Val Leu Gly Phe Leu Tyr Tyr Ser Ala Trp Lys Leu His Leu
                20                  25                  30

Leu Gln Trp Glu Asp Ser Asn Ser Leu Ile Leu Ser Leu Asp Ser Ala
                35                  40                  45

Gly Gln Thr Leu Gly Thr Glu Tyr Asp Arg Leu Gly Phe Leu Leu Lys
            50                  55                  60

Leu Asp Ser Lys Leu Pro Ala Glu Leu Ala Thr Lys Tyr Ala Asn Phe
65                  70                  75                  80

Ser Glu Gly Ala Cys Lys Pro Gly Tyr Ala Ser Ala Met Met Thr Ala
                85                  90                  95

Ile Phe Pro Arg Phe Ser Lys Pro Ala Pro Met Phe Leu Asp Asp Ser
                100                 105                 110

Phe Arg Lys Trp Ala Arg Ile Arg Glu Phe Val Pro Pro Phe Gly Ile
            115                 120                 125

Lys Gly Gln Asp Asn Leu Ile Lys Ala Ile Leu Ser Val Thr Lys Glu
130                 135                 140

Tyr Arg Leu Thr Pro Ala Leu Asp Ser Leu His Cys Arg Arg Cys Ile
145                 150                 155                 160

Ile Val Gly Asn Gly Gly Val Leu Ala Asn Lys Ser Leu Gly Ser Arg
                165                 170                 175

Ile Asp Asp Tyr Asp Ile Val Ile Arg Leu Asn Ser Ala Pro Val Lys
            180                 185                 190

Gly Phe Glu Lys Asp Val Gly Ser Lys Thr Thr Leu Arg Ile Thr Tyr
        195                 200                 205

Pro Glu Gly Ala Met Gln Arg Pro Glu Gln Tyr Glu Arg Asp Ser Leu
210                 215                 220

Phe Val Leu Ala Gly Phe Lys Trp Gln Asp Phe Lys Trp Leu Lys Tyr
225                 230                 235                 240

Ile Val Tyr Lys Glu Arg Val Ser Ala Ser Asp Gly Phe Trp Lys Ser
                245                 250                 255

Val Ala Thr Arg Val Pro Lys Glu Pro Pro Glu Ile Arg Ile Leu Asn
            260                 265                 270

Pro Tyr Phe Ile Gln Glu Ala Ala Phe Thr Leu Ile Gly Leu Pro Phe
        275                 280                 285

Asn Asn Gly Leu Met Gly Arg Gly Asn Ile Pro Thr Leu Gly Ser Val
290                 295                 300

Ala Val Thr Met Ala Leu Asp Gly Cys Asp Glu Val Ala Val Ala Gly
305                 310                 315                 320

Phe Gly Tyr Asp Met Asn Thr Pro Asn Ala Pro Leu His Tyr Tyr Glu
                325                 330                 335

Thr Val Arg Met Ala Ala Ile Lys Glu Ser Trp Thr His Asn Ile Gln
                340                 345                 350
```

```
Arg Glu Lys Glu Phe Leu Arg Lys Leu Val Lys Ala Arg Val Ile Thr
            355                 360                 365

Asp Leu Ser Ser Gly Ile
    370
```

<210> SEQ ID NO 19
<211> LENGTH: 555
<212> TYPE: PRT
<213> ORGANISM: Homo sapiens
<220> FEATURE:
<223> OTHER INFORMATION: human full-length
      UDP-N-acetylgalactosaminyltransferase 2 (GalNAcT2)

<400> SEQUENCE: 19

```
Met Arg Arg Arg Ser Arg Met Leu Leu Cys Phe Ala Phe Leu Trp Val
  1               5                  10                  15

Leu Gly Ile Ala Tyr Tyr Met Tyr Ser Gly Gly Ser Ala Leu Ala
             20                  25                  30

Gly Gly Ala Gly Gly Ala Gly Arg Lys Glu Asp Trp Asn Glu Ile
         35                  40                  45

Asp Pro Ile Lys Lys Asp Leu His His Ser Asn Gly Glu Glu Lys
 50                  55                  60

Ala Gln Ser Met Glu Thr Leu Pro Pro Gly Lys Val Arg Trp Pro Asp
 65                  70                  75                  80

Phe Asn Gln Glu Ala Tyr Val Gly Gly Thr Met Val Arg Ser Gly Gln
                 85                  90                  95

Asp Pro Tyr Ala Arg Asn Lys Phe Asn Gln Val Glu Ser Asp Lys Leu
            100                 105                 110

Arg Met Asp Arg Ala Ile Pro Asp Thr Arg His Asp Gln Cys Gln Arg
        115                 120                 125

Lys Gln Trp Arg Val Asp Leu Pro Ala Thr Ser Val Val Ile Thr Phe
    130                 135                 140

His Asn Glu Ala Arg Ser Ala Leu Leu Arg Thr Val Val Ser Val Leu
145                 150                 155                 160

Lys Lys Ser Pro Pro His Leu Ile Lys Glu Ile Ile Leu Val Asp Asp
                165                 170                 175

Tyr Ser Asn Asp Pro Glu Asp Gly Ala Leu Leu Gly Lys Ile Glu Lys
            180                 185                 190

Val Arg Val Leu Arg Asn Asp Arg Arg Glu Gly Leu Met Arg Ser Arg
        195                 200                 205

Val Arg Gly Ala Asp Ala Ala Gln Ala Lys Val Leu Thr Phe Leu Asp
    210                 215                 220

Ser His Cys Glu Cys Asn Glu His Trp Leu Glu Pro Leu Leu Glu Arg
225                 230                 235                 240

Val Ala Glu Asp Arg Thr Arg Val Val Ser Pro Ile Ile Asp Val Ile
                245                 250                 255

Asn Met Asp Asn Phe Gln Tyr Val Gly Ala Ser Ala Asp Leu Lys Gly
            260                 265                 270

Gly Phe Asp Trp Asn Leu Val Phe Lys Trp Asp Tyr Met Thr Pro Glu
        275                 280                 285

Gln Arg Arg Ser Arg Gln Gly Asn Pro Val Ala Pro Ile Lys Thr Pro
    290                 295                 300

Met Ile Ala Gly Gly Leu Phe Val Met Asp Lys Phe Tyr Phe Glu Glu
305                 310                 315                 320

Leu Gly Lys Tyr Asp Met Met Met Asp Val Trp Gly Gly Glu Asn Leu
                325                 330                 335
```

```
Glu Ile Ser Phe Arg Val Trp Gln Cys Gly Gly Ser Leu Glu Ile
            340                 345                 350
Pro Cys Ser Arg Val Gly His Val Phe Arg Lys Gln His Pro Tyr Thr
        355                 360                 365
Phe Pro Gly Gly Ser Gly Thr Val Phe Ala Arg Asn Thr Arg Arg Ala
    370                 375                 380
Ala Glu Val Trp Met Asp Glu Tyr Lys Asn Phe Tyr Tyr Ala Ala Val
385                 390                 395                 400
Pro Ser Ala Arg Asn Val Pro Tyr Gly Asn Ile Gln Ser Arg Leu Glu
                405                 410                 415
Leu Arg Lys Lys Leu Ser Cys Lys Pro Phe Lys Trp Tyr Leu Glu Asn
            420                 425                 430
Val Tyr Pro Glu Leu Arg Val Pro Asp His Gln Asp Ile Ala Phe Gly
        435                 440                 445
Ala Leu Gln Gln Gly Thr Asn Cys Leu Asp Thr Leu Gly His Phe Ala
    450                 455                 460
Asp Gly Val Val Gly Val Tyr Glu Cys His Asn Ala Gly Gly Asn Gln
465                 470                 475                 480
Glu Trp Ala Leu Thr Lys Glu Lys Ser Val Lys His Met Asp Leu Cys
                485                 490                 495
Cys Arg Glu Asn Asp Ser Arg Gln Lys Trp Glu Gln Ile Glu Gly Asn
            500                 505                 510
Ser Lys Leu Arg His Val Gly Ser Asn Leu Cys Leu Asp Ser Arg Thr
        515                 520                 525
Ala Lys Ser Gly Gly Leu Ser Val Glu Val Cys Gly Pro Ala Leu Ser
    530                 535                 540
Gln Gln Trp Lys Phe Thr Leu Asn Leu Gln Gln
545                 550                 555

<210> SEQ ID NO 20
<211> LENGTH: 1713
<212> TYPE: DNA
<213> ORGANISM: Homo sapiens
<220> FEATURE:
<223> OTHER INFORMATION: human full-length
      UDP-N-acetylgalactosaminyltransferase 2 (GalNAcT2)

<400> SEQUENCE: 20
atgcggcggc gctcgcggat gctgctctgc ttcgccttcc tgtgggtgct gggcatcgcc      60
tactacatgt actcgggggg cggctctgcg ctggccgggg cgcgggcgg cggcgccggc      120
aggaaggagg actggaatga aattgacccc attaaaaaga agaccttca tcacagcaat      180
ggagaagaga agcacaaag catggagacc ctccctccag ggaaagtacg gtggccagac      240
tttaaccagg aagcttatgt tggagggacg atggtccgct ccgggcagga cccttacgcc      300
cgcaacaagt tcaaccaggt ggagagtgat aagcttcgaa tggacagagc catccctgac      360
acccggcatg accagtgtca gcggaagcag tggcgggtgg atctgccggc caccagcgtg      420
gtgatcacgt tcacaatga agccaggtcg gccctactca ggaccgtggt cagcgtgctt      480
aagaaaagcc cgccccatct cataaaagaa atcatcttgg tggatgacta cagcaatgat      540
cctgaggacg gggctctctt ggggaaaatt gagaaagtgc gagttcttag aaatgatcga      600
cgagaaggcc tcatgcgctc acgggttcgg ggggccgatg ctgcccaagc caaggtcctg      660
accttcctgg acagtcactg cgagtgtaat gagcactggc tggagcccct cctggaaagg      720
gtggcggagg acaggactcg ggttgtgtca cccatcatcg atgtcattaa tatggacaac      780
```

```
tttcagtatg tggggggcatc tgctgacttg aagggcggtt ttgattggaa cttggtattc      840
aagtgggatt acatgacgcc tgagcagaga aggtcccggc aggggaaccc agtcgcccct      900
ataaaaaccc ccatgattgc tggtgggctg tttgtgatgg ataagttcta ttttgaagaa      960
ctggggaagt acgacatgat gatggatgtg tggggaggag agaacctaga gatctcgttc     1020
cgcgtgtggc agtgtggtgg cagcctggag atcatcccgt gcagccgtgt gggacacgtg     1080
ttccggaagc agcaccccta cacgttcccg ggtggcagtg gcactgtctt tgcccgaaac     1140
acccgccggg cagcagaggt ctggatggat gaatacaaaa atttctatta tgcagcagtg     1200
ccttctgcta gaaacgttcc ttatggaaat attcagagca gattggagct taggaagaaa     1260
ctcagctgca agcctttcaa atggtacctt gaaaatgtct atccagagtt aagggttcca     1320
gaccatcagg atatagcttt tggggccttg cagcagggaa ctaactgcct cgacactttg     1380
ggacactttg ctgatggtgt ggttggagtt tatgaatgtc acaatgctgg gggaaaccag     1440
gaatgggcct tgacgaagga gaagtcggtg aagcacatgg atttgtgcct tactgtggtg     1500
gaccgggcac cgggctctct tataaagctg cagggctgcc gagaaaatga cagcagacag     1560
aaatgggaac agatcgaggg caactccaag ctgaggcacg tgggcagcaa cctgtgcctg     1620
gacagtcgca cggccaagag cgggggccta agcgtggagg tgtgtggccc ggccctttcg     1680
cagcagtgga agttcacgct caacctgcag cag                                  1713
```

<210> SEQ ID NO 21
<211> LENGTH: 520
<212> TYPE: PRT
<213> ORGANISM: Artificial Sequence
<220> FEATURE:
<223> OTHER INFORMATION: Description of Artificial Sequence:delta51
    UDP-N-acetylgalactosaminyltransferase 2
    (delta51GalNAcT2)

<400> SEQUENCE: 21

```
Lys Lys Lys Asp Leu His His Ser Asn Gly Glu Glu Lys Ala Gln Ser
  1               5                  10                  15

Met Glu Thr Leu Pro Pro Gly Lys Val Arg Trp Pro Asp Phe Asn Gln
             20                  25                  30

Glu Ala Tyr Val Gly Gly Thr Met Val Arg Ser Gly Gln Asp Pro Tyr
         35                  40                  45

Ala Arg Asn Lys Phe Asn Gln Val Glu Ser Asp Lys Leu Arg Met Asp
     50                  55                  60

Arg Ala Ile Pro Asp Thr Arg His Asp Gln Cys Gln Arg Lys Gln Trp
 65                  70                  75                  80

Arg Val Asp Leu Pro Ala Thr Ser Val Val Ile Thr Phe His Asn Glu
                 85                  90                  95

Ala Arg Ser Ala Leu Leu Arg Thr Val Val Ser Val Leu Lys Lys Ser
            100                 105                 110

Pro Pro His Leu Ile Lys Glu Ile Ile Leu Val Asp Asp Tyr Ser Asn
        115                 120                 125

Asp Pro Glu Asp Gly Ala Leu Leu Gly Lys Ile Glu Lys Val Arg Val
    130                 135                 140

Leu Arg Asn Asp Arg Arg Glu Gly Leu Met Arg Ser Arg Val Arg Gly
145                 150                 155                 160

Ala Asp Ala Ala Gln Ala Lys Val Leu Thr Phe Leu Asp Ser His Cys
                165                 170                 175

Glu Cys Asn Glu His Trp Leu Glu Pro Leu Leu Glu Arg Val Ala Glu
```

```
                    180              185              190
Asp Arg Thr Arg Val Ser Pro Ile Ile Asp Val Ile Asn Met Asp
            195              200              205
Asn Phe Gln Tyr Val Gly Ala Ser Ala Asp Leu Lys Gly Gly Phe Asp
        210              215              220
Trp Asn Leu Val Phe Lys Trp Asp Tyr Met Thr Pro Glu Gln Arg Arg
225              230              235              240
Ser Arg Gln Gly Asn Pro Val Ala Pro Ile Lys Thr Pro Met Ile Ala
            245              250              255
Gly Gly Leu Phe Val Met Asp Lys Phe Tyr Phe Glu Glu Leu Gly Lys
        260              265              270
Tyr Asp Met Met Met Asp Val Trp Gly Gly Glu Asn Leu Glu Ile Ser
            275              280              285
Phe Arg Val Trp Gln Cys Gly Gly Ser Leu Glu Ile Ile Pro Cys Ser
        290              295              300
Arg Val Gly His Val Phe Arg Lys Gln His Pro Tyr Thr Phe Pro Gly
305              310              315              320
Gly Ser Gly Thr Val Phe Ala Arg Asn Thr Arg Arg Ala Ala Glu Val
            325              330              335
Trp Met Asp Glu Tyr Lys Asn Phe Tyr Tyr Ala Ala Val Pro Ser Ala
            340              345              350
Arg Asn Val Pro Tyr Gly Asn Ile Gln Ser Arg Leu Glu Leu Arg Lys
            355              360              365
Lys Leu Ser Cys Lys Pro Phe Lys Trp Tyr Leu Glu Asn Val Tyr Pro
        370              375              380
Glu Leu Arg Val Pro Asp His Gln Asp Ile Ala Phe Gly Ala Leu Gln
385              390              395              400
Gln Gly Thr Asn Cys Leu Asp Thr Leu Gly His Phe Ala Asp Gly Val
            405              410              415
Val Gly Val Tyr Glu Cys His Asn Ala Gly Gly Asn Gln Glu Trp Ala
            420              425              430
Leu Thr Lys Glu Lys Ser Val Lys His Met Asp Leu Cys Leu Thr Val
        435              440              445
Val Asp Arg Ala Pro Gly Ser Leu Ile Lys Leu Gln Gly Cys Arg Glu
        450              455              460
Asn Asp Ser Arg Gln Lys Trp Glu Gln Ile Glu Gly Asn Ser Lys Leu
465              470              475              480
Arg His Val Gly Ser Asn Leu Cys Leu Asp Ser Arg Thr Ala Lys Ser
            485              490              495
Gly Gly Leu Ser Val Glu Val Cys Gly Pro Ala Leu Ser Gln Gln Trp
            500              505              510
Lys Phe Thr Leu Asn Leu Gln Gln
        515              520

<210> SEQ ID NO 22
<211> LENGTH: 1560
<212> TYPE: DNA
<213> ORGANISM: Artificial Sequence
<220> FEATURE:
<223> OTHER INFORMATION: Description of Artificial Sequence:delta51
      UDP-N-acetylgalactosaminyltransferase 2
      (delta51GalNAcT2)

<400> SEQUENCE: 22
aaaaagaaag accttcatca cagcaatgga gaagagaaag cacaaagcat ggagaccctc        60
```

-continued

```
cctccaggga aagtacggtg gccagacttt aaccaggaag cttatgttgg agggacgatg    120
gtccgctccg ggcaggaccc ttacgcccgc aacaagttca accaggtgga gagtgataag    180
cttcgaatgg acagagccat ccctgacacc cggcatgacc agtgtcagcg gaagcagtgg    240
cgggtggatc tgccggccac cagcgtggtg atcacgtttc acaatgaagc caggtcggcc    300
ctactcagga ccgtggtcag cgtgcttaag aaaagcccgc cccatctcat aaaagaaatc    360
atcttggtgg atgactacag caatgatcct gaggacgggg ctctcttggg gaaaattgag    420
aaagtgcgag ttcttagaaa tgatcgacga gaaggcctca tgcgctcacg ggttcggggg    480
gccgatgctg cccaagccaa ggtcctgacc ttcctggaca gtcactgcga gtgtaatgag    540
cactggctgg agcccctcct ggaaagggtg gcggaggaca ggactcgggt tgtgtcaccc    600
atcatcgatg tcattaatat ggacaacttt cagtatgtgg gggcatctgc tgacttgaag    660
ggcggttttg attggaactt ggtattcaag tgggattaca tgacgcctga gcagagaagg    720
tcccggcagg ggaacccagt cgcccctata aaaacccca tgattgctgg tgggctgttt    780
gtgatggata agttctattt tgaagaactg gggaagtacg acatgatgat ggatgtgtgg    840
ggaggagaga acctagagat ctcgttccgc gtgtggcagt gtggtggcag cctggagatc    900
atcccgtgca gccgtgtggg acacgtgttc cggaagcagc accctacac gttcccgggt    960 ggcagtggca ctgtctttgc ccgaaacacc cgccgggcag cagaggtctg gatggatgaa   1020
tacaaaaatt tctattatgc agcagtgcct tctgctagaa cgttcctta tggaaatatt   1080 cagagcagat tggagcttag gaagaaactc agctgcaagc ctttcaaatg gtaccttgaa   1140
aatgtctatc cagagttaag ggttccagac catcaggata tagcttttgg ggccttgcag   1200
cagggaacta actgcctcga cactttggga cactttgctg atggtgtggt tggagtttat   1260
gaatgtcaca atgctggggg aaaccaggaa tgggccttga cgaaggagaa gtcggtgaag   1320
cacatggatt tgtgccttac tgtggtggac cgggcaccgg gctctcttat aaagctgcag   1380
ggctgccgag aaaatgacag cagacagaaa tgggaacaga tcgagggcaa ctccaagctg   1440
aggcacgtgg gcagcaacct gtgcctggac agtcgcacgg ccaagagcgg gggcctaagc   1500
gtggaggtgt gtgcccccgc cctttcgcag cagtggaagt tcacgctcaa cctgcagcag   1560
```

<210> SEQ ID NO 23
<211> LENGTH: 691
<212> TYPE: PRT
<213> ORGANISM: Artificial Sequence
<220> FEATURE:
<223> OTHER INFORMATION: Description of Artificial Sequence:maltose
binding protein-Gal beta-1,3-GalNAc alpha-2,3-sialyltransferase 1
(MBP-ST3Gal1) fusion protein

<400> SEQUENCE: 23

```
Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95
```

```
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
        370                 375                 380

Glu Gly Arg Ile Ser Glu Phe Gly Ser Glu Leu Ser Glu Asn Phe Lys
385                 390                 395                 400

Lys Leu Met Lys Tyr Pro Tyr Arg Pro Cys Thr Cys Thr Arg Cys Ile
                405                 410                 415

Glu Glu Gln Arg Val Ser Ala Trp Phe Asp Glu Arg Phe Asn Arg Ser
            420                 425                 430

Met Gln Pro Leu Leu Thr Ala Lys Asn Ala His Leu Glu Glu Asp Thr
        435                 440                 445

Tyr Lys Trp Trp Leu Arg Leu Gln Arg Glu Lys Gln Pro Asn Asn Leu
        450                 455                 460

Asn Asp Thr Ile Arg Glu Leu Phe Gln Val Val Pro Gly Asn Val Asp
465                 470                 475                 480

Pro Leu Leu Glu Lys Arg Leu Val Ser Cys Arg Arg Cys Ala Val Val
                485                 490                 495

Gly Asn Ser Gly Asn Leu Lys Glu Ser Tyr Tyr Gly Pro Gln Ile Asp
            500                 505                 510
```

```
Ser His Asp Phe Val Leu Arg Met Asn Lys Ala Pro Thr Glu Gly Phe
        515                 520                 525

Glu Ala Asp Val Gly Ser Lys Thr Thr His His Phe Val Tyr Pro Glu
        530                 535                 540

Ser Phe Arg Glu Leu Ala Gln Glu Val Ser Met Ile Leu Val Pro Phe
545                 550                 555                 560

Lys Thr Thr Asp Leu Glu Trp Val Ile Ser Ala Thr Thr Thr Gly Arg
                565                 570                 575

Ile Ser His Thr Tyr Val Pro Val Pro Ala Lys Ile Lys Val Lys Lys
            580                 585                 590

Glu Lys Ile Leu Ile Tyr His Pro Ala Phe Ile Lys Tyr Val Phe Asp
        595                 600                 605

Arg Trp Leu Gln Gly His Gly Arg Tyr Pro Ser Thr Gly Ile Leu Ser
        610                 615                 620

Val Ile Phe Ser Leu His Ile Cys Asp Glu Val Asp Leu Tyr Gly Phe
625                 630                 635                 640

Gly Ala Asp Ser Lys Gly Asn Trp His His Tyr Trp Glu Asn Asn Pro
                645                 650                 655

Ser Ala Gly Ala Phe Arg Lys Thr Gly Val His Asp Gly Asp Phe Glu
            660                 665                 670

Ser Asn Val Thr Thr Ile Leu Ala Ser Ile Asn Lys Ile Arg Ile Phe
        675                 680                 685

Lys Gly Arg
    690

<210> SEQ ID NO 24
<211> LENGTH: 841
<212> TYPE: PRT
<213> ORGANISM: Artificial Sequence
<220> FEATURE:
<223> OTHER INFORMATION: Description of Artificial Sequence:maltose
      binding protein-starch binding domain-Gal beta-1,3-GalNAc
      alpha-2,3-sialyltransferase 1 (MBP-SBD-ST3Gal1) fusion protein

<400> SEQUENCE: 24

Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
```

-continued

```
                165                 170                 175
Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
370                 375                 380

Glu Gly Arg Ile Ser Glu Phe Gly Ser Ile Val Ala Thr Gly Gly Thr
385                 390                 395                 400

Thr Thr Thr Ala Thr Pro Thr Gly Ser Gly Ser Val Thr Ser Thr Ser
                405                 410                 415

Lys Thr Thr Ala Thr Ala Ser Lys Thr Ser Thr Ser Thr Ser Ser Thr
                420                 425                 430

Ser Cys Thr Thr Pro Thr Ala Val Ala Val Thr Phe Asp Leu Thr Ala
            435                 440                 445

Thr Thr Thr Tyr Gly Glu Asn Ile Tyr Leu Val Gly Ser Ile Ser Gln
            450                 455                 460

Leu Gly Asp Trp Glu Thr Ser Asp Gly Ile Ala Leu Ser Ala Asp Lys
465                 470                 475                 480

Tyr Thr Ser Ser Asp Pro Leu Trp Tyr Val Thr Val Thr Leu Pro Ala
                485                 490                 495

Gly Glu Ser Phe Glu Tyr Lys Phe Ile Arg Ile Glu Ser Asp Asp Ser
                500                 505                 510

Val Glu Trp Glu Ser Asp Pro Asn Arg Glu Tyr Thr Val Pro Gln Ala
            515                 520                 525

Cys Gly Thr Ser Thr Ala Thr Val Thr Asp Thr Trp Arg Gly Ser Glu
            530                 535                 540

Leu Ser Glu Asn Phe Lys Lys Leu Met Lys Tyr Pro Tyr Arg Pro Cys
545                 550                 555                 560

Thr Cys Thr Arg Cys Ile Glu Glu Gln Arg Val Ser Ala Trp Phe Asp
                565                 570                 575

Glu Arg Phe Asn Arg Ser Met Gln Pro Leu Leu Thr Ala Lys Asn Ala
            580                 585                 590
```

-continued

```
His Leu Glu Glu Asp Thr Tyr Lys Trp Trp Leu Arg Leu Gln Arg Glu
            595                 600                 605

Lys Gln Pro Asn Asn Leu Asn Asp Thr Ile Arg Glu Leu Phe Gln Val
        610                 615                 620

Val Pro Gly Asn Val Asp Pro Leu Leu Glu Lys Arg Leu Val Ser Cys
625                 630                 635                 640

Arg Arg Cys Ala Val Val Gly Asn Ser Gly Asn Leu Lys Glu Ser Tyr
                645                 650                 655

Tyr Gly Pro Gln Ile Asp Ser His Asp Phe Val Leu Arg Met Asn Lys
            660                 665                 670

Ala Pro Thr Glu Gly Phe Glu Ala Asp Val Gly Ser Lys Thr Thr His
        675                 680                 685

His Phe Val Tyr Pro Glu Ser Phe Arg Glu Leu Ala Gln Glu Val Ser
    690                 695                 700

Met Ile Leu Val Pro Phe Lys Thr Thr Asp Leu Glu Trp Val Ile Ser
705                 710                 715                 720

Ala Thr Thr Thr Gly Arg Ile Ser His Thr Tyr Val Pro Val Pro Ala
                725                 730                 735

Lys Ile Lys Val Lys Lys Glu Lys Ile Leu Ile Tyr His Pro Ala Phe
            740                 745                 750

Ile Lys Tyr Val Phe Asp Arg Trp Leu Gln Gly His Gly Arg Tyr Pro
        755                 760                 765

Ser Thr Gly Ile Leu Ser Val Ile Phe Ser Leu His Ile Cys Asp Glu
    770                 775                 780

Val Asp Leu Tyr Gly Phe Gly Ala Asp Ser Lys Gly Asn Trp His His
785                 790                 795                 800

Tyr Trp Glu Asn Asn Pro Ser Ala Gly Ala Phe Arg Lys Thr Gly Val
                805                 810                 815

His Asp Gly Asp Phe Glu Ser Asn Val Thr Thr Ile Leu Ala Ser Ile
            820                 825                 830

Asn Lys Ile Arg Ile Phe Lys Gly Arg
        835                 840

<210> SEQ ID NO 25
<211> LENGTH: 793
<212> TYPE: PRT
<213> ORGANISM: Artificial Sequence
<220> FEATURE:
<223> OTHER INFORMATION: Description of Artificial Sequence:maltose
      binding protein-alpha-N-acetylgalactosaminide alpha-2,
      6-sialyltransferase I mouse truncation fusion protein
      (MBP-mST6GalNAcI S127)
<220> FEATURE:
<221> NAME/KEY: MOD_RES
<222> LOCATION: (708)
<223> OTHER INFORMATION: Xaa = any amino acid

<400> SEQUENCE: 25

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
```

```
                65                  70                  75                  80
        Thr Pro Asp Lys Ala Phe Gln Asp Lys Leu Tyr Pro Phe Thr Trp Asp
                        85                  90                  95

Ala Val Arg Tyr Asn Gly Lys Leu Ile Ala Tyr Pro Ile Ala Val Glu
                        100                 105                 110

Ala Leu Ser Leu Ile Tyr Asn Lys Asp Leu Leu Pro Asn Pro Pro Lys
                        115                 120                 125

Thr Trp Glu Glu Ile Pro Ala Leu Asp Lys Glu Leu Lys Ala Lys Gly
                        130                 135                 140

Lys Ser Ala Leu Met Phe Asn Leu Gln Glu Pro Tyr Phe Thr Trp Pro
        145                 150                 155                 160

Leu Ile Ala Ala Asp Gly Gly Tyr Ala Phe Lys Tyr Glu Asn Gly Lys
                        165                 170                 175

Tyr Asp Ile Lys Asp Val Gly Val Asp Asn Ala Gly Ala Lys Ala Gly
                        180                 185                 190

Leu Thr Phe Leu Val Asp Leu Ile Lys Asn Lys His Met Asn Ala Asp
                        195                 200                 205

Thr Asp Tyr Ser Ile Ala Glu Ala Ala Phe Asn Lys Gly Glu Thr Ala
                        210                 215                 220

Met Thr Ile Asn Gly Pro Trp Ala Trp Ser Asn Ile Asp Thr Ser Lys
        225                 230                 235                 240

Val Asn Tyr Gly Val Thr Val Leu Pro Thr Phe Lys Gly Gln Pro Ser
                        245                 250                 255

Lys Pro Phe Val Gly Val Leu Ser Ala Gly Ile Asn Ala Ala Ser Pro
                        260                 265                 270

Asn Lys Glu Leu Ala Lys Glu Phe Leu Glu Asn Tyr Leu Leu Thr Asp
                        275                 280                 285

Glu Gly Leu Glu Ala Val Asn Lys Asp Lys Pro Leu Gly Ala Val Ala
                        290                 295                 300

Leu Lys Ser Tyr Glu Glu Leu Ala Lys Asp Pro Arg Ile Ala Ala
        305                 310                 315                 320

Thr Met Glu Asn Ala Gln Lys Gly Glu Ile Met Pro Asn Ile Pro Gln
                        325                 330                 335

Met Ser Ala Phe Trp Tyr Ala Val Arg Thr Ala Val Ile Asn Ala Ala
                        340                 345                 350

Ser Gly Arg Gln Thr Val Asp Glu Ala Leu Lys Asp Ala Gln Thr Asn
                        355                 360                 365

Ser Ser Ser Asn Asn Asn Asn Asn Asn Asn Asn Asn Leu Gly Ile
                        370                 375                 380

Glu Gly Arg Ile Ser Glu Phe Gly Ser Ser Glu His Leu Asp Lys Val
        385                 390                 395                 400

Pro Arg Thr Pro Gly Ala Leu Ser Thr Arg Lys Thr Pro Met Ala Thr
                        405                 410                 415

Gly Ala Val Pro Ala Lys Lys Val Val Gln Ala Thr Lys Ser Pro
                        420                 425                 430

Ala Ser Ser Pro His Pro Thr Thr Arg Arg Gln Arg Leu Lys Ala
                        435                 440                 445

Ser Glu Phe Lys Ser Glu Pro Arg Trp Asp Phe Glu Glu Tyr Ser
                        450                 455                 460

Leu Asp Met Ser Ser Leu Gln Thr Asn Cys Ser Ala Ser Val Lys Ile
        465                 470                 475                 480

Lys Ala Ser Lys Ser Pro Trp Leu Gln Asn Ile Phe Leu Pro Asn Ile
                        485                 490                 495
```

Thr Leu Phe Leu Asp Ser Gly Arg Phe Thr Gln Ser Glu Trp Asn Arg
             500                 505                 510

Leu Glu His Phe Ala Pro Pro Phe Gly Phe Met Glu Leu Asn Gln Ser
             515                 520                 525

Leu Val Gln Lys Val Val Thr Arg Phe Pro Val Arg Gln Gln Gln
530                 535                 540

Leu Leu Leu Ala Ser Leu Pro Thr Gly Tyr Ser Lys Cys Ile Thr Cys
545                 550                 555                 560

Ala Val Val Gly Asn Gly Gly Ile Leu Asn Asp Ser Arg Val Gly Arg
             565                 570                 575

Glu Ile Asp Ser His Asp Tyr Val Phe Arg Leu Ser Gly Ala Val Ile
             580                 585                 590

Lys Gly Tyr Glu Gln Asp Val Gly Thr Arg Thr Ser Phe Tyr Gly Phe
             595                 600                 605

Thr Ala Phe Ser Leu Thr Gln Ser Ile Leu Ile Leu Gly Arg Arg Gly
             610                 615                 620

Phe Gln His Val Pro Leu Gly Lys Asp Val Arg Tyr Leu His Phe Leu
625                 630                 635                 640

Glu Gly Thr Arg Asn Tyr Glu Trp Leu Glu Ala Met Phe Leu Asn Gln
             645                 650                 655

Thr Leu Ala Lys Thr His Leu Ser Trp Phe Arg His Arg Pro Gln Glu
             660                 665                 670

Ala Phe Arg Asn Ala Leu Asp Leu Asp Arg Tyr Leu Leu Leu His Pro
             675                 680                 685

Asp Phe Leu Arg Tyr Met Lys Asn Arg Phe Leu Arg Ser Lys Thr Leu
690                 695                 700

Asp Thr Ala Xaa Trp Arg Ile Tyr Arg Pro Thr Thr Gly Ala Leu Leu
705                 710                 715                 720

Leu Leu Thr Ala Leu His Leu Cys Asp Lys Val Ser Ala Tyr Gly Phe
             725                 730                 735

Ile Thr Glu Gly His Glu Arg Phe Ser Asp His Tyr Tyr Asp Thr Ser
             740                 745                 750

Trp Lys Arg Leu Ile Phe Tyr Ile Asn His Asp Phe Arg Leu Glu Arg
             755                 760                 765

Met Val Trp Lys Arg Leu His Asp Glu Gly Ile Trp Leu Tyr Gln
             770                 775                 780

Arg Pro Gln Ser Asp Lys Ala Lys Asn
785                 790

<210> SEQ ID NO 26
<211> LENGTH: 958
<212> TYPE: PRT
<213> ORGANISM: Artificial Sequence
<220> FEATURE:
<223> OTHER INFORMATION: Description of Artificial Sequence:maltose
      binding protein-alpha-N-acetylgalactosaminide alpha-2,
      6-sialyltransferase I human truncation fusion protein
      (MBP-hST6GalNAcI K36)

<400> SEQUENCE: 26

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
             35                  40                  45

```
Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg Ile Ser Glu Phe Gly Ser Lys Glu Pro Gln Thr Lys Pro
385                 390                 395                 400

Ser Arg His Gln Arg Thr Glu Asn Ile Lys Glu Arg Ser Leu Gln Ser
                405                 410                 415

Leu Ala Lys Pro Lys Ser Gln Ala Pro Thr Arg Ala Arg Arg Thr Thr
                420                 425                 430

Ile Tyr Ala Glu Pro Val Pro Glu Asn Asn Ala Leu Asn Thr Gln Thr
            435                 440                 445

Gln Pro Lys Ala His Thr Thr Gly Asp Arg Gly Lys Glu Ala Asn Gln
        450                 455                 460
```

```
Ala Pro Pro Glu Glu Gln Asp Lys Val Pro His Thr Ala Gln Arg Ala
465                 470                 475                 480

Ala Trp Lys Ser Pro Glu Lys Glu Lys Thr Met Val Asn Thr Leu Ser
            485                 490                 495

Pro Arg Gly Gln Asp Ala Gly Met Ala Ser Gly Arg Thr Glu Ala Gln
        500                 505                 510

Ser Trp Lys Ser Gln Asp Thr Lys Thr Thr Gln Gly Asn Gly Gly Gln
        515                 520                 525

Thr Arg Lys Leu Thr Ala Ser Arg Thr Val Ser Glu Lys His Gln Gly
        530                 535                 540

Lys Ala Ala Thr Thr Ala Lys Thr Leu Ile Pro Lys Ser Gln His Arg
545                 550                 555                 560

Met Leu Ala Pro Thr Gly Ala Val Ser Thr Arg Thr Arg Gln Lys Gly
            565                 570                 575

Val Thr Thr Ala Val Ile Pro Pro Lys Glu Lys Pro Gln Ala Thr
            580                 585                 590

Pro Pro Pro Ala Pro Phe Gln Ser Pro Thr Thr Gln Arg Asn Gln Arg
        595                 600                 605

Leu Lys Ala Ala Asn Phe Lys Ser Glu Pro Arg Trp Asp Phe Glu Glu
        610                 615                 620

Lys Tyr Ser Phe Glu Ile Gly Gly Leu Gln Thr Thr Cys Pro Asp Ser
625                 630                 635                 640

Val Lys Ile Lys Ala Ser Lys Ser Leu Trp Leu Gln Lys Leu Phe Leu
                645                 650                 655

Pro Asn Leu Thr Leu Phe Leu Asp Ser Arg His Phe Asn Gln Ser Glu
            660                 665                 670

Trp Asp Arg Leu Glu His Phe Ala Pro Pro Phe Gly Phe Met Glu Leu
        675                 680                 685

Asn Tyr Ser Leu Val Gln Lys Val Val Thr Arg Phe Pro Pro Val Pro
        690                 695                 700

Gln Gln Gln Leu Leu Ala Ser Leu Pro Ala Gly Ser Leu Arg Cys
705                 710                 715                 720

Ile Thr Cys Ala Val Val Gly Asn Gly Gly Ile Leu Asn Asn Ser His
                725                 730                 735

Met Gly Gln Glu Ile Asp Ser His Asp Tyr Val Phe Arg Leu Ser Gly
            740                 745                 750

Ala Leu Ile Lys Gly Tyr Glu Gln Asp Val Gly Thr Arg Thr Ser Phe
        755                 760                 765

Tyr Gly Phe Thr Ala Phe Ser Leu Thr Gln Ser Leu Leu Ile Leu Gly
        770                 775                 780

Asn Arg Gly Phe Lys Asn Val Pro Leu Gly Lys Asp Val Arg Tyr Leu
785                 790                 795                 800

His Phe Leu Glu Gly Thr Arg Asp Tyr Glu Trp Leu Glu Ala Leu Leu
            805                 810                 815

Met Asn Gln Thr Val Met Ser Lys Asn Leu Phe Trp Phe Arg His Arg
        820                 825                 830

Pro Gln Glu Ala Phe Arg Glu Ala Leu His Met Asp Arg Tyr Leu Leu
        835                 840                 845

Leu His Pro Asp Phe Leu Arg Tyr Met Lys Asn Arg Phe Leu Arg Ser
        850                 855                 860

Lys Thr Leu Asp Gly Ala His Trp Arg Ile Tyr Arg Pro Thr Thr Gly
865                 870                 875                 880

Ala Leu Leu Leu Leu Thr Ala Leu Gln Leu Cys Asp Gln Val Ser Ala
```

```
                885                 890                 895
Tyr Gly Phe Ile Thr Glu Gly His Glu Arg Phe Ser Asp His Tyr Tyr
                900                 905                 910

Asp Thr Ser Trp Lys Arg Leu Ile Phe Tyr Ile Asn His Asp Phe Lys
                915                 920                 925

Leu Glu Arg Glu Val Trp Lys Arg Leu His Asp Glu Gly Ile Ile Arg
        930                 935                 940

Leu Tyr Gln Arg Pro Gly Pro Gly Thr Ala Lys Ala Lys Asn
945                 950                 955

<210> SEQ ID NO 27
<211> LENGTH: 402
<212> TYPE: PRT
<213> ORGANISM: Bos taurus
<220> FEATURE:
<223> OTHER INFORMATION: full length bovine beta-1,
      4-galactosyltransferase (GalT1)

<400> SEQUENCE: 27

Met Lys Phe Arg Glu Pro Leu Leu Gly Gly Ser Ala Ala Met Pro Gly
  1               5                  10                  15

Ala Ser Leu Gln Arg Ala Cys Arg Leu Leu Val Ala Val Cys Ala Leu
                 20                  25                  30

His Leu Gly Val Thr Leu Val Tyr Tyr Leu Ala Gly Arg Asp Leu Arg
             35                  40                  45

Arg Leu Pro Gln Leu Val Gly Val His Pro Pro Leu Gln Gly Ser Ser
         50                  55                  60

His Gly Ala Ala Ala Ile Gly Gln Pro Ser Gly Glu Leu Arg Leu Arg
 65                  70                  75                  80

Gly Val Ala Pro Pro Pro Pro Leu Gln Asn Ser Ser Lys Pro Arg Ser
                 85                  90                  95

Arg Ala Pro Ser Asn Leu Asp Ala Tyr Ser His Pro Gly Pro Gly Pro
            100                 105                 110

Gly Pro Gly Ser Asn Leu Thr Ser Ala Pro Val Pro Ser Thr Thr Thr
        115                 120                 125

Arg Ser Leu Thr Ala Cys Pro Glu Glu Ser Pro Leu Leu Val Gly Pro
    130                 135                 140

Met Leu Ile Glu Phe Asn Ile Pro Val Asp Leu Lys Leu Ile Glu Gln
145                 150                 155                 160

Gln Asn Pro Lys Val Lys Leu Gly Gly Arg Tyr Thr Pro Met Asp Cys
                165                 170                 175

Ile Ser Pro His Lys Val Ala Ile Ile Leu Phe Arg Asn Arg Gln
            180                 185                 190

Glu His Leu Lys Tyr Trp Leu Tyr Tyr Leu His Pro Met Val Gln Arg
        195                 200                 205

Gln Gln Leu Asp Tyr Gly Ile Tyr Val Ile Asn Gln Ala Gly Glu Ser
    210                 215                 220

Met Phe Asn Arg Ala Lys Leu Leu Asn Val Gly Phe Lys Glu Ala Leu
225                 230                 235                 240

Lys Asp Tyr Asp Tyr Asn Cys Phe Val Phe Ser Asp Val Asp Leu Ile
                245                 250                 255

Pro Met Asn Asp His Asn Thr Tyr Arg Cys Phe Ser Gln Pro Arg His
            260                 265                 270

Ile Ser Val Ala Met Asp Lys Phe Gly Phe Ser Leu Pro Tyr Val Gln
        275                 280                 285
```

```
Tyr Phe Gly Gly Val Ser Ala Leu Ser Lys Gln Gln Phe Leu Ser Ile
    290                 295                 300

Asn Gly Phe Pro Asn Asn Tyr Trp Gly Trp Gly Glu Asp Asp Asp
305                 310                 315                 320

Ile Tyr Asn Arg Leu Ala Phe Arg Gly Met Ser Val Ser Arg Pro Asn
                325                 330                 335

Ala Val Ile Gly Lys Cys Arg Met Ile Arg His Ser Arg Asp Lys Lys
                340                 345                 350

Asn Glu Pro Asn Pro Gln Arg Phe Asp Arg Ile Ala His Thr Lys Glu
                355                 360                 365

Thr Met Leu Ser Asp Gly Leu Asn Ser Leu Thr Tyr Met Val Leu Glu
    370                 375                 380

Val Gln Arg Tyr Pro Leu Tyr Thr Lys Ile Thr Val Asp Ile Gly Thr
385                 390                 395                 400

Pro Ser
```

<210> SEQ ID NO 28
<211> LENGTH: 343
<212> TYPE: PRT
<213> ORGANISM: Sus scrofa
<220> FEATURE:
<223> OTHER INFORMATION: full length porcine Gal beta-1,3-GalNAc
      alpha-2,3-sialyltransferase 1 (ST3Gal1)

<400> SEQUENCE: 28

```
Met Ala Pro Met Arg Lys Lys Ser Thr Leu Lys Leu Thr Leu Leu
1               5                   10                  15

Val Leu Phe Ile Phe Leu Thr Ser Phe Leu Asn Tyr Ser His Thr
                20                  25                  30

Val Val Thr Thr Ala Trp Phe Pro Lys Gln Met Val Ile Glu Leu Ser
                35                  40                  45

Glu Asn Phe Lys Lys Leu Met Lys Tyr Pro Tyr Arg Pro Cys Thr Cys
    50                  55                  60

Thr Arg Cys Ile Glu Glu Gln Arg Val Ser Ala Trp Phe Asp Glu Arg
65                  70                  75                  80

Phe Asn Arg Ser Met Gln Pro Leu Leu Thr Ala Lys Asn Ala His Leu
                85                  90                  95

Glu Glu Asp Thr Tyr Lys Trp Trp Leu Arg Leu Gln Arg Glu Lys Gln
                100                 105                 110

Pro Asn Asn Leu Asn Asp Thr Ile Arg Glu Leu Phe Gln Val Val Pro
            115                 120                 125

Gly Asn Val Asp Pro Leu Leu Glu Lys Arg Leu Val Ser Cys Arg Arg
130                 135                 140

Cys Ala Val Val Gly Asn Ser Gly Asn Leu Lys Glu Ser Tyr Tyr Gly
145                 150                 155                 160

Pro Gln Ile Asp Ser His Asp Phe Val Leu Arg Met Asn Lys Ala Pro
                165                 170                 175

Thr Glu Gly Phe Glu Ala Asp Val Gly Ser Lys Thr Thr His His Phe
                180                 185                 190

Val Tyr Pro Glu Ser Phe Arg Glu Leu Ala Gln Glu Val Ser Met Ile
                195                 200                 205

Leu Val Pro Phe Lys Thr Thr Asp Leu Glu Trp Val Ile Ser Ala Thr
    210                 215                 220

Thr Thr Gly Thr Ile Ser His Thr Tyr Val Pro Val Pro Ala Lys Ile
225                 230                 235                 240
```

```
Lys Val Lys Lys Glu Lys Ile Leu Ile Tyr His Pro Ala Phe Ile Lys
                245                 250                 255

Tyr Val Phe Asp Arg Trp Leu Gln Gly His Gly Arg Tyr Pro Ser Thr
            260                 265                 270

Gly Ile Leu Ser Val Ile Phe Ser Leu His Ile Cys Asp Glu Val Asp
            275                 280                 285

Leu Tyr Gly Phe Gly Ala Asp Ser Lys Gly Asn Trp His His Tyr Trp
        290                 295                 300

Glu Asn Asn Pro Ser Ala Gly Ala Phe Arg Lys Thr Gly Val His Asp
305                 310                 315                 320

Gly Asp Phe Glu Ser Asn Val Thr Thr Ile Leu Ala Ser Ile Asn Lys
                325                 330                 335

Ile Arg Ile Phe Lys Gly Arg
                340

<210> SEQ ID NO 29
<211> LENGTH: 600
<212> TYPE: PRT
<213> ORGANISM: Homo sapiens
<220> FEATURE:
<223> OTHER INFORMATION: human alpha-N-acetylgalactosaminide
      alpha-2,6-sialyltransferase I (ST6GalNAcTI)

<400> SEQUENCE: 29

Met Arg Ser Cys Leu Trp Arg Cys Arg His Leu Ser Gln Gly Val Gln
  1               5                  10                  15

Trp Ser Leu Leu Leu Ala Val Leu Val Phe Leu Phe Ala Leu Pro
                 20                  25                  30

Ser Phe Ile Lys Glu Pro Gln Thr Lys Pro Ser Arg His Gln Arg Thr
                 35                  40                  45

Glu Asn Ile Lys Glu Arg Ser Leu Gln Ser Leu Ala Lys Pro Lys Ser
 50                  55                  60

Gln Ala Pro Thr Arg Ala Arg Arg Thr Thr Ile Tyr Ala Glu Pro Val
 65                  70                  75                  80

Pro Glu Asn Asn Ala Leu Asn Thr Gln Thr Gln Pro Lys Ala His Thr
                 85                  90                  95

Thr Gly Asp Arg Gly Lys Glu Ala Asn Gln Ala Pro Pro Glu Glu Gln
                100                 105                 110

Asp Lys Val Pro His Thr Ala Gln Arg Ala Ala Trp Lys Ser Pro Glu
                115                 120                 125

Lys Glu Lys Thr Met Val Asn Thr Leu Ser Pro Arg Gly Gln Asp Ala
                130                 135                 140

Gly Met Ala Ser Gly Arg Thr Glu Ala Gln Ser Trp Lys Ser Gln Asp
145                 150                 155                 160

Thr Lys Thr Thr Gln Gly Asn Gly Gly Gln Thr Arg Lys Leu Thr Ala
                165                 170                 175

Ser Arg Thr Val Ser Glu Lys His Gln Gly Lys Ala Ala Thr Thr Ala
                180                 185                 190

Lys Thr Leu Ile Pro Lys Ser Gln His Arg Met Leu Ala Pro Thr Gly
                195                 200                 205

Ala Val Ser Thr Arg Thr Arg Gln Lys Gly Val Thr Thr Ala Val Ile
                210                 215                 220

Pro Pro Lys Glu Lys Pro Gln Ala Thr Pro Pro Ala Pro Phe
225                 230                 235                 240

Gln Ser Pro Thr Thr Gln Arg Asn Gln Arg Leu Lys Ala Ala Asn Phe
                245                 250                 255
```

Lys Ser Glu Pro Arg Trp Asp Phe Glu Lys Tyr Ser Phe Glu Ile
            260                 265                 270

Gly Gly Leu Gln Thr Thr Cys Pro Asp Ser Val Lys Ile Lys Ala Ser
        275                 280                 285

Lys Ser Leu Trp Leu Gln Lys Leu Phe Leu Pro Asn Leu Thr Leu Phe
    290                 295                 300

Leu Asp Ser Arg His Phe Asn Gln Ser Glu Trp Asp Arg Leu Glu His
305                 310                 315                 320

Phe Ala Pro Pro Phe Gly Phe Met Glu Leu Asn Tyr Ser Leu Val Gln
                325                 330                 335

Lys Val Val Thr Arg Phe Pro Val Pro Gln Gln Leu Leu Leu
            340                 345                 350

Ala Ser Leu Pro Ala Gly Ser Leu Arg Cys Ile Thr Cys Ala Val Val
        355                 360                 365

Gly Asn Gly Gly Ile Leu Asn Asn Ser His Met Gly Gln Glu Ile Asp
    370                 375                 380

Ser His Asp Tyr Val Phe Arg Leu Ser Gly Ala Leu Ile Lys Gly Tyr
385                 390                 395                 400

Glu Gln Asp Val Gly Thr Arg Thr Ser Phe Tyr Gly Phe Thr Ala Phe
                405                 410                 415

Ser Leu Thr Gln Ser Leu Leu Ile Leu Gly Asn Arg Gly Phe Lys Asn
            420                 425                 430

Val Pro Leu Gly Lys Asp Val Arg Tyr Leu His Phe Leu Glu Gly Thr
        435                 440                 445

Arg Asp Tyr Glu Trp Leu Glu Ala Leu Leu Met Asn Gln Thr Val Met
    450                 455                 460

Ser Lys Asn Leu Phe Trp Phe Arg His Arg Pro Gln Glu Ala Phe Arg
465                 470                 475                 480

Glu Ala Leu His Met Asp Arg Tyr Leu Leu Leu His Pro Asp Phe Leu
                485                 490                 495

Arg Tyr Met Lys Asn Arg Phe Leu Arg Ser Lys Thr Leu Asp Gly Ala
            500                 505                 510

His Trp Arg Ile Tyr Arg Pro Thr Thr Gly Ala Leu Leu Leu Leu Thr
        515                 520                 525

Ala Leu Gln Leu Cys Asp Gln Val Ser Ala Tyr Gly Phe Ile Thr Glu
    530                 535                 540

Gly His Glu Arg Phe Ser Asp His Tyr Tyr Asp Thr Ser Trp Lys Arg
545                 550                 555                 560

Leu Ile Phe Tyr Ile Asn His Asp Phe Lys Leu Glu Arg Glu Val Trp
                565                 570                 575

Lys Arg Leu His Asp Glu Gly Ile Ile Arg Leu Tyr Gln Arg Pro Gly
            580                 585                 590

Pro Gly Thr Ala Lys Ala Lys Asn
        595                 600

<210> SEQ ID NO 30
<211> LENGTH: 566
<212> TYPE: PRT
<213> ORGANISM: Gallus gallus
<220> FEATURE:
<223> OTHER INFORMATION: chicken alpha-N-acetylgalactosaminide
    alpha-2,6-sialyltransferase I (ST6GalNAcTI)

<400> SEQUENCE: 30

Met Gly Phe Leu Ile Arg Arg Leu Pro Lys Asp Ser Arg Ile Phe Arg

```
              1               5              10              15
            Trp Leu Leu Ile Leu Thr Val Phe Ser Phe Ile Ile Thr Ser Phe Ser
                         20                  25                  30

Ala Leu Phe Gly Met Glu Lys Ser Ile Phe Arg Gln Leu Lys Ile Tyr
                         35                  40                  45

Gln Ser Ile Ala His Met Leu Gln Val Asp Thr Gln Asp Gln Gln Gly
                         50                  55                  60

Ser Asn Tyr Ser Ala Asn Gly Arg Ile Ser Lys Val Gly Leu Glu Arg
             65                  70                  75                  80

Asp Ile Ala Trp Leu Glu Leu Asn Thr Ala Val Ser Thr Pro Ser Gly
                         85                  90                  95

Glu Gly Lys Glu Gln Lys Lys Thr Val Lys Pro Val Ala Lys Val
                        100                 105                 110

Glu Glu Ala Lys Glu Lys Val Thr Val Lys Pro Phe Pro Glu Val Met
                        115                 120                 125

Gly Ile Thr Asn Thr Thr Ala Ser Thr Ala Ser Val Val Glu Arg Thr
                        130                 135                 140

Lys Glu Lys Thr Thr Ala Arg Pro Val Pro Gly Val Gly Glu Ala Asp
            145                 150                 155                 160

Gly Lys Arg Thr Thr Ile Ala Leu Pro Ser Met Lys Glu Asp Lys Glu
                        165                 170                 175

Lys Ala Thr Val Lys Pro Ser Phe Gly Met Lys Val Ala His Ala Asn
                        180                 185                 190

Ser Thr Ser Lys Asp Lys Pro Lys Ala Glu Glu Pro Ala Ser Val
                        195                 200                 205

Lys Ala Ile Arg Pro Val Thr Gln Ala Ala Thr Val Thr Glu Lys Lys
            210                 215                 220

Lys Leu Arg Ala Ala Asp Phe Lys Thr Glu Pro Gln Trp Asp Phe Asp
            225                 230                 235                 240

Asp Glu Tyr Ile Leu Asp Ser Ser Pro Val Ser Thr Cys Ser Glu
                        245                 250                 255

Ser Val Arg Ala Lys Ala Ala Lys Ser Asp Trp Leu Arg Asp Leu Phe
                        260                 265                 270

Leu Pro Asn Ile Thr Leu Phe Ile Asp Lys Ser Tyr Phe Asn Val Ser
                        275                 280                 285

Glu Trp Asp Arg Leu Glu His Phe Ala Pro Pro Tyr Gly Phe Met Glu
                        290                 295                 300

Leu Asn Tyr Ser Leu Val Glu Glu Val Met Ser Arg Leu Pro Pro Asn
            305                 310                 315                 320

Pro His Gln Gln Leu Leu Leu Ala Asn Ser Ser Ser Asn Val Ser Thr
                        325                 330                 335

Cys Ile Ser Cys Ala Val Val Gly Asn Gly Gly Ile Leu Asn Asn Ser
                        340                 345                 350

Gly Met Gly Gln Glu Ile Asp Ser His Asp Tyr Val Phe Arg Val Ser
                        355                 360                 365

Gly Ala Val Ile Lys Gly Tyr Glu Lys Asp Val Gly Thr Lys Thr Ser
                        370                 375                 380

Phe Tyr Gly Phe Thr Ala Tyr Ser Leu Val Ser Ser Leu Gln Asn Leu
            385                 390                 395                 400

Gly His Lys Gly Phe Lys Lys Ile Pro Gln Gly Lys His Ile Arg Tyr
                        405                 410                 415

Ile His Phe Leu Glu Ala Val Arg Asp Tyr Glu Trp Leu Lys Ala Leu
                        420                 425                 430
```

```
Leu Leu Asp Lys Asp Ile Arg Lys Gly Phe Leu Asn Tyr Tyr Gly Arg
        435                 440                 445

Arg Pro Arg Glu Arg Phe Asp Glu Asp Phe Thr Met Asn Lys Tyr Leu
450                 455                 460

Val Ala His Pro Asp Phe Leu Arg Tyr Leu Lys Asn Arg Phe Leu Lys
465                 470                 475                 480

Ser Lys Asn Leu Gln Lys Pro Tyr Trp Arg Leu Tyr Arg Pro Thr Thr
                485                 490                 495

Gly Ala Leu Leu Leu Leu Thr Ala Leu His Leu Cys Asp Arg Val Ser
                500                 505                 510

Ala Tyr Gly Tyr Ile Thr Glu Gly His Gln Lys Tyr Ser Asp His Tyr
                515                 520                 525

Tyr Asp Lys Glu Trp Lys Arg Leu Val Phe Tyr Val Asn His Asp Phe
        530                 535                 540

Asn Leu Glu Lys Gln Val Trp Lys Arg Leu His Asp Glu Asn Ile Met
545                 550                 555                 560

Lys Leu Tyr Gln Arg Ser
                565
```

<210> SEQ ID NO 31
<211> LENGTH: 495
<212> TYPE: PRT
<213> ORGANISM: Artificial Sequence
<220> FEATURE:
<223> OTHER INFORMATION: Description of Artificial Sequence:mouse
      alpha-N-acetylgalactosaminide
      alpha-2,6-sialyltransferase I (ST6GalNAcTI)
      beginning at residue 32 of the native mouse protein

<400> SEQUENCE: 31

```
Asp Pro Arg Ala Lys Asp Ser Arg Cys Gln Phe Ile Trp Lys Asn Asp
 1               5                  10                  15

Ala Ser Ala Gln Glu Asn Gln Gln Lys Ala Glu Pro Gln Val Pro Ile
            20                  25                  30

Met Thr Leu Ser Pro Arg Val His Asn Lys Glu Ser Thr Ser Val Ser
        35                  40                  45

Ser Lys Asp Leu Lys Lys Gln Glu Arg Glu Ala Val Gln Gly Glu Gln
    50                  55                  60

Ala Glu Gly Lys Glu Lys Arg Lys Leu Glu Thr Ile Arg Pro Ala Pro
65                  70                  75                  80

Glu Asn Pro Gln Ser Lys Ala Glu Pro Ala Ala Lys Thr Pro Val Ser
                85                  90                  95

Glu His Leu Asp Lys Leu Pro Arg Thr Pro Gly Ala Leu Ser Thr Arg
            100                 105                 110

Lys Thr Pro Met Ala Thr Gly Ala Val Pro Ala Lys Lys Val Val
        115                 120                 125

Gln Ala Thr Lys Ser Pro Ala Ser Ser Pro His Pro Thr Thr Arg Arg
    130                 135                 140

Arg Gln Arg Leu Lys Ala Ser Glu Phe Lys Ser Glu Pro Arg Trp Asp
145                 150                 155                 160

Phe Glu Glu Glu Tyr Ser Leu Asp Met Ser Ser Leu Gln Thr Asn Cys
                165                 170                 175

Ser Ala Ser Val Lys Ile Lys Ala Ser Lys Ser Pro Trp Leu Gln Asn
            180                 185                 190

Ile Phe Leu Pro Asn Ile Thr Leu Phe Leu Asp Ser Gly Arg Phe Thr
        195                 200                 205
```

```
Gln Ser Glu Trp Asn Arg Leu Glu His Phe Ala Pro Pro Phe Gly Phe
    210                 215                 220

Met Glu Leu Asn Gln Ser Leu Val Gln Lys Val Val Thr Arg Phe Pro
225                 230                 235                 240

Pro Val Arg Gln Gln Gln Leu Leu Leu Ala Ser Leu Pro Thr Gly Tyr
                245                 250                 255

Ser Lys Cys Ile Thr Cys Ala Val Val Gly Asn Gly Gly Ile Leu Asn
                260                 265                 270

Asp Ser Arg Val Gly Arg Glu Ile Asp Ser His Asp Tyr Val Phe Arg
            275                 280                 285

Leu Ser Gly Ala Val Ile Lys Gly Tyr Glu Gln Asp Val Gly Thr Arg
            290                 295                 300

Thr Ser Phe Tyr Gly Phe Thr Ala Phe Ser Leu Thr Gln Ser Ile Leu
305                 310                 315                 320

Ile Leu Gly Arg Arg Gly Phe Gln His Val Pro Leu Gly Lys Asp Val
                325                 330                 335

Arg Tyr Leu His Phe Leu Glu Gly Thr Arg Asn Tyr Glu Trp Leu Glu
                340                 345                 350

Ala Met Phe Leu Asn Gln Thr Leu Ala Lys Thr His Leu Ser Trp Phe
            355                 360                 365

Arg His Arg Pro Gln Glu Ala Phe Arg Asn Ala Leu Asp Leu Asp Arg
            370                 375                 380

Tyr Leu Leu Leu His Pro Asp Phe Leu Arg Tyr Met Lys Asn Arg Phe
385                 390                 395                 400

Leu Arg Ser Lys Thr Leu Asp Thr Ala His Trp Arg Ile Tyr Arg Pro
                405                 410                 415

Thr Thr Gly Ala Leu Leu Leu Thr Ala Leu His Leu Cys Asp Lys
                420                 425                 430

Val Ser Ala Tyr Gly Phe Ile Thr Glu Gly His Gln Arg Phe Ser Asp
            435                 440                 445

His Tyr Tyr Asp Thr Ser Trp Lys Arg Leu Ile Phe Tyr Ile Asn His
    450                 455                 460

Asp Phe Arg Leu Glu Arg Met Val Trp Lys Arg Leu His Asp Glu Gly
465                 470                 475                 480

Ile Ile Trp Leu Tyr Gln Arg Pro Gln Ser Asp Lys Ala Lys Asn
                485                 490                 495

<210> SEQ ID NO 32
<211> LENGTH: 363
<212> TYPE: PRT
<213> ORGANISM: Homo sapiens
<220> FEATURE:
<223> OTHER INFORMATION: full length human core 1
      UDP-galactose:N-acetylgalactosamine-alpha-R
      beta-1,3-galactosyltransferase (Core 1 GalT1)

<400> SEQUENCE: 32

Met Ala Ser Lys Ser Trp Leu Asn Phe Leu Thr Phe Leu Cys Gly Ser
1               5                   10                  15

Ala Ile Gly Phe Leu Leu Cys Ser Gln Leu Phe Ser Ile Leu Leu Gly
                20                  25                  30

Glu Lys Val Asp Thr Gln Pro Asn Val Leu His Asn Asp Pro His Ala
            35                  40                  45

Arg His Ser Asp Asp Asn Gly Gln Asn His Leu Glu Gly Gln Met Asn
        50                  55                  60
```

Phe Asn Ala Asp Ser Ser Gln His Lys Asp Glu Asn Thr Asp Ile Ala
 65                  70                  75                  80

Glu Asn Leu Tyr Gln Lys Val Arg Ile Leu Cys Trp Val Met Thr Gly
                 85                  90                  95

Pro Gln Asn Leu Glu Lys Lys Ala Lys His Val Lys Ala Thr Trp Ala
            100                 105                 110

Gln Arg Cys Asn Lys Val Leu Phe Met Ser Ser Glu Glu Asn Lys Asp
        115                 120                 125

Phe Pro Ala Val Gly Leu Lys Thr Lys Glu Gly Arg Asp Gln Leu Tyr
    130                 135                 140

Trp Lys Thr Ile Lys Ala Phe Gln Tyr Val His Glu His Tyr Leu Glu
145                 150                 155                 160

Asp Ala Asp Trp Phe Leu Lys Ala Asp Asp Asp Thr Tyr Val Ile Leu
                165                 170                 175

Asp Asn Leu Arg Trp Leu Leu Ser Lys Tyr Asp Pro Glu Glu Pro Ile
            180                 185                 190

Tyr Phe Gly Arg Arg Phe Lys Pro Tyr Val Lys Gln Gly Tyr Met Ser
        195                 200                 205

Gly Gly Ala Gly Tyr Val Leu Ser Lys Glu Ala Leu Lys Arg Phe Val
    210                 215                 220

Asp Ala Phe Lys Thr Asp Lys Cys Thr His Ser Ser Ser Ile Glu Asp
225                 230                 235                 240

Leu Ala Leu Gly Arg Cys Met Glu Ile Met Asn Val Glu Ala Gly Asp
                245                 250                 255

Ser Arg Asp Thr Ile Gly Lys Gly Thr Phe His Pro Phe Val Pro Glu
            260                 265                 270

His His Leu Ile Lys Gly Tyr Leu Pro Arg Thr Phe Trp Tyr Trp Asn
        275                 280                 285

Tyr Asn Tyr Tyr Pro Pro Val Glu Gly Pro Gly Cys Cys Ser Asp Leu
    290                 295                 300

Ala Val Ser Phe His Tyr Val Asp Ser Thr Thr Met Tyr Glu Leu Glu
305                 310                 315                 320

Tyr Leu Val Tyr His Leu Arg Pro Tyr Gly Tyr Leu Tyr Arg Tyr Gln
                325                 330                 335

Pro Thr Leu Pro Glu Arg Ile Leu Lys Glu Ile Ser Gln Ala Asn Lys
            340                 345                 350

Asn Glu Asp Thr Lys Val Lys Leu Gly Asn Pro
        355                 360

<210> SEQ ID NO 33
<211> LENGTH: 341
<212> TYPE: PRT
<213> ORGANISM: Drosophila melanogaster
<220> FEATURE:
<223> OTHER INFORMATION: Drosophila core 1
     UDP-galactose:N-acetylgalactosamine-alpha-R
     beta-1,3-galactosyltransferase (Core 1 GalT1)

<400> SEQUENCE: 33

Glu Phe Met Pro Tyr Asp Gly His Arg His Gly Asp Val Asn Asp Ala
 1               5                  10                  15

His His Ser His Asp Met Met Glu Met Ser Gly Pro Glu Gln Asp Val
             20                  25                  30

Gly Gly His Glu His Val His Glu Asn Ser Thr Ile Ala Glu Arg Leu
         35                  40                  45

Tyr Ser Glu Val Arg Val Leu Cys Trp Ile Met Thr Asn Pro Ser Asn

```
            50                  55                  60
His Gln Lys Lys Ala Arg His Val Lys Arg Thr Trp Gly Lys Arg Cys
 65                  70                  75                  80

Asn Lys Leu Ile Phe Met Ser Ser Ala Lys Asp Asp Glu Leu Asp Ala
                 85                  90                  95

Val Ala Leu Pro Val Gly Glu Gly Arg Asn Asn Leu Trp Gly Lys Thr
            100                 105                 110

Lys Glu Ala Tyr Lys Tyr Ile Tyr Glu His His Ile Asn Asp Ala Asp
        115                 120                 125

Trp Phe Leu Lys Ala Asp Asp Asp Thr Tyr Thr Ile Val Glu Asn Met
    130                 135                 140

Arg Tyr Met Leu Tyr Pro Tyr Ser Pro Glu Thr Pro Val Tyr Phe Gly
145                 150                 155                 160

Cys Lys Phe Lys Pro Tyr Val Lys Gln Gly Tyr Met Ser Gly Gly Ala
                165                 170                 175

Gly Tyr Val Leu Ser Arg Glu Ala Val Arg Arg Phe Val Val Glu Ala
            180                 185                 190

Leu Pro Asn Pro Lys Leu Cys Lys Ser Asp Asn Ser Gly Ala Glu Asp
        195                 200                 205

Val Glu Ile Gly Lys Cys Leu Gln Asn Val Asn Val Leu Ala Gly Asp
    210                 215                 220

Ser Arg Asp Ser Asn Gly Arg Gly Arg Phe Phe Pro Phe Val Pro Glu
225                 230                 235                 240

His His Leu Ile Pro Ser His Thr Asp Lys Lys Phe Trp Tyr Trp Gln
                245                 250                 255

Tyr Ile Phe Tyr Lys Thr Asp Glu Gly Leu Asp Cys Cys Ser Asp Asn
            260                 265                 270

Ala Ile Ser Phe His Tyr Val Ser Pro Asn Gln Met Tyr Val Leu Asp
        275                 280                 285

Tyr Leu Ile Tyr His Leu Arg Pro Tyr Gly Ile Ile Asn Thr Pro Asp
    290                 295                 300

Ala Leu Pro Asn Lys Leu Ala Val Gly Glu Leu Met Pro Glu Ile Lys
305                 310                 315                 320

Glu Gln Ala Thr Glu Ser Thr Ser Asp Gly Val Ser Lys Arg Ser Ala
                325                 330                 335

Glu Thr Lys Thr Gln
            340

<210> SEQ ID NO 34
<211> LENGTH: 341
<212> TYPE: PRT
<213> ORGANISM: Drosophila melanogaster
<220> FEATURE:
<223> OTHER INFORMATION: Drosophila core 1
      UDP-galactose:N-acetylgalactosamine-alpha-R
      beta-1,3-galactosyltransferase (Core 1 GalT1)

<400> SEQUENCE: 34

Glu Phe Met Pro Tyr Asp Gly His Arg His Gly Asp Val Asn Asp Ala
 1               5                  10                  15

His His Ser His Asp Met Met Glu Met Ser Gly Pro Glu Gln Asp Val
                20                  25                  30

Gly Gly His Glu His Val His Glu Asn Ser Thr Ile Ala Glu Arg Leu
        35                  40                  45

Tyr Ser Glu Val Arg Val Leu Cys Trp Ile Met Thr Asn Pro Ser Asn
    50                  55                  60
```

His Gln Lys Lys Ala Arg His Val Lys Arg Thr Trp Gly Lys Arg Cys
 65                  70                  75                  80

Asn Lys Leu Ile Phe Met Ser Ser Ala Lys Asp Asp Glu Leu Asp Ala
                 85                  90                  95

Val Ala Leu Pro Val Gly Glu Gly Arg Asn Asn Leu Trp Gly Lys Thr
            100                 105                 110

Lys Glu Ala Tyr Lys Tyr Ile Tyr Glu His His Ile Asn Asp Ala Asp
        115                 120                 125

Trp Phe Leu Lys Ala Asp Asp Asp Thr Tyr Thr Ile Val Glu Asn Met
    130                 135                 140

Arg Tyr Met Leu Tyr Pro Tyr Ser Pro Glu Thr Pro Val Tyr Phe Gly
145                 150                 155                 160

Cys Lys Phe Lys Pro Tyr Val Lys Gln Gly Tyr Met Ser Gly Gly Ala
                165                 170                 175

Gly Tyr Val Leu Ser Arg Glu Ala Val Arg Arg Phe Val Val Glu Ala
            180                 185                 190

Leu Pro Asn Pro Lys Leu Cys Lys Ser Asp Asn Ser Gly Ala Glu Asp
        195                 200                 205

Val Glu Ile Gly Lys Cys Leu Gln Asn Val Asn Val Leu Ala Gly Asp
    210                 215                 220

Ser Arg Asp Ser Asn Gly Arg Gly Arg Phe Phe Pro Phe Val Pro Glu
225                 230                 235                 240

His His Leu Ile Pro Ser His Thr Asp Lys Lys Phe Trp Tyr Trp Gln
                245                 250                 255

Tyr Ile Phe Tyr Lys Thr Asp Glu Gly Leu Asp Cys Cys Ser Asp Asn
            260                 265                 270

Ala Ile Ser Phe His Tyr Val Ser Pro Asn Gln Met Tyr Val Leu Asp
        275                 280                 285

Tyr Leu Ile Tyr His Leu Arg Pro Tyr Gly Ile Ile Asn Thr Pro Asp
    290                 295                 300

Ala Leu Pro Asn Lys Leu Ala Val Gly Glu Leu Met Pro Glu Ile Lys
305                 310                 315                 320

Glu Gln Ala Thr Glu Ser Thr Ser Asp Gly Val Ser Lys Arg Ser Thr
                325                 330                 335

Glu Thr Lys Thr Gln
            340

<210> SEQ ID NO 35
<211> LENGTH: 371
<212> TYPE: PRT
<213> ORGANISM: Yersinia pseudotuberculosis
<220> FEATURE:
<223> OTHER INFORMATION: maltose binding protein (MBP)

<400> SEQUENCE: 35

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Ile Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Leu
 65                  70                  75                  80

```
Thr Pro Ser Lys Ala Phe Gln Glu Lys Leu Phe Pro Phe Thr Trp Asp
            85                  90                  95

Ala Val Arg Phe Asn Gly Lys Leu Ile Gly Tyr Pro Val Ala Val Glu
            100                 105                 110

Ala Leu Ser Leu Ile Tyr Asn Lys Asp Leu Val Lys Glu Ala Pro Lys
            115                 120                 125

Thr Trp Glu Glu Ile Pro Ala Leu Asp Lys Thr Leu Arg Ala Asn Gly
            130                 135                 140

Lys Ser Ala Ile Met Trp Asn Leu Gln Glu Pro Tyr Phe Thr Trp Pro
145                 150                 155                 160

Val Ile Ala Ala Asp Gly Gly Tyr Ala Phe Lys Phe Glu Asn Gly Val
            165                 170                 175

Tyr Asp Ala Lys Asn Val Gly Val Asn Asn Ala Gly Ala Gln Ala Gly
            180                 185                 190

Leu Gln Phe Ile Val Asp Leu Val Lys Asn Lys His Ile Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Lys Ser Lys
225                 230                 235                 240

Ile Asn Tyr Gly Val Thr Leu Leu Pro Thr Phe His Gly Gln Pro Ser
            245                 250                 255

Lys Pro Phe Val Gly Val Leu Thr Ala Gly Ile Asn Ala Ala Ser Pro
            260                 265                 270

Asn Lys Glu Leu Ala Thr Glu Phe Leu Glu Asn Tyr Leu Ile Thr Asp
            275                 280                 285

Gln Gly Leu Ala Glu Val Asn Lys Asp Lys Pro Leu Gly Ala Val Ala
            290                 295                 300

Leu Lys Ser Phe Gln Glu Gln Leu Ala Lys Asp Pro Arg Ile Ala Ala
305                 310                 315                 320

Thr Met Asp Asn Ala Thr Asn Gly Glu Ile Met Pro Asn Ile Pro Gln
            325                 330                 335

Met Ala Ala Phe Trp Tyr Ala Thr Arg Ser Ala Val Leu Asn Ala Ile
            340                 345                 350

Thr Gly Arg Gln Thr Val Glu Ala Ala Leu Asn Asp Ala Ala Thr Arg
            355                 360                 365

Ile Thr Lys
    370

<210> SEQ ID NO 36
<211> LENGTH: 369
<212> TYPE: PRT
<213> ORGANISM: Escherichia coli
<220> FEATURE:
<223> OTHER INFORMATION: maltose binding protein (MBP)

<400> SEQUENCE: 36

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60
```

```
His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
             85                  90                  95

Ala Val Arg Tyr Asn Gly Lys Leu Ile Ala Tyr Pro Ile Ala Val Glu
        100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
        180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
        290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser

<210> SEQ ID NO 37
<211> LENGTH: 381
<212> TYPE: PRT
<213> ORGANISM: Pyrococcus furiosus
<220> FEATURE:
<223> OTHER INFORMATION: maltose binding protein (MBP)

<400> SEQUENCE: 37

Met Lys Ile Glu Glu Gly Lys Val Val Ile Trp His Ala Met Gln Pro
 1               5                  10                  15

Asn Glu Leu Glu Val Phe Gln Ser Leu Ala Glu Glu Tyr Met Ala Leu
             20                  25                  30

Ser Pro Glu Val Glu Ile Val Phe Glu Gln Lys Pro Asn Leu Glu Asp
         35                  40                  45
```

```
Ala Leu Lys Ala Ala Ile Pro Thr Gly Gln Gly Pro Asp Leu Phe Ile
    50                  55                  60

Trp Ala His Asp Trp Ile Gly Lys Phe Ala Glu Ala Gly Leu Leu Glu
 65                  70                  75                  80

Pro Ile Asp Glu Tyr Val Thr Glu Asp Leu Leu Asn Glu Phe Ala Pro
                 85                  90                  95

Met Ala Gln Asp Ala Met Gln Tyr Lys Gly His Tyr Tyr Ala Leu Pro
            100                 105                 110

Phe Ala Ala Glu Thr Val Ala Ile Ile Tyr Asn Lys Glu Met Val Ser
        115                 120                 125

Glu Pro Pro Lys Thr Phe Asp Glu Met Lys Ala Ile Met Glu Lys Tyr
    130                 135                 140

Tyr Asp Pro Ala Asn Glu Lys Tyr Gly Ile Ala Trp Pro Ile Asn Ala
145                 150                 155                 160

Tyr Phe Ile Ser Ala Ile Ala Gln Ala Phe Gly Gly Tyr Tyr Phe Asp
                165                 170                 175

Asp Lys Thr Glu Gln Pro Gly Leu Asp Lys Pro Glu Thr Ile Glu Gly
            180                 185                 190

Phe Lys Phe Phe Phe Thr Glu Ile Trp Pro Tyr Met Ala Pro Thr Gly
        195                 200                 205

Asp Tyr Asn Thr Gln Gln Ser Ile Phe Leu Glu Gly Arg Ala Pro Met
    210                 215                 220

Met Val Asn Gly Pro Trp Ser Ile Asn Asp Val Lys Lys Ala Gly Ile
225                 230                 235                 240

Asn Phe Gly Val Val Pro Leu Pro Pro Ile Ile Lys Asp Gly Lys Glu
                245                 250                 255

Tyr Trp Pro Arg Pro Tyr Gly Gly Val Lys Leu Ile Tyr Phe Ala Ala
            260                 265                 270

Gly Ile Lys Asn Lys Asp Ala Ala Trp Lys Phe Ala Lys Trp Leu Thr
        275                 280                 285

Thr Ser Glu Glu Ser Ile Lys Thr Leu Ala Leu Glu Leu Gly Tyr Ile
    290                 295                 300

Pro Val Leu Thr Lys Val Leu Asp Asp Pro Glu Ile Lys Asn Asp Pro
305                 310                 315                 320

Val Ile Tyr Gly Phe Gly Gln Ala Val Gln His Ala Tyr Leu Met Pro
                325                 330                 335

Lys Ser Pro Lys Met Ser Ala Val Trp Gly Gly Val Asp Gly Ala Ile
            340                 345                 350

Asn Glu Ile Leu Gln Asp Pro Gln Asn Ala Asp Ile Glu Gly Ile Leu
        355                 360                 365

Lys Lys Tyr Gln Gln Glu Ile Leu Asn Asn Met Gln Gly
    370                 375                 380

<210> SEQ ID NO 38
<211> LENGTH: 412
<212> TYPE: PRT
<213> ORGANISM: Thermococcus litoralis
<220> FEATURE:
<223> OTHER INFORMATION: maltose binding protein (MBP)

<400> SEQUENCE: 38

Met Lys Ile Glu Glu Gly Lys Ile Val Phe Ala Val Gly Gly Ala Pro
  1               5                  10                  15

Asn Glu Ile Glu Tyr Trp Lys Gly Val Ile Ala Glu Phe Glu Lys Lys
             20                  25                  30
```

Tyr Pro Gly Val Thr Val Glu Leu Lys Arg Gln Ala Thr Asp Thr Glu
         35                  40                  45

Gln Arg Arg Leu Asp Leu Val Asn Ala Leu Arg Gly Lys Ser Ser Asp
 50                  55                  60

Pro Asp Val Phe Leu Met Asp Val Ala Trp Leu Gly Gln Phe Ile Ala
 65                  70                  75                  80

Ser Gly Trp Leu Glu Pro Leu Asp Asp Tyr Val Gln Lys Asp Asn Tyr
                 85                  90                  95

Asp Leu Ser Val Phe Phe Gln Ser Val Ile Asn Leu Ala Asp Lys Gln
                 100                 105                 110

Gly Gly Lys Leu Tyr Ala Leu Pro Val Tyr Ile Asp Ala Gly Leu Leu
             115                 120                 125

Tyr Tyr Arg Lys Asp Leu Leu Glu Lys Tyr Gly Tyr Ser Lys Pro Pro
130                 135                 140

Glu Thr Trp Gln Glu Leu Val Glu Met Ala Gln Lys Ile Gln Ser Gly
145                 150                 155                 160

Glu Arg Glu Thr Asn Pro Asn Phe Trp Gly Phe Val Trp Gln Gly Lys
                 165                 170                 175

Gln Tyr Glu Gly Leu Val Cys Asp Phe Val Glu Tyr Val Tyr Ser Asn
             180                 185                 190

Gly Gly Ser Leu Gly Glu Phe Lys Asp Gly Lys Trp Val Pro Thr Leu
         195                 200                 205

Asn Lys Pro Glu Asn Val Glu Ala Leu Gln Phe Met Val Asp Leu Ile
210                 215                 220

His Lys Tyr Lys Ile Ser Pro Pro Asn Thr Tyr Thr Glu Met Thr Glu
225                 230                 235                 240

Glu Pro Val Arg Leu Met Phe Gln Gln Gly Asn Ala Ala Phe Glu Arg
                 245                 250                 255

Asn Trp Pro Tyr Ala Trp Gly Leu His Asn Ala Asp Asp Ser Pro Val
             260                 265                 270

Lys Gly Lys Val Gly Val Ala Pro Leu Pro His Phe Pro Gly His Lys
         275                 280                 285

Ser Ala Ala Thr Leu Gly Gly Trp His Ile Gly Ile Ser Lys Tyr Ser
290                 295                 300

Asp Asn Lys Ala Leu Ala Trp Glu Phe Val Lys Phe Val Glu Ser Tyr
305                 310                 315                 320

Ser Val Gln Lys Gly Phe Ala Met Asn Leu Gly Trp Asn Pro Gly Arg
                 325                 330                 335

Val Asp Val Tyr Asp Asp Pro Ala Val Val Ser Lys Ser Pro His Leu
             340                 345                 350

Lys Glu Leu Arg Ala Val Phe Glu Asn Ala Val Pro Arg Pro Ile Val
         355                 360                 365

Pro Tyr Tyr Pro Gln Leu Ser Glu Ile Ile Gln Lys Tyr Val Asn Ser
370                 375                 380

Ala Leu Ala Gly Lys Ile Ser Pro Gln Glu Ala Leu Asp Lys Ala Gln
385                 390                 395                 400

Lys Glu Ala Glu Glu Leu Val Lys Gln Tyr Ser Lys
                 405                 410

<210> SEQ ID NO 39
<211> LENGTH: 378
<212> TYPE: PRT
<213> ORGANISM: Thermatoga maritime
<220> FEATURE:
<223> OTHER INFORMATION: maltose binding protein (MBP)

<400> SEQUENCE: 39

```
Met Lys Ile Glu Gln Thr Lys Leu Thr Ile Trp Ser Ser Glu Lys Gln
1               5                   10                  15

Val Asp Ile Leu Gln Lys Leu Gly Glu Phe Lys Ala Lys Tyr Gly
            20                  25                  30

Ile Pro Val Glu Val Gln Tyr Val Asp Phe Gly Ser Ile Lys Ser Lys
            35                  40                  45

Phe Leu Thr Ala Ala Pro Gln Gly Gln Gly Ala Asp Ile Ile Val Gly
        50                  55                  60

Ala His Asp Trp Val Gly Glu Leu Ala Val Asn Gly Leu Ile Glu Pro
65                  70                  75                  80

Ile Pro Asn Phe Ser Asp Leu Lys Asn Phe Tyr Asp Thr Ala Leu Lys
                85                  90                  95

Ala Phe Ser Tyr Gly Gly Lys Leu Tyr Gly Val Pro Tyr Ala Met Glu
            100                 105                 110

Ala Val Ala Leu Ile Tyr Asn Lys Asp Tyr Val Asp Ser Val Pro Lys
        115                 120                 125

Thr Met Asp Glu Leu Ile Glu Lys Ala Lys Gln Ile Asp Glu Glu Tyr
130                 135                 140

Gly Gly Glu Val Arg Gly Phe Ile Tyr Asp Val Ala Asn Phe Tyr Phe
145                 150                 155                 160

Ser Ala Pro Phe Ile Leu Gly Tyr Gly Gly Tyr Val Phe Lys Glu Thr
                165                 170                 175

Pro Gln Gly Leu Asp Val Thr Asp Ile Gly Leu Ala Asn Glu Gly Ala
            180                 185                 190

Val Lys Gly Ala Lys Leu Ile Lys Arg Met Ile Asp Glu Gly Val Leu
        195                 200                 205

Thr Pro Gly Asp Asn Tyr Gly Thr Met Asp Ser Met Phe Lys Glu Gly
210                 215                 220

Leu Ala Ala Met Ile Ile Asn Gly Leu Trp Ala Ile Lys Ser Tyr Lys
225                 230                 235                 240

Asp Ala Gly Ile Asn Tyr Gly Val Ala Pro Ile Pro Glu Leu Glu Pro
                245                 250                 255

Gly Val Pro Ala Lys Pro Phe Val Gly Val Gln Gly Phe Met Ile Asn
            260                 265                 270

Ala Lys Ser Pro Asn Lys Val Ile Ala Met Glu Phe Leu Thr Asn Phe
        275                 280                 285

Ile Ala Arg Lys Glu Thr Met Tyr Lys Ile Tyr Leu Ala Asp Pro Arg
290                 295                 300

Leu Pro Ala Arg Lys Asp Val Leu Glu Leu Val Lys Asp Asn Pro Asp
305                 310                 315                 320

Val Val Ala Phe Thr Gln Ser Ala Ser Met Gly Thr Pro Met Pro Asn
                325                 330                 335

Val Pro Glu Met Ala Pro Val Trp Ser Ala Met Gly Asp Ala Leu Ser
            340                 345                 350

Ile Ile Ile Asn Gly Gln Ala Ser Val Glu Asp Ala Leu Lys Glu Ala
        355                 360                 365

Val Asp Lys Ile Lys Ala Gln Ile Glu Lys
370                 375
```

<210> SEQ ID NO 40
<211> LENGTH: 372
<212> TYPE: PRT

<213> ORGANISM: Vibrio cholerae
<220> FEATURE:
<223> OTHER INFORMATION: maltose binding protein (MBP)

<400> SEQUENCE: 40

```
Met Lys Ile Glu Glu Gly Gln Leu Thr Ile Trp Ile Asn Gly Asp Lys
  1               5                  10                  15

Gly Tyr Asn Gly Leu Ala Glu Val Gly Lys Lys Phe Glu Ala Asp Thr
             20                  25                  30

Gly Ile Lys Val Thr Val Ala His Pro Asp Ala Leu Gln Asp Lys Phe
         35                  40                  45

Pro Gln Thr Ala Ala Thr Gly Asp Gly Pro Asp Ile Val Phe Trp Ala
     50                  55                  60

His Asp Arg Phe Gly Gly Tyr Ala Glu Ala Gly Leu Leu Val Glu Ile
 65                  70                  75                  80

Lys Pro Ser Ala Lys Ile Gln Glu Gly Ile Val Asp Phe Ala Trp Asp
                 85                  90                  95

Ala Val Lys Tyr Asn Gly Lys Ile Ile Gly Tyr Pro Ile Ala Val Glu
            100                 105                 110

Ser Leu Ser Leu Ile Tyr Asn Lys Asp Leu Val Pro Asn Pro Pro Lys
        115                 120                 125

Ser Trp Glu Glu Val Ala Glu Leu Asp Ala Lys Leu Lys Lys Glu Gly
    130                 135                 140

Lys Ser Ala Ile Met Trp Asn Leu Lys Glu Pro Tyr Phe Thr Trp Pro
145                 150                 155                 160

Leu Met Ala Ala Asp Gly Gly Tyr Ala Phe Lys Tyr Gly Val Asp Gly
                165                 170                 175

Tyr Asp Val Lys Asp Ala Gly Ile Asn Asn Lys Gly Val Lys Asp Ala
            180                 185                 190

Met Asn Phe Val Lys Gly Leu Val Asp Lys Gly Val Ile Ser Pro Asp
        195                 200                 205

Met Asp Tyr Ser Val Ser Glu Ser Ala Phe Asn Gln Gly Asn Thr Ala
    210                 215                 220

Met Thr Ile Asn Gly Pro Trp Ser Trp Gly Asn Ile Glu Lys Ser Gly
225                 230                 235                 240

Ile Asn Tyr Gly Val Thr Thr Leu Pro Lys Phe Asn Gly Gln Ala Ser
                245                 250                 255

Lys Pro Phe Val Gly Val Leu Thr Ala Gly Ile Ser Thr Ala Ser Pro
            260                 265                 270

Asn Lys Asp Leu Ala Val Glu Phe Ile Glu Asn Tyr Leu Leu Thr Asn
        275                 280                 285

Asp Gly Leu Arg Met Val Asn Asn Asp Lys Pro Leu Gly Ala Val Ala
    290                 295                 300

Leu Asn Ser Phe Gln Arg Glu Leu Asp Ala Asp Ala Arg Ile Ala Ala
305                 310                 315                 320

Thr Met Asp Asn Ala Met Asn Gly Glu Ile Met Pro Asn Ile Pro Gln
                325                 330                 335

Met Asn Ala Phe Trp Ser Ser Ala Lys Asn Ala Ile Ile Asn Ile Val
            340                 345                 350

Asp Gly Arg Gln Thr Val Asp Ala Ala Leu Ala Asp Ala Glu Lys Gln
        355                 360                 365

Met Thr Lys Pro
    370
```

-continued

```
<210> SEQ ID NO 41
<211> LENGTH: 559
<212> TYPE: PRT
<213> ORGANISM: Homo sapiens
<220> FEATURE:
<223> OTHER INFORMATION: human UDP-N-acetylgalactosaminyltransferase 1
      (GalNAcT1)

<400> SEQUENCE: 41

Met Arg Lys Phe Ala Tyr Cys Lys Val Val Leu Ala Thr Ser Leu Ile
 1               5                  10                  15

Trp Val Leu Leu Asp Met Phe Leu Leu Leu Tyr Phe Ser Glu Cys Asn
            20                  25                  30

Lys Cys Asp Glu Lys Lys Glu Arg Gly Leu Pro Ala Gly Asp Val Leu
        35                  40                  45

Glu Pro Val Gln Lys Pro His Glu Gly Pro Gly Glu Met Gly Lys Pro
    50                  55                  60

Val Val Ile Pro Lys Glu Asp Gln Glu Lys Met Lys Glu Met Phe Lys
65                  70                  75                  80

Ile Asn Gln Phe Asn Leu Met Ala Ser Glu Met Ile Ala Leu Asn Arg
                85                  90                  95

Ser Leu Pro Asp Val Arg Leu Glu Gly Cys Lys Thr Lys Val Tyr Pro
            100                 105                 110

Asp Asn Leu Pro Thr Thr Ser Val Val Ile Val Phe His Asn Glu Ala
        115                 120                 125

Trp Ser Thr Leu Leu Arg Thr Val His Ser Val Ile Asn Arg Ser Pro
    130                 135                 140

Arg His Met Ile Glu Glu Ile Val Leu Val Asp Asp Ala Ser Glu Arg
145                 150                 155                 160

Asp Phe Leu Lys Arg Pro Leu Glu Ser Tyr Val Lys Lys Leu Lys Val
                165                 170                 175

Pro Val His Val Ile Arg Met Glu Gln Arg Ser Gly Leu Ile Arg Ala
            180                 185                 190

Arg Leu Lys Gly Ala Ala Val Ser Lys Gly Gln Val Ile Thr Phe Leu
        195                 200                 205

Asp Ala His Cys Glu Cys Thr Val Gly Trp Leu Glu Pro Leu Leu Ala
    210                 215                 220

Arg Ile Lys His Asp Arg Arg Thr Val Val Cys Pro Ile Ile Asp Val
225                 230                 235                 240

Ile Ser Asp Asp Thr Phe Glu Tyr Met Ala Gly Ser Asp Met Thr Tyr
                245                 250                 255

Gly Gly Phe Asn Trp Lys Leu Asn Phe Arg Trp Tyr Pro Val Pro Gln
            260                 265                 270

Arg Glu Met Asp Arg Arg Lys Gly Asp Arg Thr Leu Pro Val Arg Thr
        275                 280                 285

Pro Thr Met Ala Gly Gly Leu Phe Ser Ile Asp Arg Asp Tyr Phe Gln
    290                 295                 300

Glu Ile Gly Thr Tyr Asp Ala Gly Met Asp Ile Trp Gly Gly Glu Asn
305                 310                 315                 320

Leu Glu Ile Ser Phe Arg Ile Trp Gln Cys Gly Gly Thr Leu Glu Ile
                325                 330                 335

Val Thr Cys Ser His Val Gly His Val Phe Arg Lys Ala Thr Pro Tyr
            340                 345                 350

Thr Phe Pro Gly Gly Thr Gly Gln Ile Ile Asn Lys Asn Asn Arg Arg
        355                 360                 365
```

```
Leu Ala Glu Val Trp Met Asp Glu Phe Lys Asn Phe Phe Tyr Ile Ile
            370                 375                 380
Ser Pro Gly Val Thr Lys Val Asp Tyr Gly Asp Ile Ser Ser Arg Val
385                 390                 395                 400
Gly Leu Arg His Lys Leu Gln Cys Lys Pro Phe Ser Trp Tyr Leu Glu
                405                 410                 415
Asn Ile Tyr Pro Asp Ser Gln Ile Pro Arg His Tyr Phe Ser Leu Gly
                420                 425                 430
Glu Ile Arg Asn Val Glu Thr Asn Gln Cys Leu Asp Asn Met Ala Arg
                435                 440                 445
Lys Glu Asn Glu Lys Val Gly Ile Phe Asn Cys His Gly Met Gly Gly
450                 455                 460
Asn Gln Val Phe Ser Tyr Thr Ala Asn Lys Glu Ile Arg Thr Asp Asp
465                 470                 475                 480
Leu Cys Leu Asp Val Ser Lys Leu Asn Gly Pro Val Thr Met Leu Lys
                485                 490                 495
Cys His His Leu Lys Gly Asn Gln Leu Trp Glu Tyr Asp Pro Val Lys
                500                 505                 510
Leu Thr Leu Gln His Val Asn Ser Asn Gln Cys Leu Asp Lys Ala Thr
                515                 520                 525
Glu Glu Asp Ser Gln Val Pro Ser Ile Arg Asp Cys Asn Gly Ser Arg
530                 535                 540
Ser Gln Gln Trp Leu Leu Arg Asn Val Thr Leu Pro Glu Ile Phe
545                 550                 555

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 42

Lys Met Leu Leu
  1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 43

Ile Trp Val Leu
  1

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence:consensus
      peptide

<400> SEQUENCE: 44

Arg Ala Ile Pro Asp
  1               5
```

```
<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence:consensus
      peptide

<400> SEQUENCE: 45

Thr Ser Val Val Ile
 1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence:consensus
      peptide

<400> SEQUENCE: 46

Phe His Asn Glu Ala
 1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence:consensus
      peptide

<400> SEQUENCE: 47

Leu Leu Arg Thr Val
 1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence:consensus
      peptide

<400> SEQUENCE: 48

Glu Ile Ile Leu Val Asp Asp
 1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence:consensus
      peptide

<400> SEQUENCE: 49

Gly Leu Ile Arg Ala Arg Leu Lys Gly Ala
 1               5                  10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence:consensus
      peptide

<400> SEQUENCE: 50
```

```
Val Ile Thr Phe Leu Asp Ala His Cys Glu Cys
1               5                   10

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence:consensus
      peptide

<400> SEQUENCE: 51

Trp Leu Glu Pro Leu Leu
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence:consensus
      peptide

<400> SEQUENCE: 52

Pro Ile Ile Asp Val Ile
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence:consensus
      peptide

<400> SEQUENCE: 53

Tyr Met Ala Ala Ser
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence:consensus
      peptide

<400> SEQUENCE: 54

Pro Ile Lys Thr Pro
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence:consensus
      peptide

<400> SEQUENCE: 55

Ile Ala Gly Gly Leu Phe
1               5

<210> SEQ ID NO 56
<211> LENGTH: 25
<212> TYPE: PRT
<213> ORGANISM: Artificial Sequence
```

<220> FEATURE:
<223> OTHER INFORMATION: Description of Artificial Sequence:consensus
      peptide

<400> SEQUENCE: 56

Met Asp Ile Trp Gly Gly Glu Asn Leu Glu Ile Ser Phe Arg Ile Trp
 1               5                  10                  15

Gln Cys Gly Gly Ser Leu Glu Ile Ile
             20                  25

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence:consensus
      peptide

<400> SEQUENCE: 57

Val Gly His Val Phe Arg Lys
 1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence:consensus
      peptide

<400> SEQUENCE: 58

Pro Tyr Thr Phe Pro Gly Gly Ser Gly
 1               5

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence:consensus
      peptide

<400> SEQUENCE: 59

Ala Glu Val Trp Met Asp Glu Phe Lys Asn Phe Phe Tyr
 1               5                  10

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 60

Cys Lys Pro Phe
 1

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence:consensus
      peptide

<400> SEQUENCE: 61

```
Trp Tyr Leu Glu Asn Ile Tyr Pro Asp
1               5
```

```
<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 62

Val Gly Ile Phe
1
```

```
<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 63

Gly Gly Asn Gln
1
```

```
<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 64

Asp Leu Cys Leu
1
```

```
<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence:consensus
      peptide

<400> SEQUENCE: 65

Ser Gln Gln Trp
1
```

```
<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence:anti-FLAG
      antibody epitope tag, "FLAG tag"

<400> SEQUENCE: 66

Asp Tyr Lys Asp Asp Asp Asp Lys
1               5
```

```
<210> SEQ ID NO 67
<211> LENGTH: 6
<212> TYPE: PRT
<213> ORGANISM: Artificial Sequence
<220> FEATURE:
```

```
<223> OTHER INFORMATION: Description of Artificial Sequence:
      hexahistidine affinity tag, polyhistidine purification tag, poly
      His, metal chelate affinity ligand

<400> SEQUENCE: 67

His His His His His His
  1               5

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence:PCR
      amplification sense primer Sial 5'Tm

<400> SEQUENCE: 68
tttggatcca agctacactt actccaatgg                                      30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence:PCR
      amplification antisense primer Sial 3' Whole

<400> SEQUENCE: 69
tttgaattct cagataccac tgcttaagtc                                      30

<210> SEQ ID NO 70
<211> LENGTH: 31
<212> TYPE: DNA
<213> ORGANISM: Artificial Sequence
<220> FEATURE:
<223> OTHER INFORMATION: Description of Artificial Sequence:PCR
      amplification sense primer ST3BAMH1

<400> SEQUENCE: 70
taatggattc aagctacact tactccaatg g                                    31

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence:PCR
      amplification antisense primer ST3XBA1

<400> SEQUENCE: 71
gcgctctaga tcagatacca ctgcttaagt                                      30

<210> SEQ ID NO 72
<211> LENGTH: 35
<212> TYPE: DNA
<213> ORGANISM: Artificial Sequence
<220> FEATURE:
<223> OTHER INFORMATION: Description of Artificial Sequence:PCR 5'
      primer ST3 BamH1 delta73

<400> SEQUENCE: 72
tgtatcggat ccctggccac caagtacgct aactt                                35

<210> SEQ ID NO 73
<211> LENGTH: 38
<212> TYPE: DNA
<213> ORGANISM: Artificial Sequence
```

```
<220> FEATURE:
<223> OTHER INFORMATION: Description of Artificial Sequence:PCR 5'
      primer ST3 BamH1 delta85

<400> SEQUENCE: 73
tgtatcggat cctgcaaacc cggctacgct tcagccat                           38

<210> SEQ ID NO 74
<211> LENGTH: 35
<212> TYPE: DNA
<213> ORGANISM: Artificial Sequence
<220> FEATURE:
<223> OTHER INFORMATION: Description of Artificial Sequence:PCR 5'
      primer ST3 BamH1 delta86

<400> SEQUENCE: 74
tgtatcggat ccaaacccgg ctacgcttca gccat                             35

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence:PCR common
      3' primer ST3-Xho1

<400> SEQUENCE: 75
ggtctcctcg agtcagatac cactgcttaa                                   30

<210> SEQ ID NO 76
<211> LENGTH: 37
<212> TYPE: DNA
<213> ORGANISM: Artificial Sequence
<220> FEATURE:
<223> OTHER INFORMATION: Description of Artificial Sequence:mutagenic
      oligonucleotide GnT1 R120A C121H+

<400> SEQUENCE: 76
ccgcagcact gttcgggccc acctggacaa gctgctg                            37

<210> SEQ ID NO 77
<211> LENGTH: 37
<212> TYPE: DNA
<213> ORGANISM: Artificial Sequence
<220> FEATURE:
<223> OTHER INFORMATION: Description of Artificial Sequence:mutagenic
      oligonucleotide GnT1 R120A C121H-

<400> SEQUENCE: 77
cagcagcttg tccaggtggg cccgaacagt gctgcgg                            37

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence:mutagenic
      oligonucleotide GnT1C123A+

<400> SEQUENCE: 78
agcactgttc ggcgcgccct ggacaagctg ctg                               33

<210> SEQ ID NO 79
<211> LENGTH: 33
<212> TYPE: DNA
<213> ORGANISM: Artificial Sequence
<220> FEATURE:
```

```
<223> OTHER INFORMATION: Description of Artificial Sequence:mutagenic
      oligonucleotide GnT1C123A-

<400> SEQUENCE: 79
cagcagcttg tccagggcgc gccgaacagt gct                                    33

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence:MuC-2-like
      GalNAc peptide acceptor

<400> SEQUENCE: 80

Met Val Thr Pro Thr Pro Thr Pro Thr Cys
1               5                   10
```

What is claimed is:

1. A method of refolding an insoluble, recombinant, eukaryotic α(2,3)sialyltransferase (ST3Gal3) protein, wherein the ST3Gal3 protein comprises a maltose binding protein domain (MBD), the method comprising the steps of
   (a) solubilizing the insoluble, recombinant, eukaryotic ST3Gal3 protein in a solubilization buffer; and
   (b) contacting the soluble eukaryotic ST3Gl13 protein with a refolding buffer comprising a redox couple and polyethylene glycol) (PEG) and/or lauryl maltoside to refold the eukaryotic ST3Gal3 protein,
   wherein the refolded eukaryotic ST3Gal3 protein catalyzes the transfer of a sialic acid sugar from a donor substrate to an acceptor substrate.

2. The method of claim 1, wherein the eukaryotic ST3Gal3 protein further comprises a purification domain selected from the group consisting of a starch binding domain, a thioredoxin domain, a SUMO domain, a poly-His domain, a myc epitope domain, and a glutathione-S-transferase domain.

3. The method of claim 1, wherein the eukaryotic ST3Gal3 protein is expressed in a bacterial host cell as an insoluble inclusion body.

4. The method of claim 1, wherein a second insoluble, recombinant eukaryotic glycosyltransferase is refolded with the eukaryotic ST3Gal3 protein.

5. The method of claim 4, wherein a third insoluble, recombinant eukaryotic glycosyltransferase is refolded with the eukaryotic ST3Gal3 protein and the second eukaryotic glycosyltransferase.

6. The method of claim 1, wherein the redox couple is selected from the group consisting of reduced glutathione/oxidized glutathione (GSH/GSSG) and cysteine/cystamine.

7. The method of claim 1, wherein the acceptor substrate is selected from the group consisting of a protein, a peptide, a glycoprotein, and a glycopeptide.

8. The method of claim 1, wherein the donor substrate is a CMP-sialic acid PEG molecule and the acceptor substrate is selected from the group consisting of a protein, a peptide, a glycoprotein, and a glycopeptide.

9. A method of refolding an insoluble, recombinant, eukaryotic α(2,3)sialyltransferase (ST3Gal3) protein, wherein the ST3Gal3 protein comprises a maltose binding protein domain (MBD) and is truncated to remove all or a portion of a stem region, the method comprising the steps of
   (a) solubilizing the insoluble, recombinant, eukaryotic ST3Gal3protein in a solubilization buffer; and
   (b) contacting the soluble eukaryotic ST3Gal3 protein with a refolding buffer comprising a redox couple and poly (ethylene glycol) (PEG) and/or lauryl maltoside to refold the eukaryotic ST3Gal3 protein,
   wherein the refolded eukaryotic ST3Gal3 protein catalyzes the transfer of a sialic acid sugar from a donor substrate to an acceptor substrate.

10. A method of refolding an insoluble, recombinant, eukaryotic α(2,3)sialyltransferase (ST3Gal3) protein, wherein the ST3Gal3 protein comprises a maltose binding protein domain (MBD) and wherein an unpaired cysteine is removed by substitution with a non-cysteine amino acid, the method comprising the steps of
   (a) solubilizing the insoluble, recombinant, eukaryotic ST3Gal3 protein in a solubilization buffer; and
   (b) contacting the soluble eukaryotic ST3Gal3 protein with a refolding buffer comprising a redox couple and poly (ethylene glycol) (PEG) and/or lauryl maltoside to refold the eukaryotic ST3Gal3 protein,
   wherein the refolded eukaryotic ST3Gal3 protein catalyzes the transfer of a sialic acid sugar from a donor substrate to an acceptor substrate.

11. The method of claim 1, wherein the refolding buffer comprises PEG and lauryl maltoside.

12. The method of claim 11, wherein the refolding buffer comprises about 0.02-10 mM reduced glutathione (GSH), 0.005-10 mM oxidized glutathione (GSSG), 0.005-10 mM lauryl maltoside, 50-250 mM NaCl, 2-10 mM KCl, 0.01-0.05% PEG 3350, and 150-550 mM L-arginine.

13. The method of claim 9, wherein the refolding buffer comprises PEG and lauryl maltoside.

14. The method of claim 13, wherein the refolding buffer comprises about 0.02-10 mM reduced glutathione (GSH), 0.005-10 mM oxidized glutathione (GSSG), 0.005-10 mM lauryl maltoside, 50-250 mM NaCl, 2-10 mM KCl, 0.01-0.05% PEG 3350, and 150-550 mM L-arginine.

15. The method of claim 10, wherein the refolding buffer comprises PEG and lauryl maltoside.

16. The method of claim 15, wherein the refolding buffer comprises about 0.02-10 mM reduced glutathione (GSH), 0.005-10 mM oxidized glutathione (GSSG), 0.005-10 mM lauryl maltoside, 50-250 mM NaCl, 2-10 mM KCl, 0.01-0.05% PEG 3350, and 150-550 mM L-arginine.

* * * * *